US011725232B2

(12) United States Patent
Chu Ip et al.

(10) Patent No.: US 11,725,232 B2
(45) Date of Patent: Aug. 15, 2023

(54) COMPOSITIONS, METHODS AND KITS FOR DETECTION OF GENETIC VARIANTS FOR ALZHEIMER'S DISEASE

(71) Applicant: The Hong Kong University of Science and Technology, Hong Kong (CN)

(72) Inventors: Nancy Yuk-Yu Chu Ip, Hong Kong SAR (CN); Kit Yu Fu, Hong Kong SAR (CN); Yu Chen, Hong Kong SAR (CN); Xiaopu Zhou, Chongqing (CN)

(73) Assignee: The Hong Kong University of Science and Technology, Kowloon (HK)

( * ) Notice: Subject to any disclaimer, the term of this patent is extended or adjusted under 35 U.S.C. 154(b) by 0 days.

(21) Appl. No.: 15/797,583

(22) Filed: Oct. 30, 2017

(65) Prior Publication Data

US 2018/0142287 A1   May 24, 2018

Related U.S. Application Data

(60) Provisional application No. 62/507,344, filed on May 17, 2017, provisional application No. 62/457,640, filed on Feb. 10, 2017, provisional application No. 62/415,236, filed on Oct. 31, 2016.

(51) Int. Cl.
*C12Q 1/6827* (2018.01)
*C12Q 1/6883* (2018.01)
*G01N 33/53* (2006.01)

(52) U.S. Cl.
CPC ......... *C12Q 1/6827* (2013.01); *C12Q 1/6883* (2013.01); *G01N 33/5308* (2013.01); *C12Q 2600/118* (2013.01); *C12Q 2600/156* (2013.01); *G01N 2800/2821* (2013.01)

(58) Field of Classification Search
CPC .............. C12Q 1/6827; C12Q 1/6883; C12Q 2600/118; C12Q 2600/156
See application file for complete search history.

(56) References Cited

U.S. PATENT DOCUMENTS

| | | | |
|---|---|---|---|
| 4,897,268 A | 1/1990 | Tice et al. |
| 5,075,109 A | 12/1991 | Tice et al. |
| 5,424,186 A | 6/1995 | Fodor et al. |
| 5,451,683 A | 9/1995 | Barrett et al. |
| 5,811,128 A | 9/1998 | Tice et al. |
| 5,814,344 A | 9/1998 | Tice et al. |
| 5,820,883 A | 10/1998 | Tice et al. |
| 5,837,832 A | 11/1998 | Chee et al. |
| 5,853,763 A | 12/1998 | Tice et al. |
| 5,858,659 A | 1/1999 | Sapolsky et al. |
| 5,928,647 A | 7/1999 | Rock |
| 5,942,252 A | 8/1999 | Tice et al. |
| 6,040,138 A | 3/2000 | Lockhart et al. |
| 6,207,392 B1 | 3/2001 | Weiss et al. |
| 6,300,063 B1 | 10/2001 | Lipshutz et al. |
| 6,306,597 B1 | 10/2001 | Macevicz |
| 6,797,470 B2 | 9/2004 | Barany et al. |
| 6,858,412 B2 | 2/2005 | Willis et al. |
| 6,969,589 B2 | 11/2005 | Patil et al. |
| 7,037,687 B2 | 5/2006 | Williams et al. |
| 7,083,917 B2 | 8/2006 | Barany et al. |
| 7,166,434 B2 | 1/2007 | Barany et al. |
| 7,169,560 B2 | 1/2007 | Lapidus et al. |
| 7,232,656 B2 | 6/2007 | Balasubramanian et al. |
| 7,320,865 B2 | 1/2008 | Barany et al. |
| 7,332,285 B2 | 2/2008 | Barany et al. |
| 7,364,858 B2 | 4/2008 | Barany et al. |
| 7,429,453 B2 | 9/2008 | Barany et al. |
| 7,598,035 B2 | 10/2009 | Macevicz |
| 7,645,596 B2 | 1/2010 | Williams et al. |
| 7,769,400 B2 | 8/2010 | Backholm et al. |
| 2002/0012930 A1 | 1/2002 | Rothberg et al. |
| 2003/0068629 A1 | 4/2003 | Rothberg et al. |
| 2003/0100102 A1 | 5/2003 | Rothberg et al. |
| 2003/0148344 A1 | 8/2003 | Rothberg et al. |
| 2003/0207295 A1 | 11/2003 | Gunderson et al. |
| 2003/0215821 A1 | 11/2003 | Gunderson et al. |
| 2004/0014109 A1 | 1/2004 | Pericak-Vance et al. |
| 2004/0018491 A1 | 1/2004 | Gunderson et al. |
| 2004/0248161 A1 | 12/2004 | Rothberg et al. |
| 2005/0079510 A1 | 4/2005 | Berka et al. |
| 2005/0100893 A1 | 5/2005 | Gunderson et al. |
| 2005/0100932 A1 | 5/2005 | Lapidus et al. |
| 2005/0124022 A1 | 6/2005 | Srinivasan et al. |
| 2006/0012784 A1 | 1/2006 | Ulmer |
| 2006/0012793 A1 | 1/2006 | Harris |
| 2006/0024678 A1 | 2/2006 | Buzby |
| 2006/0024711 A1 | 2/2006 | Lapidus et al. |

(Continued)

FOREIGN PATENT DOCUMENTS

| | | |
|---|---|---|
| WO | WO-9210092 A1 | 6/1992 |
| WO | WO-9511995 A1 | 5/1995 |

(Continued)

OTHER PUBLICATIONS

Lalli (Molecular Psychiatry, 2015, 20, 1294-1300).*
Scarpini (Lancet Neurol 2003, 2: 539-47).*
Jaio (PLOS ONE 10(12), 2015, 1-10).*
RefSNP cluster report rs6857, available at ncbi.nlm.nih.gov, printed Oct. 2019, pp. 1-3.*
Vellas (Lancet Neurolo, 2012, 11:851-59).*
Araya-Quintanilla (Neurologia 2020, vol. 35, 105-114).*
Vallen Graham et al. (Annu. Rev. Med, 2017, 68:413-30).*

(Continued)

*Primary Examiner* — Sarae L Bausch

(74) *Attorney, Agent, or Firm* — Kilpatrick Townsend & Stockton LLP

(57) ABSTRACT

Provided herein are methods, kits, and devices related to genetic variations of neurological disorders. For example, methods, kits, and devices for using such genetic variations to assess susceptibility of developing Alzheimer's disease.

16 Claims, 9 Drawing Sheets

Specification includes a Sequence Listing.

(56) References Cited

U.S. PATENT DOCUMENTS

| | | | |
|---|---|---|---|
| 2006/0078909 | A1 | 4/2006 | Srinivasan et al. |
| 2007/0269827 | A1 | 11/2007 | Harley |
| 2009/0130683 | A1 | 5/2009 | Gaffney et al. |
| 2010/0035266 | A1 | 2/2010 | Atwood |
| 2010/0183610 | A1 | 7/2010 | Li et al. |
| 2011/0189668 | A1 | 8/2011 | Bergman et al. |
| 2011/0200564 | A1 | 8/2011 | Tanzi et al. |
| 2013/0102692 | A1 | 4/2013 | Atwood |
| 2013/0324431 | A1 | 12/2013 | Szigeti et al. |
| 2014/0134186 | A1 | 5/2014 | Li et al. |
| 2015/0153364 | A1 | 6/2015 | Crary |
| 2015/0337375 | A1 | 11/2015 | Crary et al. |
| 2017/0016072 | A1 | 1/2017 | Atwood |

FOREIGN PATENT DOCUMENTS

| | | | |
|---|---|---|---|
| WO | WO-9820019 | A1 | 5/1998 |
| WO | WO-2008103472 | A2 | 8/2008 |
| WO | WO-2008103472 | A3 | 5/2009 |
| WO | 2013071119 | A2 | 5/2013 |
| WO | 2016025602 | A1 | 2/2016 |

OTHER PUBLICATIONS

RefSNP cluster report rs1257592, available at ncbi.nlm.nih.gov, printed Oct. 2019, pp. 1-3.*
Kaasinen (Eur. J. Medical Genetics, 2014, vol. 57, pp. 543-551).*
DbSNP (ncbi.nlm.nih.gov/snp/) Reference SNP report, rs157592, pp. 1-10, released Apr. 9, 2021.*
DbSNP reference SNP cluster report rs11791561, available at ncbi.nlm.nih.gov, pp. 1-3, printed Oct. 2019.*
DbSNP reference SNP cluster report: rs10204137, available at ncbi.nlm.nih.gov, pp. 1-3, printer Oct. 2019.*
Zhou, et al. "Identification of genetic risk factors in the Chinese population implicates a role of immune system in Alzheimer's disease pathogenesis." Proceedings of the National Academy of Sciences 115, No. 8 (2018): 1697-1706.
Zhou, et al. "Non-coding variability at the APOE locus contributes to the Alzheimer's risk." Nature communications 10, No. 1 (2019): 3310.
Floudas, Charalampos S., Nara Um, M. Ilyas Kamboh, Michael M. Barmada, and Shyam Visweswaran. "Identifying Genetic Interactions Associated with Late-Onset Alzheimer's Disease." PeerJ PrePrints (2013).
Masoodi, Tariq Ahmad, Sulaiman A. Al Shammari, May N. Al-Muammar, and Adel A. Alhamdan. "Screening and evaluation of deleterious SNPs in APOE gene of Alzheimer's disease." Neurology research international 2012 (2012).
Ridge, Perry G., Shubhabrata Mukherjee, Paul K. Crane, and John SK Kauwe. "Alzheimer's disease: analyzing the missing heritability." PloS one 8, No. 11 (2013): e79771.
Altschul et al., Gapped BLAST and PSI-BLAST: a new generation of protein database search programs, Nucl. Acids. Res. 25(17):3389-3402 (1997).
Amarzguioui, et al. Approaches for chemically synthesized siRNA and vector-mediated RNAi. FEBS Lett. Oct. 31, 2005;579(26):5974-81. Epub Sep. 20, 2005.
Bedell, et al. In vivo genome editing using a high-efficiency TALEN system. Nature. Sep. 23, 2012. doi: 10.1038/nature11537. [Epub ahead of print].
Bennett, C. Efficiency of antisense oligonucleotide drug discovery. Antisense Nucleic Acid Drug Dev. Jun. 2002;12(3):215-24.
Bibkova et al. High-throughput DNA methylation profiling using universal bead arrays. Genome Res. 16:383-393 (2006).
BIRD et al. Single-chain antigen-binding proteins. Science 242:423-442 (1988).
Brummelkamp, et al. A system for stable expression of short interfering RNAs in mammalian cells. Science. Apr. 19, 2002;296(5567):550-3. Epub Mar. 21, 2002.
Chen, H. Clinical development of antisense oligonucleotides as anti-cancer therapeutics. Methods Mol Med. 2003;75:621-36.
Chouraki, et al. Evaluation of a Genetic Risk Score to Improve Risk Prediction for Alzheimer's Disease, J Alzheimers, Dis. Jun. 18, 2016; 53(3): 921-932.
Desikan, et al. Genetic assessment of age-associated Alzheimer disease risk: Development and validation of a polygenic hazard score, PLoS Med, 2017, Mar. 21, 14(3): e1002258.
Dias, et al. Antisense oligonucleotides: basic concepts and mechanisms. Mol. Cancer Ther. Mar. 2002;1(5):347-55.
Fan, et al. Donor IL-18 rs5744247 polymorphism as a new biomarker of tacrolimus elimination in Chinese liver transplant patients during the early post-transplantation period: results from two cohort studies, Pharmacogenomics, 2015, 16(3):239-50.
Fire, et al. Potent and specific genetic interference by double-stranded RNA in Caenorhabditis Eelegans, Nature. Feb. 19, 1998;391(6669):806-11.
Gravina, et al. The darkside of circulating nucleic acids, Aging Cell, Jun. 2016, 15(3):398-9.
Harris et al. Single-molecule DNA sequencing of a viral genome. Science 320:106-109 (2008).
Harrison, et al. An Alzheimer's Disease Genetic Risk Score Predicts Longitudinal Thinning of Hippocampal Complex Subregions in Healthy Older Adults, Eneuro, Methods/New Tools, Jun. 2016, 13 pages.
Huston, et al. Protein engineering of antibody binding sites: recovery of specific activity in an anti-digoxin single-chain Fv analogue produced in *Escherichia coli*. Proc Natl Acad. Sci. U.S.A. Aug. 1988; 85(16):5879-83.
Kim, et al. Strategies for silencing human disease using RNA interference. Nat Rev Genet. Mar. 2007;8(3):173-84.
Kim, et al., Synthetic dsRNA dicer substrates enhance RNAi potency and efficacy. Nature biotechnology. 2005; 23(2): 222-226.
Kraus, et al. Detection and isolation of novel protein-tyrosine kinase genes employing reduced stringency hybridization. Methods Enzymol. 1991;200:546-56.
Kurreck, J. Antisense technologies. Improvement through novel chemical modifications. Eur J Biochem. Apr. 2003;270(8):1628-44.
Kutyavin, et al. A novel endonuclease IV post-PCR genotyping system. Nucleic Acids Res. 2006;34(19):e128. Epub Sep. 29, 2006.
Lavery, et al. Antisense and RNAi: powerful tools in drug target discovery and validation. Curr Opin. Drug Discov. Devel. Jul. 2003;6(4):561-9.
Limon-Sztencel, et al. The algorithm for Alzheimer risk assessment based on APOE promoter polymorphisms based on APOE promoter polymorphisms, research and Therapy, 2016, 8:19.
Margulies, et al. Genome sequencing in microfabricated high-density picolitre reactors. Nature. Sep. 15, 2005;437(7057):376-80. Epub Jul. 31, 2005.
Marques, et al. A structural basis for discriminating between self and nonself double-stranded RNAs in mammalian cells. Nat Biotechnol. May 2006;24(5):559-65. Epub Apr. 30, 2006.
McCaughan, et al. Single-molecule genomics. J Pathol. Jan. 2010; 220(2):297-306. Doi: 10.1002/path.2647.
Nielsen et al. Sequence-selective recognition of DNA by strand displacement with a thymine-substituted polyamide. Science 254:1497-1500 (1991).
Podlesniy, et al. Mitochondrial DNA differentiates Alzheimer's disease from Creutzfeldt-Jakob disease, Alzheimers Dement, May 2016, 12(5):546-55.
Siolas, et al. Synthetic shRNAs as potent RNAi triggers. Nat Biotechnol. Feb. 2005;23(2):227-31. Epub Dec. 26, 2004.
Smith, et al. A high-density admixture map for disease gene discovery in African Americans. Am J Hum Genet. May 2004;74(5):1001-13. Epub Apr. 14, 2004.
Soni et al. Progress toward ultrafast DNA sequencing using solid-state nanopores. Clin Chem 53:1996-2001 (2007).
Stephens, et al. Antisense oligonucleotide therapy in cancer. Curr Opin Mol. Ther. Apr. 2003;5(2):118-22.
Thompson. Applications of antisense and siRNAs during preclinical drug development. Drug Discov Today. Sep. 1, 2002;7(17):912-7.
Urnov, et al. Genome editing with engineered zinc finger nucleases. Nat Rev Genet. Sep. 2010;11(9):636-46.
Wang, et al. Antisense anticancer oligonucleotide therapeutics. Curr Cancer Drug Targets. Nov. 2001;1(3):177-96.

(56) References Cited

OTHER PUBLICATIONS

Ward, et al. Binding activities of a repertoire of single immunoglobulin variable domains secreted from *Escherichia coli*. Nature (1989) 341:544-46.

Yusa, et al. Targeted gene correction of α1-antitrypsin deficiency in induced pluripotent stem cells. Nature. Oct. 12, 2011; 478(7369):391-4. Doi: 10.1038/nature10424.

Yu et al. Interleukin-18 promoter polymorphisms and risk of late onset Alzheimer's disease. Brain research. Feb. 9, 2009;1253:169-75.

\* cited by examiner

Figure 2A
Figure 2B
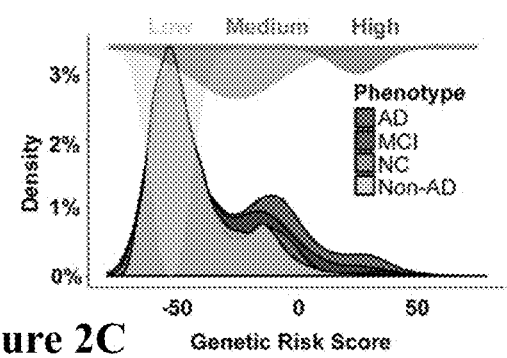
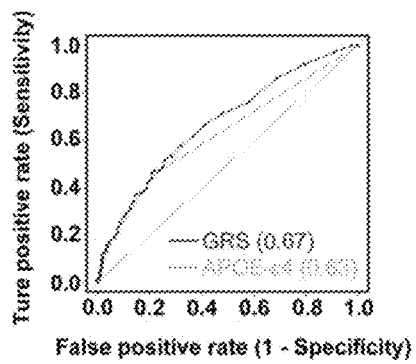
Figure 2C
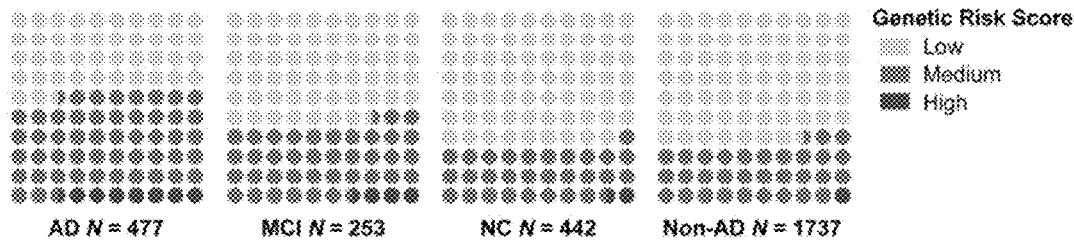
Figure 2

Figure 7A 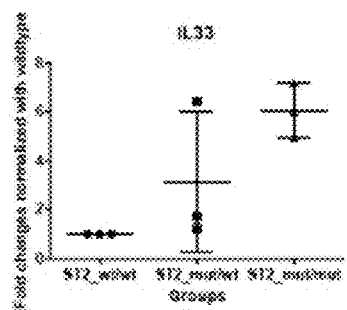 Figure 7B 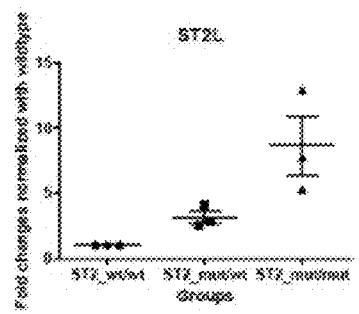 Figure 7C 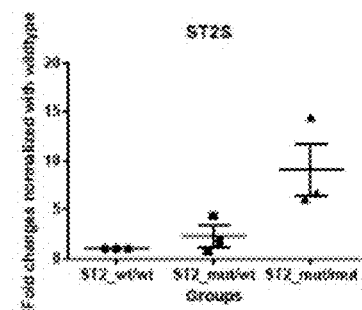
Figure 7

Figure 8A
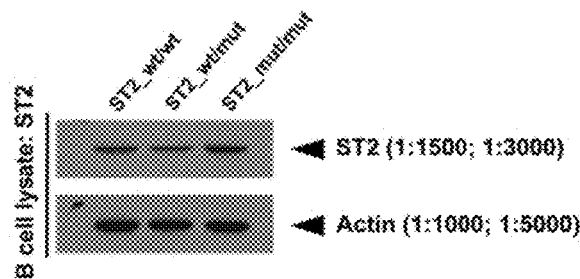
Figure 8B
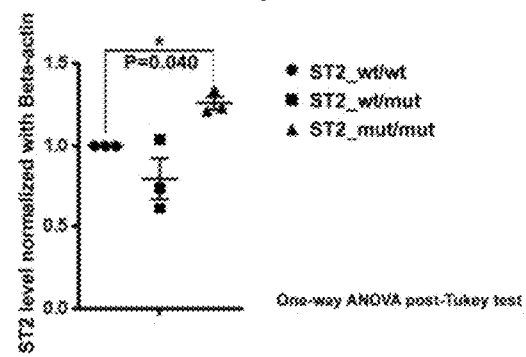
Figure 8C
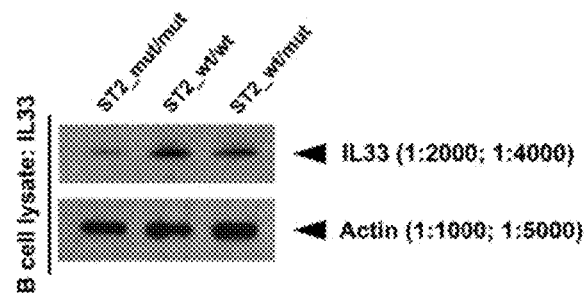
Figure 8D
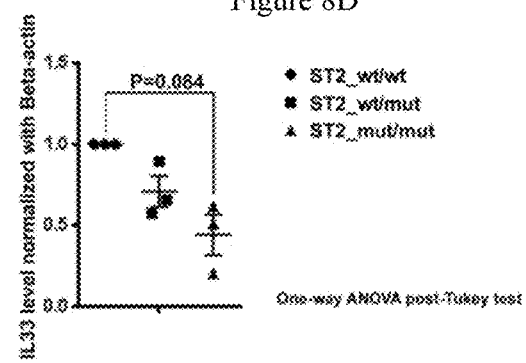
Figure 8

Figure 9A
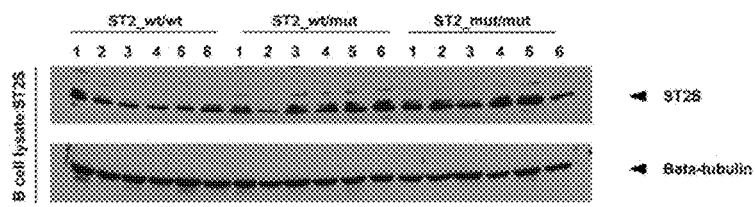
Figure 9B
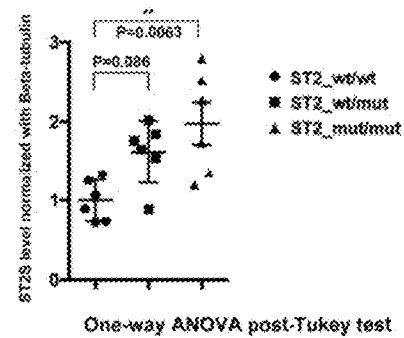
Figure 9

COMPOSITIONS, METHODS AND KITS FOR DETECTION OF GENETIC VARIANTS FOR ALZHEIMER'S DISEASE

CROSS-REFERENCE

This application claims the benefit of U.S. Provisional Application Nos. 62/507,344 filed May 17, 2017; 62/457,640 filed Feb. 10, 2017; and 62/415,236 filed Oct. 31, 2016, which are incorporated by reference herein in their entirety.

SEQUENCE LISTING

The instant application contains a Sequence Listing which has been submitted electronically in ASCII format and is hereby incorporated by reference in its entirety. Said ASCII copy, created on Jan. 18, 2018, is named 52226-701_201_SL.txt and is 98,095 bytes in size.

BACKGROUND

Alzheimer's disease (AD) is an age-related neurodegenerative disease. As populations worldwide age, its prevalence is increasing such that it has become one of the leading causes of mortality in the elderly population in recent years. AD is the most common type of dementia, affecting more than 46.88 million people worldwide. In China, a meta-analysis has revealed a fast-growing dementia population over the past decades, with the total number of AD patients rising from 1.9 million in 1990 to 5.7 million in 2010.

BRIEF SUMMARY

One aspect provides a method for detecting a genetic variant in a subject suspected of having Alzheimer's disease (AD), said method comprising:
a. obtaining a biological sample from said subject;
b. contacting said biological sample with a probe specific for said genetic variant that comprises one or more single nucleotide polymorphism (SNP) listed in Table 1; and
c. detecting binding between said probe and said genetic variant. In some aspects, said SNP comprises rs12339504, rs11603664, rs72713460, rs12442709, rs12606254, rs4806915, rs73052335, rs2836293, rs2591054, rs928771 or a combination thereof.

In some aspects, said subject is a mammal. In some aspects, said mammal is a human. In some aspects, said biological sample comprises a nucleic acid. In some aspects, the method further comprises purifying said nucleic acid from said biological sample. In some aspects, said detecting comprises amplifying said nucleic acid. In some aspects, said detecting comprises sequencing said nucleic acid. In some aspects, said biological sample is collected from blood, saliva, urine, serum, tears, skin, tissue, or hair. In some aspects, said detecting comprises use of at least one of polymerase chain reaction (PCR), enzyme-linked immunosorbent assay (ELISA), mass spectrometry, sequencing, northern blot, immunohistochemistry, genotyping array, microarray, RNA expression array, or any combination thereof. In some aspects, said sequencing comprises high-throughput sequencing. In some aspects, said high-throughput sequencing comprises massively parallel signature sequencing (MPSS), polony sequencing, 454 pyrosequencing, illumina sequencing, SOLiD sequencing, ion semiconductor sequencing, DNA nanoball sequencing, heliscope single molecule sequencing, single molecule real time (SMRT) sequencing, nanopore DNA sequencing, or any combination thereof. In some aspects, said subject is at least about 20 years old, at least about 30 years old, at least about 40 years old, at least about 50 years old, at least about 60 years old, or at least about 70 years old. In some aspects, said subject is asymptomatic of AD. In some aspects, said subject has a symptom of AD. In some aspects, said symptom comprises wandering and getting lost, trouble handling money and paying bills, repeating questions, taking longer to complete normal daily tasks, losing things or misplacing them in odd places, personality and behavior changes, increased memory loss and confusion, problems recognizing family and friends, inability to learn new things, difficulty carrying out multistep tasks, problems coping with new situations, hallucinations, delusions, paranoia, impulsive behavior, inability to communicate, weight loss, seizures, skin infections, difficulty swallowing, groaning, moaning, grunting, increased sleeping, lack of control of bowel and bladder, or any combination thereof.

In some aspects, the method further comprises assessing a risk of AD in said subject based on a presence of said genetic variant. In some aspects, the method further comprises assessing said risk of AD in said subject based on a presence of a genetic variant listed in Table 3. In some aspects, the method further comprises assessing said risk of AD in said subject based on a presence of a haplotype listed in Table 12. In some aspects, the method further comprises assessing said risk of AD in said subject based on a presence of a haplotype listed in Table 13. In some aspects, the method further comprises assessing said risk of AD in said subject based on a presence of a genetic variant listed in Table 4. In some aspects, the method further comprises assessing said risk of AD in said subject based on a clinical information. In some aspects, said clinical information comprises age, gender, education level, cognitive performance score, smoking, diabetes, hypertension, abnormal cholesterol levels, said subject having a family history of one or more of AD, dementia, abnormal cholesterol levels, stroke, cerebral infarction, diabetes, hypertension, or any combination thereof. In some aspects, said clinical information comprises age, cognitive performance, and family history of AD or cerebral infarction, or any combination thereof. In some aspects, the method further comprises measuring a transcript level of a target gene or a part thereof. In some aspects, said target gene is listed in Table 8. In some aspects, the method further comprises assessing a status of AD in said subject based on said presence of said genetic variant, said haplotype, said clinical information and/or said transcript level. In some aspects, the method further comprises measuring a level of a target metabolite. In some aspects, said target metabolite is listed in Table 9. In some aspects, the method further comprises assessing said status of AD in said subject based on said presence of said genetic variant, said haplotype, said clinical information and/or said level of said target metabolite. In some aspects, the method further comprises evaluating a brain image data of said subject. In some aspects, said brain image data is generated by computed tomography (CT), magnetic resonance imaging (MRI), functional MRI (fMRI), positron emission tomography (PET), or any combination thereof. In some aspects, the method further comprises assessing a status of AD in said subject. In some aspects, said assessing is based on an assessment by a medical doctor, a psychologist, a neurologist, a psychiatrist, or other professionals who can screen said subject for AD. In some aspects, said assessment comprises an evaluation of said subject's motor skills, autonomic function, neuropsychiatry, mood, cognition, behavior, thoughts, ability to sense, past medical history, or a combination thereof. In some aspects, said evaluation is performed by observation, a questionnaire, a checklist, a test, or any combination thereof. In some aspects, said subject is East Asian in ethnicity. In some aspects, said subject is Chinese. In some aspects, said subject is Caucasian. In some aspects, method further comprises generating a genetic risk score (GRS) based on said genetic variant.

In some aspects, said GRS is indicative of a status of AD. In some aspects, said status of AD comprises a low risk, a medium risk, or a high risk. In some aspects, the method further comprises stratifying said subject to a category for a further course of action. In some aspects, said category for said further course of action comprises a further diagnosis category, a drug discovery category, a drug evaluation category, or a therapeutic category. In some aspects, said category for said further course of action comprises said therapeutic category and wherein said method further comprises administering a treatment to said subject. In some aspects, the method further comprises administering a treatment to said subject. In some aspects, said administering said treatment comprises administering donepezil, galantamine, rivastigmine, an acetylcholinesterase inhibitor, a glutamate receptor blocker, memantine, citalopram, fluoxetine, paroxeine, sertraline, trazodone, lorazepam, oxazepam, aripiprazole, clozapine, haloperidol, olanzapine, quetiapine, risperidone, ziprasidone, nortriptyline, trazodone, tricyclic antidepressants, benzodiazepines, lorazepam, oxazepam, temazepam, zolpidem, zaleplon, chloral hydrate, risperidone, onlanzapine, quetiap, haloperidol, coenzyme Q10, ubiquinone, coral calcium, *Ginkgo biloba*, huperzine A, omega-3 fatty acids, phosphatidylserine, or a combination thereof.

One aspect provides a method for identifying a compound useful for treating Alzheimer's disease (AD), said method comprising:
  a. providing a cell that expresses a gene comprising a genetic variant, wherein said genetic variant comprises one or more single nucleotide polymorphism (SNP) listed in Table 1;
  b. contacting said cell with a compound; and
  c. measuring an expression level of said gene relative to said expression level of said gene in the absence of said compound, wherein, said compound is identified as useful for treating Alzheimer's disease (AD) based on said expression level of said gene in the presence of said compound.

In some aspects, said expression of said gene in the presence of said compound is reduced relative to said expression level of said gene in the absence of said compound. In some aspects, said expression of said gene is enhanced relative to said expression level of said gene in the absence of said compound. In some aspects, said expression of said gene in the presence of said compound is same as said expression level of said gene in the absence of said compound. In some aspects, said cell is a mammalian cell. In some aspects, said mammalian cell is a human cell or a rodent cell. In some aspects, measuring said expression level of said gene, in (c), comprises measuring expression levels of RNA transcribed from said gene. In some aspects, said gene is recombinantly expressed by said cell. In some aspects, said compound comprises an acetylcholinesterase inhibitor, a glutamate receptor blocker, a cholinesterase inhibitor, or any combination thereof.

One aspects provides a method for detecting a presence of Alzheimer's disease (AD) or an increased risk of developing AD in a subject, comprising detecting in a biological sample taken from said subject a presence of:
  a. one or more single nucleotide polymorphisms (SNPs) listed in Table 3; or
  b. one or more haplotypes listed in Tables 12 and 13.

In some aspects, the method comprises said detecting of said increased risk of developing AD in the subject. In some aspects, the method further comprises assessing said increased risk of AD. In some aspects, said assessing of said risk of AD based on a clinical information of said subject. In some aspects, said clinical information comprises age, gender, education level, cognitive performance score, smoking, diabetes, hypertension, abnormal cholesterol levels, said subject having a family history of one or more of AD, dementia, abnormal cholesterol levels, stroke, cerebral infarction, diabetes, hypertension, or any combination thereof. In some aspects, said clinical information comprises age, cognitive performance, and family history of AD or cerebral infarction, or any combination thereof. In some aspects, the method further comprises measuring a level of a target metabolite in said biological sample. In some aspects, said target metabolite is listed in Table 9. In some aspects, the method further comprises assessing said increased risk of AD in said subject based on said presence of said one or more SNPs, said one or more haplotypes, said clinical information, said level of said target metabolite, or any combination thereof. In some aspects, the method further comprises evaluating a brain image data of said subject. In some aspects, said brain image data is generated by computed tomography (CT), magnetic resonance imaging (MRI), functional MRI (fMRI), positron emission tomography (PET), or any combination thereof. In some aspects, the method further comprises assessing a status of AD in said subject. In some aspects, said assessing is based on an assessment by a medical doctor, a psychologist, a neurologist, a psychiatrist, or other professionals who can screen said subject for AD. In some aspects, said assessment comprises an evaluation of said subject's motor skills, autonomic function, neuropsychiatry, mood, cognition, behavior, thoughts, ability to sense, past medical history, or a combination thereof. In some aspects, said evaluation is performed by observation, a questionnaire, a checklist, a test, or any combination thereof. In some aspects, said subject is an East Asian in ethnicity. In some aspects, said subject is Chinese or Japanese. In some aspects, said subject has a family history of AD but does not exhibit symptoms of AD. In some aspects, said sample is a blood sample. In some aspects, said detecting step comprises an amplification reaction. In some aspects, said amplification reaction is a polymerase chain reaction (PCR). In some aspects, the method further comprises stratifying said subject to a category for a further course of action. In some aspects, said category for said further course of action comprises a further diagnosis category, a drug discovery category, a drug evaluation category, or a therapeutic category. In some aspects, said category for said further course of action comprises said therapeutic category and wherein said method further comprises administering a treatment to said subject. In some aspects, the method further comprises administering a treatment to said subject. In some aspects, said administering said treatment comprises administering donepezil, galantamine, rivastigmine, an acetylcholinesterase inhibitor, a glutamate receptor blocker, memantine, citalopram, fluoxetine, paroxeine, sertraline, trazodone, lorazepam, oxazepam, aripiprazole, clozapine, haloperidol, olanzapine, quetiapine, risperidone, ziprasidone, nortriptyline, trazodone, tricyclic antidepressants, benzodiazepines, lorazepam, oxazepam, temazepam, zolpidem, zaleplon, chloral hydrate, risperidone, onlanzapine, quetiap, haloperidol, coenzyme Q10, ubiquinone, coral calcium, *Ginkgo biloba*, huperzine A, omega-3 fatty acids, phosphatidylserine, or a combination thereof. In some aspects, the method further comprises administering a treatment to said subject upon determining said subject as having AD or having an increased risk of developing AD.

One aspect provides a kit comprising:
  a. a first probe for detecting a first single nucleotide polymorphism (SNP);
  b. a second probe for detecting a second SNP, wherein said first SNP and said second SNP are comprised in Table 1, wherein said first SNP and said second SNP are different; and
  c. a reagent for detecting an interaction between:
    i. said first probe and said first SNP or
    ii. said second probe and said second SNP.

In some aspects, said first SNP or said second SNP comprises rs12339504, rs11603664, rs72713460, rs12442709, rs12606254, rs4806915, rs73052335, rs2836293, rs2591054, rs928771, or any combination thereof. In some aspects, said first probe or said second probe comprises an antibody. In some aspects, said antibody comprises a sequence having at least 80% homology to any one of SEQ ID Nos. 165-179. In some aspects, said first probe or said second probe comprises a polynucleotide. In some aspects, said polynucleotide comprises a sequence having at least 80% homology to at least 8 consecutive polynucleotides of any one of SEQ ID Nos. 66-164.

One aspect provides a kit comprising:
  a. a first probe for detecting a target metabolite;
  b. a second probe for detecting a genetic variant, wherein said genetic variant comprises a single polymorphism (SNP) listed in Table 1; and
  c. a reagent for detecting an interaction between:
    i. said first probe and said metabolite or
    ii. said second probe and said SNP.

In some aspects, said SNP comprises rs12339504, rs11603664, rs72713460, rs12442709, rs12606254, rs4806915, rs73052335, rs2836293, rs2591054, rs928771, or any combination thereof. In some aspects, said target metabolite is listed in Table 9. In some aspects, said first probe or said second probe comprises an antibody. In some aspects, said antibody comprises a sequence having at least 80% homology to any one of SEQ ID Nos. 165-179. In some aspects, said first probe or said second probe comprises a polynucleotide. In some aspects, said polynucleotide comprises a sequence having at least 80% homology to at least 8 consecutive polynucleotides of any one of SEQ ID Nos. 66-164.

One aspect provides a kit comprising:
  a. a first probe for detecting a target gene;
  b. a second probe for detecting a genetic variant, wherein said genetic variant comprises a single polymorphism (SNP) listed in Table 1; and
  c. a reagent for detecting an interaction between:
    i. said first probe and said target gene or
    ii. said second probe and said SNP.

In some aspects, said SNP comprises rs12339504, rs11603664, rs72713460, rs12442709, rs12606254, rs4806915, rs73052335, rs2836293, rs2591054, rs928771 or a combination thereof. In some aspects, said target gene is listed in Table 8. In some aspects, said first probe or said second probe comprises an antibody. In some aspects, said antibody comprises a sequence having at least 80% homology to any one of SEQ ID Nos. 165-179. In some aspects, said first probe or said second probe comprises a polynucleotide. In some aspects, said polynucleotide comprises a sequence having at least 80% homology to at least 8 consecutive polynucleotides of any one of SEQ ID Nos. 66-164.

In one aspect, disclosed herein is method for detecting a genetic variant in a subject suspected of having Alzheimer's disease (AD). The method can comprise (a) obtaining a biological sample from a subject; (b) contacting a biological sample with a probe specific for a genetic variant that comprises one or more single nucleotide polymorphism (SNP) listed in Table 1; and (c) detecting binding between a probe and a genetic variant. In some embodiments, a SNP can comprise rs12339504, rs11603664, rs72713460, rs12442709, rs12606254, rs4806915, rs73052335, rs2836293, rs2591054, rs928771 or a combination thereof. In some embodiments, a subject can be a mammal. The mammal can be a human. In some embodiments, a biological sample can comprise a nucleic acid. In some embodiments, the method can further comprise purifying a nucleic acid from a biological sample. In some embodiments, detecting can comprise amplifying a nucleic acid. The detecting can comprise sequencing a nucleic acid. In some embodiments, a biological sample can be collected from blood, saliva, urine, serum, tears, skin, tissue, and/or hair. In some embodiments, detecting can comprise use at least one of polymerase chain reaction (PCR), mass spectrometry, sequencing, northern blot, immunohistochemistry, genotyping array, microarray, RNA expression array, or any combination thereof. In some embodiments, sequencing can comprise high-throughput sequencing. High-throughput sequencing can comprise massively parallel signature sequencing (MPSS), polony sequencing, 454 pyrosequencing, illumina sequencing, SOLiD sequencing, ion semiconductor sequencing, DNA nanoball sequencing, heliscope single molecule sequencing, single molecule real time (SMRT) sequencing, nanopore DNA sequencing or a combination thereof. A subject can be at least about 20 years old, at least about 30 years old, at least about 40 years old, at least about 50 years old, at least about 60 years old, or at least about 70 years old. The subject can be asymptomatic of AD. A subject can have a symptom of AD. A symptom can comprise wandering and getting lost, trouble handling money and paying bills, repeating questions, taking longer to complete normal daily tasks, losing things or misplacing them in odd places, personality and behavior changes, increased memory loss and confusion, problems recognizing family and friends, inability to learn new things, difficulty carrying out multistep tasks, problems coping with new situations, hallucinations, delusions, paranoia, impulsive behavior, inability to communicate, weight loss, seizures, skin infections, difficulty swallowing, groaning, moaning, grunting, increased sleeping, lack of control of bowel and bladder, or a combination thereof. In some embodiments, the method can further comprise assessing a risk of AD in a subject based on a presence of one or more genetic variants in Tables 1 and/or 3. In some embodiments, the method can further comprise assessing a risk of AD in a subject based on a presence of one or more genetic variants listed in Table 1, Table 3, Table 4, and/or Table 11. In some embodiments, the method can further comprise assessing a risk of AD in a subject based on a presence of a haplotype listed in Table 12 and/or Table 13. In some embodiments, the method can further comprise measuring a transcript level of a target gene or a part thereof. The target gene can be listed in Table 8. In some embodiments, the method can further comprise assessing a status of AD in a subject based on presence of a genetic variant and a transcript level. In some embodiments, the method can comprise assessing a status of AD in a subject based on a presence of a haplotype listed in Table 12 and/or Table 13. In some embodiments, the method can further comprise assessing a status of AD in a subject based on a presence of one or more genetic variants listed in Table 1, Table 3, Table 4, and/or Table 11. In some embodiments, the method can further comprise measuring a level of a target metabolite. The target metabolite can be listed in Table 9. In some embodiments, the method can further comprise assessing a status of AD in a subject based on presence of a genetic variant and a level of a target metabolite. In some embodiments, the method can further comprise evaluating a brain image data of a subject. A brain image data can be generated by computed tomography (CT), magnetic resonance imaging (MRI), functional MRI (fMRI), positron emission tomography (PET) or a combination thereof. In some embodiments, the method can further comprise assessing a status of AD in a subject. The assessing can be based on an assessment by a medical doctor, a psychologist, a neurologist, a psychiatrist, or other professionals who screen subjects for AD. The assessment can comprise an evaluation of a subject's motor skills, autonomic function, neuropsychiatry, mood, cognition, behavior, thoughts, ability to sense, past medical history, or a combination thereof. The evaluation can be performed by observation, a questionnaire, a checklist, a test, or a combination thereof. In some embodiments, a subject can be East Asian in ethnicity. In some embodiments, a subject can be Chinese. In some embodiments, a subject can be Caucasian. In some embodiments, the method can further comprise generating a genetic risk score (GRS) based on a genetic variant. The GRS can be indicative of a status of AD. The status of AD can comprise low risk, medium risk, or high risk. In some embodiments, a method can further comprise administering a treatment to a subject. The treatment can comprise donepezil, galantamine, rivastigmine, an acetylcholinesterase inhibitor, a glutamate receptor blocker, memantine, citalopram, fluoxetine, paroxeine, sertraline, trazodone, lorazepam, oxazepam, aripiprazole, clozapine, haloperidol, olanzapine, quetiapine, risperidone, ziprasidone, nortriptyline, trazodone, tricyclic antidepressants, benzodiazepines, lorazepam, oxazepam, temazepam, zolpidem, zaleplon, chloral hydrate, risperidone, onlanzapine, quetiap, haloperidol, coenzyme Q10, ubiquinone, coral calcium, *Ginkgo biloba*, huperzine A, omega-3 fatty acids, phosphatidylserine, or a combination thereof.

In one aspect, disclosed herein is a method for identifying a compound useful for treating Alzheimer's disease (AD). A method can comprise: (a) providing a cell that expresses a gene comprising a genetic variant, (b) wherein the genetic variant comprises one or more single nucleotide polymorphism (SNP) listed in Table 1; (c) contacting a cell with a compound; and (d) measuring an expression level of a gene relative to an expression level of the gene in the absence of a compound. In some instances, when a compound reduces the expression level of a gene, the compound can be identified as useful for treating Alzheimer's disease (AD). In some embodiments, the cell can be a mammalian cell. In some embodiments, the mammalian cell can be a human cell or a rodent cell. In some embodiments, the method can comprise measuring RNA levels transcribed from a gene. In some embodiments, the gene can be recombinantly expressed by the cell. In some embodiments, the compound can comprise an acetylcholinesterase inhibitor, a glutamate receptor blocker, a cholinesterase inhibitor, or a combination thereof.

In another aspect, disclosed herein are kits. A kit can comprise (a) a first probe for detecting a first single nucleotide polymorphism (SNP); (b) a second probe for detecting a second SNP, wherein a first SNP and a second SNP can be comprised in Table 1. A SNP and a second SNP can be different. A kit can further comprise (c) a reagent for detecting an interaction between: (i) a first probe and a first SNP or (ii) a second probe and a second SNP. In some embodiments, a first SNP or a second SNP can comprise rs12339504, rs11603664, rs72713460, rs12442709, rs12606254, rs4806915, rs73052335, rs2836293, rs2591054, rs928771 or a combination thereof. In some embodiments, a first probe or a second probe can comprise an antibody. In some embodiments, an antibody can comprise a sequence having at least 80% homology to SEQ ID Nos 165-179. In some embodiments, a first probe or a second probe can comprise a polynucleotide. In some embodiments, a polynucleotide can comprise a sequence having at least 80% homology to at least 8 consecutive polynucleotides of SEQ ID. Nos 66-164.

In another aspect, disclosed herein are kits. A kit can comprise: (a) a first probe for detecting a metabolite; (b) a second probe for detecting a genetic variant. A genetic variant can comprise a single polymorphism (SNP) listed in Table 1. A kit can further comprise a reagent for detecting an interaction between: (i) a first probe and a metabolite or (ii) a second probe and a SNP. In some embodiments, a SNP can comprise rs12339504, rs11603664, rs72713460, rs12442709, rs12606254, rs4806915, rs73052335, rs2836293, rs2591054, rs928771 or a combination thereof. In some embodiments, a metabolite can be listed in Table 9. In some embodiments, a first probe or a second probe can comprise an antibody. In some embodiments, an antibody can comprise a sequence having at least 80% homology to SEQ ID Nos 165-179. In some embodiments, a first probe or a second probe can comprise a polynucleotide. In some embodiments, a polynucleotide can comprise a sequence having at least 80% homology to at least 8 consecutive polynucleotides of SEQ ID. Nos 66-164.

In yet another aspect, disclosed herein are kits. A kit can comprise: (a) a first probe for detecting a target gene; and (b) a second probe for detecting a genetic variant. A genetic variant can comprise a single polymorphism (SNP) listed in Table 1. A kit can further comprise (c) a reagent for detecting an interaction between: (i) a first probe and a target gene or (ii) a second probe and a SNP. In some embodiments, a SNP can comprise rs12339504, rs11603664, rs72713460, rs12442709, rs12606254, rs4806915, rs73052335, rs2836293, rs2591054, rs928771 or a combination thereof. In some embodiments, a target gene can be listed in Table 8. In some embodiments, a first probe or a second probe can comprise an antibody. In some embodiments, an antibody can comprise a sequence having at least 80% homology to SEQ ID Nos 165-179. In some embodiments, a first probe or a second probe can comprise a polynucleotide. In some embodiments, a polynucleotide can comprise a sequence having at least 80% homology to at least 8 consecutive polynucleotides of SEQ ID. Nos 66-164.

In one aspect, disclosed herein are methods for detecting genetic variations in a subject. A method can comprise determining nucleotide sequence in the subject's genomic DNA at one or more of single nucleotide polymorphism (SNP) sites listed in Table 17. In some embodiments, one or more SNP sites can be selected from IL33 SNP rs11791561; IL33 SNP rs11792633; IL1RL1 SNP rs4988956; IL1RL1 SNP rs10204137; IL1RL1 SNP rs10192157; and IL1RL1 SNP rs10206753. In some embodiments, a nucleotide sequence can be determined by analyzing a biological sample obtained from the subject (1) genomic DNA sequence of IL33 and/or IL1RL1; (2) mRNA sequence of IL33 and/or IL1RL1; or (3) amino acid sequence of IL33 and/or IL1RL1 protein. In some embodiments, a biological sample can be a sample of tissue or bodily fluid. The biological sample can be a whole blood sample. The biological sample can be an oral swab. In some embodiments, the method can further comprise detecting a G allele at IL33 SNP rs11791561 and determining the subject as having Alzheimer's disease (AD) or having an increased risk of developing AD. In some embodiments, the method can further comprise detecting mRNA or protein level of IL33/IL1RL/soluble ST2 in a biological sample taken from a subject. In some embodiments, the method can further comprise detecting a G allele at IL1RL1 SNP rs4988956 and determining a subject as having AD or having an increased risk of developing AD. In some embodiments, the method can further comprise detecting a G allele at IL1RL1 SNP rs10204137 and determining a subject as having or having an increased risk of developing AD. In some embodiments, the method can further comprise the step of detecting a T allele at IL1RL1 SNP rs10192157 and determining a subject as having or having an increased risk of developing AD. In some embodiments, the method can further comprise the step of detecting a T allele at IL1RL1 SNP rs10206753 and determining the subject as having AD or having an increased risk of developing AD. In some embodiments, the method can further comprise detecting a C allele at IL33 SNP rs11792633 and determining a subject as having AD or having an increased risk of developing AD. In some embodiments, the method can further comprise detecting mRNA or protein level of IL33/IL1RL1/soluble ST2 in a biological sample taken from the subject. In some embodiments, the method can further comprise administering to the subject a therapeutic agent effect for treating AD.

In one aspect, disclosed herein are kits. A kit can be used to detect genetic variations in a subject. A kit can comprise reagents for determining nucleotide sequence in a subject's genomic DNA at one or more of SNP sites listed in Table 17. In some embodiments, one or more SNP sites are selected from IL33 SNP rs11791561; IL33 SNP rs11792633; IL1RL1 SNP rs4988956; IL1RL1 SNP rs10204137; IL1RL1 SNP rs10192157; and IL1RL1 SNP rs10206753. In some embodiments, the kit can further comprise an instruction manual for using reagents for detecting genetic variations.

In one aspect, disclosed herein are methods for detecting the presence of Alzheimer's Disease (AD) or an increased risk of developing AD in a subject. In some embodiments, a method can comprise detecting in a biological sample taken from a patient a presence of (1) one or more of the single nucleotide polymorphisms (SNPs) in Table 3 or (2) one or more of the haplotypes in Tables 12 and 13.

In some embodiments, a subject can be East Asian in ethnicity. In some embodiments, a subject can be Chinese or Japanese. In some embodiments, a subject can have a family history of AD. In some embodiments, a subject may not exhibit symptoms of AD. In some embodiments, a sample can be a blood sample. In some embodiments, detecting can comprise an amplification reaction to amplify a genetic variant(s). An amplification reaction can be a polymerase chain reaction (PCR). In some embodiments, the method can further comprise administering to a subject an agent effective for treating AD upon determining the subject as having AD or having an increased risk of developing AD.

In one aspect, disclosed herein is a method for detecting a presence of Alzheimer's Disease (AD) or an increased risk of developing AD in a subject. The method can comprise detecting in a biological sample taken from a subject a presence of SNP APOE-ε4 variant rs429358 and the presence of one or more of the SNPs selected from rs360716, rs7106524, rs1783563, rs7951170, rs60462066, rs7120611, rs1264436, or rs56389899. In some embodiments, a subject can be East Asian in ethnicity. In some embodiments, the subject can be Chinese or Japanese. In some embodiments, a subject can have a family history of AD but does not exhibit symptoms of AD. In some embodiments, a biological sample can be a blood sample. In some embodiments, detecting step can comprise an amplification reaction to amplify the SNPs. An amplification reaction can be a polymerase chain reaction (PCR). In some embodiments, the method can further comprise administering to the subject an agent effective for treating AD upon determining the subject as having AD or having an increased risk of developing AD.

In one aspect, disclosed herein is a kit for detecting the presence of Alzheimer's Disease (AD) or an increased risk of developing AD in a subject. A kit can comprise: (a) a first agent for detecting in a biological sample taken from a subject a presence of one or more of the SNPs in Table 11, and a second agent for detecting a presence of one or more haplotypes in Tables 12 and 13; or (b) a first agent for detecting in a biological sample taken from a subject the presence of SNP APOE-ε4 variant rs429358, and a second agent for detecting a presence of one or more SNPs selected from rs360716, rs7106524, rs1783563, rs7951170, rs60462066, rs7120611, rs1264436, or rs56389899. In some embodiments, a biological sample can be a blood sample. In some embodiments, a kit can comprise (A) a first agent comparing (a) a set of primers for amplification of one or more SNPs in Table 11; or (b) a polynucleotide probe that specifically hybridizes to one or more of the SNPs in Table 11, and a second agent that can comprise (i) a set of primers for amplification of one or more of the haplotypes in Tables 12 and 13; or (ii) a polynucleotide probe that can specifically hybridize to one or more of the haplotypes in Tables 12 and 13; or (B) a first agent that can comprise (a) a set of primers for amplification of SNP APOE-ε4 variant rs429358; or (b) a polynucleotide probe that specifically hybridizes to APOE-ε4 variant rs429358, and a second agent comprises (i) a set of primers for amplification of one SNP selected from the group consisting of rs360716, rs7106524, rs1783563, rs7951170, rs60462066, rs7120611, rs1264436, and rs5689899; or (ii) a polynucleotide probe that specifically hybridizes to one SNP selected from rs360716, rs7106524, rs1783563, rs7951170, rs60462066, rs7120611, rs1264436, or rs56389899. In some embodiments, a kit can further comprise an instruction manual for detecting the presence of AD or an increased risk of developing AD.

INCORPORATION BY REFERENCE

All publications, patents, and patent applications mentioned in this specification are herein incorporated by reference in their entireties to the same extent as if each individual publication, patent, or patent application was specifically and individually indicated to be incorporated by reference in their entireties.

BRIEF DESCRIPTION OF THE DRAWINGS

The novel features described herein are set forth with particularity in the appended claims. A better understanding of the features and advantages of the features described herein will be obtained by reference to the following detailed description that sets forth illustrative examples, in which the principles of the features described herein are utilized, and the accompanying drawings of which:

FIG. 2 illustrates an outcome for GRS in prediction of AD. FIG. 2A depicts a density plot for GRS across different phenotypes. FIG. 2B depicts a comparison between GRS using the APOE-ε4 dosage for the prediction of AD. FIG. 2C depicts dot plots for the distribution of low, medium and high risk categories in each phenotypic group.

FIG. 7 depicts dose-dependent regulation of IL33/IL1RL1 transcript level by mutations in human B lymphoblastoid cell lines. FIG. 7A shows transcript level of IL33. FIG. 7B shows transcript level of ST2L. FIG. 7C shows transcript level of ST2S.

FIG. 8 depicts regulation of IL33/IL1RL1 protein levels by IL1RL1 mutations in human B lymphoblastoid cell lines. FIG. 8A shows ST2 expression levels in LCLs harboring ST2 wild type and mutant genotypes. FIG. 8B shows normalized ST2 expression in LCLs harboring ST2 wild type and mutant genotypes. FIG. 8C shows IL33 expression levels in wild type and mutant. FIG. 8D shows normalized IL33 expression levels in LCLs harboring ST2 wild type and mutant genotypes.

FIG. 9 depicts regulation of soluble ST2 protein (ST2S) levels by IL1RL1 mutations in human B lymphoblastoid cell lines. FIG. 9A shows expression level of ST2 in wild type and mutant.

FIG. 9B shows normalized expression of ST2 in wild type and mutant.

DETAILED DESCRIPTION

Figure 1:
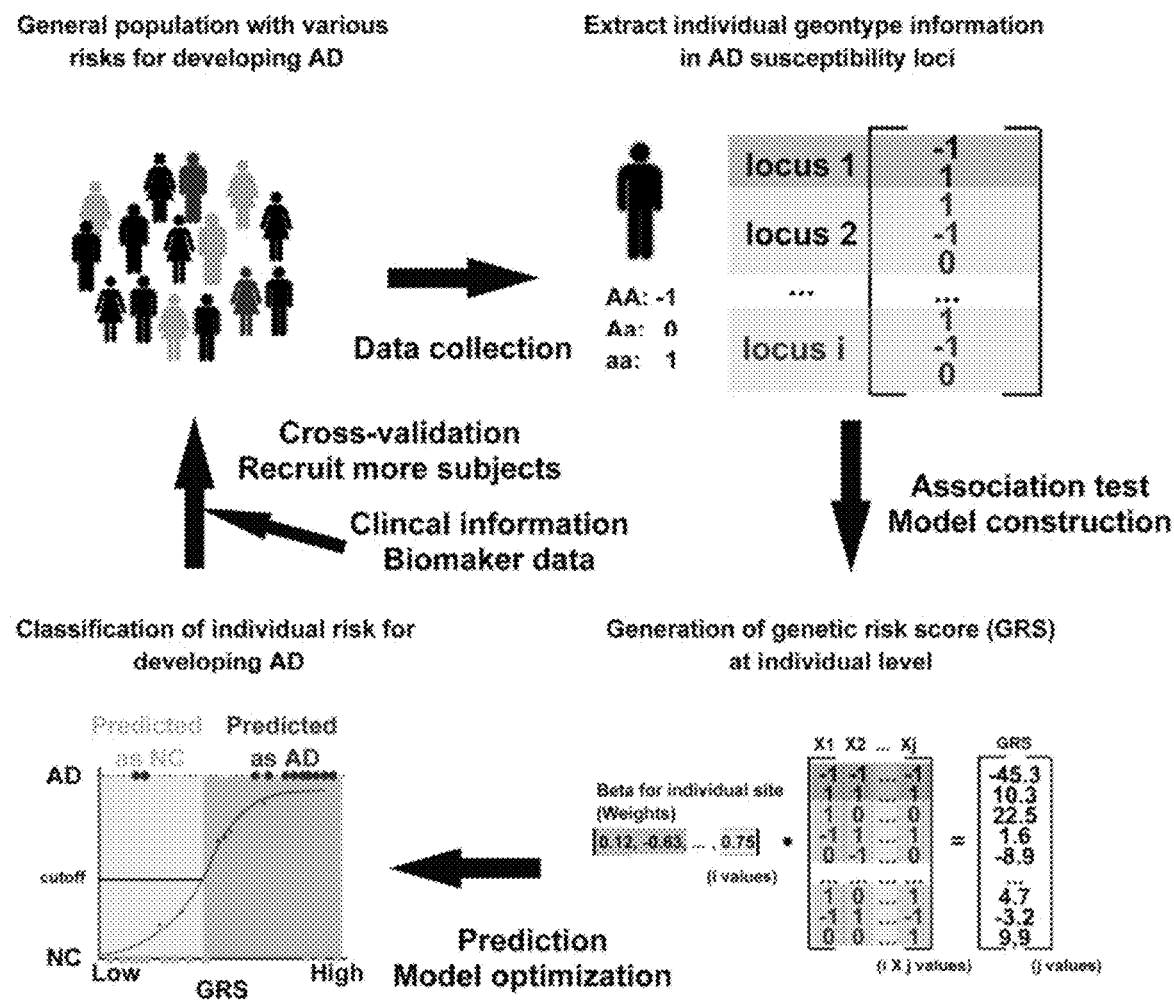
FIG. 1 depicts a mathematical model for a genetic risk score (GRS) and prediction of AD.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Unless defined otherwise, all technical and scientific terms used in this disclosure have the same meanings as commonly understood by one of ordinary skill in the art to which this disclosure belongs.

The term "antibody" can include intact antibodies and binding fragments thereof. The term "antibody" can also include bispecific antibody, humanized antibody, monoclonal antibody and polyclonal antibody. An antibody can specifically bind to a particular spatial and polar organization of another molecule. An antibody can be monoclonal, polyclonal, or a recombinant antibody, and can be prepared by techniques that are well known in the art such as immunization of a host and collection of sera (polyclonal) or by preparing continuous hybrid cell lines and collecting the secreted protein (monoclonal), or by cloning and expressing nucleotide sequences or mutagenized versions thereof, coding at least for the amino acid sequences required for specific binding of natural antibodies. A naturally occurring antibody can be a protein comprising at least two heavy (H) chains and two light (L) chains inter-connected by disulfide bonds. Each heavy chain can be comprised of a heavy chain variable region ($V_H$) and a heavy chain constant region. The heavy chain constant region can be comprised of three domains, $C_{H1}$, $C_{H2}$ and $C_{H3}$. Each light chain can be comprised of a light chain variable region ($V_L$) and a light chain constant region. The light chain constant region can be comprised of one domain, $C_L$. The $V_H$ and $V_L$ regions can be further subdivided into regions of hypervariability, termed complementary determining regions (CDR), interspersed with regions that are more conserved, termed framework regions (FR). Each $V_H$ and $V_L$ can be composed of three CDRs and four FRs arranged from amino-terminus to carboxy-terminus in the following order: $FR_1$, $CDR_1$, $FR_2$, $CDR_2$, $FR_3$, $CDR_3$, and FR4. The constant regions of the antibodies may mediate the binding of the immunoglobulin to host tissues or factors, including various cells of the immune system (e.g., effector cells) and the first component (C1q) of the classical complement system. The antibodies can be of any isotype (e.g., IgG, IgE, IgM, IgD, IgA and IgY), class (e.g., $IgG_1$, $IgG_2$, $IgG_3$, $IgG_4$, $IgA_1$ and $IgA_2$), subclass or modified version thereof. Antibodies may include a complete immunoglobulins or fragments thereof. An antibody fragment can refer to one or more fragments of an antibody that retain the ability to specifically bind to a target analyte, such as an antigen. In addition, aggregates, polymers, and conjugates of immunoglobulins or their fragments can be used where appropriate so long as binding affinity for a particular molecule is maintained. Examples of antibody fragments include a Fab fragment, a monovalent fragment consisting of the $V_L$, $V_H$, $C_L$ and CHI domains; a F(ab)₂ fragment, a bivalent fragment comprising two Fab fragments linked by a disulfide bridge at the hinge region; an Fd fragment consisting of the $V_H$ and CHI domains; an Fv fragment consisting of the $V_L$ and $V_H$ domains of a single arm of an antibody; a single domain antibody (dAb) fragment (Ward et al., (1989) Nature 341:544-46), which consists of a $V_H$ domain; and an isolated CDR and a single chain Fragment (scFv) in which the $V_L$ and $V_H$ regions pair to form monovalent molecules (known as single chain Fv (scFv); See, e.g., Bird et al., (1988) Science 242:423-26; and Huston et al., (1988) PNAS 85:5879-83). Thus, antibody fragments include Fab, F(ab)₂, scFv, Fv, dAb, and the like. Although the two domains $V_L$ and $V_H$ are coded for by separate genes, they can be joined, using recombinant methods, by an artificial peptide linker that enables them to be made as a single protein chain. Such single chain antibodies include one or more antigen binding moieties. These antibody fragments can be obtained using conventional techniques known to those of skill in the art, and the fragments can be screened for utility in the same manner as are intact antibodies. Antibodies can be human, humanized, chimeric, isolated, dog, cat, donkey, sheep, any plant, animal, or mammal.

The terms "attach", "bind", "couple", "hybridize", and "link" can be used interchangeably and can refer to covalent interactions (e.g., by chemically coupling), or non-covalent interactions (e.g., ionic interactions, hydrophobic interactions, hydrogen bonds, hybridization, etc.). The terms "specific", "specifically", or specificity" can refer to the preferential recognition, contact, and formation of a stable complex between a first molecule and a second molecule compared to that of the first molecule with any one of a plurality of other molecules (e.g., substantially less to no recognition, contact, or formation of a stable complex between the first molecule and any one of the plurality of other molecules). For example, two molecules may be specifically attached, specifically bound, specifically coupled, or specifically linked. For example, specific hybridization between a first polynucleotide and a second polynucleotide can refer to the binding, duplexing, or hybridizing of the first polynucleotide preferentially to a particular nucleotide sequence of the second polynucleotide under stringent conditions. In some instances, sufficient number complementary base pairs in a polynucleotide sequence may be required to specifically hybridize with a nucleic acid sequence. A high degree of complementarity may be needed for specificity and sensitivity involving hybridization, although it need not be 100%.

The term "symptom" can refer to a subjective evidence of a disease, such as altered gait, as perceived by the patient. A "sign" can refer to objective evidence of a disease as observed by a physician.

"Cognitive function" can refer to mental processes such as any, all of, but not limited to attention, memory, producing and understanding language, solving problems, and taking an interest in one's surroundings and self-care. "Enhanced cognitive function" or "improved cognitive function" can refer to improvement relative to a baseline, for example, diagnosis or initiation of treatment. "Decline of cognitive function" can refer to a decrease in function relative to such a base line.

"Pharmaceutically acceptable" can refer to molecular entities and compositions that are physiologically tolerable and do not typically produce an allergic or similar untoward reaction, such as gastric upset, dizziness and the like, when administered to a human.

A "packaging material" can refer to a physical structure housing the components of a kit. The packaging material can maintain the components sterilely and can be made of material commonly used for such purposes (e.g., paper, corrugated fiber, glass, plastic, foil, ampules, etc.). The label or packaging insert can include appropriate written instructions. Kits, therefore, can additionally include labels or instructions for using the kit components in any method of the disclosure. A kit can include a compound in a pack, or dispenser together with instructions for administering the compound in a method described herein.

"Prevention" can refer to prophylaxis, prevention of onset of symptoms, prevention of progression of a disease or disorder. "Inhibition", "prevention", "treatment" and "treating" can be used interchangeably and can refer to, for example, stasis of symptoms, prolongation of survival, partial or full amelioration of symptoms, and partial or full eradication of a condition, disease or disorder.

"Nucleotide," "nucleoside," "nucleotide residue," and "nucleoside residue," as used herein, can mean a deoxyribonucleotide or ribonucleotide residue, or other similar nucleoside analogue. A "nucleic acid", or grammatical equivalents, can refer to either a single nucleotide or at least two nucleotides covalently linked together.

A "polynucleotide" or grammatical equivalents can refer to at least two nucleotides covalently linked together. A polynucleotide comprises a molecule containing two or more nucleotides. A polynucleotide comprises a specific sequence of four nucleotide bases: adenine (A); cytosine (C); guanine (G); and thymine (T) (uracil (U) for thymine (T) when the polynucleotide is RNA).

A "polypeptide" can refer to a molecule comprising at least two amino acids. A polypeptide can comprise a single peptide. A polypeptide can comprise two or more peptides. Examples of polypeptides include, but are not limited to, amino acid chains, proteins, peptides, hormones, polypeptide saccharides, lipids, glycolipids, phospholipids, antibodies, enzymes, kinases, receptors, transcription factors, and ligands.

A "subject", "individual", "host" or "patient" can refer to a living or nonliving organism such as mammals. Examples of subjects include, but are not limited to, horses, cows, camels, sheep, pigs, goats, dogs, cats, rabbits, guinea pigs, rats, mice (e.g., humanized mice), gerbils, non-human primates (e.g., macaques), humans and the like, non-mammals, including, e.g., non-mammalian vertebrates, such as birds (e.g., chickens or ducks) fish (e.g., sharks) or frogs (e.g., *Xenopus*), and non-mammalian invertebrates, as well as transgenic species thereof. In certain aspects, a subject can refer to a single organism (e.g., human). A subject from whom a sample is obtained can either be afflicted with a disease and/or disorder and can be compared against a negative control subject which is not affected by the disease and/or disorder.

A "kit" can refer to a delivery system for delivering materials or reagents for carrying out a method disclosed herein. kits can include systems that allow for the storage, transport, or delivery of reaction reagents (e.g., probes, enzymes, etc. in the appropriate containers) and/or supporting materials (e.g., buffers, written instructions for performing the assessment etc.) from one location to another. For example, kits can include one or more enclosures (e.g., boxes) containing the relevant reaction reagents and/or supporting materials. Such contents can be delivered to the intended recipient together or separately. For example, a first container can contain an enzyme for use in an assay, while a second container can contain a plurality of primers.

"Treat" or "treatment" can refer to a therapeutic treatment wherein the object is to eliminate or lessen symptoms.

The terminology used herein is for the purpose of describing particular cases only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term comprising.

The term "about" or "approximately" can mean within an acceptable error range for the particular value as determined by one of ordinary skill in the art, which will depend in part on how the value is measured or determined, i.e. the limitations of the measurement system. For example, "about" can mean within 1 or more than 1 standard deviation, per the practice in the art. Alternatively, "about" can mean a range of up to 20%, up to 10%, up to 5%, or up to 1% of a given value. Where particular values are described in the application and claims, unless otherwise stated the term "about" meaning within an acceptable error range for the particular value should be assumed. The term "about" has the meaning as commonly understood by one of ordinary skill in the art. In some embodiments, the term "about" refers to ±10%. In some embodiments, the term "about" refers to ±5%.

Human gene symbols generally are italicized, with all letters in uppercase for example, (APOE). Human protein designations are the same as the gene symbol, but are generally not italicized (APOE).

Overview

Disease and disease risk can be conferred by subtle changes in an individual genome. Genes can differ between individuals due to genomic variability, the most frequent of which can be due to single nucleotide polymorphisms (SNPs). Additional genetic polymorphisms in a human genome can be caused by duplication, insertion, deletion, translocation and/or inversion, of short and/or long stretches of DNA. Genetic variations may encode protein variants that can result in an increased susceptibility to a disease or result in disease onset, for example Alzheimer's disease (AD). Alzheimer's disease (AD) can be marked by gradual but progressive decline in learning and memory, and is a leading cause of mortality in the elderly. Currently, more than 46.88 million people worldwide are afflicted with the disease but this figure is expected to rise significantly to 100 million by 2050 due to longer life expectancies. There are at least four FDA approved drugs available to AD patients currently, many of these treatments alleviate symptoms rather than alter disease pathology (they cannot reverse the condition or prevent further deterioration) and are ineffective in severe conditions. Thus, early therapeutic intervention is critical in the management of AD. Research has confirmed that AD affects the brain long before actual symptoms of memory loss or cognitive decline actually manifest. To date, however, there are no diagnostic tools for early detection; by the time a patient is diagnosed with AD using methods currently available, which involves subjective clinical assessment, often the pathological symptoms are already at an advanced state. As such, for the purpose of improving AD treatment and long term management, there exists an urgent need for developing new and effective methods for early diagnosis and stratification of AD or an increased risk of developing AD both for pre-screening also the drug application.

Diseases such as AD may be associated with one or more genetic variations, where the presence of a genetic variation may increase the risk of developing AD or is indicative of AD. Genetic analysis can be used to determine the presence of such a genetic variation. In instances where a subject presents symptoms for closely related diseases, for example AD, dementia, Lewy bodies, and Parkinson's disease, a genetic analysis can be used to differentiate related diseases. For example, a genetic analysis can be performed to determine a presence or absence of a diseases associated genetic variation. This approach can therefore rule out or confirm a disease. Thus, allowing for a correct diagnosis and proper treatment.

Described herein, in some embodiments, are methods, kits and devices to assess the risk for Alzheimer's disease (AD) by determining whether certain genetic variations, for example, a single nucleotide polymorphism (SNP) is present. The genetic variants disclosed herein, such as in Table 1, Table 3, Table 4, Table 7, Table 8, Table 9, or any combination thereof, can be used as causative biomarkers for AD, genetic biomarkers for diagnosis and prognosis of AD, genetic biomarkers for AD as a drug therapeutic target, genetic biomarker for evalutaing a drug response in AD patients, or any combination thereof. In addition, the methods disclosed herein can be used for stratification of individuals to different categories of AD and determine a further course of action depending on the category, such as perform further diagnosis after identification of a genetic variant in an individual, use the genetic variant information identified in an individual for drug discovery, for evalutaing a response of a therapeutic candidate or a known drug, for prognosis using a therapeutic candidate or a known drug, for predicting response to a therapeutic candidate or a known drug. In some cases, an individual can be stratified into more than one category and accordingly be administered more than one further courser of action. As used herein, the term "causative biomarkers" can refer to biomarkers that can be classified as causal of a disease or a condition. For example, in case of a genetic variant, it can be classified as a causative biomarker or a causative mutation, used interchangeably herein, if said genetic variant causes the disease or condition. Such causative association can be measured, for example, by verifying that the genetic variant causes a change in the protein product of the gene. The causative biomarkers or mutations can also be used as indicators of a pathogenic process or condition, such as evaluation of a drug response.

SNPs can have many important uses in drug discovery, screening, and development. A high probability exists that, for any gene/protein selected as a potential drug target, variants of that gene/protein will exist in a patient population. Thus, determining the impact of gene/protein variants on the selection and delivery of a therapeutic agent can be an integral aspect of the drug discovery and development process.

In particular, the presence of a genetic variation associated with AD can be indicative of AD or an increased risk of AD. Following the detection of a SNP, a medicament for AD can be administered to a subject to treat AD or symptoms attributed to AD. Knowledge of the genetic variants of a particular therapeutic target (e.g., a gene, mRNA transcript, or protein associated with AD) can enable parallel screening of the variants and can lead to identification of therapeutic candidates (e.g., small molecule compounds, antibodies, antisense or RNAi nucleic acid compounds) that can demonstrate efficacy across the genetic variants. Such therapeutic candidates, developed by screening against a wide array of genetic variants associated with AD, can show equal efficacy across a larger segment of an AD patient population, thereby leading to a larger benefit for the therapeutic candidate.

Furthermore, identifying genetic variants of AD can lead to identifying the most prevalent form of the AD to be used for selection of therapeutic candidates, thereby helping to ensure that the experimental activity that is observed for the selected candidates reflects the real activity expected in the largest proportion of a patient population. Additionally, screening therapeutic candidates against a large number of genetic variants of AD can enable the early identification of potential toxicities and adverse reactions relating to particular variants. Variability in the frequency and, indeed, the types of genetic variants among ethnic populations can be a common theme underlying ethnic-specific beneficial and adverse drug responses. Thus, in some cases, SNPs located in AD therapeutic targets (e.g., a gene, mRNA transcript, or protein associated with AD, or drug metabolizing genes) can be identified, and this information can be utilized during the drug development process to minimize variability in drug disposition and develop therapeutic agents that are safer across a wider range of an AD patient population. For instance, drug responses can be evaluated, by correlating variability in drug absorption, distribution, metabolism and excretion (ADME) with the presence, absence, or frequency of the genetic variants disclosed herein.

To assess Alzheimer's disease (AD), nucleic acids can be extracted from a sample and purified. The purified nucleic acids can be incorporated in an amplification reaction with primers and/or probes specific to a genetic variant. The presence or absence of a specific genetic variation can thereafter be determined. In some cases, a purified nucleic acid can be sequenced to determine the presence or absence of a genetic variation. The presence of a genetic variation associated with AD can be indicative of AD or an increased risk of AD. A genetic variation and/or a combination of genetic variations that can be indicative of AD or an increased risk of AD can be an APOE, e.g., APOE-ε4, genetic mutation. A genetic variation can be as disclosed in Table 1, Table 3, Table 4, Table 7, Table 8, and/or Table 9. A genetic variation and/or a combination of genetic variations that can be indicative of AD or an increased risk of AD can be a novel and non-APOE mutation. In various embodiments, a genetic mutation can be a SNP. Following the detection of a genetic mutation, a medicament can be administered to a subject to treat AD or symptoms attributed to AD. A therapeutically effective amount of such medicament can be administered orally, intraperitoneally, buccally, intravenously, parenterally, rectally, intradermally, transdermally, pulmonary, intracranially, nasally, topically, or by inhalation spray.

TABLE 1

Genetic variants/SNPs associated with AD

| rsID | SNP region | SEQ ID NO. |
|---|---|---|
| rs7106524 | GCTCAAGCAGTCCTCAGCATCCTGA[A/G]AGTTCTACAGGCATGCACCAACAC | 66 |
| rs1783563 | GGGCCCAGCCTTCCCCGACCTTACA[C/T]CCTCGCCCCTCCAGGGCCTTCTCGG | 67 |
| rs7951170 | ATTAGACCTTCTTGACTTACTGAAT[A/G]CTGTCAACCCAATGCTTTTATTATC | 68 |
| rs60462066 | TGTTTGTTTGTTTGTTTGTTTTTTT[-/TTT]GCTTTTTGTTTTTCTTATTGAGATG | 69 |
| rs7120611 | GGCACGCACCACCATGCCCAGCTAA[C/T]TTTTGTATTTTTAGTAGCAACAGGG | 70 |
| rs1264436 | ccaaagagttgggattataggcgtg[A/G]gccaccacgccaggccAAtttttt | 71 |
| rs5639899 | CAAAGCGAGAACCGAAGGTGTTTGG[A/G]CTAGGAAAATGTTATTCTTGATGTT | 72 |
| rs12339504 | TATGGCTGGTTTTGTTGTTTTTTTT[G/T]TTTTTTTTTTTCACAAGAAAGAGGA | 73 |
| rs11603664 | AGACTCCATCTCAAATAAAAAAAAA[A/C]AAAAAAAACAAAAACTGTTTTTTA | 74 |
| rs72713460 | GTGGATCAGAATCTGATCTACCTAA[G/T]TTGGGTGCAGTGGTGCATGCCTGTG | 75 |
| rs12442709 | TGTAATCCCAGCACTTTGGGAGGCC[A/G]AGGCGGGCGGATCACGAGGTCAGGA | 76 |
| rs12606254 | AACATCTTTGATTTCTTTTTCTTTT[C/T]TTTTTTTTTTTTTTGGCCCGGACT | 77 |
| rs4806915 | gagattccgtctcaaaaaaaaaaaa[A/C]aaaacacaaacaaaaaaaaaAAACT | 78 |
| rs73052335 | ACTCTGTCTCAAAAAAAAAAAAAAA[A/C]AAAAAAAAAACAAGATGGTCTTGCC | 79 |
| rs2836293 | TTTTAGGTCAGGCATATAATCCTAA[A/G]ATAAAAAAATATGTATTAATCGTGA | 80 |
| rs404935 | ggagtgcagtgatgcgatctcggct[C/T]actgcaagctccgcctcctgggttc | 81 |
| rs35338085 | GTTTTCAAAGTGTGACCTGCAGACC[C/T]CATGGGGTCCCTGAGATTTTTCAGA | 82 |
| rs78237068 | TATTTTTATGTAACGCCTGTTCACA[C/T]GAAAGAACGCGATGTGAGGGAAGAA | 83 |
| rs11223248 | AGTAACTGAGTAATGCCACTATGAA[A/C]AATTGCATGTAAGTCTTTGTGGGAC | 84 |
| rs74762471 | TCCAGGAATGTCAGGTGTCTATCAG[A/G]TGATGGTCATGCAGTTGTTAAACTG | 85 |
| rs76589214 | GGTCACAGCCAGCACCAGGGAAAGA[C/G]AGTCTCCCAATTGATAGAAAACAGC | 86 |
| rs11223250 | CTCCCAGGTTCCCTCCTCTTTGACC[A/C/G/T]GGCCTGCCAGGGTGCCTCCTTCCTC | 87 |
| rs11223251 | TATGAGGTAACGCAGCAGAAATGCA[A/G]AAGATCTAAGTAGCATTGTTTATAC | 88 |
| rs11605454 | CCCTGGCTGCCACAGAGGGCGATAG[A/G]GCCGGCACTTGGGCATTAGCTCCGC | 89 |
| rs11223254 | ATAGGAGAAATGAAATCATACGCTC[A/G]GCCCAACAGAGGAAACACGGCTCCT | 90 |
| rs11223255 | TCAGGTAAATTCTTTGTGAAGCTAG[A/G]GATTCTGCCACACCAAGGGGATGCT | 91 |
| rs1962519 | TGCTTGGATGCCGTGGACTGTTTAG[A/G]TGTTGTGATTCCTTCCTCACTAGCA | 92 |
| rs4797101 | TCCACTGCATTCGCCAGGCCTACGT[C/G]GGACTTTCAATTCTTTACCTCCCAG | 93 |
| rs566476 | TTCCCTGTGAAGGAGTCCCGTCCGC[A/T]TGTTCTCCTGGCCCCCTTAGTTCCC | 94 |
| rs490218 | CCTCCATGGCGTCCACCACAAGTGG[C/T]CTCAGCCCATTCAGACGCGGGTCTG | 95 |
| rs518669 | CAAGTGGTCTCAGCCCATTCAGACG[C/T]GGGTCTGAGGGAGTTGGTGCTGGTT | 96 |
| rs11669999 | CGGGAGGCTCCGGGGCCCGCCCCCG[C/G]CCCCCCTGCGTCAGGCCTGTACCCG | 97 |

TABLE 1-continued

Genetic variants/SNPs associated with AD

| rsID | SNP region | SEQ ID NO. |
|---|---|---|
| rs545909 | GGTGTGTGGCGGGCAGCAGGGAGAT[C/G/T]GTCGCGGTGCGTGGCGGGCAGCAGG | 98 |
| rs477511 | GGGGGGTCCGTGTGCAGCTCAGGTG[C/T]GCGGAGCAGGGACCCCTGAGCTGCG | 99 |
| rs507218 | CAGGAGAATAGATTGAACCCGGGAG[A/G]TGGAGGCTGCAGTGAGCCGAGATTG | 100 |
| rs529910 | CTGTGGGCATGGACCCGGCACGCGT[C/T]CATGGCCCCTGTGACCCGTTATGTC | 101 |
| rs529914 | TGGGCATGGACCCGGCACGCGTTCA[C/T]GGCCCCTGTGACCCGTTATGTCGGG | 102 |
| rs311614 | CTTCCCCCAGTGATCATATCTtttt[G/T]ttttgttttgttttgtttttttgag | 103 |
| rs312072 | GACCCACTGCAAATCCCCGTTCCCC[C/T]GCACTCCTCTTCTCCCAGCCCATCC | 104 |
| rs57875940 | TGTGAAGGGGCTGAGGGTGAGTGGT[A/G]TGGTTATAGTAAGGCAACGCGATAG | 105 |
| rs150825385 | CTGAGGTGAGAGAATGGCGTGAACC[C/T]GGGAGGTGGAGCTTGCAGTGAGCCG | 106 |
| rs55935131 | CCTGTAGTAGCTACAAAAAAAAAAA[A/G]AGAGAGAGAGAGATGCTACTTAAAC | 107 |
| rs2878170 | GGCTGGAGTGCAGTGGCATGATCTC[A/G]GCTCACTGCAAGCTCTGCCTCCCAG | 108 |
| rs115448952 | attgagagaaaaaggcttcagacga[A/G]caaactactccaagctaaaggagga | 109 |
| rs148308391 | ttaaaaaaattagacgaatggctaa[C/T]tagaataaccaatgcagagaagtcc | 110 |
| rs150918078 | TGCTGTATTCAGGAAACCCATCTCA[C/T]GTGCAGAGACACACATAGGCTCAAA | 111 |
| rs146123422 | AAAAGATCAATAAAATTGATAGACC[A/G]CTAGCAAGACTAATAAAGAAGAAAA | 112 |
| rs60851395 | GATAGCATTAGGAGATATACCTAAT[A/G]TTAAATGACGAGTTAATGGGTGCAG | 113 |
| rs59750960 | CTGCAGTGAGCTATGATTACACCAC[G/T]GCATTCCAGCCTGGGTGACAGAACA | 114 |
| rs55881030 | ACTCCAGCCTGGGCAACAGAGCAAG[G/T]CCCTGTCTCAAAAAAAAAAAAAAAA | 115 |
| rs111537263 | TTGAACTCCCAGCCTCAGGTGATCC[A/G]CCCTCCTCAGCCTCTCAAAGTGCTG | 116 |
| rs3783639 | GCTATTCTCATCCTCTCAGCCAGCC[C/T]TGTCACAAACACTACGTTTCTTGGT | 117 |
| rs11626210 | CATCCAAGTAAGTACCATCAGAGTG[C/T]GCAAGCCACCATCATTAGTGACAGA | 118 |
| rs58293795 | ACTTTGGGAGGCCAAGGCAGGCGTA[C/T]CATTTGAGGTCAGGAGTTCGAGACC | 119 |
| rs67620272 | CCTCTCCCTGCCTTGCAGTTGCTTG[C/G]AGATTTTGTACGCTAGCCCCAGGAA | 120 |
| rs72713477 | GACAGTGATTTGTACCTCTTTTCAG[C/T]GAACCAGTCAAGATCCACATTGCTC | 121 |
| rs8020798 | ACAAAAAAAACACCAGTTATTGTCC[C/T]GACTTTACAGATGAGGACACAGATA | 122 |
| rs17128052 | AGCTCCAGCAAGGAAATGAGACAGA[C/G]TGGTTTCTCAGATTAACTGTGCACT | 123 |
| rs34544088 | ATAATCTCTAAACCAGCATGGACAC[A/G]TTCTGCAAAAAACAAACAACCCAAA | 124 |
| rs57095876 | GACCATCTACAGTTCCACTTTTCAC[A/G]GTTTCAGTTACCCTTGGTCAAACAT | 125 |
| rs7147201 | agactgcaaaagctatggccacagc[A/G]catggtaagtgcttagttaagatgg | 126 |
| rs3783641 | ATTACAGTCCTCATATAGAAATCAC[A/C/T]GGCAAATGAGTCAGGTGGGGAATGC | 127 |
| rs72713482 | GTATTTAGTACTAATACAAGTTGAA[A/T]TGTGCCATTCGCCAAAAAAGATATG | 128 |
| rs8017210 | AACCTTTTGTGATTGCTCATTTCA[A/G]TATGAAGTGTCTAAGATGCATTTTT | 129 |
| rs11247317 | CAAAGCTTCGCTTGGGGGAAAAACT[G/T]AAACCTAGAGTTGGGACTAAAGTGG | 130 |
| rs311616 | GCCCATCTCCTTCCTTCCATCATGG[A/G]CCCCACACACCAAGCCGCTGCCTC | 131 |
| rs13382069 | agatccagagggtgaagcctgtgtc[A/G]ctgctgctgcagcactggcaggggc | 132 |
| rs186339 | TGGGGGGTGCCCGAGTGGAAAAGCA[C/G]CGGCTTAGGCCGGGGTGGGGAAAGT | 133 |
| rs149256323 | CTGTAGTCCCAACTACTCTGGAGGC[A/C/T]GAGGCAGGAGAATGGCGTGAACCCG | 134 |
| rs4806916 | aaaaaaaaaaaaaacacaaacaaa[A/C]aaaaaAAACTTATTCTCCTGCTCTC | 135 |

TABLE 1-continued

Genetic variants/SNPs associated with AD

| rsID | SNP region | SEQ ID NO. |
|---|---|---|
| rs311620 | CCTCCTGTGGTCCTCAGTGCTGAGG[C/G]CGATGCTGGCACCCAGCGGACGGGC | 136 |
| rs311621 | GCCCCACACACGGGTCACCTGCCCC[A/G]GGAACAGCCAGGCCATTCCCCTGCT | 137 |
| rs2304249 | GAGGGCCTCAGGGTGGGTGTCGTGG[A/G]GCTGAAACAGGCCCGGCTCTTGCCC | 138 |
| rs1978729 | GCGGAGGTCATGGGGTGCGGGAGCC[A/G]GGCGGGGGTGACTGTGGCCTTGCCT | 139 |
| rs59377097 | GATCACCTGTCAGGAGTTCGAGACC[C/T]GCCTAACGTGTTGAAACCCTGTCTC | 140 |
| rs28372911 | CTGGAGACGGTGGGTGCCCCTTTCA[C/T]GGATGGGTCCGGRGCTCTGCGGAGC | 141 |
| rs2836255 | ATATCTGCTAGGAGGTAAAGAAAAT[A/G]TAATGAATCCTGGAGCACCTGGCTG | 142 |
| rs928771 | AGACACAGTGTTGAGATCAGAAGCA[G/T]GGACTATGGATTCCAACATACCTTG | 143 |
| rs10975489 | GTCAGGAGATCGAGACCATCCTGGC[C/T]AACACAGTGAAACCCCGTCTCTACT | 144 |
| rs11791561 | TTGGGAGGCCGAGGTGGGTGAATCG[C/G]CTGAGGTCAGGAGTTTGCAGCCAGC | 145 |
| rs9657650 | AGATTAAGACCATCCTGGGTAACAC[A/G/T]GTGAAACCCCGTCTCTACTAAAAAA | 146 |
| rs9657651 | TCAGGAGGCTGAGGCAGGAGAATGG[C/T]GTGAGCCCGGGAGGCGGAGCTTGCA | 147 |
| rs10979217 | ATCTTCATAAAGGTATCTTCAAGTT[A/G]TCAGTCTCCCCAGTCTGTGCAGAGT | 148 |
| rs73041479 | AGCTCTGTTATAACAGGTAATAATT[C/T]GAGCTCACTTAGAGAAAAATCTCAA | 149 |
| rs56013432 | CTCTTTTAGAGCATTGTTTTCTTTT[C/T]TTCTTTTTTTGTAAGATTACACAGT | 150 |
| rs522941 | ACAGCTCTGCTTTATACTGGGCACA[A/G]CTTTCCCTCTTTCTTCACTCATCTG | 151 |
| rs556075 | TGTCCCCACCTTTCGCCCCTCACCC[C/T]AGCTCCCCAACGCCAAAGACAAGG | 152 |
| rs510724 | CAGCGCGGCTGGCGGGGCGGTTCGC[C/G]GCGGTGCCCACAGGACCTCAGGGCG | 153 |
| rs11551095 | ACATGCTGAAGGCGTCTTGTCTGCC[G/T]CTCGGCTTCATCGTCTTCCTGCCCG | 154 |
| rs537248 | CCATGGCCGGGCCAAGCGTCCCGCG[C/T]CCCTGGAGCCCTAAGTCCCCTCTCT | 155 |
| rs475814 | GTGGCGGGCAGCAGGGAGATCGTCG[C/T]GGTGCGTGGCGGGCAGCAGGGAGAT | 156 |
| rs545850 | GGGCAGCAGGGAGATCGTCGCGGTG[C/T]GTGGCGGGCAGCAGGGAGATCGTCG | 157 |
| rs311618 | GGCCTGCGTCACTCCACAGTGGCAC[A/G]GGCGCTGGGCTCCGCATCCCATGGG | 158 |
| rs519271 | GATCTCCTGACCTCATGATTTGCCC[A/T]CCTCAGCCTCCCAAAGTGCTCGGAT | 159 |
| rs311622 | gtcccctcccagccccagaaccccc[A/G]gcatgtgcgcatccgtcccagtgcc | 160 |
| rs311623 | gaacagatcctacactgtggacaaa[C/G]tcttttggatctggcttctctcact | 161 |
| rs311624 | GGGATTGAATACAGGAGGGGAGCGA[C/T]CACAGCTGCCCACTGGACGTGGCAG | 162 |
| rs312074 | AACCCTCCACCCCGCAGACCAGGCG[A/C/G/T]CGTGTGTGTGTGGGAGAGAAGGAGG | 163 |
| rs7275784 | CTCTGTGGGATTCCCTCCCCATTCC[C/T]GGAGATAGCTGGTTCGCCCTGCTTG | 164 |
| rs2591054 | TGATGGCACCAGGCCGTCACCACCG[C/T]GGTGACAGCACACACATCCACAC | 243 |

In some embodiments wherein [X/Y] can identify a genetic variation, X can be the effect allele and Y can be the reference allele. In some embodiments wherein [X/Y] can identify a genetic variation, Y can be the effect allele and X can be the reference allele. The reference allele can be an allele present in the wild-type having no genetic variation at the identified location.

To assess Alzheimer's disease (AD), polypeptides and/or proteins can be extracted from a sample and purified. The purified polypeptides and/or proteins can be incorporated in hybridization reaction with antibodies and/or probes specific to a genetic variant. The presence or absence of a specific genetic variation can thereafter be determined. In some cases, a purified polypeptide and/or protein can be sequenced to determine the presence or absence of a genetic variation. The presence of a genetic variation associated with AD can be indicative of AD or an increased risk of AD. A genetic variation and/or a combination of genetic variations that can be indicative of AD or an increased risk of AD can be an APOE, e.g., APOE-ε4, genetic mutation. A genetic variant can be detected by hybridizing, binding, attaching, and/or interacting one or more of polypeptide, protein, and/or a part thereof in Table 2. In some cases, proteins encoded by the genes marked by the intronic variants, for example, a combination of 5 genes including OPCML, FAM169B, MYOM1, NCLN and KCNJ15 can be indicative of AD or an increased risk of AD. In some case, proteins encoded by a combination of 4 genes including marked by the 2 intergenic variants including KLF4-ACTL7B and SAMD4A-GCH1 can be indicative of AD or an increased risk of AD. In some cases, APOE locus such as PVRL2, TOMM40, APOE and APOC1 can be indicative of AD or an increased risk of AD. In some cases, IL33/IL1RL1, e.g., IL-33, ST2/IL1RL1, can be indicative of AD or an increased risk of AD. A genetic variation can be as disclosed in Table 1, Table 3, Table 4, Table 7, Table 8, and/or Table 9. A genetic variation and/or a combination of genetic variations that can be indicative of AD or an increased risk of AD can be a novel and non-APOE mutation. In various embodiments, a genetic mutation can be a SNP. Following the detection of a genetic mutation, a medicament can be administered to a subject to treat AD or symptoms attributed to AD. A therapeutically effective amount of such medicament can be administered orally, intraperitoneally, buccally, intravenously, parenterally, rectally, intradermally, transdermally, pulmonary, intracranially, nasally, topically, or by inhalation spray.

TABLE 2

Polypeptides for detecting genetic variants/SNPs associated with AD

| Categories | Gene | Uniprot Sequence ID | Amino acid sequences | SEQ ID No. |
| --- | --- | --- | --- | --- |
| WGS | KLF4 | O43474-3 | MRQPPGESDMAVSDALLPSFSTFASGPAGREKT LRQAGAPNNRWREELSHMKRLPPVLPGRPYDLA AATVATDLESGGAGAACGGSNLAPLPRRETEEF NDLLDLDFILSNSLTHPPESVAATVSSSASASS SSSPSSSGPASAPSTCSFTYPIRAGNDPGVAPG GTGGGLLYGRESAPPPTAPFNLADINDVSPSGG FVAELLRPELDPVYIPPQQPQPPGGGLMGKFVL KASLSAPGSEYGSPSVISVSKGSPDGSHPVVVA PYNGGPPRTCPKIKQEAVSSCTHLGAGPPLSNG HRPAAHDFPLGRQLPSRTTPTLGLEEVLSSRDC HPALPLPPGFHPHPGPNYPSFLPDQMQPQVPPL HYQGQSRGFVARAGEPCVCWPHFGTHGMMLTPP SSPLELMPPGSCMPEEPKPKRGRRSWPRKRTAT HTCDYAGCGKTYTKSSHLKAHLRTHTGEKPYHC DWDGCGWKFARSDELTRHYRKHTGHRPFQCQKC DRAFSRSDHLALHMKRHF | 165 |
| | ACTL7B | Q9Y614-1 | MATRNSPMPLGTAQGDPGEAGTRPGPDASLRDT GAATQLKMKPRKVHKIKAVIIDLGSQYCKCGYA GEPRPTYFISSTVGKRCPEAADAGDTRKWTLVG HELLNTEAPLKLVNPLKHGIVVDWDCVQDIWEY IFRTAMKILPEEHAVLVSDPPLSPSSNREKYAE LMFETFGIPAMHVTSQSLLSIYSYGKTSGLVVE SGHGVSHVVPISEGDVLPGLTSRADYAGGDLTN YLMQLLNEAGHAFTDDHLHIIEHIKKKCCYAAF LPEEELGLVPEELRVDYELPDGKLITIGQERFR CSEMLFQPSLAGSTQPGLPELTAACLGRCQDTG FKEEMAANVLLCGGCTMLDGFPERFQRELSLLC PGDSPAVAAAPERKTSVWTGGSILASLQAFQQL WVSKEEFEERGSVAIYSKC | 166 |
| | OPCML | Q14982-1 | MGVCGYLFLPWKCLVVVSLRLLFLVPTGVPVRS GDATFPKAMDNVTVRQGESATLRCTIDDRVTRV AWLNRSTILYAGNDKWSIDPRVIILVNTPTQYS IMIQNVDVYDEGPYTCSVQTDNHPKTSRVHLIV QVPPQIMNISSDITVNEGSSVTLLCLAIGRPEP TVTWRHLSVKEGQGFVSEDEYLEISDIKRDQSG EYECSALNDVAAPDVRKVKITVNYPPYISKAKN TGVSVGQKGILSCEASAVPMAEFQWFKEETRLA TGLDGMRIENKGRMSTLTFFNVSEKDYGNYTCV ATNKLGNTNASITLYGPGAVIDGVNSASRALAC LWLSGTLLAHFFIKF | 167 |
| | SAMD4A | Q9UPU9-1 | MMFRDQVGVLAGWFKGWNECEQTVALLSLLKRV SQTQARFLQLCLEHSLADCAELHVLEREANSPG IINQWQQESKDKVISLLLTHLPLLKPGNLDAKV EYMKLLPKILAHSIEHNQHIEESRQLLSYALIH PATSLEDRSALAMWLNHLEDRTSTSFGGQNRGR SDSVDYGQTHYYHQRQNSDDKLNGWQNSRDSGI CINASNWQDKSMGCENGHVPLYSSSSVPTTINT IGTSTSTILSGQAHHSPLKRSVSLTPPMNVPNQ PLGHGWMSHEDLRARGPQCLPSDHAPLSPQSSV ASSGSGGSEHLEDQTTARNTFQEEGSGMKDVPA WLKSLRLHKYAALFSQMTYEEMMALTECQLEAQ NVTKGARHKIVISIQKLKERQNLLKSLERDIIE GGSLRIPLQELHQMILTPIKAYSSPSTTPEARR REPQAPRQPSLMGPESQSPDCKDGAAATGATAT PSAGASGGLQPHQLSSCDGELAVAPLPEGDLPG QFTRVMGKVCTQLLVSRPDEENISSYLQLIDKC LIHEAFTETQKKRLLSWKQQVQKLFRSFPRKTL LDISGYRQQRNRGFGQSNSLPTAGSVGGGMGRR | 168 |

TABLE 2-continued

Polypeptides for detecting genetic variants/SNPs associated with AD

| Categories | Gene | Uniprot Sequence ID | Amino acid sequences | SEQ ID No. |
|---|---|---|---|---|
| | | | NPRQYQIPSRNVPSARLGLLGTSGFVSSNQRNT TATPTIMKQGRQNLWFANPGGSNSMPSRTHSSV QRTRSLPVHTSPQNMLMFQQPEFQLPVTEPDIN NRLESLCLSMTEHALGDGVDRTSTI | |
| | GCH1 | P30793-1 | MEKGPVRAPAEKPRGARCSNGFPERDPPRPGPS RPAEKPPRPEAKSAQPADGWKGERPRSEEDNEL NLPNLAAAYSSILSSLGENPQRQGLLKTPWRAA SAMQFFTKGYQETISDVLNDAIFDEDHDEMVIV KDIDMFSMCEHHLVPFVGKVHIGYLPNKQVLGL SKLARIVEIYSRRLQVQERLTKQIAVAITEALR PAGVGVVVEATHMCMVMRGVQKMNSKTVTSTML GVFREDPKTREEFLTLIRS | 169 |
| | FAM169B | Q8N8A8-1 | MKVQSFGERVVLFILNAIIFGRLERNLDDDDMF FLPHSVKEQAKILWRRGAAVGFYTTKMKGRLCG DGTGACYLLPVFDTVFIRRKHWHRGLGTAMLRD FCETFPEDEALGVSCSMSPAMYQAHPGNSEDVS RHARTSQNDRPRQPAPGDGSKERMCGEELEDTK DDPECGVEEEDAGLAGQPPGKLTRSSP | 170 |
| | MYOM1 | P52179-1 | MSLPFYQRCHQHYDLSYRNKDVRSTVSHYQREK KRSAVYTQGSTAYSSRSSAAHRRESEAFRRASA SSSQQQASQHALSSEVSRKAASAYDGSSHGLT DSSLLLDDYSSKLSPKPKRAKHSLLSGEEKENL PSDYMVPIFSGRQKHVSGITDTEEERIKEAAAY IAQRNLLASEEGITTSKQSTASKQTTASKQSTA SKQSTASKQSTASRQSTASRQSVVSKQATSALQ QEETSEKKSRKVVIREKAERLSLRKTLEETETY HAKLNEDHLLHAPEFIIKPRSHTVWEKENVKLH CSIAGWPEPRVTWYKNQVPINVHANPGKYIIES RYGMHTLEINGCDFEDTAQYRASAMNVKGELSA YASVVVKRYKGEFDETRFHAGASTMPLSFGVTP YGYASRFEIHFDDKFDVSFGREGETMSLGCRVV ITPEIKHFQPEIQWYRNGVPLSPSKWVQTLWSG ERATLTFSHLNKEDEGLYTIRVRMGEYYEQYSA YVFVRDADAEIEGAPAAPLDVKCLEANKDYIII SWKQPAVDGGSPILGYFIDKCEVGTDSWSQCND TPVKFARFPVTGLIEGRSYIFRVRAVNKMGIGF PSRVSEPVAALDPAEKARLKSRPSAPWTGQIIV TEEEPSEGIVPGPPTDLSVTEATRSYVVLSWKP PGQRGHEGIMYFVEKCEAGTENWQRVNTELPVK SPRFALFDLAEGKSYCFRVRCSNSAGVGEPSEA TEVTVVGDKLDIPKAPGKIIPSRNTDTSVVVSW EESKDAKELVGYYIEASVAGSGKWEPCNNNPVK GSRFTCHGLVTGQSYIFRVRAVNAAGLSEYSQD SEAIEVKAAIGGGVSPDVCPALSDEPGGLTASR GRVHEASPPTFQKDALLGSKPNKPSLPSSSQNL GQTEVSKVSETVQEELTPPPQKAAPQGKSKSDP LKKKTDRAPPSPPCDITCLESFRDSMVLGWKQP DKIGGAEITGYYVNYREVIDGVPGKWREANVKA VSEEAYKISNLKENMVYQFQVAAMNMAGLGAPS AVSECFKCEEWTIAVPGPPHSLKCSEVRKDSLV LQWKPPVHSGRTPVTGYFVDLKEAKAKEDQWRG LNEAAIKNVYLKVRGLKEGVSYVFRVRAINQAG VGKPSDLAGPVVAETRPGTKEVVVNVDDDGVIS LNFECDKMTPKSEFSWSKDYVSTEDSPRLEVES KGNKTKMTFKDLGMDDLGIYSCDVTDTDGIASS YLIDEEELKRLLALSHEHKFPTVPVKSELAVEI LEKGQVRFWMQAEKLSGNAKVNYIFNEKEIFEG PKYKMHIDRNTGIIEMFMEKLQDEDEGTYTFQL QDGKATNHSTVVLVGDVFKKLQKEAEFQRQEWI RKQGPHFVEYLSWEVTGECNVLLKCKVANIKKE THIVWYKDEREISVDEKHDFKDGICTLLITEFS KKDAGIYEVILKDDRGKDKSRLKLVDEAFKELM MEVCKKIALSATDLKIQSTAEGIQLYSFVTYYV EDLKVNWSHNGSAIRYSDRVKTGVTGEQIWLQI NEPTPNDKGKYVMELFDGKTGHQKTVDLSGQAY DEAYAEFQRLKQAAIAEKNRARVLGGLPDVVTI QEGKALNLTCNVWGDPPPEVSWLKNEKALASDD HCNLKFEAGRTAYFTINGVSTADSGKYGLVVKN KYGSETSDFTVSVFIPEEEARMAALESLKGGKK AK | 171 |
| | NCLN | Q969V3-1 | MLEEAGEVLENMLKASCLPLGFIVFLPAVLLLV APPLPAADAAHEFTVYRMQQYDLQGQPYGTRNA VLNTEARTMAAEVLSRRCVLMRLLDFSYEQYQK ALRQSAGAVVIILPRAMAAVPQDVVRQFMEIEP EMLAMETAVPVYFAVEDEALLSIYKQTQAASAS | 172 |

TABLE 2-continued

Polypeptides for detecting genetic variants/SNPs associated with AD

| Categories | Gene | Uniprot Sequence ID | Amino acid sequences | SEQ ID No. |
|---|---|---|---|---|
| | | | QGSASAAEVLLRTATANGFQMVTSGVQSKAVSD WLIASVEGRLTGLGGEDLPTIVIVAHYDAFGVA PWLSLGADSNGSGVSVLLELARLFSRLYTYKRT HAAYNLLFFASGGGKFNYQGTKRWLEDNLDHTD SSLLQDNVAFVLCLDTVGRGSSLHLHVSKPPRE GTLQHAFLRELETVAAHQFPEVRFSMVHKRINL AEDVLAWEHERFAIRRLPAFTLSHLESHRDGQR SSIMDVRSRVDSKTLTRNTRIIAEALTRVIYNL TEKGTPPDMPVFTEQMQIQQEQLDSVMDWLTNQ PRAAQLVDKDSTFLSTLEHHLSRYLKDVKQHHV KADKRDPEFVFYDQLKQVMNAYRVKPAVFDLLL AVGIAAYLGMAYVAVQHFSLLYKTVQRLLVKAK TQ | |
| | KCNJ15 | Q99712-1 | MDAIHIGMSSTPLVKHTAGAGLKANRPRVMSKS GHSNVRIDKVDGIYLLYLQDLWTTVIDMKWRYK LTLFAATFVMTWFLFGVIYYAIAFIHGDLEPGE PISNHTPCIMKVDSLTGAFLFSLESQTTIGYGV RSITEECPHAIFLLVAQLVITTLIEIFITGTFL AKIARPKKRAETIKFSHCAVITKQNGKLCLVIQ VANMRKSLLIQCQLSGKLLQTHVTKEGERILLN QATVKFHVDSSSESPFLILPMTFYHVLDETSPL RDLTPQNLKEKEFELVVLLNATVESTSAVCQSR TSYIPEEIYWGFEFVPVVSLSKNGKYVADFSQF EQIRKSPDCTFYCADSEKQQLEEKYRQEDQRER ELRTLLLQQSNV | 173 |
| APOE locus | PVRL2 | Q92692-1 | MARAAALLPSRSPPTPLLWPLLLLLLLETGAQD VRVQVLPEVRGQLGGTVELPCHLLPPVPGLYIS LVTWQRPDAPANHQNVAAFHPKMGPSFPSPKPG SERLSFVSAKQSTGQDTEAELQDATLALHGLTV EDEGNYTCEFATFPKGSVRGMTWLRVIAKPKNQ AEAQKVTFSQDPTTVALCISKEGRPPARISWLS SLDWEAKETQVSGTLAGTVTVTSRFTLVPSGRA DGVTVTCKVEHESFEEPALIPVTLSVRYPPEVS ISGYDDNWYLGRTDATLSCDVRSNPEPTGYDWS TTSGTFPTSAVAQGSQLVIHAVDSLFNTTFVCT VTNAVGMGRAEQVIFVRETPNTAGAGATGGIIG GIIAAIIATAVAATGILICRQQRKEQTLQGAEE DEDLEGPPSYKPPTPKAKLEAQEMPSQLFTLGA SEHSPLKTPYFDAGASCTEQEMPRYHELPTLEE RSGPLHPGATSLGSPIPVPPGPPAVEDVSLDLE DEEGEEEEYLDKINPIYDALSYSSPSDSYQGK GFVMSRAMYV | 174 |
| | TOMM40 | O960080-1 | MGNVLAASSPPAGPPPPPAPALVGLPPPPPSPP GFTLPPLGGSLGAGTSTSRSSERTPGAATASAS GAAEDGACGCLPNPGTFEECHRKCKELFPIQME GVKLTVNKGLSNIVQVNHTVALSTIGESNYHFG VTYVGTKQLSPTEAFPVLVGDMDNSGSLNAQVI HQLGPGLRSKMAIQTQQSKFVNWQVDGEYRGSD FTAAVTLGNPDVLVGSGILVAHYLQSITPCLAL GGELVYHRRPGEEGTVMSLAGKYTLNNWLATVT LGQAGMHATYYHKASDQLQVGVEFEASTRMQDT SVSFGYQLDLPKANLLFKGSVDSNWIVGATLEK KLPPLPLTLALGAFLNHRKNKFQCGFGLIG | 175 |
| | APOE | P02649-1 | MKVLWAALLVTFLAGCQAKVEQAVETEPEPELR QQTEWQSGQRWELALGRFWDYLRWVQTLSEQVQ EELLSSQVTQELRALMDETMKELKAYKSELEEQ LTPVAEETRARLSKELQAAQARLGADMEDVCGR LVQYRGEVQAMLGQSTEELRVRLASHLRKLRKR LLRDADDLQKRLAVYQAGAREGAERGLSAIRER LGPLVEQGRVRAATVGSLAGQPLQERAQAWGER LRARMEEMGSRTRDRLDEVKEQVAEVRAKLEEQ AQQIRLQAEAFQARLKSWFEPLVEDMQRQWAGL VEKVQAAVGTSAAPVPSDNH | 176 |
| | APOC1 | P02654-1 | MRLFLSLPVLVVVLSIVLEGPAPAQGTPDVSSA LDKLKEFGNTLEDKARELISRIKQSELSAKMRE WFSETFQKVKEKLKIDS | 177 |
| IL33/IL1RL1 | IL33 | O95760-1 | MKPKMKYSTNKISTAKWKNTASKALCFKLGKSQ QKAKEVCPMYFMKLRSGLMIKKEACYFRRETTK RPSLKTGRKHKRHLVLAACQQQSTVECFAFGIS GVQKYTRALHDSSITGISPITEYLASLSTYNDQ SITFALEDESYEIYVEDLKKDEKKDVLLSYYE SQHPSNESGDGVDGKMLMVTLSPTKDFWLHANN KEHSVELHKCEKPLPDQAFFVLHNMHSNCVSFE | 178 |

TABLE 2-continued

Polypeptides for detecting genetic variants/SNPs associated with AD

| Categories | Gene | Uniprot Sequence ID | Amino acid sequences | SEQ ID No. |
|---|---|---|---|---|
| | | | CKTDPGVFIGVKDNHLALIKVDSSENLCTENIL FKLSET | |
| | IL1RL1 | Q01638-1 | MGFWILAILTILMYSTAAKFSKQSWGLENEALI VRCPRQGKPSYTVDWYYSQTNKSIPTQERNRVF ASGQLLKFLPAAVADSGIYTCIVRSPTFNRTGY ANVTIYKKQSDCNVPDYLMYSTVSGSEKNSKIY CPTIDLYNWTAPLEWFKNCQALQGSRYRAHKSF LVIDNVMTEDAGDYTCKFIHNENGANYSVTATR SFTVKDEQGFSLFPVIGAPAQNEIKEVEIGKNA NLTCSACFGKGTQFLAAVLWQLNGTKITDFGEP RIQQEEGQNQSFSNGLACLDMVLRIADVKEEDL LLQYDCLALNLHGLRRHTVRLSRKNPIDHHSIY CIIAVCSVFLMLINVLVIILKMFWIEATLLWRD IAKPYKTRNDGKLYDAYVVYPRNYKSSTDGASR VEHPVHQILPDVLENKCGYTLCIYGRDMLPGED VVTAVETNIRKSRRHIFILTPQITHNKEFAYEQ EVALHCALIQNDAKVILIEMEALSELDMLQAEA LQDSLQHLMKVQGTIKWREDHIANKRSLNSKFW KHVRYQMPVPSKIPRKASSLTPLAAQKQ | 179 |

GRS Value

In some embodiments, the combination effects of genetic variants can be quantified in the form of a GRS and a classification can be based on a GRS value. An assessment can be done using the category test (e.g., Fisher or Chi-square test) comparing a relative risk of having Alzheimer's disease (AD) or mild cognitive impairment (MCI) for individuals in medium and high risk groups with the individuals in low risk group. In some cases, odds ratio (OR) can be used to quantify risk effects (see Table 10). The OR for AD in AD high risk group can be at least about 1, 2, 3, 4, 5, 6, 7, 8, 9, 10, 11, 12, 13, 14, 15, 16, 17, 18, 19, 20, 25, 30, 40, 45, 50 or more. The OR for AD in AD high risk group can be at least about 1, 2, 3, 4, 5, 6, 7, 8, 9, 10, 11, 12, 13, 14, 15, 16, 17, 18, 19, 20, 25, 30, 40, 45, 50 or less. The OR for AD in AD high risk group can be between 1 and 100, 2 and 40, 3 and 30, 4 and 20, 5 and 25, or 12 and 15. The OR for MCI in AD high risk group can be at least about 0.1, 0.5, 1, 2, 3, 4, 5, 6, 7, 8, 9, 10, 15, 20, or more. The OR for MCI in AD high risk group can be at least about 0.1, 0.5, 1, 2, 3, 4, 5, 6, 7, 8, 9, 10, 15, 20, or less. The OR for MCI in AD high risk group can be between 0.1 and 20, 0.2 and 15, 1 and 10, 2 and 8, 3 and 6, or 4 and 5. For example, for an AD high risk group, ORs for AD and MCI can be 14.8 and 5.2, respectively, when compared with the low risk group.

The OR for AD in AD medium risk group can be at least about 0.1, 0.5, 1, 2, 3, 4, 5, 6, 7, 8, 9, 10, 11, 12, 13, 14, 15, 16, 17, 18, 19, 20, or more. The OR for AD in AD medium risk group can be at least about 0.1, 0.5, 1, 2, 3, 4, 5, 6, 7, 8, 9, 10, 11, 12, 13, 14, 15, 16, 17, 18, 19, 20, or less. The OR for AD in AD medium risk group can be between 0.1 and 20, 0.2 and 15, 1 and 10, 2 and 8, 3 and 6, 4 and 5, or 2 and 3. The OR for MCI in AD medium risk group can be at least about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.5, 3, 4, 5, 10, or more. The OR for MCI in AD high risk group can be at least about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.5, 3, 4, 5, 10, or less. The OR for MCI in AD medium risk group can be between 0.1 and 10, 0.2 and 15, 1 and 5, 2 and 4, or 2 and 3. For example, for an AD medium risk group, the ORs for AD and MCI can be 2.5 and 1.5, respectively, when compared with the low risk group.

A risk of AD in a subject can be classified in one, two, three or more categories. For example, AD subjects can be classified as high risk, medium risk or low risk. In some embodiments, a threshold value can be determined for classifying the risk of AD. Classification can be based on a GRS value alone. A classification of individuals as low, medium or high risk of having AD can be based on an estimation of probabilities that individuals belong to any of those 3 categories. In some cases, Bayesian classifier can be used. In some cases, when a posterior probability an individual belonging to a specific category exceeded the value of 0.1, 0.2, 0.3, 0.4, 0.5, or 0.6, the classification is accepted. An AD high risk group can have a mean GRS value of about −100, −90, −80, −70, −60, −50, −40, −30, −20, −10, 0, 10, 20, 30, 40, 50, or more. An AD high risk group or individual can have a mean GRS value of about −100, −90, −80, −70, −60, −50, −40, −30, −20, −10, 0, 10, 20, 30, 40, 50, or less. An AD high risk group can have a mean GRS value between −100 and 50, −90 and 40, −80 and 30, −70 and 20, −60 and 10, −80 and −50, −60 and −50, or −70 and −40. For example, an AD high risk group can have mean GRS value of between −50 and −55.

An AD medium risk group or individual can have a mean GRS value of about −100, −90, −80, −70, −60, −50, −40, −30, −20, −10, 0, 10, 20, 30, 40, 50, or more. An AD medium risk group or individual can have a mean GRS value of about −100, −90, −80, −70, −60, −50, −40, −30, −20, −10, 0, 10, 20, 30, 40, 50, or less. An AD medium risk group or individual can have a mean GRS value between −100 and 50, −90 and 40, −80 and 30, −70 and 20, −60 and 10, −80 and −50, −60 and −50, −70 and −40, −50 and −10, −40 and −15, or −20 and −10. For example, an AD medium risk group or individual can have mean GRS value of between −20 and −15.

An AD low risk group or individual can have a mean GRS value of about 1, 10, 20, 30, 40, 50, 60, 70, 80, 90, 100, 150, 200, or more. An AD low risk group can have a mean GRS value of about 1, 10, 20, 30, 40, 50, 60, 70, 80, 90, 100, 150, 200, or less. An AD low risk group or individual can have a mean GRS value between 1 and 200, 10 and 100, 15 and 90, 10 and 50, 20 and 40, or 25 and 35. For example, an AD low risk group or individual can have mean GRS value of between 30 and 35.

Genetic Variations and Neurological Disorders

Genomic sequences within populations exhibit variability between individuals at many locations in the genome. For example, the human genome exhibits sequence variations that can occur on average every 500 base pairs or less. Such genetic variations in nucleic acid sequences are commonly referred to as polymorphisms or polymorphic sites. For instance, single nucleotide polymorphism can occur on average about every 100 to 300 base pairs. As used herein, a polymorphism, e.g. genetic variation, includes a variation in the sequence of a gene in the genome amongst a population, such as allelic variations and other variations that arise or are observed. Thus, a polymorphism can refer to the occurrence of two or more genetically determined alternative sequences or alleles in a population. These differences can occur in coding and non-coding portions of the genome, and can be manifested or detected as differences in nucleic acid sequences, gene expression, including, for example transcription, processing, translation, transport, protein processing, trafficking, DNA synthesis, expressed proteins, other gene products or products of biochemical pathways or in post-translational modifications and any other differences manifested amongst members of a population. A single nucleotide polymorphism (SNP) includes to a polymorphism that arises as the result of a single base change, such as an insertion, deletion or change in a base. A polymorphic marker or site can be the locus at which divergence occurs. Such site can be as small as one base pair (a SNP). Polymorphic markers include, but are not limited to, restriction fragment length polymorphisms, variable number of tandem repeats (VNTR's), hypervariable regions, minisatellites, dinucleotide repeats, trinucleotide repeats, tetranucleotide repeats and other repeating patterns, simple sequence repeats and insertional elements, such as Alu. Polymorphic forms also are manifested as different mendelian alleles for a gene. Polymorphisms can be observed by differences in proteins, protein modifications, RNA expression modification, DNA and RNA methylation, regulatory factors that alter gene expression and DNA replication, and any other manifestation of alterations in genomic nucleic acid or organelle nucleic acids.

As used herein, "genetic variation" includes point mutations, polymorphisms, translocations, insertions, deletions, amplifications, inversions, interstitial deletions, copy number variations (CNVs), loss of heterozygosity, or any combination thereof. As genetic variation includes any deletion, insertion or base substitution of the genomic DNA of one or more individuals in a first portion of a total population which thereby can result in a difference at the site of the deletion, insertion or base substitution relative to one or more individuals in a second portion of the total population. Thus, the term "genetic variation" encompasses "wild type" or the most frequently occurring variation, and also includes "mutant," or the less frequently occurring variation. In some cases, a genetic variation can be a variation as compared to a wild type sequence.

Polymorphisms (e.g. polymorphic markers, genetic variations, or genetic variants) can comprise any nucleotide position at which two or more sequences are possible in a subject population. In some cases, each version of a nucleotide sequence with respect to the polymorphism can represent a specific allele, of the polymorphism. Genomic DNA from a subject can contain two alleles for any given polymorphic marker, representative of each copy of the marker on each chromosome. In some cases, an allele can be a nucleotide sequence of a given location on a chromosome. Polymorphisms can comprise any number of specific alleles.

In some cases of the disclosure, a polymorphism can be characterized by the presence of two or more alleles in a population. A polymorphism can be characterized by the presence of three or more alleles. An allele can be associated with one or more diseases or disorders, for example, a neurological disorder risk allele can be an allele that is associated with increased or decreased risk of developing a neurological disorder. Genetic variations and alleles can be used to associate an inherited phenotype, for example, a neurological disorder, with a responsible genotype. In some cases, a neurological disorder risk allele can be a variant allele that is statistically associated with a screening of one or more neurological disorders. In some cases, genetic variations can be of any measurable frequency in the population, for example, a frequency higher than 10%, 20%, 30%, 40%, 50%, 60%, 70%, 80%, 90%, 99%, or higher; a frequency between 5% and 10%, a frequency between 1% and 5%, or frequency below 1%. As used herein, variant alleles can be alleles that differ from a reference allele. As used herein, a variant can be a segment of DNA that differs from a reference DNA, such as a genetic variation. Genetic variations can be used to track the inheritance of a gene that has not yet been identified, but whose approximate location is known.

As used herein, a "haplotype" can be information regarding the presence or absence of one or more genetic markers in a given chromosomal region in a subject. A haplotype can be a segment of DNA characterized by one or more alleles arranged along the segment, for example, a haplotype can comprise one member of the pair of alleles for each genetic variation or locus. In some cases, the haplotype can comprise two or more alleles, three or more alleles, four or more alleles, five or more alleles, or any combination thereof, wherein, each allele can comprise one or more genetic variations along the segment. In some cases, haplotype can refer to a set of single-nucleotide polymorphisms (SNPs) on one chromosome that tend to always occur together, i.e., that are associated statistically, especially associated with the presence of one or more defined disease or condition, such as AD, or an heightened risk of later developing such disease or condition.

A genetic variation can be a functional aberration that can alter gene function, gene expression, polypeptide expression, polypeptide function, or any combination thereof. A genetic variation can be a loss-of-function mutation, gain-of-function mutation, dominant negative mutation, or reversion. A genetic variation can be part of a gene's coding region or regulatory region. Regulatory regions can control gene expression and thus polypeptide expression. In some cases, a regulatory region can be a segment of DNA wherein regulatory polypeptides, for example, transcription factors, can bind. A regulatory region can be positioned near the gene being regulated, for example, positions upstream of the gene being regulated. A regulatory region (e.g., enhancer element) can be several thousands of base pairs upstream or downstream of a gene.

Variants can include changes that affect a polypeptide, such as a change in expression level, sequence, function, localization, binding partners, or any combination thereof. In some cases, a genetic variation can be a frameshift mutation, nonsense mutation, missense mutation, neutral mutation, or silent mutation. For example, sequence differences, when compared to a reference nucleotide sequence, can include the insertion or deletion of a single nucleotide, or of more than one nucleotide, resulting in a frame shift; the change of at least one nucleotide, resulting in a change in the encoded amino acid; the change of at least one nucleotide, resulting in the generation of a premature stop codon; the deletion of several nucleotides, resulting in a deletion of one or more amino acids encoded by the nucleotides; the insertion of one or several nucleotides, such as by unequal recombination or gene conversion, resulting in an interruption of the coding sequence of a reading frame; duplication of all or a part of a sequence; transposition; or a rearrangement of a nucleotide sequence. A genetic variation associated with a neurological disorder can be a synonymous change in one or more nucleotides, for example, a change that does not result in a change in the amino acid sequence. Such a polymorphism can, for example, alter splice sites, affect the stability or transport of mRNA, or otherwise affect the transcription or translation of an encoded polypeptide. A synonymous mutation can result in the polypeptide product having an altered structure due to rare codon usage that impacts polypeptide folding during translation, which in some cases may alter its function and/or drug binding properties if it is a drug target. The changes that can alter DNA and increase the possibility that structural changes, such as amplifications or deletions, occur at the somatic level. A polypeptide encoded by a reference nucleotide sequence can be a reference polypeptide with a particular reference amino acid sequence, and polypeptides encoded by variant nucleotide sequences can be variant polypeptides with variant amino acid sequences.

One or more variant polypeptides can be associated with one or more diseases or disorders, such as AD. Variant polypeptides and changes in expression, localization, and interaction partners thereof, can be used to associate an inherited phenotype, for example, a neurological disorder, with a responsible genotype. A neurological disorder associated variant polypeptide can be statistically associated with a diagnosis, prognosis, or theranosis of one or more neurological disorders. Neurological disorder and neurological disease are used interchangeably. "Neurological disorder" "neurological diseases" and "neurodegenerative disease" are use interchangeable.

The most common sequence variants comprise base variations at a single base position in the genome, and such sequence variants, or polymorphisms, are commonly called single nucleotide polymorphisms (SNPs) or single nucleotide variants (SNVs). In some cases, a SNP represents a genetic variant present at greater than or equal to 1% occurrence in a population. In some cases, a SNP can represent a genetic variant present at any frequency level in a population. A SNP can be a nucleotide sequence variation occurring when a single nucleotide at a location in the genome differs between members of a species or between paired chromosomes in a subject. SNPs can include variants of a single nucleotide, for example, at a given nucleotide position, some subjects can have a 'G', while others can have a 'C'. SNPs can occur in a single mutational event, and therefore there can be two possible alleles possible at each SNP site; the original allele and the mutated allele. SNP polymorphisms can have two alleles, for example, a subject can be homozygous for one allele of the polymorphism wherein both chromosomal copies of the individual have the same nucleotide at the SNP location, or a subject can be heterozygous wherein the two sister chromosomes of the subject contain different nucleotides. The SNP nomenclature as reported herein is the official Reference SNP (rs) ID identification tag as assigned to each unique SNP by the National Center for Biotechnological Information (NCBI). In some cases SNPs can affect susceptibility to neurological disorders.

Another genetic variation of the disclosure can be copy number variations (CNVs). As used herein, "CNVs" include alterations of the DNA of a genome that results in an abnormal number of copies of one or more sections of DNA. Other types of sequence variants can be found in the human genome and can be associated with a disease or disorder, including but not limited to, microsatellites. A polymorphic microsatellite can comprise multiple small repeats of bases, for example, CA repeats, at a particular site wherein the number of repeat lengths varies in a population. In some cases, microsatellites, for example, variable number of tandem repeats (VNTRs), can be short segments of DNA that have one or more repeated sequences, for example, about 2 to 5 nucleotides long, that can occur in non-coding DNA. In some cases, changes in microsatellites can occur during genetic recombination of sexual reproduction, increasing or decreasing the number of repeats found at an allele, or changing allele length.

Neurological Disorders

"Neurological disorders", as used herein, include Acquired Epileptiform Aphasia, Acute Disseminated Encephalomyelitis, Adrenoleukodystrophy, Agenesis of the corpus callosum, Agnosia, Aicardi syndrome, Alexander disease, Alpers' disease, Alternating hemiplegia, Alzheimer's disease, Amyotrophic lateral sclerosis (see Motor Neuron Disease), Anencephaly, Angelman syndrome, Angiomatosis, Anoxia, Aphasia, Apraxia, Arachnoid cysts, Arachnoiditis, Arnold-Chiari malformation, Arteriovenous malformation, Asperger's syndrome, Ataxia Telangiectasia, Attention Deficit Hyperactivity Disorder, Autism, Auditory processing disorder, Autonomic Dysfunction, Back Pain, Batten disease, Behcet's disease, Bell's palsy, Benign Essential Blepharospasm, Benign Focal Amyotrophy, Benign Intracranial Hypertension, Bilateral frontoparietal polymicrogyria, Binswanger's disease, Blepharospasm, Bloch-Sulzberger syndrome, Brachial plexus injury, Brain abscess, Brain damage, Brain injury, Brain tumor, Brown-Sequard syndrome, Canavan disease, Carpal tunnel syndrome (CTS), Causalgia, Central pain syndrome, Central pontine myelinolysis, Centronuclear myopathy, Cephalic disorder, Cerebral aneurysm, Cerebral arteriosclerosis, Cerebral atrophy, Cerebral gigantism, Cerebral palsy, Charcot-Marie-Tooth disease, Chiari malformation, Chorea, Chronic inflammatory demyelinating polyneuropathy (CIDP), Chronic pain, Chronic regional pain syndrome, Coffin Lowry syndrome, Coma, including Persistent Vegetative State, Congenital facial diplegia, Corticobasal degeneration, Cranial arteritis, Craniosynostosis, Creutzfeldt-Jakob disease, Cumulative trauma disorders, Cushing's syndrome, Cytomegalic inclusion body disease (CIBD), Cytomegalovirus Infection, Dandy-Walker syndrome, Dawson disease, De Morsier's syndrome, Dejerine-Klumpke palsy, Dejerine-Sottas disease, Delayed sleep phase syndrome, Dementia, Dermatomyositis, Neurological Dyspraxia, Diabetic neuropathy, Diffuse sclerosis, Dysautonomia, Dyscalculia, Dysgraphia, Dyslexia, Dystonia, Early infantile epileptic encephalopathy, Empty sella syndrome, Encephalitis, Encephalocele, Encephalotrigeminal angiomatosis, Encopresis, Epilepsy, Erb's palsy, Erythromelalgia, Essential tremor, Fabry's disease, Fahr's syndrome, Fainting, Familial spastic paralysis, Febrile seizures, Fisher syndrome, Friedreich's ataxia, FART Syndrome, Gaucher's disease, Gerstmann's syndrome, Giant cell arteritis, Giant cell inclusion disease, Globoid cell Leukodystrophy, Gray matter heterotopia, Guillain-Barre syndrome, HTLV-1 associated myelopathy, Hallervorden-Spatz disease, Head injury, Headache, Hemifacial Spasm, Hereditary Spastic Paraplegia, Heredopathia atactica polyneuritiformis, Herpes zoster oticus, Herpes zoster, Hirayama syndrome, Holoprosencephaly, Huntington's disease, Hydranencephaly, Hydrocephalus, Hypercortisolism, Hypoxia, Immune-Mediated encephalomyelitis, Inclusion body myositis, Incontinentia pigmenti, Infantile phytanic acid storage disease, Infantile Refsum disease, Infantile spasms, Inflammatory myopathy, Intracranial cyst, Intracranial hypertension, Joubert syndrome, Kearns-Sayre syndrome, Kennedy disease, Kinsboume syndrome, Klippel Feil syndrome, Krabbe disease, Kugelberg-Welander disease, Kuru, Lafora disease, Lambert-Eaton myasthenic syndrome, Landau-Kleffner syndrome, Lateral medullary (Wallenberg) syndrome, Learning disabilities, Leigh's disease, Lennox-Gastaut syndrome, Lesch-Nyhan syndrome, Leukodystrophy, Lewy body dementia, Lissencephaly, Locked-In syndrome, Lou Gehrig's disease, Lumbar disc disease, Lyme disease—Neurological Sequelae, Machado-Joseph disease (Spinocerebellar ataxia type 3), Macrencephaly, Maple Syrup Urine Disease, Megalencephaly, Melkersson-Rosenthal syndrome, Menieres disease, Meningitis, Menkes disease, Metachromatic leukodystrophy, Microcephaly, Migraine, Miller Fisher syndrome, Mini-Strokes, Mitochondrial Myopathies, Mobius syndrome, Monomelic amyotrophy, Motor Neuron Disease, Motor skills disorder, Moyamoya disease, Mucopolysaccharidoses, Multi-Infarct Dementia, Multifocal motor neuropathy, Multiple sclerosis, Multiple system atrophy, Muscular dystrophy, Myalgic encephalomyelitis, Myasthenia gravis, Myelinoclastic diffuse sclerosis, Myoclonic Encephalopathy of infants, Myoclonus, Myopathy, Myotubular myopathy, Myotonia congenita, Narcolepsy, Neurofibromatosis, Neuroleptic malignant syndrome, Neurological manifestations of AIDS, Neurological sequelae of lupus, Neuromyotonia, Neuronal ceroid lipofuscinosis, Neuronal migration disorders, Niemann-Pick disease, Non 24-hour sleep-wake syndrome, Nonverbal learning disorder, O'Sullivan-McLeod syndrome, Occipital Neuralgia, Occult Spinal Dysraphism Sequence, Ohtahara syndrome, Olivopontocerebellar atrophy, Opsoclonus myoclonus syndrome, Optic neuritis, Orthostatic Hypotension, Overuse syndrome, Palinopsia, Paresthesia, Parkinson's disease, Paramyotonia Congenita, Paraneoplastic diseases, Paroxysmal attacks, Parry-Romberg syndrome (also known as Rombergs Syndrome), Pelizaeus-Merzbacher disease, Periodic Paralyses, Peripheral neuropathy, Persistent Vegetative State, Pervasive neurological disorders, Photic sneeze reflex, Phytanic Acid Storage disease, Pick's disease, Pinched Nerve, Pituitary Tumors, PMG, Polio, Polymicrogyria, Polymyositis, Porencephaly, Post-Polio syndrome, Postherpetic Neuralgia (PHN), Postinfectious Encephalomyelitis, Postural Hypotension, Prader-Willi syndrome, Primary Lateral Sclerosis, Prion diseases, Progressive Hemifacial Atrophy also known as Rombergs Syndrome, Progressive multifocal leukoencephalopathy, Progressive Sclerosing Poliodystrophy, Progressive Supranuclear Palsy, Pseudotumor cerebri, Ramsay-Hunt syndrome (Type I and Type II), Rasmussen's encephalitis, Reflex sympathetic dystrophy syndrome, Refsum disease, Repetitive motion disorders, Repetitive stress injury, Restless legs syndrome, Retrovirus-associated myelopathy, Rett syndrome, Reye's syndrome, Rombergs Syndrome, Rabies, Saint Vitus dance, Sandhoff disease, Schytsophrenia, Schilder's disease, Schizencephaly, Sensory Integration Dysfunction, Septo-optic dysplasia, Shaken baby syndrome, Shingles, Shy-Drager syndrome, Sjogren's syndrome, Sleep apnea, Sleeping sickness, Snatiation, Sotos syndrome, Spasticity, Spina bifida, Spinal cord injury, Spinal cord tumors, Spinal muscular atrophy, Spinal stenosis, Steele-Richardson-Olszewski syndrome, Progressive Supranuclear Palsy, Spinocerebellar ataxia, Stiff-person syndrome, Stroke, Sturge-Weber syndrome, Subacute sclerosing panencephalitis, Subcortical arteriosclerotic encephalopathy, Superficial siderosis, Sydenham's chorea, Syncope, Synesthesia, Syringomyelia, Tardive dyskinesia, Tay-Sachs disease, Temporal arteritis, Tethered spinal cord syndrome, Thomsen disease, Thoracic outlet syndrome, Tic Douloureux, Todd's paralysis, Tourette syndrome, Transient ischemic attack, Transmissible spongiform encephalopathies, Transverse myelitis, Traumatic brain injury, Tremor, Trigeminal neuralgia, Tropical spastic paraparesis, Trypanosomiasis, Tuberous sclerosis, Vasculitis including temporal arteritis, Von Hippel-Lindau disease (VHL), Viliuisk Encephalomyelitis (VE), Wallenberg's syndrome, Werdnig-Hoffman disease, West syndrome, Whiplash, Williams syndrome, Wilson's disease, X-Linked Spinal and Bulbar Muscular Atrophy, and Zellweger syndrome. Neurological conditions can comprise difficulty remembering recent events (short-term memory loss), for example Alzheimer's disease (AD).

Alzheimer's Disease

Alzheimer's disease (AD), also referred to simply as Alzheimer's, is a chronic neurodegenerative disease that usually starts slowly and worsens over time. It is the most common form of dementia in the world, accounting for about 60% to 70% of cases of dementia. It is an irreversible degenerative brain disease and a leading cause of mortality in the elderly. The hallmarks of the disease are deposition of extracellular β-amyloid (Aβ) plaques and intracellular neurofibrillary tangles, which result in declining memory, reasoning, judgment, and locomotion abilities, with symptoms worsening over time. The most common early symptom is difficulty in remembering recent events (short-term memory loss). As the disease advances, symptoms can include problems with language, disorientation (including easily getting lost), mood swings, loss of motivation, not managing self-care, and behavioral issues.

AD can be classified into two types based on the onset-age of the disease: familial AD (also known as early-onset AD) with an onset-age on or before 45, and late-onset AD where onset-age is on or after 65. Early-onset AD accounts for about 10% of all cases and tends to pre-dominate in certain families due to the inheritance of specific and rare missense mutations in for example APP, PSEN1 or PSEN2. Late-onset AD accounts for about 90% of all cases. Polymorphisms in APOE can be a risk factor for late-onset AD.

In some embodiments, IL33 variations can be a potential genetic risk factor based on genetic and transcriptomics studies. In some embodiments, protective single nucleotide polymorphism (SNP) sites in the IL33 region (SNP rs1157505, rs11792633 and rs7044343) can harbor protective effects against AD together with less cerebral amyloid angiopathy (CAA) in the brains of non-APOE ε4 AD cases. In a Chinese cohort, SNP sites, rs1157505, rs11792633 and rs7044343 were evaluated in Chinese Han or simply referred to as "Chinese" AD cohort and the T allele of the SNP rs11792633 can reduce the risk of AD in Chinese patients.

In some embodiments, individuals diagnosed with mild cognitive impairment (MCI) can have a higher serum level of soluble ST2 (sST2, the decoy receptor of IL33) compared with age-matched controls. In some embodiments, missense variants located within the IL1RL1 gene including SNPs rs6749114 (Q501K), rs4988956 (A433T), rs10204137 (Q501R), rs10192157 (T549I), rs10206753 (L551S), and rs1041973 (A78E) can be significantly associated with sST2 expression. In other embodiments, intracellular domain variants (A433T, T549I, Q501K, Q501R, and L551S) can be significantly associated with increased sST2 expression in different cell types.

APOE variants can be one of the most reliable genetic markers for late-onset AD. Table 3 lists APOE SNPs that can be associated with AD. Although several studies conducted in Caucasian and Asian populations have highlighted the existence of haplotype structure in the APOE locus, together with possible association with AD, cognitive performance and human longevity, the variant pools they identified are incomplete due to the limitation of detection technologies. Disclosed herein are methods, kits, and devices for re-evaluating the contributions of APOE locus for AD pathogenies in humans, and identification of several long-range haplotypes in APOE locus that commonly exist in the general population and are linked with the disease. In some embodiments, a human can be Asian. In other embodiments, the human can be East Asian, and in some cases, the human can be Chinese. The disclosed methods comprise the largest variant pools phased and reported (novel variants that are linked with AD were also identified) for providing impact on the stratification of individuals with potential disease risk for AD, and other neurological disorders.

TABLE 3

APOE SNPs that can be associated with AD.

| SNP | Sequence | SEQ ID No. |
| --- | --- | --- |
| rs404935 | ggagtgcagtgatgcgatctcggct[C/T]actgcaagctccgcctcctgggttc | 180 |
| rs395908 | ACAAGCCTCCCCACATCCTCCTGGC[C/T]GCCCTCCAAGCTGTTAGAATAGTGA | 181 |
| rs519113 | GGGTGGCCTCTCTGGGTAACATTAC[C/G]AGGTGTGAGTATAGGCAGTTTCTGG | 182 |
| rs34278513 | AGAAACACAATCCGGCCCCAAGGCA[C/T]GGAGCCAAAGAGGAAAAGCACAAAG | 183 |
| rs412776 | ATTTCCAGTTCGGTGTCTGTCTGGG[C/G/T]GGGTGGAGCTGACCCTCCCCTGGGT | 184 |
| rs3865427 | GGGGGTGTGGCCCCCAAGCTCATAG[A/C]TTTGTGAGGACCCCACAGCACATTC | 185 |
| rs11668861 | GCCCCCAAGCTCATAGCTTTGTGAG[G/T]ACCCCACAGCACATTCAGGGAGGGC | 186 |
| rs6859 | CTTGGGACTTGGAGGGAGGTGGAAC[A/G]GCACACTGGACTTCTCCCGTCTCTA | 187 |
| rs3852860 | GGTTTTTACCCGCGTCACCTCTGCT[C/T]TCCCAAGCCTCCATGCCTCCTCTGT | 188 |
| rs3852861 | GACCCAGTAAGGACATGCCCGTGAT[G/T]CCCTCATGCAGCCTCATTGACCTCC | 189 |
| rs71352237 | CCGTGATGCCCTCATGCAGCCTCAT[C/T]GACCTCCACAGACCCCACCAAGCCC | 190 |
| rs34224078 | GACCCCACCAAGCCCTGTGCCAGGC[A/G]GTGCTGGGGCTGCAGCTGTGGCCTG | 191 |
| rs35879138 | CAGTGCTGGGGCTGCAGCTGTGGCC[A/T]GCACAGACCCAGTGCCGTCCTCCGG | 192 |
| rs12972156 | tttgagacaggatctcactctgtcc[C/G]tcaggctagagttcagtggtataat | 193 |
| rs12972970 | cctagctagttttgtattttgta[A/G]agacagggttttgccatgttgccca | 194 |
| rs34342646 | ACAGGAACTTTAACCTAATTTGAGG[A/G]ACAGGAAGGCACTTCATTTATTCAT | 195 |
| rs283811 | atcccagcactttgggaggccgagg[C/T]gggcagatcacctgaggtcaggagt | 196 |
| rs283812 | tcaaattaaaaaaaaaaaaaaaaaa[A/G]aaagaaaGAAAGATCagccaggcgt | 197 |
| rs283815 | ctgggattacaggtgtgagccacca[C/T]gcctgaccAGATAATCAATTTTCAT | 198 |
| rs6857 | ATGAGGCTCACCCTGTCTGACCCTA[A/G]GCTGGGGCTGCTTGCTTGGTAGGCA | 199 |
| rs71352238 | GGAAGGGTGGGAGGGGCGCCGTGGC[C/T]ACCCTGCGAGTGAGAACCAATACAA | 200 |
| rs184017 | CCCGAGATCCAGGCCATCGCAGCCC[A/C]GCGGGGCCCCTCGCCCCTCACCCT | 201 |
| rs157580 | GTCACGGTGTCAGCAAGGTGTCAGC[A/G]AGGTTCCTTGGGTATGGGACCCAAA | 202 |
| rs2075650 | GAGATGAGAGTTGGTGTGGGGTTGG[A/G]GTGGAGTGTGACAGCGTTTCTCTTC | 203 |
| rs157581 | TAAGGACACCAGGAAGGCTCACCTG[A/G]AAATGGTTACTCAACCCTTTGTTGA | 204 |
| rs34404554 | ATCCAGAGGTACTGTCTCCCCATAG[C/G]AGCTAGGCTGGAGTGAAGGAACAGG | 205 |
| rs11556505 | CAATCGGGGAGTCCAACTACCACTT[C/T]GGGGTCACATATGTGGGACAAAGC | 206 |
| rs157582 | TTTGGCTACAAATTTGTTATTAGAA[A/G]GATACAATGAATGGATGAAAAAGGA | 207 |
| rs59007384 | GGGCAAAACTGGAGGCCCAGACAGG[G/T]TTGGGGGGACTGAATGAGGTCTCTG | 208 |
| rs405697 | CACCTACCTTTTAACAAGTGTTCCC[C/T]GGTAATGTGGAGGCCCACAGGGTGG | 209 |

TABLE 3-continued

APOE SNPs that can be associated with AD.

| SNP | Sequence | SEQ ID No. |
|---|---|---|
| rs10119 | CAGAATCCTGCGTGCCCCTCAATTC[C/T]GGAATCCCTCCCGGGACCCCAGGCC | 210 |
| rs405509 | AAGGGAGGACACCTCGCCCAGTAAT[A/C]CAGACACCCTCCTCCATTCTGGGGG | 211 |
| rs440446 | CTAGAAAGAGCTGGGACCCTGGGAA[C/G]CCCTGGCCTCCAGGTAGTCTCAGGA | 212 |
| rs769449 | ACCTCAACCTCCTGGCCCCATTCAG[A/G]CAGACCCTGGGCCCCCTCTTCTGAG | 213 |
| rs429358 | GCTGGGCGCGGACATGGAGGACGTG[C/T]GCGGCCGCCTGGTGCAGTACCGCGG | 214 |
| rs75627662 | TGGTGCCTTTATTCTAAGCTATTTT[C/T]ATTTTTTTTCTGCTGTCATTATTCT | 215 |
| rs439401 | CCCAGGAGCCGCCGGCACTCTCTTC[C/T]CCTCCCACCCCCTCAGTTCTCAGAG | 216 |
| rs10414043 | TCTGTCACCCAAGCTGGAGTGCAGT[A/G]GCACAATCTTGGCTCACTGCAACCT | 217 |
| rs7256200 | CTCCCAAAGTTCTGGGAATACAGGC[A/G/T]TGAGCCACTGCAACCAGCCAGTAGC | 218 |
| rs483082 | CCAGCTCAGAGCTTCCAGTCCCTGT[A/C]AGCCCCAGGGGCCCCCCTACTTCCC | 219 |
| rs584007 | AGGAGGGGCGTCAGAGGGTGAATAA[A/G]AGCAGATAGAGTGTTTGGGGGAGGT | 220 |
| rs438811 | CCACCACGCTCGGCTAATTTTTGAA[C/T]TTTTTTGTAGAGATGAGGTCTCCCT | 221 |
| rs5117 | CACCGTGGTCTCGATCTCCTGACTT[C/T]GTGATCCGCCTGCCTCGACCTCCCA | 222 |
| rs3826688 | ATTTTTggccgggcagggtggctca[C/T]gcctgtaatcccagcactttgggag | 223 |
| rs73052335 | ACTCTGTCTCAAAAAAAAAAAAAAA[A/C]AAAAAAAAAACAAGATGGTCTTGCC | 224 |
| rs12721046 | CCAAAAAGAAAAAAAACTCCTGGC[A/G]CGGTGGCTCACGCCAGTAATCCCAG | 225 |
| rs484195 | tctcgatctcctgacctggtgatcc[A/G]cccgcctcggcctcccaaagtgctg | 226 |
| rs12721051 | CGAACTCCTGACCTCAAGTGATCAG[C/G]CTACCTCGGCCTCCCAAAGTGTTGG | 227 |
| rs56131196 | TCCCATAAGGGCATTGAGGCCCAGA[A/G]AGGTGAAGTTACTTGTATAAGGTCA | 228 |
| rs4420638 | AATGTCACTATGCTACACTTTTCCT[A/G]GTGTGGTCTACCCGAGATGAGGGGC | 229 |
| rs157594 | gtgaggagcgcctcttcccggccgc[A/C]catcgtctgagatgtggggagcgcc | 230 |
| rs157595 | acctcctgggttcaagcgattctca[C/T]gcctcagcctactgagtagctggga | 231 |
| rs111789331 | GGTGGTGGGTGCCTGTAGTCTCAGC[A/T]ACTTGGGAGGCTGAGGCATGAGAAT | 232 |
| rs66626994 | ATTACAGGCCTGTGCCACCACACCC[A/G]GCTAATTTTTTCTATTTTTGACAGG | 233 |
| rs60049679 | TCTAGGGACACGGTGTGAATGAGGG[C/G]GGGATGAGATCACAGGGTTATTACT | 234 |
| rs4803766 | TGAGGAGTGATTGGAGGAGTGGACG[A/G]AGGTAGAAGGGAGCTGGGACGAGAG | 244 |

In some embodiments, SNP can be associated with AD are listed in Table 4.

TABLE 4

SNPs that can be associated with AD.

| SNP | Sequence | SEQ ID No. |
|---|---|---|
| rs4988956 | TCTTGTATGACTAGATGTAGTCACT[A/G]CAGTGGAAACCAACATACGAAAGAG | 235 |
| rs10204137 | GCTGAGGCGCTTCAGGACTCCCTCC[A/G]GCATCTTATGAAAGTACAGGGGACC | 236 |
| rs10192157 | ATTCCCAGAAAGGCCTCTAGTTTGA[C/T]TCCCTTGGCTGCCCAGAAGCAATAG | 237 |
| rs10206753 | AGAAAGGCCTCTAGTTTGACTCCCT[C/T]GGCTGCCCAGAAGCAATAGTGCCTG | 238 |
| rs3825610 | TGTTTTTTCTATAAAAATAAAAAAA[A/T]TTTAAAAAGAAACAAACATTAAAAA | 239 |

TABLE 4-continued

SNPs that can be associated with AD.

| SNP | Sequence | SEQ ID No. |
|---|---|---|
| rs507872 | ACTCCCAGAAGACCTAGCGCGCCAG[A/C/G]CAGGCACTTCCTTTTCTCTTTATCC | 240 |
| rs507905 | GACCTAGCGCGCCAGGCAGGCACTT[C/T]CTTTTCTCTTTATCCCCAACTTCCT | 241 |
| rs395908 | ACAAGCCTCCCCACATCCTCCTGGC[C/T]GCCCTCCAAGCTGTTAGAATAGTGA | 181 |
| rs283812 | tcaaattaaaaaaaaaaaaaaaaaa[A/G]aaagaaaGAAAGATCagccaggcgt | 197 |
| rs60049679 | TCTAGGGACACGGTGTGAATGAGGG[C/G]GGGATGAGATCACAGGGTTATTACT | 234 |
| rs525761 | TCAGAAACTCCCTTTCTAGCCGGGC[A/G]CGGTAGCTCACGCCTGTAATTTACA | 242 |

To date, most of the genetic studies including APOE locus have been conducted on individuals with Caucasian ancestry. Given the huge impact environmental factors may have had on humans throughout history, as well as the diversities in genomic content across different ethnic groups, the genetic risk factors for AD may be different between populations of Asian and Caucasian origins, e.g., Chinese and Caucasian populations.

Disclosed herein are methods, kits, and devices provide for whole-genome sequencing data obtained from a Chinese cohort with 2,909 subjects. The study identified eight loci including APOE and 7 novel loci, which can be associated with AD. In some cases, further investigations are performed to unravel the putative biological functions of those AD-risk loci, and to identify genes and metabolites that can be regulated by those loci. In some cases, a genetic risk score (GRS) can be designed for predicting the relative risks of having AD based on the genetic information from these genomic regions. In some cases, other biomarker information can be integrated for further optimization of such a system. Exemplary biomarker information include, but is not limited to, brain magnetic resonance imaging (MRI), proteomic data, and/or transcriptomic data from human subjects. Such a system can result in a superior performance compared to using single variants, for example (APOE, rs429358), alone for prediction of disease.

AD Diagnosis

While physicians can determine if a person has dementia, it can be difficult to determine the exact cause. Diagnosing Alzheimer's can require careful medical evaluation, including but not limited to, a thorough medical history, mental status and mood testing, a physical and neurological exam, blood tests and/or brain imaging to rule out other causes of dementia-like symptoms. In some cases, a subject suspected of AD can be assessed for behavioral and physical activities. The assessment can be performed by a healthcare professional including, but is not limited to, a physician, a medical doctor, a psychologist, a neurologist, a psychiatrist, a nurse, a nurse practitioner, and/or a professional who screens subjects for AD. Exemplary assessments for AD include evaluating a subject's motor skills, autonomic function, neuropsychiatry, mood, cognition, behavior, thoughts, ability of sense, past medical history, and/or a combination thereof. Evaluation can be performed by observation, a questionnaire, a checklist, a test, and/or a combination thereof.

Symptoms of AD may comprise wandering and getting lost, trouble handling money and paying bills, repeating questions, taking longer to complete normal daily tasks, losing things or misplacing them in odd places, personality and behavior changes, increased memory loss and confusion, problems recognizing family and friends, inability to learn new things, difficulty carrying out multistep tasks, problems coping with new situations, hallucinations, delusions, paranoia, impulsive behavior, inability to communicate, weight loss, seizures, skin infections, difficulty swallowing, groaning, moaning, grunting, increased sleeping, lack of control of bowel and bladder, or a combination thereof.

Additional testing can be performed to help confirm the diagnosis. The testing can comprise use of imaging techniques such as MRI, functional MRI (fMRI), position emission tomography (PET), fluorodeoxyglucose (FDG)-PET, computed tomography (CT), and/or ultrasound to evaluate the brain. The testing can comprise an evaluation of biomarkers in cell-free nucleic acid, (DNA or RNA). The testing can comprise an evaluation of biomarkers in cell-free DNA (cfDNA) obtained from blood, plasma, and/or bodily fluid, and/or a urine examination for odor signature of AD. Cell-free DNA can be circulating cell-free DNA.

In some embodiments, the methods disclosed herein can be used to monitor a neurological disorder such as AD. To monitor a neurological disorder, a method as disclosed herein can be repeated to assess a subject. Detection of genetic variations disclosed herein can be used in combination with one or more imaging techniques disclosed herein to detect a neurological disorder or a risk of developing a neurological disorder and/or susceptibility to a neurological disorder. In some embodiments, a detection of a genetic variation, e.g., a SNP, or a combination thereof, and abnormal in vivo imaging indicates AD.

A brain scan, using either computed tomography (CT) or magnetic resonance imaging (MRI), can be generally included in the standard evaluation for Alzheimer's disease and other forms of dementia. CT and MRI scans, which reveal the anatomic structure of the brain, can be used to rule out such problems as tumor, hemorrhage, stroke, and hydrocephalus, which can masquerade as Alzheimer's disease. These scans can also show the loss of brain mass associated with Alzheimer's disease and other dementias. In Alzheimer's disease, the region of the brain known as the hippocampus may be disproportionately atrophied.

Other brain scans may be performed if CT and MRI scans are inconclusive. Positron emission tomography (PET) and single-photon emission computed tomography provide images of brain activity based on blood flow, oxygen consumption, or glucose use. These techniques can help narrow down a diagnosis by revealing deficits common in Alzheimer's disease that are distinct from findings for other dementias, such as frontotemporal lobar degeneration and dementia with Lewy bodies. In some cases, Pittsburgh Compound-B (PiB PET) is used. PiB PET is a kind of PET scan that uses a chemical tracer that binds specifically to amyloid deposits in the brain, allowing them to show up clearly on the brain scans. These tests may help doctors and/or healthcare professionals diagnose the disease before symptoms appear, as well as assess new treatments.

MRI techniques can be used to measure brain atrophy and diagnose Alzheimer's disease with greater accuracy. Functional MRI (fMRI), which records blood flow changes linked to brain activity, may be used to distinguish among different forms of dementia.

An electroencephalogram (EEG) may be done to detect abnormal brain-wave activity. Although the EEG is usually normal in people with mild Alzheimer's disease and many other types of dementia, EEG abnormalities do occur in delirium and Creutzfeldt-Jakob disease, which is a cause of dementia.

AD Treatment

In some embodiments, medications may not cure Alzheimer's disease or stop it from progressing. In some embodiments, a medication or treatment disclosed herein may help lessen symptoms, such as memory loss, behavioral changes, and/or sleep changes, for a limited time. Treatment may include medications and/or non-drug approaches. In some embodiments, treatment can comprise administering one or more of donepezil, galantamine, rivastigmine, acetylcholinesterase inhibitor, Cognex (tacrine), Razadyne ER (galantamine), Aricept ODT (donepezil), Exelon (rivastigmine), Aricept (donepezil), Razadyne (galantamine), Namzaric (donepezil/memantine), glutamate receptor blocker, glutamate receptor agonist, glutamate receptor antagonist, N-methyl-D-aspartate (NMDA) receptor, memantine, citalopram, fluoxetine, paroxeine, sertraline, trazodone, lorazepam, oxazepam, aripiprazole, clozapine, haloperidol, olanzapine, quetiapine, risperidone, ziprasidone, nortriptyline, trazodone, tricyclic antidepressants, benzodiazepines, lorazepam, oxazepam, temazepam, zolpidem, zaleplon, chloral hydrate, risperidone, onlanzapine, quetiap, haloperidol, coenzyme Q10, ubiquinone, coral calcium, Ginkgo biloba, huperzine A, omega-3 fatty acids, phosphatidylserine, aminocyclopropanecarboxylic acid; D-Cycloserine, cis-2,3-Piperidinedicarboxylic acid, aspartic acid, glutamic acid, quinolinate, homocysteic acid, D-Serine, L-Serine, D-Alanine, L-Alanine, ACPL, Nebostinel, curcumin, 3,5-Dibromo-L-phenylalanine, apimostinel (NRX-1074), Rapastinel (GLYX-13), AP5, conantokins, dextromethorphan, dexanabinol, diethyl ether, dizocilpine (MK-801), ketamine, nitrous oxide, phencyclidine, xenon, methoxetamine, agmatine, 4-Chlorokynurenine (AV-101), 7-chlorokynurenic acid, amantadine, atomoxetine, dextropropoxyphene, ethanol, guaifenisen, huperzine A, ibogaine, ketobemidone, methadone tramadol, kynurenic acid, aminoglycosides, CDK5, polyamines, reelin, Src kinase, tianeptine, Na+, K+, Ca2+, Zn2+, Cu2+, Pb2, glutathione, lipoic acid, pyrroloquinoline quinone, or a combination thereof to a subject in need thereof.

Genetic Risk Score (GRS) and Pilot Study

Genetic risk score (GRS) can be an important measure for inherited disease risk. As the GRS of an individual can be typically based on the predisposing genotype he/she carries, it allows for measuring his/her individualized inherited risk. Furthermore, since genotype information of an individual generally does not change over time, it allows assessment of lifetime risk.

GRS can also be a more robust predictor of disease risk compared to other traditional methods (eg. family history). Thus, GRS can be vitally important for individuals who may not have access to family history data, while GRS can also be used to supplement an individual's family history to improve his/her risk prediction.

Furthermore, in some embodiments because of the way in which GRS may be calculated-based on the sum of predisposing genotypes that each individual carries, either unweighted or weighted by the effect size of the specific predisposing genotypes—it may be found to account for more genetic variance compared to risk prediction via family history alone.

In various embodiments, the model in the pilot study described herein can be classified into 4 parts: (1) selection of a variant pool for the construction of GRS score, (2) calculating the GRS, (3) quality control (QC) for the GRS, and (4) GRS for Alzheimer's disease prediction. Further description is provided below.

Selection of a Variant Pool for the Construction of GRS Score

Variant pool can be determined by using results from an association test (Fisher Exact test, Chi-square test or logistic regression test), and the most prominent sites can be selected (application of nominal p-value $<1\times10^{-7}$ as threshold yielded 44 sites in pilot study). Further expansion of variant pool can be favored to refine a model by adding more informative variants (additional sites may be included using pre-calculated LD (Linkage-disequilibrium) measurements ($r^2$ the pilot study) in the corresponding loci, with pairwise $r^2$ bigger or equal to 0.6 to the aforementioned 44 sites to include more sites).

Calculating the GRS

A logistic regression model can be applied for each variant to estimate the individual contributions for the disease risk, with the beta (slope) for each variant returned as weight for GRS calculation. Furthermore, individual genotypes can be obtained and recorded as −1, 0 and 1, which can denote the carrying of 0, 1 and 2 copies of effective alleles in consistent with the alleles for the calculation of beta, respectively. Dot product can be applied for the vector of beta values with genotype matrix in the matched order, to generate the GRS value for each individual.

Quality Control (QC) for GRS

Before carrying out the construction of prediction models, the effects, or the association between GRS and disease statues, can be assessed. During the pilot study, a histogram of the GRSs for different groups can be plotted, and further estimated the proportions of each group by fitting the data with mixture Gaussian models. The lambdas for each subcategory can be obtained, with corresponding means and standard deviations (e.g., the fitting results from the non-AD group and AD group, with 2 and 3 categories identifiable after selecting the number of clusters for fitting can be used). A Naïve Bayesian classifier can be used by using a fitted probability density functions, together with the population prior of AD set as 5% (e.g., based on the meta-study for the AD prevalence in China (Chan et al., 2013; Wu et al, 2013)). Subjects can be classified into categories by examining the three posterior probabilities for each individual so as to fit them into corresponding categories (e.g., individuals are classified into a certain category once the certain posterior probability exceeds the value of 0.5). In some embodiments, subjects can be classified into 1, 2, 3, 4, 5, 6, 7, 8, 9, 10 or more categories. The lambda can be updated according to prediction results. One may re-do the classification process until the lambdas converge. In some embodiments, lambda can converge within 1, 2, 3, 4, 5, 6, 7, 8, 9, 10 or more loops. Categories can be named for example as low, medium or high risk according to the mean GRS values from each group. In the pilot trial described herein, the statistical metrics for the GRS distribution after the classification can be: low risk group (GRS −70.23--39.82, mean=−53.68); medium risk group (GRS-39.75-18.03, mean=−19.76); high risk group (GRS 18.27-63.52, mean=31.66). In the pilot trial, further examination can be performed for the relative risks of having the disease (e.g., including MCI and AD) for individuals classified into medium and high risk groups by comparing the result with low risk groups using a 2 by 2 table with category test (e.g., Fisher Exact test or Chi-square test). The result can indicate that the GRS is associated with the pathogenies of both MCI and AD.

GRS for AD Prediction

The logistic regression model with GRS value and binary phenotypes of having the disease or not (e.g., 1 for yes and 0 for no) can be trained. Accordingly, the model can be added by using genotype dosage of APOE-ε4 variant (rs429358) alone as control to compare model performance. A random sampling process can be performed with the combination of different cut-offs to generate series of empirical metrics including sensitivity and specificity. The receiver operating characteristic (ROC) curve and the area under the curve (AUC) values can then be obtained for the model judgment and selection.

In various embodiments, thresholds for the classification of risk levels based on GRS can be determined. The thresholds can be adjustable in order to meet the requirement for sensitivity and specificity during application. The thresholds can be highly variable according to the training data. Thus, all parameters can be adaptive to the data features. Predictions for the risk of AD can be determined by the presence or absence of a combination of genetic variants, for example, at least 2, 3, 4, 5, 6, 7, 8, 9, 10, 15, 20, 50, 100, 200, 500, 1000, or more. In some cases, the number of genetic variants in a combination is less than 2, 3, 4, 5, 6, 7, 8, 9, 10, 15, 20, 50, 100, 200, 500, or 1000. In some cases, the number of genetic variants in a combination is between 2-1000, 3-500, 5-100, 10-50, 15-20, 2-8, or 1-3. Depending on the presence or absence of genetic variants in for example, Table 1 and/or Table 9, the risk of AD can be classified in a category. In some embodiments a category can be low risk, medium risk or high risk.

The sensitivity of determining a risk of AD can be controlled by the setting of the threshold for splitting the AD and NC (normal control) subjects. For a logistical regression model, a lower cut-off may classify more individuals into 'Predicted AD' and increase the sensitivity at the cost of reduction of specificity. Table 5 includes different thresholds with corresponding metrics for both sensitivities and specificities for AD classification. The sensitivity and specificity can be determined by the selection of cut-offs for the logistic regression models. In some embodiments, higher cut-off values can render more subjects to be classified as controls, namely, with a higher specificity while a lower sensitivity. In some embodiments, a proper cut-off can be selected in order to balance the sensitivity and specificity.

TABLE 5

Sensitivity and Specificity for the GRS prediction models

| Cut-off | Sensitivity-GRS | Specificity-GRS |
|---|---|---|
| 0 | 1 | 0 |
| 0.01 | 1 | 0 |
| 0.02 | 1 | 0 |
| 0.03 | 1 | 0 |
| 0.04 | 1 | 0 |
| 0.05 | 1 | 0 |
| 0.06 | 1 | 0 |
| 0.07 | 1 | 0 |
| 0.08 | 0.998 | 0.029 |
| 0.09 | 0.971 | 0.093 |
| 0.1 | 0.92 | 0.206 |
| 0.11 | 0.861 | 0.315 |
| 0.12 | 0.761 | 0.419 |
| 0.13 | 0.713 | 0.52 |
| 0.14 | 0.664 | 0.59 |
| 0.15 | 0.62 | 0.633 |
| 0.16 | 0.579 | 0.678 |
| 0.17 | 0.536 | 0.715 |
| 0.18 | 0.516 | 0.742 |
| 0.19 | 0.49 | 0.749 |
| 0.2 | 0.473 | 0.765 |
| 0.21 | 0.474 | 0.781 |
| 0.22 | 0.464 | 0.792 |
| 0.23 | 0.44 | 0.792 |
| 0.24 | 0.425 | 0.805 |
| 0.25 | 0.4 | 0.81 |
| 0.26 | 0.388 | 0.823 |
| 0.27 | 0.38 | 0.837 |
| 0.28 | 0.373 | 0.854 |
| 0.29 | 0.344 | 0.862 |
| 0.3 | 0.311 | 0.876 |
| 0.31 | 0.293 | 0.889 |
| 0.32 | 0.279 | 0.896 |
| 0.33 | 0.249 | 0.912 |
| 0.34 | 0.231 | 0.921 |
| 0.35 | 0.21 | 0.923 |
| 0.36 | 0.188 | 0.934 |
| 0.37 | 0.17 | 0.953 |
| 0.38 | 0.158 | 0.959 |
| 0.39 | 0.153 | 0.964 |
| 0.4 | 0.14 | 0.966 |
| 0.41 | 0.132 | 0.966 |
| 0.42 | 0.128 | 0.968 |
| 0.43 | 0.119 | 0.977 |
| 0.44 | 0.109 | 0.98 |
| 0.45 | 0.105 | 0.98 |
| 0.46 | 0.103 | 0.98 |
| 0.47 | 0.1 | 0.98 |
| 0.48 | 0.099 | 0.979 |
| 0.49 | 0.092 | 0.98 |
| 0.51 | 0.086 | 0.982 |
| 0.52 | 0.08 | 0.982 |
| 0.53 | 0.076 | 0.982 |
| 0.54 | 0.071 | 0.984 |
| 0.55 | 0.069 | 0.984 |
| 0.56 | 0.065 | 0.984 |
| 0.57 | 0.065 | 0.984 |
| 0.58 | 0.061 | 0.987 |
| 0.59 | 0.054 | 0.986 |
| 0.6 | 0.05 | 0.986 |
| 0.61 | 0.046 | 0.989 |
| 0.62 | 0.038 | 0.989 |
| 0.63 | 0.032 | 0.989 |
| 0.64 | 0.025 | 0.989 |
| 0.65 | 0.023 | 0.993 |
| 0.66 | 0.019 | 0.993 |
| 0.67 | 0.013 | 0.995 |
| 0.68 | 0.01 | 0.995 |
| 0.69 | 0.008 | 0.995 |
| 0.7 | 0.008 | 0.995 |
| 0.71 | 0.006 | 0.998 |
| 0.72 | 0.006 | 1 |
| 0.73 | 0.004 | 1 |
| 0.74 | 0.004 | 1 |
| 0.75 | 0.002 | 1 |
| 0.76 | 0.002 | 1 |

TABLE 5-continued

Sensitivity and Specificity for the GRS prediction models

| Cut-off | Sensitivity-GRS | Specificity-GRS |
|---|---|---|
| 0.77 | 0 | 1 |
| 0.78 | 0 | 1 |
| 0.79 | 0 | 1 |
| 0.8 | 0 | 1 |
| 0.81 | 0 | 1 |
| 0.82 | 0 | 1 |
| 0.83 | 0 | 1 |
| 0.84 | 0 | 1 |
| 0.85 | 0 | 1 |
| 0.86 | 0 | 1 |
| 0.87 | 0 | 1 |
| 0.88 | 0 | 1 |
| 0.89 | 0 | 1 |
| 0.9 | 0 | 1 |
| 0.91 | 0 | 1 |
| 0.92 | 0 | 1 |
| 0.93 | 0 | 1 |
| 0.94 | 0 | 1 |
| 0.95 | 0 | 1 |
| 0.96 | 0 | 1 |
| 0.97 | 0 | 1 |
| 0.98 | 0 | 1 |
| 0.99 | 0 | 1 |
| 1 | 0 | 1 |

In addition to the genetic variants, the methods disclosed herein can use clinical information of the subject, to assess a risk of AD. Examples of clinical information in the datasets can include one or more of the following information regarding the one or more subjects: age, gender, education level, cognitive performance score, such as the Mini Mental State Exam (MMSE) score, Montreal Congnitive Assessment (MoCA) score, smoking habits, whether the subjects have diabetes, hypertension, or abnormal cholesterol levels, whether the subjects have a family history of AD, dementia, abnormal cholesterol levels, stroke, cerebral infarction, diabetes, hypertension. For instance, presence of smoking can be positively correlated with AD; strong correlation between cholesterol abnormalies and AD can also be seen in some subjects; and suggestive trends of association can be seen between AD and one or both of diabetes and hypertension. In case of smoking, there can be seen in some subjects, a positive correlation between the number of years the subject has been a smoker and the risk of AD. For instance, smoking in young adults, aged from about 17 years to about 21 years, in youg to middle aged adults, aged from about 25 years to about 60 years, and in elders, aged 60 or higher, can in some examples be associated with increased risk of AD. A subject with increased risk of AD can have a genetic variation as described above and be a smoker for a number of years, such as for 5-10 years, 10-15 years, 15-20 years, 20-25 years, 30-35 years, or longer. In some cases, the subject with positive correlation between smoking and risk of AD can be of East Asian ethnicity. In yet other examples, a subject can have a reduced risk of AD based on a genetic variation as described above and the number of years the subject has been a smoker, for example, 5-10 years, 10-15 years, 15-20 years, 20-25 years, 30-35 years, or longer. In certain instances, negative correlation can be seen between number of years a subject has lived with cholesterol abnormalities and the risk of AD. Similar negative correlations can be seen, in some subjects, when associating number of years a subject has been suffering from diabetes, hypertension, or both, and the risk of AD. In some examples, a subject may have lived for about 10-15 years with cholesterol abnormalities, diabetes, hypertension, or any combination of the three conditions, and said subject can be assessed to have reduced risk of AD. When gender information is used by the methods disclosed herein, in some cases it can be observed that a female subject can have a higher risk of AD than a male subject. Suggestive disease indicators, such as MMSE and MoCA scores, can be used in some cases to assess the risk of AD and typically a subject with AD or high risk of AD can have a lower MMSE score, or lower MoCA score, or both. In some cases, a subject can be assessed to have a high risk of AD based on a MMSE score lower than 30, for example, 23 or lower, 22 or lower, 21 or lower, 20 or lower, 19 or lower, 18 or lower, 17 or lower, 16 or lower, 15 or lower, 14 or lower, 13 or lower, 12 or lower, 11 or lower, 10 or lower, 9 or lower, 8 or lower, 7 or lower, 6 or lower, 5 or lower, 4 or lower, 3 or lower, 2 or lower, 1, or 0. In some cases, a subject can be assessed to have a high risk of AD based on a MoCA score lower than 30, for example, 26 or lower, 25 or lower, 24 or lower, 23 or lower, 22 or lower, 21 or lower, 20 or lower, 19 or lower, 18 or lower, 17 or lower, 16 or lower, 15 or lower, 14 or lower, 13 or lower, 12 or lower, 11 or lower, 10 or lower, 9 or lower, 8 or lower, 7 or lower, 6 or lower, 5 or lower, 4 or lower, 3 or lower, 2 or lower, 1, or 0. Family history of the subjects can also be used to assess the risk of AD. A family history of AD can be a risk factor for AD. The method disclosed herein can use additional family history information, such as dementia, abnormal cholesterol levels, stroke, cerebral infarction, diabetes, hypertension, or any combination thereof, to assess a risk of AD. Thus, in some examples, methods disclosed herein can be used to assess a risk of AD based on genetic variation in combination with a clinical information as described above.

Subject

A subject, can be an individual of any age or sex from whom a sample can be obtained. A subject can include for example, a male or female adult, child, newborn, or fetus. A subject can be of any ethnicity. A subject can be Asian, East Asian, Chinese, Caucasian, Hispanic, African, or combinations thereof. In some embodiments, a subject can be a target of therapeutic administration. In some embodiments, a subject can be a test subject or a reference subject. In some embodiments, a subject can be associated with a condition or disease or disorder, asymptomatic or symptomatic, have increased or decreased susceptibility to a disease or disorder, be associated or unassociated with a treatment or treatment regimen, or any combination thereof. As used in the present disclosure a cohort can represent an ethnic group, a patient group, a particular age group, a group not associated with a particular disease or disorder, a group associated with a particular disease or disorder, a group of asymptomatic subjects, a group of symptomatic subjects, or a group or subgroup of subjects associated with a particular response to a treatment regimen or clinical trial. In some embodiments, a patient can be a subject afflicted with a disease or disorder. In some embodiments, a patient can be a subject not afflicted with a disease or disorder. In some embodiments, a subject can be a test subject, a patient or a candidate for a therapeutic, wherein a sample from the subject, patient, or candidate is obtained for analysis by one or more methods of the present disclosure. In some embodiments, a sample can be obtained prenatally from a fetus or embryo or from the mother, for example, from fetal or embryonic cells in the maternal circulation.

The present disclosure also provides methods for assessing genetic variations in subjects who are members of a target population. Such a target population is in some embodiments a population or group of subjects at risk of developing the disease, based on, for example, other genetic factors, biomarkers, biophysical parameters, family history of a neurological disorder, previous screening or medical history, or any combination thereof.

Although AD is known to affect older adults more frequently than children, subjects of all ages are contemplated in the present disclosure. In some embodiments subjects can be from specific age subgroups, such as those over the age of 1, over the age of 2, over the age of 3, over the age of 4, over the age of 5, over the age of 6, over the age of 7, over the age of 8, over the age of 9, over the age of 10, over the age of 15, over the age of 20, over the age of 25, over the age of 30, over the age of 35, over the age of 40, over the age of 45, over the age of 50, over the age of 55, over the age of 60, over the age of 65, over the age of 70, over the age of 75, over the age of 80, or over the age of 85. Other embodiments of the disclosure pertain to other age groups, such as subjects aged less than 85, such as less than age 80, less than age 75, less than age 70, less than age 65, less than age 60, less than age 55, less than age 50, less than age 45, less than age 40, less than age 35, less than age 30, less than age 25, less than age 20, less than age 15, less than age 10, less than age 9, less than age 8, less than age 6, less than age 5, less than age 4, less than age 3, less than age 2, or less than age 1. Other embodiments relate to subjects with age at onset of the disease in any of particular age or age ranges defined by the numerical values described in the above or other numerical values bridging these numbers. It is also contemplated that a range of ages can be relevant in certain embodiments, such as age at onset at more than age 15 but less than age 120. Other age ranges are however also contemplated, including all age ranges bracketed by the age values listed in the above.

Genetic variations of the present disclosure can identify an association in human populations. Particular embodiments comprising subject human populations are thus also contemplated and within the scope of the disclosure. Such embodiments relate to human subjects that are from one or more human populations including, but not limited to, Caucasian, European, American, Eurasian, Asian, Central/South Asian, East Asian, Middle Eastern, African, Hispanic, and Oceanic populations. European populations include, but are not limited to, Swedish, Norwegian, Finnish, Russian, Danish, Icelandic, Irish, Kelt, English, Scottish, Dutch, Belgian, French, German, Spanish, Portuguese, Italian, Polish, Bulgarian, Slavic, Serbian, Bosnian, Czech, Greek and Turkish populations. The racial contribution in subjects can also be determined by genetic analysis, for example, genetic analysis of ancestry can be carried out using unlinked microsatellite markers such as those set out in Smith et al. (Am J Hum Genet 74, 1001-13 (2004)).

It is also well known to the person skilled in the art that certain genetic variations have different population frequencies in different populations, or are polymorphic in one population but not in another. A person skilled in the art can however apply the methods available and as taught herein to practice the present disclosure in any given human population. This can include assessment of genetic variations of the present disclosure, so as to identify those markers that give the strongest association within the specific population. Thus, the at-risk variants of the present disclosure can reside on different haplotype background and in different frequencies in various human populations.

Samples

Samples that are suitable for use in the methods, systems, devices, and kits described herein can be samples from a subject. A sample can be a mammalian tissue or derived therefrom. A sample can be a human tissue or derived therefrom, for example brain tissue (e.g. SN, cortex, brainstem), cells derived from brain meninges, cells derived from human skin fibroblasts. A sample can be a biological sample. A sample can comprise a nucleic acid. In some cases, a nucleic acid can comprise genomic DNA, DNA, circulating mitochondrial DNA, cell-free DNA (cfDNA), circulating cell-free DNA, RNA, polypeptides, or a combination thereof. Nucleic acids and polypeptides can be extracted from one or more samples including but not limited to, blood, saliva, urine, mucosal scrapings of the lining of the mouth, expectorant, blood, plasma, whole blood, saliva, urine, serum, tears, skin, tissue, semen, biopsy, liquid biopsy, cell-free DNA, cell-free RNA, circulating cell-free DNA, circulating cell-free RNA, circulating mitochondrial DNA, cerebrospinal fluid, amniotic fluid, bodily fluid, cervical vaginal fluid and/or tissues, hair, or a combination thereof. A sample can be assayed for nucleic acid information. "Nucleic acid information," can include a nucleic acid sequence itself, the presence/absence of genetic variation in the nucleic acid sequence, a physical property which varies depending on the nucleic acid sequence (for example, Tm), and the amount of the nucleic acid (for example, number of mRNA copies). A "nucleic acid" can be any one of DNA, RNA, DNA including artificial nucleotides, or RNA including artificial nucleotides. A "recombinant" nucleic acid molecule can include a nucleic acid molecule made by an artificial combination of two otherwise separated segments of sequence, e.g., by chemical synthesis or by the manipulation of isolated segments of nucleic acids by genetic engineering techniques. A "polypeptide" can include proteins, fragments of proteins, and peptides, whether isolated from natural sources, produced by recombinant techniques, or chemically synthesized. A polypeptide may have one or more modifications, such as a post-translational modification (e.g., glycosylation, etc.) or any other modification (e.g., pegylation, etc.). The polypeptide may contain one or more non-naturally-occurring amino acids (e.g., such as an amino acid with a side chain modification).

A sample can be processed for RNA or DNA isolation, for example, RNA or DNA in a cell or tissue sample can be separated from other components of the nucleic acid sample. Cells can be harvested from a nucleic acid sample using standard techniques known in the art, for example, by centrifuging a cell sample and resuspending the pelleted cells, for example, in a buffered solution, for example, phosphate-buffered saline (PBS). In some cases, after centrifuging the cell suspension to obtain a cell pellet, the cells can be lysed to extract DNA. In some cases, the sample can be concentrated and/or purified to isolate DNA. All samples obtained from a subject, including those subjected to any sort of further processing, are considered to be obtained from the subject. In some cases, standard techniques and kits known in the art can be used to extract RNA or DNA from a sample, including, for example, phenol extraction, a QIAamp® Tissue Kit (Qiagen, Chatsworth, Calif.), a Wizard® Genomic DNA purification kit (Promega), or a Qiagen Autopure method using Puregene chemistry, which can enable purification of highly stable DNA well-suited for archiving.

Determining the identity of an allele or determining copy number can, but need not, include obtaining a sample comprising RNA and/or DNA from a subject, and/or assessing the identity, copy number, presence or absence of one or more genetic variations and their chromosomal locations in the nucleic acid sample. The individual or organization that performs the determination need not actually carry out the physical analysis of a sample from a subject. In some cases, the methods can include using information obtained by analysis of sample by a third party. In some cases, the methods can include steps that occur at more than one site. For example, a sample can be obtained from a subject at a first site, such as at a health care provider or at the subject's home in the case of a self-testing kit. The sample can be analyzed at the same or a second site, for example, at a laboratory or other testing facility.

Methods of Screening

As used herein, "screening" a subject can include diagnosing, theranosing, or determining the susceptibility to developing (prognosing) a neurological disorder, for example, AD. In particular embodiments, the disclosure is a method of determining a presence of, or a susceptibility to, a neurological disorder, by detecting at least one genetic variation in a nucleic acid sample from a subject as described herein. Detection of particular alleles, markers, variations, or haplotypes is indicative of a presence or susceptibility to a neurological disorder.

Particular genetic variations are found more frequently in individuals with a neurological disorder, than in individuals without screening of a neurological disorder. Therefore, these genetic variations can have predictive value for detecting a neurological disorder, or a susceptibility to a neurological disorder, in an individual. Without intending to be limited, the genetic variations described herein can be associated with susceptibility of a neurological disorder and can represent functional variants predisposing to the disease. A genetic variation can confer a susceptibility of the condition, for example, carriers of the genetic variation are at a different risk of the condition than non-carriers. The presence of a genetic variation can be indicative of increased susceptibility to a neurological disorder, such as AD. The presence of a genetic variation can be indicative of having a neurological disorder, such as AD.

Screening can be performed using any of the methods disclosed, alone or in combination. Screening can be performed using Polymerase Chain Reaction (PCR). Screening can be performed using Array Comparative Genomic Hybridization (aCGH). The genetic variation information as it relates to the current disclosure can be used in conjunction with any mentioned symptomatic screening tests to screen a subject for AD, for example, using a combination of aCGH and different PET radiotracers.

Screening can comprise performing one or more of techniques including polymerase chain reaction (PCR), genome-wide association study, mass spectrometry, Taqman probe, allele specific PCR, next generation sequencing, third generation sequencing, sequencing, long-read sequencing, high-throughput sequencing, electrophoresis at single base resolution, genotyping array, microarray, northern blot, immunohistochemistry, or any combination thereof. In some embodiments, screening comprises at least one high throughput sequencing method such as Massively Parallel Signature Sequencing (MPSS), polony sequencing, 454 pyrosequencing, Illumina sequencing, SOLiD sequencing, ion semiconductor sequencing, DNA nanoball sequencing, heliscope single molecule sequencing, single molecule real time (SMRT) sequencing, RNAP sequencing, Nanopore DNA sequencing, sequencing by hybridization, and/or microfluidic Sanger sequencing.

An association with a neurological disorder can be determined by the statistical likelihood of the presence of a genetic variation in a subject with a neurological disorder, for example, an unrelated individual or a first or second-degree relation of the subject. An association with a neurological disorder can be determined by determining the statistical likelihood of the absence of a genetic variation in an unaffected reference subject, for example, an unrelated individual or a first or second-degree relation of the subject. The methods described herein can include obtaining and analyzing a nucleic acid sample from one or more suitable reference subjects.

In the present context, the term screening or assessing can comprise detecting and/or analyzing. The term screening or assessing can comprise prognosis and/or theranosis. Screening can refer to any available screening method, including those mentioned herein. As used herein, susceptibility can be proneness of a subject towards the development of a neurological condition, or towards being less able to resist a particular neurological condition than one or more control subjects. Susceptibility can encompass increased susceptibility. For example, particular nucleic acid variations of the disclosure as described herein can be characteristic of increased susceptibility to development of a neurological disorder. Susceptibility can encompass decreased susceptibility, for example, particular nucleic variations of the disclosure as described herein can be characteristic of decreased susceptibility to development of a neurological disorder.

In some cases, a presence of a genetic variant or SNP such as one or more set forth in Table 1, Table 3, Table 4, and/or Table 7 can increase susceptibility to development of a neurological disorder. In other cases, the presence of a genetic variant or SNP such as one or more set forth in Table 1, Table 3, Table 4, and/or Table 7 can decrease susceptibility to development of a neurological disorder. In some cases, the presence of a genetic variant or SNP such as rs12339504, rs11603664, rs72713460, rs12442709, rs12606254, rs4806915, rs73052335, rs2836293, rs2591054, rs928771 can increase susceptibility to development of a neurological disorder. In other cases, the presence of a genetic variant or SNP such as rs12339504, rs11603664, rs72713460, rs12442709, rs12606254, rs4806915, rs73052335, rs2591054, rs928771, or rs2836293 can decrease susceptibility to development of a neurological disorder. In various cases, the presence of a genetic variant or SNP such as rs12339504, rs11603664, rs72713460, rs12442709, rs12606254, rs4806915, rs73052335, rs2836293, rs2591054, rs928771 can increase or decrease susceptibility to development of a neurological disorder by at least 1%, 5%, 10%, 15%, 20%, 30%, 40%, 50%, 60%, 70%, 80%, 90%, 95%, 99%, or more. In various cases, the presence of a genetic variant or SNP such as rs12339504, rs11603664, rs72713460, rs12442709, rs12606254, rs4806915, rs73052335, rs2836293, rs2591054, rs928771 can increase or decrease susceptibility to development of a neurological disorder by at most 1%, 5%, 10%, 15%, 20%, 30%, 40%, 50%, 60%, 70%, 80%, 90%, 95%, 99%. In various cases, the presence of a genetic variant or SNP such as rs12339504, rs11603664, rs72713460, rs12442709, rs12606254, rs4806915, rs73052335, rs2836293, rs2591054, rs928771 can increase or decrease susceptibility to development of a neurological disorder by between about 1% and 100%, 5% and 90%, 10% and 80%, 20% and 70%, 30% and 60%, 40% and 50%, 5% and 30%, 10% and 40%, 20% and 60%, or 30% and 50%. In various cases, the presence of a genetic variant or SNP such as rs12339504, rs11603664, rs72713460, rs12442709, rs12606254, rs4806915, rs73052335, rs2836293, rs2591054, rs928771 can increase or decrease susceptibility to development of a neurological disorder in Asian, Caucasian, Hispanic, African, and/or a combination thereof. In some cases, they can increase or decrease susceptibility to development of a neurological disorder in Asian, Caucasian, Hispanic, African, and/or a combination thereof can be opposite. For example, the presence of a genetic variant or SNP such as rs12339504, rs11603664, rs72713460, rs12442709, rs12606254, rs4806915, rs73052335, rs2591054, rs928771, or rs2836293 can increase susceptibility to development of a neurological disorder in Asian, while its presence can decrease susceptibility to development of a neurological disorder in Caucasian.

In some embodiments, the presence of a combination of a genetic variant or SNP can be indicative of a risk of AD. The genetic variant can be one or more of genetic variants in Table 1. The genetic variant can be one or more of genetic variants selected from rs12339504, rs11603664, rs72713460, rs12442709, rs12606254, rs4806915, rs73052335, rs2591054, rs928771, and rs2836293. For example, the combination can comprise 2, 3, 4, 5, 6, 7, 8, 9, 10, 11, 12, 13, 14, 15, 15, 17, 18, 19, 20, 25, 30, 35, 40, 45, 50, 75, 100, 150, 200 or more genetic variants. The combination can comprise from about 1-1000, 2-500, 5-100, 10-50, 15-20, 2-8, or 1-3 genetic variants or SNPs.

As described herein, a genetic variation predictive of susceptibility to or presence of a neurological disorder can be one where the particular genetic variation is more frequently present in a subject with the condition (affected), compared to the frequency of its presence in a reference group (control), such that the presence of the genetic variation is indicative of susceptibility to or presence of the neurological disorder. The reference group can be a population sample, for example, a random sample from the general population or a mixture of two or more samples from a population. In one aspect, disease-free controls can be characterized by the absence of one or more specific disease-associated symptoms or genetic variation, for example, individuals who have not experienced symptoms associated with a neurological disorder. The disease-free control group is characterized by the absence of one or more disease-specific risk factors, for example, at least one genetic and/or environmental risk factor. A reference sequence can be referred to for a particular site of genetic variation. A reference allele can be a wild-type allele and can be chosen as either the first sequenced allele or as the allele from a control individual. One or more reference subjects can be characteristically matched with one or more affected subjects, for example, with matched aged, gender or ethnicity.

The disclosure presents a method of screening a subject for a disease or disorder comprising assaying a nucleic acid sample from the subject to detect sequence information for more than one genetic locus and comparing the sequence information to a panel of nucleic acid biomarkers and screening the subject for the presence or absence of the disease or disorder if one or more of low frequency biomarkers in the panel are present in the sequence information.

A panel can comprise at least one nucleic acid biomarker for each of the more than one genetic loci. In some embodiments, a presence or absence of a biomarker can indicate a presence or absence of a genetic variation. In some embodiments, increase expression or increase level of a biomarker can indicate a presence or absence of a genetic variation. In some embodiments, a decrease expression or decrease level of a biomarker can indicate a presence or absence of a genetic variation. The biomarkers can be one or more of biomarkers in Table 8 and/or Table 9. A biomarker can be a target gene or a metabolite. For example, the panel can comprise 2, 3, 4, 5, 6, 7, 8, 9, 10, 11, 12, 13, 14, 15, 15, 17, 18, 19, 20, 25, 30, 35, 40, 45, 50, 75, 100, 150, 200 or more nucleic acid biomarkers in Table 8 and/or Table 9 for each of the more than one genetic loci. The panel can comprise from about 1-1000, 2-500, 5-100, 10-50, 15-20, 2-8, or 1-3 nucleic acid biomarkers.

A panel can comprise at least one polypeptide biomarker for each of the more than one genetic loci. Biomarkers can be one or more biomarkers in Table 8 and/or Table 9. For example, a panel can comprise 2, 3, 4, 5, 6, 7, 8, 9, 10, 11, 12, 13, 14, 15, 15, 17, 18, 19, 20, 25, 30, 35, 40, 45, 50, 75, 100, 150, 200 or more polypeptide biomarkers in Table 8 and/or Table 9 for each of the more than one genetic loci. The panel can comprise from about 1-1000, 2-500, 5-100, 10-50, 15-20, 2-8, or 1-3 polypeptide biomarkers.

A panel can comprise at least 2 low frequency biomarkers in Table 8 and/or Table 9. For example, a panel can comprise at least 2, 3, 4, 5, 6, 7, 8, 9, 10, 11, 12, 13, 14, 15, 15, 17, 18, 19, 20, 25, 30, 35, 40, 45, 50, 55, 60, 65, 70, 75, 80, 85, 90, 95, 100, 125, 150, 175, 200, 250, 500, or 1000 or more low frequency biomarkers. A panel can comprise from about 2-1000 low frequency biomarkers. A low frequency biomarker can occur at a frequency of 0.1% or less in a population of subjects without a diagnosis of the disease or disorder. For example, a low frequency biomarker can occur at a frequency of 0.05%, 0.01%, 0.005%, 0.001%, 0.0005%, 0.0001%, 0.00005%, or 0.00001% or less in a population of subjects without a diagnosis of the disease or disorder. A low frequency biomarker can occur at a frequency from about 0.00001%-0.1% in a population of subjects without a diagnosis of the disease or disorder. For example, a low frequency biomarker can occur at a frequency of from about 0.00001%-0.00005%, 0.00001%-0.0001%, 0.00001%-0.0005%, 0.00001%-0.001%, 0.00001%-0.005%, 0.00001%-0.01%, 0.00001%-0.05%, 0.00005%-0.0001%, 0.00005%-0.0005%, 0.00005%-0.001%, 0.00005%-0.005%, 0.00005%-0.01%, 0.00005%-0.05%, 0.00005%-0.1%, 0.0001%-0.0005%, 0.0001%-0.001%, 0.0001%-0.005%, 0.0001%-0.01%, 0.0001%-0.05%, 0.0001%-0.1%, 0.0005%-0.001%, 0.0005%-0.005%, 0.0005%-0.01%, 0.0005%-0.05%, 0.0005%-0.1%, 0.001%-0.005%, 0.001%-0.01%, 0.001%-0.05%, 0.001%-0.1%, 0.005%-0.01%, 0.005%-0.05%, 0.005%-0.1%, 0.01%-0.05%, 0.01%-0.1%, or 0.05%-0.1% in a population of subjects without a diagnosis of the disease or disorder.

The presence or absence of a disease or disorder in a subject can be determined with at least 50% confidence. For example, a presence or absence of the disease or disorder in the subject can be determined with at least 50%, 55%, 60%, 65%, 70%, 75%, 80%, 85%, 90%, 95%, 98%, 99%, or 100% confidence. In one aspect, a presence or absence of a disease or disorder in a subject can be determined with a 50%-100% confidence.

The present disclosure also pertains to methods of clinical screening, for example, diagnosis, prognosis, or theranosis of a subject performed by a medical professional using the methods disclosed herein. In other embodiments, the disclosure pertains to methods of screening performed by a layman. The layman can be a customer of a genotyping service. The layman can also be a genotype service provider, who performs genotype analysis on a nucleic acid sample from an individual, in order to provide service related to genetic risk factors for particular traits or diseases, based on the genotype status of the subject obtained from use of the methods described herein. The resulting genotype information can be made available to the individual and can be compared to information about neurological disorder or risk of developing a neurological disorder associated with various genetic variations, including but not limited to, information from public literature and scientific publications. The screening applications of neurological disorder-associated genetic variations, as described herein, can, for example, be performed by an individual, a health professional, or a third party, for example, a service provider who interprets genotype information from the subject.

The information derived from analyzing sequence data (for example nucleic acid sequence) can be communicated to any particular body, including the individual from which the sample or sequence data is derived, a guardian or representative of the individual, clinician, research professional, medical professional, service provider, and medical insurer or insurance company. Medical professionals can be, for example, doctors, nurses, medical laboratory technologists, and pharmacists. Research professionals can be, for example, principle investigators, research technicians, post-doctoral trainees, and graduate students.

A professional can be assisted by determining whether specific genetic variants are present in a sample from a subject, and communicating information about genetic variants to a professional. After information about specific genetic variants is reported, a medical or a healthcare professional can take one or more actions that can affect subject care. For example, a medical or a healthcare professional can record information in the subject's medical record regarding the subject's risk of developing a neurological disorder. In one aspect, a medical or a healthcare professional can record information regarding risk assessment, or otherwise transform the subject's medical record, to reflect the subject's current medical condition. In one aspect, a medical or a healthcare professional can review and evaluate a subject's entire medical record and assess multiple treatment strategies for clinical intervention of a subject's condition.

A medical or a healthcare professional can initiate or modify treatment after receiving information regarding a subject's screening of a neurological disorder, for example. A medical or a healthcare professional can recommend a change in therapy. A medical or a healthcare professional can enroll a subject in a clinical trial based on a genetic variation. A subject can be enrolled or not be enrolled in a clinical trial based on a genetic variation.

A medical or a healthcare professional can communicate information regarding a subject's screening of developing a neurological disorder to a subject or a subject's family. A medical or a healthcare professional can provide a subject and/or a subject's family with information regarding a neurological disorder and risk assessment information, including treatment options, and referrals to specialists. A medical or a healthcare professional can provide a copy of a subject's medical records to a specialist. In one aspect, a research professional can apply information regarding a subject's risk of developing a neurological disorder to advance scientific research. In one aspect, a research professional can evaluate a subject's enrollment, or continued participation, in a research study or clinical trial. In one aspect, a research professional can communicate information regarding a subject's screening of a neurological disorder to a medical or a healthcare professional. In one aspect, a research professional can refer a subject to a medical or a healthcare professional.

Also provided herein are databases that include a list of genetic variations as described herein. The list can be stored, for example, on a flat file or computer-readable medium. The databases can further include information regarding one or more subjects, for example, whether a subject is affected or unaffected, clinical information such as endophenotype, age of onset of symptoms, any treatments administered and outcomes, for example, data relevant to pharmacogenomics, diagnostics, prognostics or theranostics, and other details, for example, data about the disorder in the subject, or environmental or other genetic factors. Further examples of clinical information in the datasets can include one or more of the following information regarding the one or more subjects: age, gender, education level, cognitive performance score, such as the Mini Mental State Exam (MMSE) score, Montreal Congnitive Assessment (MoCA) score, smoking habits, whether the subjects have diabetes, hypertension, or abnormal cholesterol levels, whether the subjects have a family history of AD, dementia, abnormal cholesterol levels, stroke, cerebral infarction, diabetes, hypertension.

The methods described herein can also include the generation of reports for use, for example, by a subject, care giver, or researcher, that include information regarding a subject's genetic variations, and optionally further information such as treatments administered, treatment history, medical history, predicted response, and actual response. The reports can be recorded in a tangible medium, e.g., a computer-readable disk, a solid state memory device, or an optical storage device.

Methods of Screening Using Variations in Polypeptides

Screening of a neurological disorder can be made by examining or comparing changes in expression, localization, binding partners, and composition of a polypeptide encoded by a nucleic acid associated with a neurological disorder, for example, in those instances where the genetic variations of the present disclosure results in a change in the composition or expression of the polypeptide and/or RNA, for example, mRNAs, miRNAs, and other noncoding RNAs (ncRNAs). Thus, screening of a neurological disorder can be made by examining expression and/or composition of one of these polypeptides and/or RNA, or another polypeptide and/or RNA encoded by a nucleic acid associated with a neurological disorder, in those instances where the genetic variation of the present disclosure results in a change in the expression, localization, binding partners, and/or composition of the polypeptide, DNA, genomic DNA, cDNA, and/or RNA. Screening can comprise diagnosing a subject. Screening can comprise determining a prognosis of a subject, for example, determining the susceptibility of developing a neurological disorder. Screening can comprise theranosing a subject.

The genetic variations described herein that show association to a neurological disorder can play a role through their effect on one or more of these nearby genes. For example, while not intending to be limited, it is generally expected that a deletion of a chromosomal segment comprising a particular gene, or a fragment of a gene, can either result in an altered composition or expression, or both, of the encoded polypeptide and/or mRNA. Likewise, duplications, or high number copy number variations, are in general expected to result in increased expression of encoded polypeptide, DNA, genomic DNA, cDNA, and/or RNA. Other possible mechanisms affecting genes within a genetic variation region include, for example, effects on transcription, effects on RNA splicing, alterations in relative amounts of alternative splice forms of mRNA, effects on RNA stability, effects on transport from the nucleus to cytoplasm, and effects on the efficiency and accuracy of translation. Thus, DNA variations can be detected directly, using the subjects unamplified or amplified genomic DNA, or indirectly, using RNA or DNA obtained from the subject's tissue(s) that are present in an aberrant form or expression level as a result of the genetic variations of the disclosure showing association to a neurological disorder.

Genetic variations of the disclosure showing association to a neurological disorder can affect polypeptide expression at the translational level. It can be appreciated by those skilled in the art that this can occur by increased or decreased expression of one or more microRNAs (miRNAs) that regulates expression of a polypeptide known to be important, or implicated, in the cause, onset, or progression of the neurological disease. Increased or decreased expression of the one or more miRNAs can result from gain or loss of the whole miRNA gene, disruption of a portion of the gene (e.g., by an indel or CNV), or even a single base change (SNP or SNV) that produces an altered, non-functional or aberrant functioning miRNA sequence. It can also be appreciated by those skilled in the art that the expression of polypeptide, for example, one known to cause a neurological disease by increased or decreased expression, can result due to a genetic variation that results in alteration of an existing miRNA binding site within the polypeptide's mRNA transcript, or even creates a new miRNA binding site that leads to aberrant polypeptide expression.

A "probe," as used herein, can include a nucleic acid fragment for examining a nucleic acid in a specimen using the hybridization reaction based on the complementarity of nucleic acid, a polypeptide fragment for examining a polypeptide fragment in a specimen using the methods for detecting polypeptide composition and/or expression levels described herein and elsewhere, or a combination thereof. A probe can bind, attach, hybridize, or interact with a targeted nucleic acid sequence. The nucleic acid sequence can be DNA, genomic DNA, cDNA, RNA, mRNA, microRNA, small RNA, or a combination thereof. The probe can be a nucleic acid fragment that has complementary sequences to the targeted nucleic acid fragment in the specimen. The probe can be a polypeptide fragment that has a motif, e.g., a structural motif sequence that recognizes and/or binds the targeted polypeptide sequence.

A variety of methods can be used for detecting polypeptide composition and/or expression levels, including but not limited to enzyme linked immunosorbent assays (ELISA), Western blots, spectroscopy, mass spectrometry, peptide arrays, colorimetry, electrophoresis, isoelectric focusing, immunoprecipitations, immunoassays, and immunofluorescence and other methods well-known in the art.

A test sample from a subject can be assessed for the presence of an alteration in the expression and/or an alteration in composition of the polypeptide encoded by a nucleic acid associated with a neurological disorder. An "alteration" in the polypeptide expression or composition, as used herein, can refer to an alteration in expression or composition in a test sample, as compared to the expression or composition of the polypeptide in a control sample. Such alteration, for example, can be an alteration in the quantitative polypeptide expression or can be an alteration in the qualitative polypeptide expression, for example, expression of a mutant polypeptide or of a different splicing variant, or a combination thereof. In some embodiments, screening of a neurological disorder can be made by detecting a particular splicing variant encoded by a nucleic acid associated with a neurological disorder, or a particular pattern of splicing variants. In some embodiments, an antibody can be used to detect the presence or absence of a mutated polypeptide.

Antibodies can be polyclonal or monoclonal and can be labeled or unlabeled. An intact antibody or a fragment thereof can be used. The term "labeled", with regard to the probe or antibody, is intended to encompass direct labeling of the probe or antibody by coupling a detectable substance to the probe or antibody, as well as indirect labeling of the probe or antibody by reactivity with another reagent that is directly labeled as previously described herein. Other non-limiting examples of indirect labeling include detection of a primary antibody using a labeled secondary antibody, for example, a fluorescently-labeled secondary antibody and end-labeling of a DNA probe with biotin such that it can be detected with fluorescently-labeled streptavidin. A label can be fluorescent or luminescent tags, metals, dyes, radioactive isotopes, and the like. Examples of labels include paramagnetic ions, radioactive isotopes; fluorochromes, metals, dyes, NMR-detectable substances, and X-ray imaging compounds. Paramagnetic ions include chromium (III), manganese (II), iron (III), iron (II), cobalt (II), nickel (II), copper (II), neodymium (II), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III). Radioactive isotopes include $^{14}$-carbon, $^{15}$chromium, $^{36}$-chlorine, $^{57}$cobalt, and the like may be utilized. Among the fluorescent labels contemplated for use include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Nucleic Acids

The nucleic acids and polypeptides described herein can be used in methods and kits of the present disclosure. In one aspect, aptamers that specifically bind the nucleic acids or polypeptides described herein can be used in methods and kits of the present disclosure. As used herein, a nucleic acid can comprise a deoxyribonucleotide (DNA) or ribonucleotide (RNA), whether singular or in polymers, naturally occurring or non-naturally occurring, double-stranded or single-stranded, coding, for example, a translated gene, or non-coding, for example, a regulatory region, or any fragments, derivatives, mimetics or complements thereof. Nucleic acids can comprise oligonucleotides, nucleotides, polynucleotides, nucleic acid sequences, genomic sequences, antisense nucleic acids, DNA regions, probes, primers, genes, regulatory regions, introns, exons, open-reading frames, binding sites, target nucleic acids and allele-specific nucleic acids.

A "probe," as used herein, can include a nucleic acid fragment for examining a nucleic acid in a specimen using the hybridization reaction based on the complementarity of nucleic acid. A probe can bind, attach, or interact with a targeted nucleic acid sequence. The nucleic acid sequence can be DNA, genomic DNA, cDNA, RNA, mRNA, microRNA, small RNA, or a combination thereof. In some embodiments, the probe can have at least 30%, 40%, 50%, 60%, 70%, 80%, 90%, 95%, or higher homology with at least 2, 3, 4, 5, 6, 7, 8, 9, 10, 11, 12, 13, 14, 15, 16, 17, 18, 19, 20, or more consecutive nucleotides of the targeted nucleic acid sequence. For example, the probe can have at least 80% of homology with at least 8 consecutive nucleotides of the targeted nucleic acid sequence. In some embodiments, the probe can have at least 30%, 40%, 50%, 60%, 70%, 80%, 90%, 95%, or higher homology with at least 30%, 40%, 50%, 60%, 70%, 80%, 90%, 95%, or more nucleotides of a standard probe for PCR amplification. For example, the probe can have at least 80% homology with at least 80% of a standard probe for PCR amplification. A standard probe for PCR amplification can comprise at least 2, 3, 4, 5, 6, 7, 8, 9, 10, 11, 12, 13, 14, 15, 16, 17, 18, 19, 20, or more nucleotides. A standard probe for PCR amplification can comprise 100, 90, 80, 70, 60, 50, 40, 30, 20, 15, 10, 5, or less nucleotides.

Nucleic acids can be fused to other coding or regulatory sequences can be considered isolated. For example, recombinant DNA contained in a vector is included in the definition of "isolated" as used herein. Isolated nucleic acids can include recombinant DNA molecules in heterologous host cells or heterologous organisms, as well as partially or substantially purified DNA molecules in solution. Isolated nucleic acids also encompass in vivo and in vitro RNA transcripts of the DNA molecules of the present disclosure. An isolated nucleic acid molecule or nucleotide sequence can be synthesized chemically or by recombinant means. Such isolated nucleotide sequences can be useful, for example, in the manufacture of the encoded polypeptide, as probes for isolating homologous sequences (e.g., from other mammalian species), for gene mapping (e.g., by in situ hybridization with chromosomes), or for detecting expression of the gene, in tissue (e.g., human tissue), such as by Northern blot analysis or other hybridization techniques disclosed herein. The disclosure also pertains to nucleic acid sequences that hybridize under high stringency hybridization conditions, such as for selective hybridization, to a nucleotide sequence described herein. Such nucleic acid sequences can be detected and/or isolated by allele- or sequence-specific hybridization (e.g., under high stringency conditions). Stringency conditions and methods for nucleic acid hybridizations are well known to the skilled person (see, e.g., Current Protocols in Molecular Biology, Ausubel, F. et al., John Wiley & Sons, (1998), and Kraus, M. and Aaronson, S., Methods Enzymol., 200:546-556 (1991), the entire teachings of which are incorporated by reference herein.

Calculations of "identity" or "percent identity" or percent homology between two or more nucleotide or amino acid sequences can be determined by aligning the sequences for optimal comparison purposes (e.g., gaps can be introduced in the sequence of a first sequence). The nucleotides at corresponding positions are then compared, and the percent identity between the two sequences is a function of the number of identical positions shared by the sequences (i.e., % identity=# of identical positions/total # of positions ×100). For example, a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

The length of a sequence aligned for comparison purposes is at least 30%, at least 40%, at least 50%, at least 60%, at least 70%, at least 80%, at least 90%, or at least 95%, of the length of the reference sequence. The actual comparison of the two sequences can be accomplished by well-known methods, for example, using a mathematical algorithm. A non-limiting example of such a mathematical algorithm is described in Karlin, S. and Altschul, S., Proc. Natl. Acad. Sci. USA, 90-5873-5877 (1993). Such an algorithm is incorporated into the NBLAST and XBLAST programs (version 2.0), as described in Altschul, S. et al., Nucleic Acids Res., 25:3389-3402 (1997). When utilizing BLAST and Gapped BLAST programs, any relevant parameters of the respective programs (e.g., NBLAST) can be used. For example, parameters for sequence comparison can be set at score=100, word length=12, or can be varied (e.g. W=5 or W=20). Other examples include the algorithm of Myers and Miller, CABIOS (1989), ADVANCE, ADAM, BLAT, and FASTA. The percent identity between two amino acid sequences can be accomplished using, for example, the GAP program in the GCG software package (Accelrys, Cambridge, UK).

Probes can be primers. Primers can be oligonucleotides that hybridize in a base-specific manner to a complementary strand of a nucleic acid molecule. Probes can be labeled as disclosed herein. Probes can include primers, which can be a single-stranded oligonucleotide probe that can act as a point of initiation of template-directed DNA synthesis using methods including but not limited to, polymerase chain reaction (PCR) and ligase chain reaction (LCR) for amplification of a target sequence. Oligonucleotides, as described herein, can include segments or fragments of nucleic acid sequences, or their complements. DNA segments can be between 5 and 10,000 contiguous bases, and can range from 5, 10, 12, 15, 20, or 25 nucleotides to 10, 15, 20, 25, 30, 40, 50, 100, 200, 500, 1000 or 10,000 nucleotides. In addition to DNA and RNA, probes and primers can include polypeptide nucleic acids (PNA), as described in Nielsen, P. et al., Science 254: 1497-1500 (1991). A probe or primer can comprise a region of nucleotide sequence that hybridizes to at least about 10, 11, 12, 13, 14, or 15, typically about 20-25, and in certain embodiments about 40, 50 or 75, consecutive nucleotides of a nucleic acid molecule. In one aspect, primers disclosed herein can share at least 10%, 15%, 20%, 30%, 40% 45%, 50%, 60%, 65%, 70%, 75%, 80%, 85%, 90%, 95%, or 100% identity or homology with a sequence disclosed herein, for example, in Table 1, Table 3, Table 4, Table 7, Table 8, or Table 9. In some embodiments, primers disclosed herein can share at least 10%, 15%, 20%, 30%, 40% 45%, 50%, 60%, 65%, 70%, 75%, 80%, 85%, 90%, 95%, or 100% identity or homology with a primer disclosed in Table 18 or Table 19. In some embodiments, primers disclosed herein can share at least 10%, 15%, 20%, 30%, 40% 45%, 50%, 60%, 65%, 70%, 75%, 80%, 85%, 90%, 95%, or 100% identity or homology with a sequence disclosed herein.

Nucleosides and derivatives thereof can be used as the building blocks of the primers described herein, except where indicated otherwise. Nothing in this application is meant to preclude the utilization of nucleoside derivatives or bases that have been chemical modified to enhance their stability or usefulness in an amplification reaction, provided that the chemical modification does not interfere with their recognition by a polymerase as deoxyguanine, deoxycytosine, deoxythymidine, or deoxyadenine, as appropriate. Nucleotide analogs can stabilize hybrid formation. In one aspect, nucleotide analogs can destabilize hybrid formation. In one aspect, nucleotide analogs can enhance hybridization specificity. In one aspect, nucleotide analogs can reduce hybridization specificity.

The present disclosure also provides isolated nucleic acids, for example, probes or primers, that contain a fragment or portion that can selectively hybridize to a nucleic acid that comprises, or consists of, a nucleotide sequence, wherein the nucleotide sequence can comprise at least one polymorphism or polymorphic allele contained in the genetic variations described herein or the wild-type nucleotide that is located at the same position, or the compliments thereof. A probe or primer can be at least 70% identical, at least 80% identical, at least 85% identical, at least 90% identical, or at least 95% identical, to a contiguous nucleotide sequence or to a complement of the contiguous nucleotide sequence.

A nucleic acid probe can be an oligonucleotide capable of hybridizing with a complementary regions of a gene associated with a neurological disorder containing a genetic variation described herein. The nucleic acid fragments of the disclosure can be used as probes or primers in assays such as those described herein.

The nucleic acids of the disclosure, such as those described above, can be identified and isolated using standard molecular biology techniques well known to the skilled person. DNA can be amplified and/or can be labeled (e.g., radiolabeled, fluorescently labeled) and used as a probe for screening, for example, a cDNA library derived from an organism. cDNA can be derived from mRNA and can be contained in a suitable vector. For example, corresponding clones can be isolated, DNA obtained following in vivo excision, and the cloned insert can be sequenced in either or both orientations by art-recognized methods to identify the correct reading frame encoding a polypeptide of the appropriate molecular weight. Using these or similar methods, the polypeptide and the DNA encoding the polypeptide can be isolated, sequenced and further characterized.

Nucleic acid can comprise one or more polymorphisms, variations, or mutations, for example, single nucleotide polymorphisms (SNPs), copy number variations (CNVs), for example, insertions, deletions, inversions, and translocations. In one aspect, a nucleic acid may be naturally or non-naturally polymorphic, for example, having one or more sequence differences, for example, additions, deletions and/or substitutions, as compared to a reference sequence. A reference sequence can be based on publicly available information, for example, the U.C. Santa Cruz Human Genome Browser Gateway (genome.ucsc.edu/cgi-bin/hg-Gateway) or the NCBI website (www.ncbi.nlm.nih.gov). A reference sequence can be determined by a practitioner of the present disclosure using methods well known in the art, for example, by sequencing a reference nucleic acid.

A probe can hybridize to an allele, SNP, or CNV as described herein. A probe can bind to another marker sequence associated with a neurological disorder as described herein.

One of skill in the art would know how to design a probe so that sequence specific hybridization can occur only if a particular allele is present in a genomic sequence from a test nucleic acid sample. The disclosure can also be reduced to practice using any convenient genotyping method, including commercially available technologies and methods for genotyping particular genetic variations.

Control probes can also be used, for example, a probe that binds a less variable sequence, for example, a repetitive DNA associated with a centromere of a chromosome, can be used as a control. In one aspect, probes can be obtained from commercial sources. Probes can be synthesized, for example, chemically or in vitro, or made from chromosomal or genomic DNA through standard techniques. In one aspect sources of DNA that can be used include genomic DNA, cloned DNA sequences, somatic cell hybrids that contain one, or a part of one, human chromosome along with the normal chromosome complement of the host, and chromosomes purified by flow cytometry or microdissection. The region of interest can be isolated through cloning, or by site-specific amplification using PCR.

One or more nucleic acids for example, a probe or primer, can also be labeled, for example, by direct labeling, to comprise a detectable label. A detectable label can comprise any label capable of detection by a physical, chemical, or a biological process for example, a radioactive label, such as 32P or 3H, a fluorescent label, such as FITC, a chromophore label, an affinity-ligand label, an enzyme label, such as alkaline phosphatase, horseradish peroxidase, or 12 galactosidase, an enzyme cofactor label, a hapten conjugate label, such as digoxigenin or dinitrophenyl, a Raman signal generating label, a magnetic label, a spin label, an epitope label, such as the FLAG or HA epitope, a luminescent label, a heavy atom label, a nanoparticle label, an electrochemical label, a light scattering label, a spherical shell label, semiconductor nanocrystal label, such as quantum dots (described in U.S. Pat. No. 6,207,392), and probes labeled with any other signal generating label known to those of skill in the art, wherein a label can allow the probe to be visualized with or without a secondary detection molecule. A nucleotide can be directly incorporated into a probe with standard techniques, for example, nick translation, random priming, and PCR labeling. A "signal," as used herein, include a signal suitably detectable and measurable by appropriate means, including fluorescence, radioactivity, chemiluminescence, and the like.

Non-limiting examples of label moieties useful for detection include, without limitation, suitable enzymes such as horseradish peroxidase, alkaline phosphatase, beta-galactosidase, or acetylcholinesterase; members of a binding pair that are capable of forming complexes such as streptavidin/biotin, avidin/biotin or an antigen/antibody complex including, for example, rabbit IgG and anti-rabbit IgG; fluorophores such as umbelliferone, fluorescein, fluorescein isothiocyanate, rhodamine, tetramethyl rhodamine, eosin, green fluorescent protein, erythrosin, coumarin, methyl coumarin, pyrene, malachite green, stilbene, lucifer yellow, Cascade Blue, Texas Red, dichlorotriazinylamine fluorescein, dansyl chloride, phycoerythrin, fluorescent lanthanide complexes such as those including Europium and Terbium, cyanine dye family members, such as Cy3 and Cy5, molecular beacons and fluorescent derivatives thereof, as well as others known in the art as described, for example, in Principles of Fluorescence Spectroscopy, Joseph R. Lakowicz (Editor), Plenum Pub Corp, 2nd edition (July 1999) and the 6th Edition of the Molecular Probes Handbook by Richard P. Hoagland; a luminescent material such as luminol; light scattering or plasmon resonant materials such as gold or silver particles or quantum dots; or radioactive material include 14C, 123I, 124I, 125I, Tc99m, 32P, 33P, 35S or 3H.

Fluorophores of different colors can be chosen. Fluorescently labeled probes can be viewed with a fluorescence microscope and an appropriate filter for each fluorophore, or by using dual or triple band-pass filter sets to observe multiple fluorophores. Techniques such as flow cytometry can be used to examine the hybridization pattern of the probes.

In other embodiments, a probe can be indirectly labeled, for example, with biotin or digoxygenin, or labeled with radioactive isotopes such as 32P and/or 3H. As a non-limiting example, a probe indirectly labeled with biotin can be detected by avidin conjugated to a detectable marker. For example, avidin can be conjugated to an enzymatic marker such as alkaline phosphatase or horseradish peroxidase. Enzymatic markers can be detected using colorimetric reactions using a substrate and/or a catalyst for the enzyme. In one aspect, catalysts for alkaline phosphatase can be used, for example, 5-bromo-4-chloro-3-indolylphosphate and nitro blue tetrazolium. In one aspect, a catalyst can be used for horseradish peroxidase, for example, diaminobenzoate.

Methods of Detecting Genetic Variations

Standard techniques for genotyping for the presence genetic variations, for example, amplification, can be used. Amplification of nucleic acids can be accomplished using methods known in the art. Generally, sequence information from the region of interest can be used to design oligonucleotide primers that can be identical or similar in sequence to opposite strands of a template to be amplified. Amplification methods can include but are not limited to, fluorescence-based techniques utilizing PCR, for example, ligase chain reaction (LCR), Nested PCR, transcription amplification, self-sustained sequence replication, nucleic acid based sequence amplification (NASBA), and multiplex ligation-dependent probe amplification (MLPA). Guidelines for selecting primers for PCR amplification are well known in the art. In some cases, a computer program can be used to design primers, for example, Oligo (National Biosciences, Inc, Plymouth Minn.), MacVector (Kodak/IBI), and GCG suite of sequence analysis programs.

Examples of PCR techniques that can be used in the present disclosure include, but are not limited to quantitative PCR, real-time quantitative PCR (qPCR), quantitative fluorescent PCR (QF-PCR), multiplex fluorescent PCR (MF-PCR), real time PCR (RT-PCR), single cell PCR, PCR-RFLP/RT-PCR-RFLP, hot start PCR and Nested PCR. Other suitable amplification methods include the ligase chain reaction (LCR), ligation mediated PCR (LM-PCR), degenerate oligonucleotide probe PCR (DOP-PCR), transcription amplification, self-sustained sequence replication, selective amplification of target polynucleotide sequences, consensus sequence primed polymerase chain reaction (CP-PCR), arbitrarily primed polymerase chain reaction (AP-PCR) and nucleic acid based sequence amplification (NABSA).

Alternative methods for the simultaneous interrogation of multiple regions include quantitative multiplex PCR of short fluorescent fragments (QMPSF), multiplex amplifiable probe hybridization (MAPH) and multiplex ligation-dependent probe amplification (MLPA).

Commercial methodologies available for genotyping, for example, SNP genotyping, can be used, but are not limited to, TaqMan genotyping assays (Applied Biosystems), SNPlex platforms (Applied Biosystems), gel electrophoresis, capillary electrophoresis, size exclusion chromatography, mass spectrometry, for example, MassARRAY system (Sequenom), minisequencing methods, real-time Polymerase Chain Reaction (PCR), Bio-Plex system (BioRad), CEQ and SNPstream systems (Beckman), array hybridization technology, for example, Affymetrix GeneChip (Perlegen), BeadArray Technologies, for example, Illumina GoldenGate and Infinium assays, array tag technology, Multiplex Ligation-dependent Probe Amplification (MLPA), and endonuclease-based fluorescence hybridization technology (Invader; Third Wave). In some cases, real-time quantitative PCR can be used to determine genetic variations, wherein quantitative PCR can permit both detection and quantification of a DNA sequence in a nucleic acid sample, for example, as an absolute number of copies or as a relative amount when normalized to DNA input or other normalizing genes. In some cases, methods of quantification can include the use of fluorescent dyes that can intercalate with double-stranded DNA, and modified DNA oligonucleotide probes that can fluoresce when hybridized with a complementary DNA.

DNA can be amplified on a bead or a solid substrate. In some cases, the amplification on the bead results in each bead carrying at least one million, at least 5 million, or at least 10 million copies of the single amplified piece of DNA molecule. Where PCR occurs in oil-emulsion mixtures, the emulsion droplets can be broken, the DNA can be denatured and the beads carrying single-stranded nucleic acids clones are deposited into a well, such as a picoliter-sized well, for further analysis according to the methods described herein. These amplification methods allow for the analysis of genomic DNA regions. Methods for using bead amplification followed by fiber optics detection are described in Margulies et al. 2005, Nature. 15; 437(7057):376-80, and as well as in US Publication Application Nos. 20020012930; 20030068629; 20030100102; 20030148344; 20040248161; 20050079510, 20050124022; and 20060078909.

Identification of genetic variations can be accomplished using hybridization methods. The presence of a specific marker allele or a particular genomic segment comprising a genetic variation, or representative of a genetic variation, can be indicated by sequence-specific hybridization of a nucleic acid probe specific for the particular allele or the genetic variation in a nucleic acid sample that has or has not been amplified by methods described herein. The presence of more than one specific marker allele or several genetic variations can be indicated by using two or more sequence-specific nucleic acid probes, wherein each is specific for a particular allele and/or genetic variation.

Hybridization can be performed by methods well known to the person skilled in the art, for example, hybridization techniques such as fluorescent in situ hybridization (FISH), Southern analysis, Northern analysis, or in situ hybridization. In some cases, hybridization refers to specific hybridization, wherein hybridization can be performed with no mismatches. Specific hybridization, if present, can use standard methods. In some cases, if specific hybridization occurs between a nucleic acid probe and the nucleic acid in the nucleic acid sample, the nucleic acid sample can contain a sequence that can be complementary to a nucleotide present in the nucleic acid probe. In some cases, if a nucleic acid probe can contain a particular allele of a polymorphic marker, or particular alleles for a plurality of markers, specific hybridization is indicative of the nucleic acid being completely complementary to the nucleic acid probe, including the particular alleles at polymorphic markers within the probe. In some cases a probe can contain more than one marker alleles of a particular haplotype, for example, a probe can contain alleles complementary to 2, 3, 4, 5 or all of the markers that make up a particular haplotype. In some cases detection of one or more particular markers of the haplotype in the nucleic acid sample is indicative that the source of the nucleic acid sample has the particular haplotype.

PCR conditions and primers can be developed that amplify a product only when the variant allele is present or only when the wild type allele is present, for example, allele-specific PCR. In some cases of allele-specific PCR, a method utilizing a detection oligonucleotide probe comprising a fluorescent moiety or group at its 3' terminus and a quencher at its 5' terminus, and an enhancer oligonucleotide, can be employed, as described by Kutyavin et al. (Nucleic Acid Res. 34:e128 (2006)).

An allele-specific primer/probe can be an oligonucleotide that is specific for a particular polymorphism can be prepared using standard methods. In some cases, allele-specific oligonucleotide probes can specifically hybridize to a nucleic acid region that contains a genetic variation. In some cases, hybridization conditions can be selected such that a nucleic acid probe can specifically bind to the sequence of interest, for example, the variant nucleic acid sequence.

Allele-specific restriction digest analysis can be used to detect the existence of a polymorphic variant of a polymorphism, if alternate polymorphic variants of the polymorphism can result in the creation or elimination of a restriction site. Allele-specific restriction digests can be performed, for example, with the particular restriction enzyme that can differentiate the alleles. In some cases, PCR can be used to amplify a region comprising the polymorphic site, and restriction fragment length polymorphism analysis can be conducted. In some cases, for sequence variants that do not alter a common restriction site, mutagenic primers can be designed that can introduce one or more restriction sites when the variant allele is present or when the wild type allele is present.

Fluorescence polarization template-directed dye-terminator incorporation (FP-TDI) can be used to determine which of multiple polymorphic variants of a polymorphism can be present in a subject.

DNA containing an amplified portion can be dot-blotted, using standard methods and the blot contacted with the oligonucleotide probe. The presence of specific hybridization of the probe to the DNA can then be detected. The methods can include determining the genotype of a subject with respect to both copies of the polymorphic site present in the genome, wherein if multiple polymorphic variants exist at a site, this can be appropriately indicated by specifying which variants are present in a subject. Any of the detection means described herein can be used to determine the genotype of a subject with respect to one or both copies of the polymorphism present in the subject's genome.

A peptide nucleic acid (PNA) probe can be used in addition to, or instead of, a nucleic acid probe in the methods described herein. A PNA can be a DNA mimic having a peptide-like, inorganic backbone, for example, N-(2-aminoethyl) glycine units with an organic base (A, G, C, T or U) attached to the glycine nitrogen via a methylene carbonyl linker.

Nucleic acid sequence analysis can also be used to detect genetic variations, for example, genetic variations can be detected by sequencing exons, introns, 5' untranslated sequences, or 3' untranslated sequences. One or more methods of nucleic acid analysis that are available to those skilled in the art can be used to detect genetic variations, including but not limited to, direct manual sequencing, automated fluorescent sequencing, single-stranded conformation polymorphism assays (SSCP); clamped denaturing gel electrophoresis (CDGE); denaturing gradient gel electrophoresis (DGGE), two-dimensional gel electrophoresis (2DGE or TDGE); conformational sensitive gel electrophoresis (CSGE); denaturing high performance liquid chromatography (DHPLC), infrared matrix-assisted laser desorption/ionization (IR-MALDI) mass spectrometry, mobility shift analysis, quantitative real-time PCR, restriction enzyme analysis, heteroduplex analysis; chemical mismatch cleavage (CMC), RNase protection assays, use of polypeptides that recognize nucleotide mismatches, allele-specific PCR, real-time pyrophosphate DNA sequencing, PCR amplification in combination with denaturing high performance liquid chromatography (dHPLC), and combinations of such methods.

Sequencing can be performed by any sequencing method known in the art. Sequencing can be performed in high throughput. Suitable next generation sequencing technologies include the 454 Life Sciences platform (Roche, Branford, Conn.) (Margulies et al., Nature, 437, 376-380 (2005)); Illumina's Genome Analyzer, GoldenGate Methylation Assay, or Infinium Methylation Assays, i.e., Infinium HumanMethylation 27K BeadArray or VeraCode GoldenGate methylation array (Illumina, San Diego, Calif.; Bibkova et al., Genome Res. 16, 383-393 (2006); and U.S. Pat. Nos. 6,306,597, 7,598,035, 7,232,656), or DNA Sequencing by Ligation, SOLID System (Applied Biosystems/Life Technologies; U.S. Pat. Nos. 6,797,470, 7,083,917, 7,166,434, 7,320,865, 7,332,285, 7,364,858, and 7,429,453); or the Helicos True Single Molecule DNA sequencing technology (Harris et al., Science, 320, 106-109 (2008); and U.S. Pat. Nos. 7,037,687, 7,645,596, 7,169,560, and 7,769,400), the single molecule, real-time (SMRT™) technology of Pacific Biosciences, and sequencing (Soni et al., Clin. Chem. 53, 1996-2001 (2007)). These systems allow multiplexed parallel sequencing of many polynucleotides isolated from a sample (Dear, Brief Funct. Genomic Proteomic, 1(4), 397-416 (2003) and McCaughan et al., J. Pathol., 220, 297-306 (2010)). In some cases, polynucleotides are sequenced by sequencing by ligation of dye-modified probes, pyrosequencing, or single-molecule sequencing. Determining the sequence of a polynucleotide may be performed by sequencing methods such as Helioscope™ single molecule sequencing, Nanopore DNA sequencing, Lynx Therapeutics' Massively Parallel Signature Sequencing (MPSS), 454 pyrosequencing, Single Molecule real time (RNAP) sequencing, Illumina (Solexa) sequencing, SOLiD sequencing, Ion Torrent™, Ion semiconductor sequencing, Single Molecule SMRT™ sequencing, Polony sequencing, DNA nanoball sequencing, and VisiGen Biotechnologies approach. Alternatively, determining the sequence of polynucleotides may use sequencing platforms, including, but not limited to, Genome Analyzer IIx, HiSeq, and MiSeq offered by Illumina, Single Molecule Real Time (SMRT™) technology, such as the PacBio RS system offered by Pacific Biosciences (California) and the Solexa Sequencer, True Single Molecule Sequencing (tSMS™) technology such as the HeliScope™ Sequencer offered by Helicos Inc. (Cambridge, Mass.). Sequencing can comprise MiSeq sequencing. Sequencing can comprise HiSeq sequencing. Determining the sequence of a polynucleotide can comprise paired-end sequencing, nanopore sequencing, high-throughput sequencing, shotgun sequencing, dye-terminator sequencing, multiple-primer DNA sequencing, primer walking, Sanger dideoxy sequencing, Maxim-Gilbert sequencing, pyrosequencing, true single molecule sequencing, or any combination thereof. Alternatively, the sequence of a polynucleotide can be determined by electron microscopy or a chemical-sensitive field effect transistor (chemFET) array.

High-throughput sequencing methods can include but are not limited to, Massively Parallel Signature Sequencing (MPSS, Lynx Therapeutics), Polony sequencing, 454 pyrosequencing, Illumina (Solexa) sequencing, SOLiD sequencing, on semiconductor sequencing, DNA nanoball sequencing, Helioscope™ single molecule sequencing, Single Molecule SMRT™ sequencing, Single Molecule real time (RNAP) sequencing, Nanopore DNA sequencing, and/or sequencing by hybridization, for example, a non-enzymatic method that uses a DNA microarray, or microfluidic Sanger sequencing. High-throughput sequencing can involve the use of technology available by Helicos BioSciences Corporation (Cambridge, Mass.) such as the Single Molecule Sequencing by Synthesis (SMSS) method as described in US Publication Application Nos. 20060024711; 20060024678; 20060012793; 20060012784; and 20050100932.

Analysis by restriction enzyme digestion can be used to detect a particular genetic variation if the genetic variation results in creation or elimination of one or more restriction sites relative to a reference sequence. In some cases, restriction fragment length polymorphism (RFLP) analysis can be conducted, wherein the digestion pattern of the relevant DNA fragment indicates the presence or absence of the particular genetic variation in the nucleic acid sample.

Arrays of oligonucleotide probes that can be complementary to target nucleic acid sequence segments from a subject can be used to identify genetic variations. An array of oligonucleotide probes can comprise an oligonucleotide array, for example, a microarray. In some cases, the present disclosure features arrays that include a substrate having a plurality of addressable areas, and methods of using them. At least one area of the plurality includes a nucleic acid probe that binds specifically to a sequence comprising a genetic variation, and can be used to detect the absence or presence of the genetic variation, for example, one or more SNPs, or microsatellites as described herein, to determine or identify an allele or genotype. For example, an array can include one or more nucleic acid probes that can be used to detect a genetic variation associated with a gene and/or gene product such as those associated with an APOE or a non-APOE locus. In some cases, the array can further comprise at least one area that includes a nucleic acid probe that can be used to specifically detect another marker associated with a neurological disorder.

Microarray hybridization can be performed by hybridizing a nucleic acid of interest, for example, a nucleic acid encompassing a genetic variation, with the array and detecting hybridization using nucleic acid probes. In some cases, the nucleic acid of interest is amplified prior to hybridization. Hybridization and detecting can be carried out according to standard methods described in Published PCT Applications: WO 92/10092 and WO 95/11995, and U.S. Pat. No. 5,424,186. For example, an array can be scanned to determine the position on the array to which the nucleic acid hybridizes. The hybridization data obtained from the scan can be, for example, in the form of fluorescence intensities as a function of location on the array.

Oligonucleotide probes forming an array can be attached to a substrate by any number of techniques, including, but not limited to, in situ synthesis, for example, high-density oligonucleotide arrays, using photolithographic techniques; spotting/printing a medium to low density on glass, nylon, or nitrocellulose; by masking; and by dot-blotting on a nylon or nitrocellulose hybridization membrane. In some cases, oligonucleotides can be immobilized via a linker, including but not limited to, by covalent, ionic, or physical linkage. Linkers for immobilizing nucleic acids and polypeptides, including reversible or cleavable linkers, are known in the art (U.S. Pat. No. 5,451,683 and WO98/20019). In some cases, oligonucleotides can be non-covalently immobilized on a substrate by hybridization to anchors, by means of magnetic beads, or in a fluid phase, for example, in wells or capillaries.

An array can comprise oligonucleotide hybridization probes capable of specifically hybridizing to different genetic variations. In some cases, oligonucleotide arrays can comprise a plurality of different oligonucleotide probes coupled to a surface of a substrate in different known locations. In some cases, oligonucleotide probes can exhibit differential or selective binding to polymorphic sites, and can be readily designed by one of ordinary skill in the art, for example, an oligonucleotide that is perfectly complementary to a sequence that encompasses a polymorphic site, for example, a sequence that includes the polymorphic site, within it, or at one end, can hybridize preferentially to a nucleic acid comprising that sequence, as opposed to a nucleic acid comprising an alternate polymorphic variant.

Arrays can include multiple detection blocks, for example, multiple groups of probes designed for detection of particular polymorphisms. In some cases, these arrays can be used to analyze multiple different polymorphisms. In some cases, detection blocks can be grouped within a single array or in multiple, separate arrays, wherein varying conditions, for example, conditions optimized for particular polymorphisms, can be used during hybridization. General descriptions of using oligonucleotide arrays for detection of polymorphisms can be found, for example, in U.S. Pat. Nos. 5,858,659 and 5,837,832. In addition to oligonucleotide arrays, cDNA arrays can be used similarly in certain embodiments.

The methods described herein can include but are not limited to providing an array as described herein; contacting the array with a sample, and detecting binding of a nucleic acid from the sample to the array. The method can comprise amplifying nucleic acid from the sample, for example, a region associated with a neurological disorder or a region that includes another region associated with a neurological disorder. The methods described herein can include using an array that can identify differential expression patterns or copy numbers of one or more genes in a sample from control and affected individuals. For example, arrays of probes to a marker described herein can be used to identify genetic variations between DNA from an affected subject, and control DNA obtained from an individual that does not have a neurological disorder. Since the nucleotides on the array can contain sequence tags or labels, their positions on the array can be accurately known relative to the genomic sequence.

It can be desirable to employ methods that can detect the presence of multiple genetic variations, for example, polymorphic variants at a plurality of polymorphic sites, in parallel or substantially simultaneously. In some cases, these methods can comprise oligonucleotide arrays and other methods, including methods in which reactions, for example, amplification and hybridization, can be performed in individual vessels, for example, within individual wells of a multi-well plate or other vessel.

Determining the identity of a genetic variation can also include or consist of reviewing a subject's medical history, where the medical history includes information regarding the identity, copy number, presence or absence of one or more alleles or SNPs in the subject, e.g., results of a genetic test.

Genetic variations can also be identified using any of a number of methods well known in the art. For example, genetic variations available in public databases, which can be searched using methods and custom algorithms or algorithms known in the art, can be used. A reference sequence can be from, for example, the human draft genome sequence, publicly available in various databases, or a sequence deposited in a database such as GenBank.

Another variation on the array-based approach can be to use the hybridization signal intensities that are obtained from the oligonucleotides employed on Affymetrix SNP arrays or in Illumina Bead Arrays. Here hybridization intensities are compared with average values that are derived from controls, such that deviations from these averages indicate a change in copy number. As well as providing information about copy number, SNP arrays have the added advantage of providing genotype information. For example, they can reveal loss of heterozygosity, which could provide supporting evidence for the presence of a deletion, or might indicate segmental uniparental disomy (which can recapitulate the effects of structural variation in some genomic regions—Prader-Willi and Angelman syndromes, for example).

Many of the basic procedures followed in microarray-based genome profiling are similar, if not identical, to those followed in expression profiling and SNP analysis, including the use of specialized microarray equipment and data-analysis tools. Since microarray-based expression profiling has been well established in the art, much can be learned from the technical advances made in this area. Examples of the use of microarrays in nucleic acid analysis that can be used are described in U.S. Pat. Nos. 6,300,063, 5,837,832, 6,969,589, 6,040,138, 6,858,412, U.S. application Ser. No. 08/529,115, U.S. application Ser. No. 10/272,384, U.S. application Ser. No. 10/045,575, U.S. application Ser. No. 10/264,571 and U.S. application Ser. No. 10/264,574. It should be noted that there are also distinct differences such as target and probe complexity, stability of DNA over RNA, the presence of repetitive DNA and the need to identify single copy number alterations in genome profiling.

The presence or absence of the disease or disorder in the subject can be determined with at least 50% confidence. For example, the presence or absence of the disease or disorder in the subject can be determined with at least 50%, 55%, 60%, 65%, 70%, 75%, 80%, 85%, 90%, 95%, 98%, 99%, or 100% confidence. The presence or absence of the disease or disorder in the subject can be determined with a 50%-100% confidence. For example, the presence or absence of the disease or disorder in the subject can be determined with a confidence of about 60%-100%, 70%-100%, 80%-100%, 90%-100%, 50%-90%, 50%-80%, 50%-70%, 50%-60%, 60%-90%, 60%-80%, 60%-70%, 70%-90%, 70%-80%, or 80%-90%.

Computer-Implemented Aspects

As understood by those of ordinary skill in the art, the methods and information described herein (genetic variation association with neurological disorders) can be implemented, in all or in part, as computer executable instructions on known computer readable media. For example, the methods described herein can be implemented in hardware. Alternatively, the method can be implemented in software stored in, for example, one or more memories or other computer readable medium and implemented on one or more processors. As is known, the processors can be associated with one or more controllers, calculation units and/or other units of a computer system, or implanted in firmware as desired. If implemented in software, the routines can be stored in any computer readable memory such as in RAM, ROM, flash memory, a magnetic disk, a laser disk, or other storage medium, as is also known. Likewise, this software can be delivered to a computing device via any known delivery method including, for example, over a communication channel such as a telephone line, the Internet, a wireless connection, etc., or via a transportable medium, such as a computer readable disk, flash drive, etc.

More generally, and as understood by those of ordinary skill in the art, the various steps described above can be implemented as various blocks, operations, tools, modules and techniques which, in turn, can be implemented in hardware, firmware, software, or any combination of hardware, firmware, and/or software. When implemented in hardware, some or all of the blocks, operations, techniques, etc. can be implemented in, for example, a custom integrated circuit (IC), an application specific integrated circuit (ASIC), a field programmable logic array (FPGA), a programmable logic array (PLA), etc.

Results from such genotyping can be stored in a data storage unit, such as a data carrier, including computer databases, data storage disks, or by other convenient data storage means. In certain embodiments, the computer database is an object database, a relational database or a post-relational database. Data can be retrieved from the data storage unit using any convenient data query method.

When implemented in software, the software can be stored in any known computer readable medium such as on a magnetic disk, an optical disk, or other storage medium, in a RAM or ROM or flash memory of a computer, processor, hard disk drive, optical disk drive, tape drive, etc. Likewise, the software can be delivered to a user or a computing system via any known delivery method including, for example, on a computer readable disk or other transportable computer storage mechanism.

The steps of the claimed methods can be operational with numerous other general purpose or special purpose computing system environments or configurations. Examples of well-known computing systems, environments, and/or configurations that can be suitable for use with the methods or system of the claims include, but are not limited to, personal computers, server computers, hand-held or laptop devices, multiprocessor systems, microprocessor-based systems, set top boxes, programmable consumer electronics, network PCs, minicomputers, mainframe computers, distributed computing environments that include any of the above systems or devices, and the like.

The steps of the methods and systems described herein can be described in the general context of computer-executable instructions, such as program modules, being executed by a computer. Generally, program modules include routines, programs, objects, components, and/or data structures that perform particular tasks or implement particular abstract data types. The methods and apparatus can also be practiced in distributed computing environments where tasks are performed by remote processing devices that are linked through a communications network. In both integrated and distributed computing environments, program modules can be located in both local and remote computer storage media including memory storage devices. Numerous alternative embodiments could be implemented, using either current technology or technology developed after the filing date of this application, which would still fall within the scope of the claims defining the disclosure.

The methods disclosed herein can be implemented in software, they can be implemented in hardware, firmware, etc., and can be implemented by any other processor. Thus, the elements described herein can be implemented in a standard multi-purpose CPU or on specifically designed hardware or firmware such as an application-specific integrated circuit (ASIC) or other hard-wired device as desired. When implemented in software, the software routine can be stored in any computer readable memory such as on a magnetic disk, a laser disk, or other storage medium, in a RAM or ROM of a computer or processor, in any database, etc. Likewise, this software can be delivered to a user or a screening system via any known or desired delivery method including, for example, on a computer readable disk or other transportable computer storage mechanism or over a communication channel, for example, a telephone line, the internet, or wireless communication. Modifications and variations can be made in the techniques and structures described and illustrated herein without departing from the spirit and scope of the present disclosure.

Computer System

Figure 3:
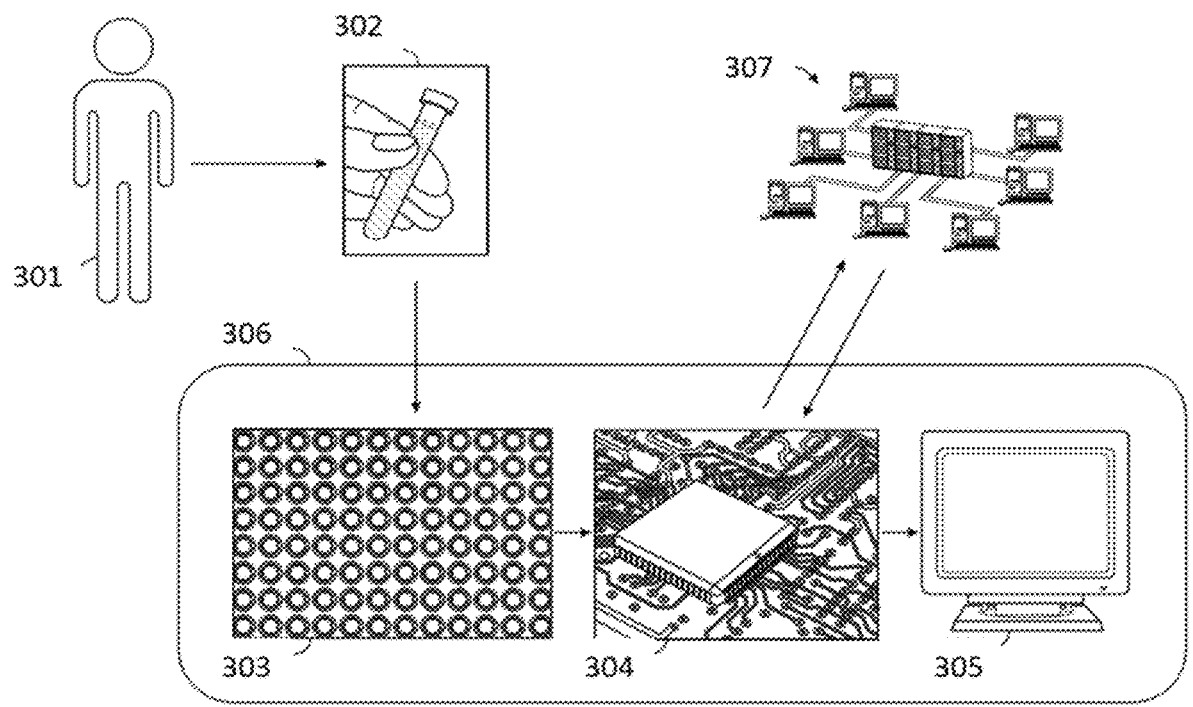
FIG. 3 depicts an exemplary method for assessing the presence of a genetic variant in a subject.

AD can be assessed using a computer or a computer system. FIG. 3 shows an exemplary method for assessing AD in a subject using a computer. A sample (FIG. 3, 302) can be obtained from a subject (FIG. 3, 301). A genetic variation or a protein mutation can be assessed (FIG. 3, 303) using a computer system (FIG. 3, 304). In some cases, a computer system can compare nucleic acid information of a sample to a reference, determine a presence or absence of a genetic variation and/or store a result of an assay or a determination of a presence or absence of a genetic variation. A reference can be stored in the computer system. Alternatively, a reference can be stored in other computers, databases, and/or servers, and accessible through a network (e.g. Internet) (FIG. 3, 307). In other instances, a result of an assay or a determination of a presence or absence of a genetic variation can be stored on remote servers, in the cloud or in a database (FIG. 3, 307). In some instances, a computer system can determine that a subject has AD, has an increased risk of AD, or has a decrease risk of AD. The result of whether a subject has AD, has a decrease risk of AD, has an increased risk of AD or a presence or absence of a genetic variant can be transmitted to an output device, e.g., a monitor (FIG. 3, 305). An assay, computer system, and an output device (FIGS. 3, 303, 304 and 305) can be integrated into a single device (FIG. 3, 306). In some cases, such a device can be a portable device, for example a smartphone. The device can be contemplated to be portable device for use in a hospital and/or a pre-hospital setting (e.g., in an ambulance or patient's home). Generally, a device can have a memory that stores executable instructions and a processor to execute the executable instructions to detect AD.

Treatment and Therapy

The disclosure provides several methods of treating or effecting prophylaxis a neurological disease or disorder, for example AD. In some cases, the disclosure provides several methods of treating AD. In some cases, the disclosure provides several methods of treating APOE SNPs related diseases, non-APOE SNPs related diseases, subjecting having a genetic variation or dementia in patients suffering from or at risk of such diseases. Patients amenable to treatment include individuals at risk of a disease disclosed herein but not showing symptoms, as well as patients presently showing symptoms or the early warning signs of synucleinopathies, for example, EEG slowing, neuropsychiatric manifestations (depression, dementia, hallucinations, anxiety, apathy, anhedonia), autonomic changes (orthostatic hypotension, bladder disturbances, constipation, fecal incontinence, sialorrhea, dysphagia, sexual dysfunction, changes in cerebral blood flow), sensory changes (olfactory, pain, color discrimination abnormal sensations), sleep disorders (REM sleep behavior disorder (RBD), restless legs syndrome/periodic extremity movements, hypersomnia, insomnia), resting tremor, muscular rigidity, bradykinesia and postural instability and miscellaneous other signs and symptoms (fatigue, diplopia, blurred vision, seborrhea, weight loss/gain). Therefore, the present methods can be administered prophylactically to individuals who have a known genetic risk of a disclosed disease. Such individuals include those having relatives who have experienced this disease and those whose risk is determined by analysis of genetic or biochemical markers.

In asymptomatic or symptomatic patients, treatment can begin at any age (e.g., 5, 10, 20, 30, 40, 50, 60 or 70). Usually, however, it may not be necessary to begin treatment until a patient reaches 35, 40, 50, 60 or 70. Treatment can entail a single dose or multiple dosing over a period of time.

In some cases, treatment can typically entail multiple dosages over a period of time. Treatment can be monitored by evaluating symptoms, assaying antibody, or activated T-cell or B-cell responses to a therapeutic agent over time. In some cases, a booster dosage can be administered. In some cases, if the response to an administered dose falls, a booster dosage can be indicated.

In prophylactic applications of a treatment described herein, a treatment e.g an antibody or a pharmaceutical composition, can be administered to a patient susceptible to, or otherwise at risk of a disease in a regime (dose, frequency and route of administration) effective to reduce the risk, lessen the severity, or delay the onset of at least one sign or symptom of the disease. In some prophylactic applications, the regime is effective to inhibit or delay accumulation of alpha synuclein and/or truncated fragments in the brain, and/or inhibit or delay its toxic effects and/or inhibit/or delay development of behavioral deficits. In therapeutic applications, a treatment is administered to a patient suspected of, or already suffering from a disease described herein in a regime (dose, frequency and route of administration) effective to ameliorate or at least inhibit further deterioration of at least one sign or symptom of the disease. In some therapeutic applications, the regime is effective to reduce or at least inhibit further increase of levels of alpha synuclein, truncated fragments, associated toxicities and/or behavioral deficits, or symptoms.

A regime can be considered therapeutically or prophylactically effective if an individual treated patient achieves an outcome more favorable than the mean outcome in a control population of comparable patients not treated by methods of the disclosure, or if a more favorable outcome is demonstrated in treated patients versus control patients in a controlled clinical trial (e.g., a phase II, phase II/III or phase III trial).

An effective dose can vary depending on many different factors, including means of administration, target site, physiological state of the patient including whether the patient is human or an animal, other medications administered, and whether treatment is prophylactic or therapeutic.

An exemplary dosage range for antibodies can be from about 0.01 to 5 mg/kg, and more usually 0.1 to 3 mg/kg or 0.15-2 mg/kg or 0.15-1.5 mg/kg or more, of patient body weight. A treatment can be administered such doses daily, on alternative days, weekly, fortnightly, monthly, quarterly, or according to any other schedule determined by empirical analysis. An exemplary treatment entails administration in multiple dosages over a prolonged period, for example, of at least six months. Additional exemplary treatment regimes entail administration once per every two weeks or once a month or once every 3 to 6 months. In some cases, a subject can be given a treatment, and there after evaluated for continued treatment.

A therapeutically effective amount of a treatment can be dependent on the weight of a subject. In some cases, the therapeutically effective amount of a treatment is at least about 1 µg of a treatment per kg of the subject, for example at least about 1, 2, 3, 4, 5, 6, 7, 8, 9, 10, 20, 30, 40, 50, 60, 70, 80, 90, 100, 200, 300, 400, 500, 600, 700, 800, 900, or 1000 µg of a treatment per kg of the subject. In some cases, the therapeutically effective amount of a treatment is at least about 1 mg of a treatment per kg of the subject, for example at least about 1, 2, 3, 4, 5, 6, 7, 8, 9, 10, 20, 30, 40, 50, 60, 70, 80, 90, 100, 200, 300, 400, 500, 600, 700, 800, 900, or 1000 mg of a treatment per kg of the subject. In some cases, the therapeutically effective amount of a treatment is less than about 1000 µg of a treatment per kg of the subject, for example less than about 1, 2, 3, 4, 5, 6, 7, 8, 9, 10, 20, 30, 40, 50, 60, 70, 80, 90, 100, 200, 300, 400, 500, 600, 700, 800, 900 or 1000 µg of a treatment per kg of the subject. In some cases, the therapeutically effective amount of a treatment is less than about 1000 mg of a treatment per kg of the subject, for example less than about 1, 2, 3, 4, 5, 6, 7, 8, 9, 10, 20, 30, 40, 50, 60, 70, 80, 90, 100, 200, 300, 400, 500, 600, 700, 800, 900 or 1000 mg of a treatment per kg of the subject. In some cases, the therapeutically effective amount of a treatment ranges from about 1 µg to 1000 µg of a treatment per kg of the subject, for example about 1-700, 1-500, 1-300, 1-100, 1-50, 1-10, 10-700, 10-500, 10-300, 10-100, 10-80, 10-60, 10-40, 10-20, 50-700, 50-500, 50-300, 50-100, 100-700, 100-500, 100-300, 300-700, 300-500, or 500-700 µg of a treatment per kg of the subject. In some cases, the therapeutically effective amount of a treatment ranges from about 1 µg to 10 µg of a treatment per kg of the subject. In some cases, the therapeutically effective amount of a treatment ranges from about 10 µg to 100 µg of a treatment per kg of the subject. In some cases, the therapeutically effective amount of a treatment ranges from about 100 µg to 500 µg of a treatment per kg of the subject. In some cases, the therapeutically effective amount of a treatment ranges from about 1 µg to 1000 mg of a treatment per kg of the subject, for example about 1-700, 1-500, 1-300, 1-100, 1-50, 1-10, 10-700, 10-500, 10-300, 10-100, 10-80, 10-60, 10-40, 10-20, 50-700, 50-500, 50-300, 50-100, 100-700, 100-500, 100-300, 300-700, 300-500, or 500-700 mg of a treatment per kg of the subject. In some cases, the therapeutically effective amount of a treatment ranges from about 16 mg to 24 mg of a treatment per kg of the subject. In some cases, the therapeutically effective amount of a treatment ranges from about 30 mg to 100 mg of a treatment per kg of the subject. In some cases, the therapeutically effective amount of a treatment ranges from about 50 mg to 140 mg of a treatment per kg of the subject. In some cases, the therapeutically effective amount of a treatment ranges from about 115 mg to 125 mg of a treatment per kg of the subject. The therapeutically effective amount of a treatment can also be the daily dosage of a treatment for the subject.

A treatment described herein can be e.g., antibodies, can be administered. Routes of administration can include topical, intravenous, oral, subcutaneous, intra-arterial, intracranial, intrathecal, intraperitoneal, intranasal or intramuscular. Some routes for administration can be intravenous or subcutaneous. A treatment, for example an antibody can be injected in the arm or leg muscles. In some methods, a treatment can be injected directly into a particular tissue where deposits have accumulated, for example intracranial injection.

Pharmaceutical compositions can be sterile and substantially isotonic and manufactured under GMP conditions. Pharmaceutical compositions can be provided in unit dosage form (i.e., the dosage for a single administration). Pharmaceutical compositions can be formulated using one or more physiologically acceptable carriers, diluents, excipients or auxiliaries. The formulation depends on the route of administration chosen. For injection, treatments can be formulated in aqueous solutions, preferably in physiologically compatible buffers such as Hank's solution, Ringer's solution, or physiological saline or acetate buffer (to reduce discomfort at the site of injection). The solution can contain formulatory agents such as suspending, stabilizing and/or dispersing agents. Alternatively treatments can be in lyophilized form for constitution with a suitable vehicle, e.g., sterile pyrogen-free water, before use.

The present regimes can be administered in combination with another agent effective in treatment or prophylaxis of the disease being treated. For example, immunotherapy against alpha synuclein WO/2008/103472, Levodopa, dopamine agonists, COMT inhibitors, MAO-B inhibitors, Amantadine, or anticholinergic agents can be used in combination with the present regimes. In some embodiments, administration can comprise a treatment disclosed herein.

A treatment described herein can increase cognitive function of a subject. In some cases, a treatment described herein can increase cognitive function of a subject afflicted with a disease disclosed herein, for example AD. Cognitive function can be measured by methods known in the art. In some cases, cognitive function can be measured using a maze in which subjects use spatial information, fear conditioning, or active avoidance.

Cognitive function can be measured by one or more of several standardized tests. Examples of a test or assay for cognitive function were described (Ruoppila and Suutama, Scand. J. Soc. Med. Suppl. 53, 44-65, 1997) and include standardized psychometric tests (e.g. Wechsler Memory Scale, the Wechsler Adult Intelligence Scale, Raven's Standard Progressive Matrices, Schaie-Thurstone Adult Mental Abilities Test), neuropsychological tests (e.g. Luria-Nebraska), metacognitive self-evaluations (e.g. Metamemory Questionnaire), visual-spatial screening tests (e.g. Poppelreuter's Figures, Clock Recognition, Honeycomb Drawing and Cancellation), cognitive screening tests (e.g. Folstein's Mini Mental State Test) and reaction time tests. Other standard tests for cognitive performance include the Alzheimer's Disease Assessment Scale-cognitive subscale (ADAS-cog); the clinical global impression of change scale (CIBIC-plus scale); the Alzheimer's Disease Cooperative Study Activities of Daily Living Scale (ADCS-ADL); the Mini Mental State Exam (MMSE); the Neuropsychiatric Inventory (NPI); the Clinical Dementia Rating Scale (CDR); the Cambridge Neuropsychological Test Automated Battery (CANTAB) or the Sandoz Clinical Assessment-Geriatric (SCAG), Stroop Test, Trail Making, Wechsler Digit Span, and the CogState computerized cognitive test. In addition, cognitive function may be measured using imaging techniques such as Positron Emission Tomography (PET), functional magnetic resonance imaging (fMRI), Single Photon Emission Computed Tomography (SPECT), or any other imaging technique that allows one to measure brain function.

Protein Kinases

Multiple small molecule kinase inhibitors have been approved by USA FDA and are available in the market, including imatinib (Gleevec), sorafenib (Nexavar), sunitinib (Sutent), rapamycin (Sirolimus) to name a few. Potential druggable kinase-related signaling pathways include protein kinase Cd, the MLK-cjun N-terminal kinase (JNK) signaling cascade, and AKT/protein kinase B (PKB) signaling cascade, all of which are kinases implicated in programmed cell death. CEP1347, a MLK inhibitor has been shown to have neuroprotective effects in a variety of neurodegenerative models. One or more protein kinase inhibitors disclosed herein can be used as a therapy to treat a neurological disease, for example AD.

Prodrugs

Prodrugs include compounds wherein an amino acid residue, or a polypeptide chain of two or more (e.g., two, three or four) amino acid residues that are covalently joined through peptide bonds to free amino, hydroxy or carboxylic acid groups of the parent compounds. Accordingly, some aspects of the disclosure provide a method for treating a neurodegenerative disease by administering a histone deacetylase inhibitor, or a derivative thereof, a prodrug thereof, or a salt thereof. Whether a particular compound is an HDAC inhibitor can be readily determined, for example, by an in vitro experimentation. Such experimental procedures are well known to one skilled in the art. Moreover, many HDAC inhibitors are well known. Exemplary HDAC inhibitors include, but are not limited to, TSA, DP AH, Tubastatin A, MGCD, hydroxamic acids (or hydroxamates), such as trichostatin A, vorinostat (SAHA), belinostat, LAQ824, and panobinostat; cyclic tetrapeptides (such as trapoxin B), and the depsipeptides; benzamides such as entinostat, CI994, and mocetinostat; electrophilic ketones; and the aliphatic acid compounds such as phenylbutyrate and valproic acid.

RNA Therapeutics

The nucleic acids and/or variants of the disclosure, or nucleic acids comprising their complementary sequence, can be used as antisense constructs to control gene expression in cells, tissues or organs. The methodology associated with antisense techniques is well known to the skilled artisan, and is described and reviewed in Antisense Drug Technology: Principles, Strategies, and Applications, Crooke, Marcel Dekker Inc., New York (2001) In general, antisense nucleic acids are designed to be complementary to a region of mRNA expressed by a gene, so that the antisense molecule hybridizes to the mRNA, thus blocking translation of the mRNA into a polypeptide. Several classes of antisense oligonucleotide are known to those skilled in the art, including cleavers and blockers. Cleavers bind to target RNA sites, activate intracellular nucleases (e.g., Rnase H or Rnase L) that cleave the target RNA. Blockers bind to target RNA, inhibit polypeptide translation by steric hindrance of the ribosomes. Examples of blockers include nucleic acids, morpholino compounds, locked nucleic acids and methylphosphonates (Thompson, Drug Discovery Today, 7:912-917 (2002)). Antisense oligonucleotides are useful directly as therapeutic agents, and are also useful for determining and validating gene function, for example, by gene knock-out or gene knock-down experiments. Antisense technology is further described in Lavery et al., Curr. Opin. Drug Discov Devel 6 561-569 (2003), Stephens et al., Curr. Opin. Mol Ther. 5.118-122 (2003), Kurreck, Eur. J. Biochem. 270.1628-44 (2003), Dias et al, Mol Cancer Ter. 1-347-55 (2002), Chen, Methods Mol Med. 75:621-636 (2003), Wang et al., Curr Cancer Drug Targets 1.177-96 (2001), and Bennett, Antisense Nucleic Acid Drug. Dev. 12 215-24 (2002).

The genetic variations described herein can be used for the selection and design of antisense reagents that are specific for particular variations (e.g., particular genetic variations, or polymorphic markers in MSA with particular genetic variations). Using information about the variations described herein, antisense oligonucleotides or other antisense molecules that specifically target mRNA molecules that contain one or more variations of the disclosure can be designed. In this manner, expression of mRNA molecules that contain one or more variations of the present disclosure (markers and/or haplotypes) can be inhibited or blocked. The antisense molecules can be designed to specifically bind a particular allelic form (i.e., one or several variations (alleles and/or haplotypes)) of a target nucleic acid, thereby inhibiting translation of a product originating from this specific allele or haplotype, but which do not bind other or alternate variants at the specific polymorphic sites of the target nucleic acid molecule.

As antisense molecules can be used to inactivate mRNA so as to inhibit gene expression, and thus polypeptide expression, the molecules can be used to treat a disease or disorder, such as a neurological disorder. The methodology can involve cleavage by means of ribozymes containing nucleotide sequences complementary to one or more regions in the mRNA that attenuate the ability of the mRNA to be translated. Such mRNA regions include, for example, polypeptide-coding regions, in particular polypeptide-coding regions corresponding to catalytic activity, substrate and/or ligand binding sites, or other functional domains of a polypeptide.

The phenomenon of RNA interference (RNAi) has been actively studied for the last decade, since its original discovery in C. elegans (Fire et al., Nature 391:806-11 (1998)), and in recent years its potential use in treatment of human disease has been actively pursued (reviewed in Kim & Rossi, Nature Rev, Genet. 8: 173-204 (2007)). RNA interference (RNAi), also called gene silencing, is based on using double-stranded RNA molecules (dsRNA) to turn off specific genes. In the cell, cytoplasmic double-stranded RNA molecules (dsRNA) are processed by cellular complexes into small interfering RNA (siRNA). The siRNA guide the targeting of a polypeptide-RNA complex to specific sites on a target mRNA, leading to cleavage of the mRNA (Thompson, Drug Discovery Today, 7:912-917 (2002)). The siRNA molecules are typically about 10-15, 20, 21, 22 or 23-25 nucleotides in length. Thus, one aspect of the disclosure relates to isolated nucleic acid sequences, and the use of those molecules for RNA interference, for example, as small interfering RNA molecules (siRNA). In some embodiments, the isolated nucleic acid sequences can be 2-30 nucleotides in length, 18-26 nucleotides in length, 19-25 nucleotides in length, 20-24 nucleotides in length, or 21, 22 or 23 nucleotides in length.

Double stranded RNA induced gene silencing can occur on at least three different levels: (i) transcription inactivation, which refers to RNA guided DNA or histone methylation; (ii) siRNA induced mRNA degradation; and (iii) mRNA induced transcriptional attenuation. It is generally considered that the major mechanism of RNA induced silencing (RNA interference, or RNAi) in mammalian cells can be mRNA degradation. RNA interference (RNAi) is a mechanism that inhibits gene expression at the stage of translation or by hindering the transcription of specific genes. Specific RNAi pathway polypeptides can be guided by the dsRNA to the targeted messenger RNA (mRNA), where they "cleave" the target, breaking it down into smaller portions that can no longer be translated into a polypeptide.

Double stranded oligonucleotides can be formed by the assembly of two distinct oligonucleotide sequences where the oligonucleotide sequence of one strand is complementary to the oligonucleotide sequence of the second strand; such double stranded oligonucleotides are generally assembled from two separate oligonucleotides (e.g., siRNA), or from a single molecule that folds on itself to form a double stranded structure (e.g., shRNA or short hairpin RNA). These double stranded oligonucleotides known in the art all have a common feature in that each strand of the duplex has a distinct nucleotide sequence, wherein only one nucleotide sequence region (guide sequence or the antisense sequence) has complementarity to a target nucleic acid sequence and the other strand (sense sequence) comprises nucleotide sequence that is homologous to the target nucleic acid sequence.

Another pathway for RNAi-mediated gene silencing originates in endogenously encoded primary microRNA (pn-miRNA) transcripts, which are processed in the cell to generate precursor miRNA (pre-miRNA). These miRNA molecules are exported from the nucleus to the cytoplasm, where they undergo processing to generate mature miRNA molecules (miRNA), which direct translational inhibition by recognizing target sites in the 3' untranslated regions of mRNAs, and subsequent mRNA degradation by processing P-bodies (reviewed in Kim & Rossi, Nature Rev. Genet. 8: 173-204 (2007)). microRNAs (miRNA) are single-stranded RNA molecules of about 21-23 nucleotides in length, which regulate gene expression. Mature miRNA molecules are partially complementary to one or more messenger RNA (mRNA) molecules, and their main function is to down-regulate gene expression.

Clinical applications of RNAi include the incorporation of synthetic siRNA duplexes, which can be approximately 20-23 nucleotides in size, and can have 3' overlaps of 2 nucleotides. Knockdown of gene expression is established by sequence-specific design for the target mRNA. Several commercial sites for optimal design and synthesis of such molecules are known to those skilled in the art.

Other applications provide longer siRNA molecules typically about 20-40 nucleotides in length, in some embodiments, 27, 28, 29, 30 or 40 nucleotides in length, as well as small hairpin RNAs (shRNAs; typically about 29 nucleotides in length). The latter are naturally expressed, as described in Amarzguioui et al. (FEBS Lett. 579:5974-81 (2005)). Chemically synthetic siRNAs and shRNAs can be substrates for in vivo processing, and in some cases provide more potent gene-silencing than shorter designs (Kim et al., Nature Biotechnol. 23:222-226 (2005); Siola et al., Nature Biotechnol. 23:227-231 (2005)). In general, siRNAs can provide for transient silencing of gene expression, because their intracellular concentration is diluted by subsequent cell divisions. By contrast, expressed shRNAs mediate long-term, stable knockdown of target transcripts, for as long as transcription of the shRNA takes place (Marques et al., Nature Biotechnol. 23.559-565 (2006), Brummelkamp et al., Science 296. 550-553 (2002)).

Since RNAi molecules, including siRNA, miRNA and shRNA, act in a sequence-dependent manner, variants described herein can be used to design RNAi reagents that recognize specific nucleic acids comprising specific genetic variations, alleles and/or haplotypes, while not recognizing nucleic acid sequences not comprising the genetic variation, or comprising other alleles or haplotypes. These RNAi reagents can thus recognize and destroy the target nucleic acid sequences. As with antisense reagents, RNAi reagents can be useful as therapeutic agents (i.e., for turning off disease-associated genes or disease-associated gene variants), but can also be useful for characterizing and validating gene function (e.g., by gene knock-out or gene knock-down experiments).

Delivery of RNAi can be performed by a range of methodologies known to those skilled in the art. Methods utilizing non-viral delivery can include cholesterol, stable nucleic acid-lipid particle (SNALP), heavy-chain antibody fragment (Fab), aptamers and nanoparticles. Viral delivery methods can include use of lentivirus, adenovirus and adeno-associated virus. The siRNA molecules can in some embodiments be chemically modified to increase their stability. This can include modifications at the 2' position of the ribose, including 2'-O-methylpunnes and 2'-fluoropyrimidmes, which provide resistance to RNase activity. Other chemical modifications are possible and known to those skilled in the art.

Antibody-Based Therapeutics

The present disclosure embodies agents that modulate a peptide sequence or RNA expressed from a gene associated with a neurological disorder. The term "biomarker", as used herein, can comprise a genetic variation of the present disclosure or a gene product, for example, RNA and polypeptides, of any one of the genes disclosed herein. A genetic variation can be one or more genetic variation disclosed herein, for example as listed in Table 1, Table 3, Table 4, Table 7, Table 8, and/or Table 9. Such modulating agents include, but are not limited to, polypeptides, peptidomimetics, peptoids, or any other forms of a molecule, which bind to, and alter the signaling or function associated with the a neurological disorder associated biomarker, have an inhibitory or stimulatory effect on the neurological disorder associated biomarkers, or have a stimulatory or inhibitory effect on the expression or activity of the a neurological disorder associated biomarkers' ligands, for example, polyclonal antibodies and/or monoclonal antibodies that specifically bind one form of the gene product but not to the other form of the gene product are also provided, or which bind a portion of either the variant or the reference gene product that contains the polymorphic site or sites.

The present disclosure provides antibody-based agents targeting a neurological disorder associated biomarkers. The antibody-based agents in any suitable form of an antibody e.g., monoclonal, polyclonal, or synthetic, can be utilized in the therapeutic methods disclosed herein. The antibody-based agents include any target-binding fragment of an antibody and also peptibodies, which are engineered therapeutic molecules that can bind to human drug targets and contain peptides linked to the constant domains of antibodies. In some embodiments, the antibodies used for targeting a neurological disorder associated biomarkers are humanized antibodies. Methods for humanizing antibodies are well known in the art. In some embodiments, the therapeutic antibodies can comprise an antibody generated against a neurological disorder associated biomarkers described in the present disclosure, wherein the antibodies are conjugated to another agent or agents, for example, a cytotoxic agent or agents.

The term "antibody" can refer to immunoglobulin molecules and immunologically active portions of immunoglobulin molecules, i.e., molecules that contain antigen-binding sites that specifically bind an antigen. A molecule that specifically binds to a polypeptide of the disclosure is a molecule that binds to that polypeptide or a fragment thereof, but does not substantially bind other molecules in a nucleic acid sample, which naturally contains the polypeptide. The disclosure provides polyclonal and monoclonal antibodies that bind to a polypeptide or nucleic acid of the disclosure.

In general, antibodies of the disclosure (e.g., a monoclonal antibody) can be used to isolate a polypeptide of the disclosure by standard techniques, such as affinity chromatography or immunoprecipitation. An antibody specific for a polypeptide of the disclosure can be used to detect the polypeptide (e.g., in a cellular lysate, cell supernatant, or tissue sample) in order to evaluate the abundance and pattern of expression of the polypeptide. Antibodies can be used diagnostically, prognostically, or theranostically to monitor polypeptide levels in tissue as part of a clinical testing procedure, e.g., to, for example, determine the efficacy of a given treatment regimen. The antibody can be coupled to a detectable substance to facilitate its detection. Examples of detectable substances include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotnazinylamine fluorescein, dansyl chloride or phycoerythnn; an example of a luminescent material includes luminol; examples of bioluminescent materials include luciferase, luciferin, and aequorin, and examples of suitable radioactive material include 125I, 131I, 35S or 3H. Antibodies can also be useful in pharmacogenomic analysis. In such embodiments, antibodies against variant polypeptides encoded by nucleic acids according to the disclosure, such as variant polypeptides that are encoded by nucleic acids that contain at least one genetic variation of the disclosure, can be used to identify individuals that can benefit from modified treatment modalities.

Antibodies can furthermore be useful for assessing expression of variant polypeptides in disease states, such as in active stages of a disease, or in an individual with a predisposition to a disease related to the function of the polypeptide, in particular a neurological disorder. Antibodies specific for a variant polypeptide of the present disclosure that is encoded by a nucleic acid that comprise at least one polymorphic marker or haplotype as described herein can be used to screen for the presence of the variant polypeptide, for example, to screen for a predisposition to a neurological disorder as indicated by the presence of the variant polypeptide.

Antibodies can be used in other methods. Thus, antibodies are useful as screening tools for evaluating polypeptides, such as variant polypeptides of the disclosure, in conjunction with analysis by electrophoretic mobility, isoelectric point, tryptic or other protease digest, or for use in other physical assays known to those skilled in the art. Antibodies can also be used in tissue typing. In one such embodiment, a specific variant polypeptide can be correlated with expression in a specific tissue type, and antibodies specific for the variant polypeptide can then be used to identify the specific tissue type.

Gene Therapy

Gene therapy can be used as a therapeutic to modulate a peptide sequence or RNA expressed from a gene associated with a developmental disorder. Gene therapy involves the use of DNA as a pharmaceutical agent to treat disease. DNA can be used to supplement or alter genes within an individual's cells as a therapy to treat disease. Gene therapy can be used to alter the signaling or function associated with the a developmental disorder associated biomarker, have an inhibitory or stimulatory effect on the developmental disorder associated biomarkers, or have a stimulatory or inhibitory effect on the expression or activity of the a developmental disorder associated biomarkers' ligands. In one embodiment, gene therapy involves using DNA that encodes a functional, therapeutic gene in order to replace a mutated gene. Other forms involve directly correcting a mutation, or using DNA that encodes a therapeutic polypeptide drug (rather than a natural human gene) to provide treatment. DNA that encodes a therapeutic polypeptide can be packaged within a vector, which can used to introduce the DNA inside cells within the body. Once inside, the DNA becomes expressed by the cell machinery, resulting in the production of the therapeutic, which in turn can treat the subject's disease.

Gene therapy agents and other agents for testing therapeutics can include plasmids, viral vectors, artificial chromosomes and the like containing therapeutic genes or polynucleotides encoding therapeutic products, including coding sequences for small interfering RNA (siRNA), ribozymes and antisense RNA, which in certain further embodiments can comprise an operably linked promoter such as a constitutive promoter or a regulatable promoter, such as an inducible promoter (e.g., IPTG inducible), a tightly regulated promoter (e.g., a promoter that permits little or no detectable transcription in the absence of its cognate inducer or derepressor) or a tissue-specific promoter. Methodologies for preparing, testing and using these and related agents are known in the art. See, e.g., Ausubel (Ed.), Current Protocols in Molecular Biology (2007 John Wiley & Sons, NY); Rosenzweig and Nabel (Eds), Current Protocols in Human Genetics (esp. Ch. 13 therein, "Delivery Systems for Gene Therapy", 2008 John Wiley & Sons, NY); Abell, Advances in Amino Acid Mimetics and Peptidomimetics, 1997 Elsevier, NY. In another embodiment, gene therapy agents may encompass zinc finger nuclease (ZFN) or transcription activator-like effector nuclease (TALEN) strategies, see for example: Urnov et al. (2010), Nature Reviews Genetics 11(9):636-46; Yusa et al. (2011), Nature 478(7369):391-4; Bedell et al. (2012), Nature ePub September 23, PubMed ID 23000899.

As a non-limiting example, one such embodiment contemplates introduction of a gene therapy agent for treating AD (e.g., an engineered therapeutic virus, a therapeutic agent-carrying nanoparticle, etc.) to one or more injection sites in a subject, without the need for imaging, surgery, or histology on biopsy specimens. Of course, periodic monitoring of the circulation for leaked therapeutic agent and/or subsequent analysis of a biopsy specimen, e.g., to assess the effects of the agent on the target tissue, can also be considered. A gene therapy can include a therapeutic polynucleotide administered before, after, or at the same time as any other therapy described herein. In some embodiments, therapeutic genes may include an antisense version of a biomarker disclosed herein, a sequence of a biomarker described herein, or an inhibitor of a biomarker disclosed herein.

Methods of Treatment

Some embodiments of the present disclosure relates to methods of using pharmaceutical compositions and kits comprising agents that can inhibit one or more neurological disorder associated biomarker to inhibit or decrease neurological disorder progression. Another embodiment of the present disclosure provides methods, pharmaceutical compositions, and kits for the treatment of subjects. The term "subject" as used herein includes humans as well as other mammals. The term "treating" as used herein includes achieving a therapeutic benefit and/or a prophylactic benefit. By therapeutic benefit is meant eradication or amelioration of a condition. Also, a therapeutic benefit is achieved with the eradication or amelioration of one or more of the physiological symptoms associated a neurological disorder such that an improvement is observed in the subject, notwithstanding the fact that the subject can still be afflicted with a neurological disorder.

For embodiments where a prophylactic benefit is desired, a pharmaceutical composition of the disclosure can be administered to a subject at risk of developing a neurological disorder, or to a subject reporting one or more of the physiological symptoms of a neurological disorder, even though a screening of the condition cannot have been made. Administration can prevent a neurological disorder from developing, or it can reduce, lessen, shorten and/or otherwise ameliorate the progression of a neurological disorder, or symptoms that develop. The pharmaceutical composition can modulate or target a neurological disorder associated biomarker. Wherein, the term modulate includes inhibition of a neurological disorder associated biomarkers or alternatively activation of a neurological disorder associated biomarkers.

Reducing the activity of one or more neurological disorder's associated biomarkers is also referred to as "inhibiting" the neurological disorder's associated biomarkers. The term "inhibits" and its grammatical conjugations, such as "inhibitory," do not require complete inhibition, but refer to a reduction in a neurological disorder's associated biomarkers' activities. In some cases such reduction is by at least 5%, at least 10%, at least 20%, at least 30%, at least 40%, at least 50%, at least 75%, at least 90%, and can be by at least 95% of the activity of the enzyme or other biologically important molecular process in the absence of the inhibitory effect, e.g., in the absence of an inhibitor. Conversely, the phrase "does not inhibit" and its grammatical conjugations refer to situations where there is less than 20%, less than 10%, and can be less than 5%, of reduction in enzyme or other biologically important molecular activity in the presence of the agent. Further the phrase "does not substantially inhibit" and its grammatical conjugations refer to situations where there is less than 30%, less than 20%, and In some cases less than 10% of reduction in enzyme or other biologically important molecular activity in the presence of the agent.

Increasing the activity and/or function of polypeptides and/or nucleic acids found to be associated with one or more neurological disorders, can also be referred to as "activating" the polypeptides and/or nucleic acids. The term "activated" and its grammatical conjugations, such as "activating," do not require complete activation, but refer to an increase in a neurological disorder associated biomarkers' activities. In some cases such increase is by at least 5%, at least 10%, at least 20%, at least 30%, at least 40%, at least 50%, at least 60%, at least 70%, at least 75%, at least 80%, at least 85%, at least 90%, and can be by at least 95% of the activity of the enzyme or other biologically important molecular process in the absence of the activation effect, e.g., in the absence of an activator. Conversely, the phrase "does not activate" and its grammatical conjugations refer to situations where there can be less than 20%, less than 10%, and less than 5%, of an increase in enzyme or other biologically important molecular activity in the presence of the agent. Further the phrase "does not substantially activate" and its grammatical conjugations refer to situations where there is less than 30%, less than 20%, and In some cases less than 10% of an increase in enzyme or other biologically important molecular activity in the presence of the agent.

The ability to reduce enzyme activity can be a measure of the potency or the activity of an agent, or combination of agents, towards or against the enzyme or other biologically important molecular process. Potency can be measured by cell free, whole cell and/or in vivo assays in terms of IC50, Ki and/or ED50 values. An IC50 value represents the concentration of an agent required to inhibit enzyme activity by half (50%) under a given set of conditions. A Ki value represents the equilibrium affinity constant for the binding of an inhibiting agent to the enzyme or other relevant biomolecule. An ED50 value represents the dose of an agent required to affect a half-maximal response in a biological assay. Further details of these measures will be appreciated by those of ordinary skill in the art, and can be found in standard texts on biochemistry, enzymology, and the like.

The present disclosure also includes kits that can be used to treat neurological disorders. These kits comprise an agent or combination of agents that inhibits a neurological disorder associated biomarker or a neurological disease associated biomarkers and In some cases instructions teaching the use of the kit according to the various methods and approaches described herein. Such kits can also include information, such as scientific literature references, package insert materials, clinical trial results, and/or summaries of these and the like, which indicate or establish the activities and/or advantages of the agent. Such information can be based on the results of various studies, for example, studies using experimental animals involving in vivo models and studies based on human clinical trials. Kits described herein can be provided, marketed and/or promoted to health providers, including physicians, nurses, pharmacists, formulary officials, and the like.

Formulations, Routes of Administration, and Effective Doses

Yet another aspect of the present disclosure relates to formulations, routes of administration and effective doses for pharmaceutical compositions comprising an agent or combination of agents of the instant disclosure. Such pharmaceutical compositions can be used to treat a neurological disorder progression and a neurological disorder associated symptoms as described above.

Compounds of the disclosure can be administered as pharmaceutical formulations including those suitable for oral (including buccal and sub-lingual), rectal, nasal, topical, transdermal patch, pulmonary, vaginal, suppository, or parenteral (including intramuscular, intra-arterial, intrathecal, intradermal, intraperitoneal, subcutaneous and intravenous) administration or in a form suitable for administration by aerosolization, inhalation or insufflation. General information on drug delivery systems can be found in Ansel et al., Pharmaceutical Dosage Forms and Drug Delivery Systems (Lippencott Williams & Wilkins, Baltimore Md. (1999).

In various embodiments, the pharmaceutical composition can include carriers and excipients (including but not limited to buffers, carbohydrates, mannitol, polypeptides, amino acids, antioxidants, bacteriostats, chelating agents, suspending agents, thickening agents and/or preservatives), water, oils including those of petroleum, animal, vegetable or synthetic origin, such as peanut oil, soybean oil, mineral oil, sesame oil and the like, saline solutions, aqueous dextrose and glycerol solutions, flavoring agents, coloring agents, detackifiers and other acceptable additives, adjuvants, or binders, other pharmaceutically acceptable auxiliary substances to approximate physiological conditions, such as pH buffering agents, tonicity adjusting agents, emulsifying agents, wetting agents and the like. Examples of excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. In some cases, the pharmaceutical preparation is substantially free of preservatives. In other embodiments, the pharmaceutical preparation can contain at least one preservative. General methodology on pharmaceutical dosage forms is found in Ansel et al., Pharmaceutical Dosage Forms and Drug Delivery Systems (Lippencott, Williams, & Wilkins, Baltimore Md. (1999)). It can be recognized that, while any suitable carrier known to those of ordinary skill in the art can be employed to administer the compositions of this disclosure, the type of carrier can vary depending on the mode of administration.

A treatment agent can also be encapsulated within liposomes using well-known technology. Biodegradable microspheres can also be employed as carriers for the pharmaceutical compositions of this disclosure. Suitable biodegradable microspheres are disclosed, for example, in U.S. Pat. Nos. 4,897,268, 5,075,109, 5,928,647, 5,811,128, 5,820,883, 5,853,763, 5,814,344 and 5,942,252. In some cases, a treatment agent can be a compound.

A treatment can be administered in liposomes or microspheres (or microparticles). The treatments or their pharmaceutically acceptable salts can be provided alone or in combination with one or more other agents or with one or more other forms. For example, a formulation can comprise one or more agents in particular proportions, depending on the relative potencies of each agent and the intended indication. For example, in compositions for targeting two different targets, and where potencies are similar, about a 1:1 ratio of agents can be used. The two forms can be formulated together, in the same dosage unit e.g., in one cream, suppository, tablet, capsule, aerosol spray, or packet of powder to be dissolved in a beverage; or each form can be formulated in a separate unit, e.g., two creams, two suppositories, two tablets, two capsules, a tablet and a liquid for dissolving the tablet, two aerosol sprays, or a packet of powder and a liquid for dissolving the powder, etc.

The term "pharmaceutically acceptable salt" can mean those salts which retain the biological effectiveness and properties of the agents used in the present disclosure, and which are not biologically or otherwise undesirable. For example, a pharmaceutically acceptable salt does not interfere with the beneficial effect of a treatment of the disclosure in inhibiting a neurological disorder, neurological disorder associated biomarker or neurological disorder biomarker's components.

A treatment can be administered in combination with one or more other treatment, forms, and/or treatments, e.g., as described above. Pharmaceutical compositions comprising combinations of a neurological disorder associated biomarker inhibitors with one or more other active agents can be formulated to comprise certain molar ratios. For example, molar ratios of about 99:1 to about 1:99 of a neurological disorder associated biomarkers' inhibitors to the other active agent can be used. In some subset of the embodiments, the range of molar ratios of neurological disorder's associated biomarkers' inhibitors: other active agents are selected from about 80:20 to about 20:80; about 75:25 to about 25:75, about 70:30 to about 30:70, about 66:33 to about 33:66, about 60:40 to about 40:60; about 50:50; and about 90:10 to about 10:90. The molar ratio of neurological disorder's associated biomarkers' inhibitors: other active agents can be about 1:9, and in some cases can be about 1:1. The treatments can be formulated together, in the same dosage unit e.g., in one cream, suppository, tablet, capsule, or packet of powder to be dissolved in a beverage; or each treatment can be formulated in separate units, e.g., two creams, suppositories, tablets, two capsules, a tablet and a liquid for dissolving the tablet, an aerosol spray a packet of powder and a liquid for dissolving the powder, etc.

If necessary or desirable, the treatments or combinations of treatments can be administered with still other treatments. The choice of treatments that can be co-administered with the treatment and/or combinations of treatments of the instant disclosure can depend, at least in part, on the condition being treated. For example, the treatments disclosed herein can additionally contain one or more conventional anti-inflammatory drugs, such as an NSAID, e.g., ibuprofen, naproxen, acetaminophen, ketoprofen, or aspirin.

The treatment(s) (or pharmaceutically acceptable salts, esters or amides thereof) can be administered per se or in the form of a pharmaceutical composition wherein the active agent(s) is in an admixture or mixture with one or more pharmaceutically acceptable carriers. A pharmaceutical composition, as used herein, can be any composition prepared for administration to a subject. Pharmaceutical compositions for use in accordance with the present disclosure can be formulated in conventional manner using one or more physiologically acceptable carriers, comprising excipients, diluents, and/or auxiliaries, e.g., which facilitate processing of the active agents into preparations that can be administered. Proper formulation can depend at least in part upon the route of administration chosen. The treatment(s) useful in the present disclosure, or pharmaceutically acceptable salts, esters, or amides thereof, can be delivered to a subject using a number of routes or modes of administration, including oral, buccal, topical, rectal, transdermal, transmucosal, subcutaneous, intravenous, and intramuscular applications, as well as by inhalation.

The compounds of the disclosure can be formulated for parenteral administration (e.g., by injection, for example, bolus injection or continuous infusion) and can be presented in unit dose form in ampoules, pre-filled syringes, small volume infusion or in multi-dose containers with an added preservative. The compositions can take such forms as suspensions, solutions, or emulsions in oily or aqueous vehicles, for example, solutions in aqueous polyethylene glycol.

For injectable formulations, the vehicle can be chosen from those known in art to be suitable, including aqueous solutions or oil suspensions, or emulsions, with sesame oil, corn oil, cottonseed oil, or peanut oil, as well as elixirs, mannitol, dextrose, or a sterile aqueous solution, and similar pharmaceutical vehicles. The formulation can also comprise polymer compositions which are biocompatible, biodegradable, such as poly(lactic-co-glycolic)acid. These materials can be made into micro or nanospheres, loaded with drug and further coated or derivatized to provide superior sustained release performance. Vehicles suitable for periocular or intraocular injection include, for example, suspensions of therapeutic agent in injection grade water, liposomes and vehicles suitable for lipophilic substances. Other vehicles for periocular or intraocular injection are well known in the art.

The composition can be formulated in accordance with routine procedures as a pharmaceutical composition adapted for intravenous administration to human beings. Typically, compositions for intravenous administration are solutions in sterile isotonic aqueous buffer. Where necessary, the composition can also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients can be mixed prior to administration.

When administration is by injection, the active compound can be formulated in aqueous solutions, specifically in physiologically compatible buffers such as Hanks solution, Ringer's solution, or physiological saline buffer. The solution can contain formulatory agents such as suspending, stabilizing and/or dispersing agents. Alternatively, the active compound can be in powder form for constitution with a suitable vehicle, e.g., sterile pyrogen-free water, before use. In some cases, the pharmaceutical composition does not comprise an adjuvant or any other substance added to enhance the immune response stimulated by the peptide. The pharmaceutical composition can comprise a substance that inhibits an immune response to the peptide. Methods of formulation are known in the art, for example, as disclosed in Remington's Pharmaceutical Sciences, latest edition, Mack Publishing Co., Easton P.

In addition to the formulations described previously, the agents can also be formulated as a depot preparation. Such long acting formulations can be administered by implantation or transcutaneous delivery (for example, subcutaneously or intramuscularly), intramuscular injection or use of a transdermal patch. Thus, for example, the agents can be formulated with suitable polymeric or hydrophobic materials (for example, as an emulsion in acceptable oil) or ion exchange resins, or as sparingly soluble derivatives, for example, as a sparingly soluble salt.

Kits

Kits useful in the methods of the disclosure comprise components useful in any of the methods described herein, including for example, primers for nucleic acid amplification, hybridization probes for detecting genetic variation, or other marker detection, restriction enzymes, nucleic acid probes, optionally labeled with suitable labels, allele-specific oligonucleotides, antibodies that bind to an altered polypeptide encoded by a nucleic acid of the disclosure as described herein or to a wild type polypeptide encoded by a nucleic acid of the disclosure as described herein, means for amplification of genetic variations or fragments thereof, means for analyzing the nucleic acid sequence of nucleic acids comprising genetic variations as described herein, means for analyzing the amino acid sequence of a polypeptide encoded by a genetic variation, or a nucleic acid associated with a genetic variation, etc. The kits can for example, include necessary buffers, nucleic acid primers for amplifying nucleic acids, and reagents for allele-specific detection of the fragments amplified using such primers and necessary enzymes (e.g., DNA polymerase). Additionally, kits can provide reagents for assays to be used in combination with the methods of the present disclosure, for example, reagents for use with other screening assays for a neurological disorder.

The disclosure pertains to a kit for assaying a sample from a subject to detect the presence of a genetic variation, wherein the kit comprises reagents necessary for selectively detecting at least one particular genetic variation in the genome of the individual. In some aspects, the disclosure pertains to a kit for assaying a sample from a subject to detect the presence of at least particular allele of at least one polymorphism associated with a genetic variation in the genome of the subject. In some aspects, the reagents can comprise at least one contiguous oligonucleotide that hybridizes to a fragment of the genome of the individual comprising at least genetic variation. In some aspects, the reagents comprise at least one pair of oligonucleotides that hybridize to opposite strands of a genomic segment obtained from a subject, wherein each oligonucleotide primer pair is designed to selectively amplify a fragment of the genome of the individual that includes at least one genetic variation, or a fragment of a genetic variation. Such oligonucleotides or nucleic acids can be designed using the methods described herein. In some aspects, the kit comprises one or more labeled nucleic acids capable of allele-specific detection of one or more specific polymorphic markers or haplotypes with a genetic variation, and reagents for detection of the label. In some aspects, a kit for detecting SNP markers can comprise a detection oligonucleotide probe, that hybridizes to a segment of template DNA containing a SNP polymorphisms to be detected, an enhancer oligonucleotide probe, detection probe, primer and/or an endonuclease, for example, as described by Kutyavin et al. (Nucleic Acid Res. 34:e128 (2006)).

The DNA template is amplified by any means of the present disclosure, prior to assessment for the presence of specific genetic variations as described herein. Standard methods well known to the skilled person for performing these methods can be utilized, and are within scope of the disclosure. In one such embodiment, reagents for performing these methods can be included in the reagent kit.

In a further aspect of the present disclosure, a pharmaceutical pack (kit) is provided, the pack can comprise a therapeutic agent and a set of instructions for administration of the therapeutic agent to humans screened for one or more variants of the present disclosure, as disclosed herein. The therapeutic agent can be a small molecule drug, an antibody, a peptide, an antisense or RNAi molecule, or other therapeutic molecules as described herein. In some aspects, an individual identified as a carrier of at least one variant of the present disclosure is instructed to take a prescribed dose of the therapeutic agent. In one such embodiment, an individual identified as a carrier of at least one variant of the present disclosure is instructed to take a prescribed dose of the therapeutic agent. In some aspects, an individual identified as a non-carrier of at least one variant of the present disclosure is instructed to take a prescribed dose of the therapeutic agent.

Also provided herein are articles of manufacture, comprising a probe that hybridizes with a region of human chromosome as described herein and can be used to detect a polymorphism described herein. For example, any of the probes for detecting polymorphisms described herein can be combined with packaging material to generate articles of manufacture or kits. The kit can include one or more other elements including: instructions for use; and other reagents such as a label or an agent useful for attaching a label to the probe. Instructions for use can include instructions for screening applications of the probe for making a diagnosis, prognosis, or theranosis to a neurological disorder in a method described herein. Other instructions can include instructions for attaching a label to the probe, instructions for performing in situ analysis with the probe, and/or instructions for obtaining a nucleic acid sample to be analyzed from a subject. The kit can include a labeled probe that hybridizes to a region of human chromosome as described herein.

The kit can also include one or more additional reference or control probes that hybridize to the same chromosome or another chromosome or portion thereof that can have an abnormality associated with a particular endophenotype. A kit that includes additional probes can further include labels, e.g., one or more of the same or different labels for the probes. In other embodiments, the additional probe or probes provided with the kit can be a labeled probe or probes. When the kit further includes one or more additional probe or probes, the kit can further provide instructions for the use of the additional probe or probes. Kits for use in self-testing can also be provided. Such test kits can include devices and instructions that a subject can use to obtain a nucleic acid sample (e.g., buccal cells, blood) without the aid of a health care provider. For example, buccal cells can be obtained using a buccal swab or brush, or using mouthwash.

Kits as provided herein can also include a mailer (e.g., a postage paid envelope or mailing pack) that can be used to return the sample for analysis, e.g., to a laboratory. The kit can include one or more containers for the sample, or the sample can be in a standard blood collection vial. The kit can also include one or more of an informed consent form, a test requisition form, and instructions on how to use the kit in a method described herein. Methods for using such kits are also included herein. One or more of the forms (e.g., the test requisition form) and the container holding the nucleic acid sample can be coded, for example, with a bar code for identifying the subject who provided the sample.

An in vitro screening test can comprise one or more devices, tools, and equipment configured to collect a sample from an individual. In some aspects of an in vitro screening test, tools to collect a sample can include one or more of a swab, a scalpel, a syringe, a scraper, a container, and other devices and reagents designed to facilitate the collection, storage, and transport of a sample. In some aspects, an in vitro screening test can include reagents or solutions for collecting, stabilizing, storing, and processing a nucleic acid sample.

Such reagents and solutions for nucleotide collecting, stabilizing, storing, and processing are well known by those of skill in the art and can be indicated by specific methods used by an in vitro screening test as described herein. In some aspects, an in vitro screening test as disclosed herein, can comprise a microarray apparatus and reagents, a flow cell apparatus and reagents, a multiplex nucleotide sequencer and reagents, and additional hardware and software necessary to assay a nucleic acid sample for certain genetic markers and to detect and visualize certain genetic markers.

The present disclosure further relates to kits for using antibodies in the methods described herein. This includes, but is not limited to, kits for detecting the presence of a variant polypeptide in a test sample. One embodiment comprises antibodies such as a labeled or labelable antibody and a compound or agent for detecting variant polypeptides in a sample, means for determining the amount or the presence and/or absence of variant polypeptide in the sample, and means for comparing the amount of variant polypeptide in the nucleic acid sample with a standard, as well as instructions for use of the kit. In certain embodiments, the kit can further comprise a set of instructions for using the reagents comprising the kit.

It should be understood that the following examples should not be construed as being limiting to the particular methodology, protocols, and compositions, etc., described herein and, as such, can vary. The following terms used herein is for the purpose of describing particular embodiments only, and is not intended to limit the scope of the embodiments disclosed herein.

Methods of Screening for Treatment Compounds

The present disclosure further provides methods of screening compounds for the treatment of neurodegenerative diseases. As described herein, a "compound" can be a chemical molecule, a biological molecule, a monomer, a polymer, and/or a conjugate. A compound can comprise two or more elements associated together. The two or more elements can be different and associated via chemical bonds. A compound can modulate transcription level of at least one gene, a downstream responder, an upstream regulator in Table 8, a gene/protein that causes a genetic variant or is a result of a genetic variant, APOE, IL33, IL1RL1, APOE, IL33, or IL1RL1. A compound can modulate transcription and/or protein expression level of at least one metabolite, a downstream responder, and/or an upstream regulator in Table 9. It is understood by one of skill in the art that the examples provided herein can be with reference to the genes or proteins disclosed herein.

Disclosed herein are methods of screening compounds for the treatment of neurodegenerative diseases. Disclosed are methods of screening compounds for decreasing the expression of a gene/protein that causes a genetic variant or is a result of a genetic variant. In some embodiments, provided herein are methods of screening compounds for increasing the expression of a gene/protein that reduces a symptom of a genetic variant or is a result of a genetic variant. In some embodiments, provided herein are methods of screening compounds, in presence of which, expression of a gene/protein that reduces a symptom of a genetic variant or is a result of a genetic variant, can be unchanged relative to the expression in absence of the compound. In some embodiments, provided herein are methods of screening compounds, in presence of which, expression of a gene/protein that reduces a symptom of a genetic variant or is a result of a genetic variant, can be increased relative to the expression in absence of the compound. In some embodiments, provided herein are methods of screening compounds, in presence of which, expression of a gene/protein that reduces a symptom of a genetic variant or is a result of a genetic variant, can be reduced relative to the expression in absence of the compound. The screening method can comprise monitoring expression of a gene/protein that causes or is the result of a genetic variant in the presence and absence of a compound. A compound that reduces, prevents or otherwise inhibits expression of a gene/protein that causes a genetic variant or is a result of a genetic variant in comparison to expression of the gene/protein in the absence of such compound (and optionally in comparison to positive and other negative controls) can be indicative that the compound is a potential treatment for a neurodegenerative disease disclosed herein. The screening method can comprise monitoring a metabolite or a target gene disclosed in Table 8 or Table 9 in the presence and absence of a compound. The screening method can comprise monitoring APOE, IL33, IL1RL1, APOE, IL33, and/or IL1RL1 in the presence and absence of a compound.

The disclosed methods further contemplate in vitro methods of screening compounds for the treatment of neurodegenerative diseases, for example AD. More specifically, disclosed are methods for determining whether a compound can attenuate toxicity induced by a gene/protein that causes a genetic variant or is a result of a genetic variant. In particular embodiments, cultures, for example primary cultures (cortical neurons or glia cells), can be transiently transfected with wild-type or mutant genes and neuronal/glia toxicity can monitored in the presence and absence of a compound. Compounds that protects against wild-type and/or mutant gene toxicity can be identified as putative treatment for neurodegenerative diseases, for example AD. The disclosure further contemplates screening cells, for example primary cells reprogrammed into induced pluripotent stem cells and further differentiated into various brain cells, e.g. neurons, astrocytes, oligodendrocytes, glia, and primary cells that has transdifferentiated into various brain cells, e.g. neurons, astrocytes, oligodendrocytes, glia.

The present disclosure further relates to transgenic models. More specifically, the present disclosure relates to transgenic models expressing genetic variants disclosed herein, for example as listed in Table 1. The transgenic animals of the present disclosure, which express a mutant human gene/protein, can exhibit one or more cardinal phenotypes of a neurodegenerative disease disclosed herein. The term "animal" can refer to any animal (e.g., a mammal) including, but not limited to, humans, non-human primates, rodents (e.g., mice, rats, etc.), and the like. In particular embodiments, the present disclosure can comprise a transgenic mouse. The term "transgenic" is used in its ordinary sense, includes germline and non-germline expression of transgenes in animals, and further includes the expression of a gene in one or more cells of an animal.

In some instances, a transgenic non-human mammal genome can comprise a human wild-type gene. The present disclosure can further provide a transgenic non-human mammal whose genome comprises a human genetic variation disclosed herein, wherein expression of the gene creates a neurodegenerative disease like phenotype. In some cases, an expression of a genetic variation can be via the Herpes Simplex Virus Amplicon expression and delivery platform. A transgenic non-human mammal of the present disclosure may be a Herpes Simplex Virus ("HSV") amplicon-based model. The transgenic non-human mammal can be an HSV amplicon-based model. The transgenic mammals can be used to test whether compounds inhibits a gene/protein that causes a genetic variant or is a result of a genetic variant and rescue or protect against one or more AD-like phenotypes. In a specific embodiment, the transgenic mammals may be used to test whether a candidate compound is protective against AD symptoms. The method may comprise exposing a transgenic non-human mammal to an effective amount of a compound to modulate activity of a gene/protein that causes a genetic variant or is a result of a genetic variant, and determining whether the compound has a significant effect on the neurodegenerative disease-like phenotype of the transgenic non-human mammal as compared to a transgenic non-human mammal expressing wild-type or mutant a gene/protein that causes a genetic variant or is a result of a genetic variant that was not exposed to the compound. A compound that has an effect on the neurodegenerative disease-like phenotype of the transgenic non-human mammal induced by activity of the expressed a gene/protein that causes a genetic variant or is a result of a genetic variant can be identified.

The method can comprise exposing the transgenic non-human mammal to an environmental stressor to accelerate expression of a neurodegenerative disease-like phenotype, exposing the transgenic non-human mammal to an effective amount of a compound to modulate activity of a gene/protein that causes a genetic variant or is a result of a genetic variant, and determining whether the compound has a significant effect on the neurodegenerative disease-like phenotype of the transgenic non-human mammal as compared to a transgenic non-human mammal expressing wild-type or a gene/protein that causes a genetic variant or is a result of a genetic variant that was not exposed to the candidate compound. The environmental stressor can be any known stressor associated with a neurodegenerative disease, and includes any stressor that accelerates a neurodegenerative disease-like phenotype. Environmental stressors may include, but are not limited to, oxidative stress, insecticides, 1-methyl-4-phenyl-1,2,3,6-tetrahydropyridine, Nitro oxide (NO) donor, proteasome inhibitors, endocrine conditions, stroke, hypertension, diabetes, smoking, head trauma, depression, infection, tumors, vitamin deficiencies, immune and metabolic conditions, and chemical exposure.

In one aspect the transgenic model can be a transgenic nematode model. The nematode can belong to the subgenus *Caenorhabditis*. The nematode can be *Caenorhabditis elegans* ("*C. elegans*"). The disclosure can provide for a transgenic nematode whose genome comprises a human wild-type gene. The present disclosure can further provide a transgenic nematode whose genome comprises a human genetic variation, wherein expression of the gene creates a neurodegenerative disease-like phenotype.

In some aspects, a compound can modulate the genes that cause a genetic variant described herein by at least 10%, 20%, 30%, 40%, 50%, 60%, 70%, 80%, 90%, 95%, or 100% relative to an untreated control. According to one approach, compounds can be added at varying concentrations to the culture medium of cells expressing the genetic variants, target genes and metabolites disclosed herein, for example disclosed in Table 1, Table 3, Table 4, Table 7, or Table 8. Gene expression of the polypeptide can then be measured, for example, by standard Northern blot analysis using any appropriate fragment prepared from the nucleic acid molecule encoding the polypeptide as a hybridization probe or by real time PCR with appropriate primers, or methods disclosed herein. The level of gene expression in the presence of the compound can be compared to the level measured in a control culture medium lacking the compound. If desired, the effect of compounds may, in the alternative, be measured at the protein level using the same general approach and standard immunological techniques, such as Western blotting or immunoprecipitation with an antibody specific to the polypeptide for example. One of skill in the art would appreciate that any method disclosed herein can be used to detect gene expression and protein expression levels. For example, immunoassays may be used to detect or monitor the level of the polypeptides disclosed herein. Polyclonal or monoclonal antibodies which are capable of binding to such polypeptides may be used in any standard immunoassay format (e.g., ELISA or RIA assay) to measure protein levels of the polypeptide. The polypeptides can also be measured using mass spectroscopy, high performance liquid chromatography, spectrophotometric or fluorometric techniques, or combinations thereof.

In another case, expression of a reporter gene that is operably linked to the promoter of a gene/protein that causes a genetic variant or is a result of a genetic variant, can also be used to identify a compound for treating or preventing a neurodegenerative disease, for example AD. Assays employing the detection of reporter gene products are sensitive and readily amenable to automation, hence making them ideal for the design of high-throughput screens. Assays for reporter genes may employ, for example, calorimetric, chemiluminescent, or fluorometric detection of reporter gene products. Many varieties of plasmid and viral vectors containing reporter gene cassettes are easily obtained. Such vectors contain cassettes encoding reporter genes such as lacZ/β-galactosidase, green fluorescent protein, and luciferase, among others. A genomic DNA fragment carrying a selected transcriptional control region (e.g., a promoter and/or enhancer) can be first cloned using standard approaches. The DNA carrying the selected transcriptional control region is then inserted, by DNA subcloning, into a reporter vector, thereby placing a vector-encoded reporter gene under the control of that transcriptional control region. The activity of the selected transcriptional control region operably linked to the reporter gene can then be directly observed and quantified as a function of reporter gene activity in a reporter gene assay. In one embodiment, for example, the transcriptional control region could be cloned upstream from a luciferase reporter gene within a reporter vector. This could be introduced into the test cells, along with an internal control reporter vector (e.g., a lacZ gene under the transcriptional regulation of the (3-actin promoter). After the cells are exposed to the test compounds, reporter gene activity can be measured and the reporter gene activity is normalized to internal control reporter gene activity. By "operably linked" can be meant that a nucleic acid molecule and one or more regulatory sequences (e.g., a promoter) are connected in such a way as to permit expression of the gene product (i.e., RNA) when the appropriate molecules (e.g., transcriptional activator proteins) are bound to the regulatory sequences.

In another case, a compound can be tested for its ability to modulate the biological activity of one or more a gene/protein that causes a genetic variant or is a result of a genetic variant in cells that naturally express such a polypeptide, after transfection with a cDNA for this polypeptide, or in cell-free solutions containing the polypeptide. Accordingly, compounds can be first contacted with a polypeptide from either disclosed herein, having some level of a characteristic biological activity (including cell survival). The exact level of activity is unimportant and may be at least 10%, 20%, 30%, 40%, 50%, 60%, 70%, 80%, 90%, 100%, or more than 100% of the biological activity of the naturally-occurring, wild-type polypeptide. The effect of a compound on the activity of the polypeptide can be tested by radioactive and non-radioactive binding assays, competition assays, and receptor signaling assays.

The present disclosure can provide methods of screening compounds for the treatment of neurodegenerative diseases, for example, acetylcholinesterase inhibitor, glutamate receptor blocker, donepezil, galantamine, rivastigmine, and/or any medicament suitable for treating Alzheimer's disease.

The disclosure is further illustrated by the following examples which should not be construed as limiting. The examples are illustrative only, and are not intended to limit, in any manner, any of the aspects described herein.

EXAMPLES

The following examples illustrate some embodiments and aspects of the disclosure. It will be apparent to those skilled in the relevant art that various modifications, additions, substitutions, and the like can be performed without altering the spirit or scope of the disclosure, and such modifications and variations are encompassed within the scope of the disclosure as defined in the claims which follow. The following examples do not in any way limit the disclosure.

Example 1—Genetic Variations Associated with AD in East Asian Population

Study Cohort and Subject Recruitment

A cohort of Chinese subjects was recruited to this study from 2007 to 2016 at the Department of Neurology, Huashan Hospital, Fudan University, Shanghai, China. There were 1,654 subjects (mean age: 69.8 years): 662 with AD, 403 with MCI, and 589 age- and gender-matched normal controls (NCs). AD patients were diagnosed on the basis of recommendations from the National Institute on Aging and the Alzheimer's Association workgroup_(McKhann et al., 2011), and had an onset age ≥50 years. MCI patients were diagnosed according to the Peterson criteria (Peteren, 2004). Individuals with any significant neurologic disease or psychiatric disorder was excluded. 250 NCs without subjective memory complaints were recruited from the community in Shanghai. The other subjects were recruited from the memory clinic and underwent laboratory screening. All recruited subjects underwent medical history assessment, neuropsychological assessment, and imaging assessment including computed tomography (CT) or magnetic resonance imaging (MRI). Some participants further undertook positron emission tomography (PET) using Pittsburgh compound B (PiB). This study was approved by the Ethics Committee of Huashan Hospital, The Hong Kong University of Science and Technology, and the HKUST Shenzhen Research Institute. All the subjects provided written informed consent for both study enrollment and sample collection. A total of 1,222 subjects (NC: 473, MCI: 260, AD: 489) passed the final quality control for the WGS library construction. Furthermore, an additional 1,737 multi-center non-AD controls from mainland China were included for the analysis.

Whole Genome Sequencing

Low-coverage whole genome sequencing (5×) was performed by Novogene Co., Ltd. In brief, genomic DNA purity was checked by a NanoPhotometer® spectrophotometer, the concentration was measured using a Qubit® DNA Assay Kit with a Qubit® 2.0 Fluorometer, and fragment distribution was measured using the DNA Nano 6000 Assay Kit with the Agilent Bioanalyzer 2100 system. DNA (1.5 µg) of each sample was fragmented by sonication to 350 bp and used to generate a sequencing library with the Truseq Nano DNA HT Sample preparation Kit (Illumina). The genomic DNA libraries were sequenced on an Illumina Hiseq X Ten platform, and paired-end reads were generated. Adapter contamination and low-quality reads were filtered from the raw data to ensure data quality; producing clean data with base quality greater than Q20 for the majority of the detected signals, and the fraction of Q30 was above 80%. The phenotypic labels were blinded for the researchers during the WGS process.

Specialized Variant Detection Protocol for Low-Pass WGS Cohort Data

A Gotcloud (Jun et al., 2015) pipeline was adapted to detect refine variants from the raw sequencing data of 1,348 samples (including 126 re-sequenced samples). An average of 15 GB Illumina sequencing data per subject was mapped to the GRCh37 reference genome containing the decoy fragments. A total of 24,742,555 SNPs were detected by glfmultiples after the initial calling steps. Hard-filter or SVM-based filtering methods were implemented in the Gotcloud pipeline using default settings of VcfCooker or Perl scripts (run_libsvm.pl) to filter low-confident calling of variants based on site information such as depth, allele balance, mapping quality, together with high-quality dataset derived from 1000 genome project or Hapmap project. Variants with high-confident calls in the range of MAF≥5% (n=4,481,200; 18.1% of raw detected sites) were subjected to Beagle (Browning and Browning, 2007; Browning and Browning, 2009) for pre-phasing and pre-imputation. Phased variants were subsequently subjected to Thunder (Li et al., 2010) to refine the variants detected during the discovery phase. In the refinement step for each candidate loci, all raw variants in the 50-kb range near the candidate gene were extracted and submitted to the same variant calling strategy with no additional filtering.

QTL Analysis Based on Database Evidences of Known GWAS Hits

A variant pool of 147 (Table 7) SNPs located in the AD susceptibility loci was submitted to a batch query of the PhenoScanner database for the annotation of known GWAS hits for possible regulations at transcript or metabolite levels. Data were collected and displayed as tables.

Model Construction for the AD Prediction

A variant pool of 147 (Table 7) SNPs located in the AD susceptibility loci were used for the construction of GRS models (FIG. 1). Briefly, FIG. 1 shows workflow for construction of GRS and the mathematical modeling on the prediction of AD. Genotype information for the cases and controls were collected for the association test, and the variant pools for AD were analyzed and determined based on the association results at single site levels. Genotype dosages, weighted by the relative risk effects of each identified susceptibility variants for AD in variant pools, were combined to generate GRS, which are subjected to modelling for the classification/prediction of AD. In the following descriptions, the models are generalized using mathematic symbols and formulas.

Genotype Matrix (G)

For a candidate variant pool containing M variants across N individuals with no missing values, the numeric matrix $G_{MN}$ were used to store the individual genotype dosage for M variants in a cohort of N subjects. Specifically, for numeric matrix $G_{MN}$, the ith row records the individual genotype information for the ith variants, and jth column records the genotype information of jth individuals. Notably, the for any element in $G_{MN}$ ($G_{ij}$ for arbitrary i,j when i belongs to [1,M] and i belongs to [1,N]), $G_{ij}$ belongs to {0, 1, 2}, with the value indicating the minor allele counts at the ith site for jth individual.

Genotype Weight Matrix (B)

To estimate relative risk for the variants from the aforementioned variant pools, the quantitative estimation of risk for AD at the single variant level was obtained. A logistic regression model taking the binary phenotype labels ({0,1| 1 for AD==True}) with age adjustment was designed to estimate the relative risk for each variants, and the corresponding beta ($B_i$) for the effective allele (ith) was recorded to generate genotype weight matrix (1 row, M columns).

$$\text{Phenotype} \sim \text{logit}(B_i * G_i * + A * \text{Age}) \text{ For obtaining } B_i$$

Generate the GRS Score (S)

Based on the aforementioned genotype matrix (G) and genotype weight matrix (B), the individual genetic risk score could be derived from the multiplication of two matrixes:

$$B_{1M} * (G_{MN} - 1) = S_{1N}$$

And S is a numeric matrix with 1 row and N columns, with ith element denoting the corresponding genotype risk score (GRS) for the ith individual.

Classification of Individuals Based on GRS Score

A mixed Gaussian model was used for the fitting of the GRS density distribution, together with the estimation of proportions for each sub-category corresponding to the low, medium or high value of the mean GRS. Model 1 was obtained when using K=2 for the GRS fitting in the non-AD groups, and model 2 was obtained when using K=3 for the GRS fitting in the AD groups; Model 1 and model 2 were used as the probability density functions for the GRS score in AD and non-AD populations.

Furthermore, a population frequency of AD was defined as 5%, so as to introduce the Naïve Bayesian classifier for classifying the GRS score. Once the predication and theoretical values converge, it is an indication that the classification process is complete.

Evaluation of GRS Model on Prediction of AD

The evaluations were accomplished in two aspects: (1) demonstrating that the high risk category (with a higher GRS) has a higher risk for developing AD as well as MCI (FIG. 2 and Table 10); and (2) demonstrating that the GRS value could have better performance for predicting AD when compared with using the APOE-ε4 site. This is suggested by both the ROC (receiver operating characteristic) curve and the AUC (Area Under the Curve) value generated by the subsampling of cases and controls for a logistic regression model taking binary phenotypes as outcome and GRS as input (FIG. 2).

$$\text{Phenotype} \sim \text{logit}(S)$$

In FIG. 2, the application of aforementioned model with pilot data set of Chinese WGS data. (FIG. 2A) Density plot for GRS across different phenotypes (AD, Alzheimer's disease; MCI, mild cognitive impairment; NC, normal control; Non-AD, non-Alzheimer's disease). The AD group of individuals was found to be shifted to the high risk score area. (FIG. 2B) GRS was out-performed when compared with that using the APOE-ε4 dosage alone for the prediction of AD (indicated by the ROC curve and the corresponding AUC values. (FIG. 2C) Dot plot for the distribution of low, medium and high risk categories in each phenotypic group (the 3 risk categories of GRS were classified using Bayesian model).

Results

A two-stage association pilot study was conducted to identify AD-associated variants in a cohort comprising 477 subjects with AD, 260 subjects with MCI, and 422 control subjects (Table 6). A total of 1,222 participants (n=1,222) including 489 Alzheimer's disease patients (AD; n=489), 260 subjects with mild-cognitive impairment (MCI; n=260), and 473 corresponding age- and gender-matched normal controls (NC; n=473) were recruited from mainland China for the pilot study aimed at identifying AD susceptibility loci in the Chinese population. Individuals with a history of neurological diseases or psychiatric disorders were excluded. Genomic DNA was extracted from whole blood of an individual and subjected to whole-genome sequencing (WGS) analysis for the association study. WGS data of 1,737 non-AD Chinese control subjects was obtained from the public database for comparison.

TABLE 6

Cohort information

| | Participants included in the pilot study (N = 1,222) | | |
|---|---|---|---|
| | NC (N = 473) | MCI (N = 260) | AD (N = 489) |
| Female (%) | 249 (53.1%) | 122 (47.2%) | 263 (53.8%) |
| Age/years (±SD) | 68.2 (±9.2) | 69.7 (±7.8) | 69.3 (±8.9) |
| APOE-ε4 carriers (%) | 100 (21.1%) | 82 (31.5%) | 219 (44.8%) |
| APOE-ε4 frequency (Allele number/%) | 108 (11.4%) | 95 (18.3%) | 271 (27.7%) |
| APOE-ε2 frequency (Allele number/%) | 77 (8.1%) | 32 (6.2%) | 34 (3.5%) |
| MMSE score (±SD) | 28.0 (±2.4) | 26.4 (±2.0) | 14.6 (±6.5) |

Genomic DNA from these individuals was subjected to low-pass whole-genome sequencing (WGS) (5×), and Gotcloud pipeline was used for variant calling and refinements. In the stage 1 association test, the aim was to identify AD susceptibly variants or loci, with a variant pool containing 3,492,083 sites with minor allele frequency (MAF) on or above 10%. Results returned 350 variants with nominal p-values less then 1E-4. Genotype information from a multi-center control cohort obtained from a non-AD control Chinese WGS dataset (N=1737, with proper filtering) were further included for the stage 2 analysis, in which 286 out of 350 sites were successfully detected and served as high-confident results, with 72 sites surviving from the same nominal p-value threshold of 1E-4. A genome-wide threshold of 1E-7 was applied to this pool of variants and finally 44 variants tagged by 8 sentinel variants located in 8 loci as the AD susceptibly variants were obtained in the Chinese AD cohort. Notably, no inflation was observed during stage 1 analysis, as suggested by the estimated genomic inflation factor ($\lambda GC=1.01$).

The variant pools were further expanded by taking other variants in linkage-disequilibrium with the 44 identified AD risk variants using pairwise $r^2 \geq 0.6$ as inclusion criteria, yielding a final variant pool of 147 SNPs located in 8 AD susceptibility loci (Table 7).

TABLE 7

The 147 candidate sites in the 8 AD susceptibility loci that are associated with AD

| # | CHR | BP (hg19) | rsID | EA | EAF | Beta | OR | P-value (adjusted for age) |
|---|---|---|---|---|---|---|---|---|
| 1 | 9 | 110869664 | rs9657650 | T | 0.07 | 0.15 | 1.16 | 3.50E−01 |
| 2 | 9 | 110869771 | rs9657651 | T | 0.07 | 0.14 | 1.15 | 3.70E−01 |
| 3 | 9 | 110875895 | rs10979217 | G | 0.07 | 0.11 | 1.12 | 4.90E−01 |
| 4 | 9 | 110879938 | rs12339504 | G | 0.07 | 0.57 | 1.77 | 1.10E−05 |
| 5 | 11 | 132721752 | rs78237068 | C | 0.14 | 0.14 | 1.15 | 2.30E−01 |
| 6 | 11 | 132722296 | rs35338085 | T | 0.14 | 0.15 | 1.16 | 2.00E−01 |
| 7 | 11 | 132724689 | rs11223248 | A | 0.13 | 0.16 | 1.18 | 1.60E−01 |
| 8 | 11 | 132726348 | rs74762471 | A | 0.14 | 0.15 | 1.16 | 2.10E−01 |
| 9 | 11 | 132726418 | rs76589214 | G | 0.14 | 0.15 | 1.16 | 2.00E−01 |
| 10 | 11 | 132728215 | rs11223250 | A | 0.16 | 0.03 | 1.03 | 7.70E−01 |
| 11 | 11 | 132728786 | rs11223251 | G | 0.16 | 0.05 | 1.05 | 6.80E−01 |
| 12 | 11 | 132731743 | rs11603664 | C | 0.17 | 0.68 | 1.97 | 8.90E−15 |
| 13 | 11 | 132734896 | rs11605454 | G | 0.16 | −0.05 | 0.95 | 6.30E−01 |
| 14 | 11 | 132735347 | rs11223254 | G | 0.15 | −0.03 | 0.97 | 7.90E−01 |
| 15 | 11 | 132736190 | rs11223255 | A | 0.15 | −0.04 | 0.96 | 7.10E−01 |
| 16 | 11 | 132736979 | rs73041479 | C | 0.15 | −0.02 | 0.98 | 8.70E−01 |
| 17 | 14 | 55297043 | rs72713460 | T | 0.1 | 0.59 | 1.8 | 4.20E−07 |
| 18 | 14 | 55301494 | rs57875940 | A | 0.1 | 0.57 | 1.78 | 8.70E−07 |
| 19 | 14 | 55330064 | rs150825385 | T | 0.12 | 0.45 | 1.57 | 1.00E−04 |
| 20 | 14 | 55331772 | rs55935131 | G | 0.12 | 0.43 | 1.54 | 2.30E−04 |
| 21 | 14 | 55335389 | rs2878170 | A | 0.11 | 0.44 | 1.55 | 2.10E−04 |
| 22 | 14 | 55338256 | rs115448952 | G | 0.12 | 0.43 | 1.53 | 3.40E−04 |
| 23 | 14 | 55338340 | rs148308391 | T | 0.12 | 0.43 | 1.53 | 3.40E−04 |
| 24 | 14 | 55339327 | rs150918078 | T | 0.11 | 0.45 | 1.57 | 1.40E−04 |
| 25 | 14 | 55340311 | rs146123422 | A | 0.11 | 0.45 | 1.57 | 1.50E−04 |
| 26 | 14 | 55343107 | rs60851395 | A | 0.11 | 0.44 | 1.56 | 1.90E−04 |
| 27 | 14 | 55343344 | rs59750960 | G | 0.1 | 0.52 | 1.68 | 1.40E−05 |
| 28 | 14 | 55346129 | rs55881030 | G | 0.11 | 0.52 | 1.68 | 1.10E−05 |
| 29 | 14 | 55347786 | rs111537263 | A | 0.1 | 0.48 | 1.61 | 8.40E−05 |
| 30 | 14 | 55347916 | rs3825610 | A | 0.11 | 0.43 | 1.53 | 4.10E−04 |
| 31 | 14 | 55348666 | rs3783639 | C | 0.11 | 0.42 | 1.53 | 5.00E−04 |
| 32 | 14 | 55349549 | rs11626210 | T | 0.11 | 0.42 | 1.53 | 4.80E−04 |
| 33 | 14 | 55351179 | rs56013432 | C | 0.11 | 0.47 | 1.6 | 6.10E−05 |
| 34 | 14 | 55351266 | rs58293795 | C | 0.11 | 0.41 | 1.51 | 6.70E−04 |
| 35 | 14 | 55351579 | rs67620272 | C | 0.11 | 0.42 | 1.52 | 5.70E−04 |
| 36 | 14 | 55352041 | rs72713477 | C | 0.11 | 0.41 | 1.51 | 6.30E−04 |
| 37 | 14 | 55353368 | rs8020798 | T | 0.11 | 0.41 | 1.51 | 6.30E−04 |
| 38 | 14 | 55356525 | rs17128052 | C | 0.11 | 0.43 | 1.53 | 4.20E−04 |
| 39 | 14 | 55357502 | rs34544088 | A | 0.12 | 0.42 | 1.52 | 3.40E−04 |
| 40 | 14 | 55357742 | rs57095876 | G | 0.11 | 0.4 | 1.49 | 8.40E−04 |
| 41 | 14 | 55358877 | rs7147201 | G | 0.12 | 0.42 | 1.52 | 2.90E−04 |
| 42 | 14 | 55360139 | rs3783641 | A | 0.12 | 0.43 | 1.54 | 1.80E−04 |
| 43 | 14 | 55360836 | rs72713482 | A | 0.11 | 0.42 | 1.53 | 4.50E−04 |
| 44 | 14 | 55361836 | rs8017210 | A | 0.12 | 0.42 | 1.52 | 2.60E−04 |
| 45 | 15 | 98926694 | rs11247317 | G | 0.34 | 0.2 | 1.22 | 1.80E−02 |
| 46 | 15 | 98935519 | rs12442709 | G | 0.36 | 0.44 | 1.56 | 1.10E−07 |
| 47 | 18 | 3187860 | rs12606254 | T | 0.2 | −0.75 | 0.47 | 7.10E−09 |
| 48 | 18 | 3188976 | rs1962519 | A | 0.16 | −0.12 | 0.89 | 2.90E−01 |
| 49 | 18 | 3191354 | rs4797101 | G | 0.16 | −0.06 | 0.94 | 5.70E−01 |
| 50 | 19 | 3184303 | rs522941 | A | 0.43 | −0.15 | 0.86 | 7.00E−02 |
| 51 | 19 | 3184630 | rs525761 | G | 0.43 | −0.15 | 0.86 | 7.20E−02 |
| 52 | 19 | 3185553 | rs507872 | G | 0.43 | −0.16 | 0.86 | 6.80E−02 |
| 53 | 19 | 3185563 | rs507905 | C | 0.43 | −0.16 | 0.85 | 5.90E−02 |
| 54 | 19 | 3185636 | rs556075 | T | 0.43 | −0.16 | 0.85 | 5.70E−02 |
| 55 | 19 | 3185874 | rs510724 | C | 0.43 | −0.14 | 0.87 | 9.30E−02 |
| 56 | 19 | 3186085 | rs11551095 | G | 0.43 | −0.15 | 0.86 | 7.00E−02 |
| 57 | 19 | 3186493 | rs537248 | T | 0.43 | −0.15 | 0.86 | 8.00E−02 |
| 58 | 19 | 3187386 | rs566476 | T | 0.43 | −0.14 | 0.87 | 9.90E−02 |
| 59 | 19 | 3189634 | rs490218 | T | 0.43 | −0.13 | 0.88 | 1.30E−01 |
| 60 | 19 | 3189652 | rs518669 | C | 0.43 | −0.09 | 0.91 | 2.80E−01 |
| 61 | 19 | 3190737 | rs11669999 | G | 0.43 | −0.15 | 0.86 | 8.00E−02 |
| 62 | 19 | 3191032 | rs475814 | T | 0.43 | −0.15 | 0.86 | 7.00E−02 |
| 63 | 19 | 3191068 | rs545850 | T | 0.43 | −0.13 | 0.87 | 1.10E−01 |

TABLE 7-continued

The 147 candidate sites in the 8 AD susceptibility loci that are associated with AD

| # | CHR | BP (hg19) | rsID | EA | EAF | Beta | OR | P-value (adjusted for age) |
|---|---|---|---|---|---|---|---|---|
| 64 | 19 | 3191089 | rs545909 | C | 0.45 | −0.13 | 0.88 | 1.20E−01 |
| 65 | 19 | 3191187 | rs477511 | T | 0.43 | −0.15 | 0.86 | 6.80E−02 |
| 66 | 19 | 3192116 | rs507218 | G | 0.43 | −0.14 | 0.87 | 9.70E−02 |
| 67 | 19 | 3192277 | rs529910 | T | 0.43 | −0.14 | 0.87 | 1.10E−01 |
| 68 | 19 | 3192280 | rs529914 | T | 0.43 | −0.13 | 0.88 | 1.20E−01 |
| 69 | 19 | 3195243 | rs311614 | G | 0.43 | −0.14 | 0.87 | 9.80E−02 |
| 70 | 19 | 3196533 | rs311616 | A | 0.49 | −0.23 | 0.8 | 7.40E−03 |
| 71 | 19 | 3196790 | rs13382069 | A | 0.41 | −0.24 | 0.79 | 6.10E−03 |
| 72 | 19 | 3196999 | rs186339 | G | 0.49 | −0.22 | 0.8 | 9.00E−03 |
| 73 | 19 | 3197210 | rs311618 | A | 0.49 | −0.23 | 0.79 | 5.60E−03 |
| 74 | 19 | 3198405 | rs149256323 | T | 0.41 | −0.24 | 0.79 | 5.80E−03 |
| 75 | 19 | 3198517 | rs4806915 | A | 0.47 | −0.53 | 0.59 | 5.70E−10 |
| 76 | 19 | 3198532 | rs4806916 | A | 0.48 | −0.31 | 0.74 | 1.80E−04 |
| 77 | 19 | 3198695 | rs311620 | C | 0.49 | −0.22 | 0.8 | 7.40E−03 |
| 78 | 19 | 3198777 | rs311621 | A | 0.49 | −0.23 | 0.8 | 6.20E−03 |
| 79 | 19 | 3199068 | rs2304249 | A | 0.41 | −0.21 | 0.81 | 1.60E−02 |
| 80 | 19 | 3199945 | rs519271 | T | 0.49 | −0.23 | 0.8 | 7.10E−03 |
| 81 | 19 | 3200790 | rs311622 | G | 0.43 | 0.16 | 1.17 | 6.60E−02 |
| 82 | 19 | 3200870 | rs311623 | C | 0.43 | 0.16 | 1.17 | 6.50E−02 |
| 83 | 19 | 3201323 | rs311624 | T | 0.43 | 0.15 | 1.17 | 6.80E−02 |
| 84 | 19 | 3201480 | rs1978729 | A | 0.41 | −0.21 | 0.81 | 1.60E−02 |
| 85 | 19 | 3203115 | rs59377097 | C | 0.41 | −0.21 | 0.81 | 1.60E−02 |
| 86 | 19 | 3204159 | rs28372911 | C | 0.41 | −0.19 | 0.83 | 2.70E−02 |
| 87 | 19 | 3208430 | rs312072 | C | 0.42 | 0.15 | 1.16 | 8.60E−02 |
| 88 | 19 | 3208890 | rs312074 | C | 0.42 | 0.14 | 1.16 | 8.80E−02 |
| 89 | 19 | 45372794 | rs404935 | A | 0.14 | 0.89 | 2.44 | 4.80E−20 |
| 90 | 19 | 45373565 | rs395908 | A | 0.14 | 0.88 | 2.41 | 5.80E−19 |
| 91 | 19 | 45376284 | rs519113 | G | 0.13 | 0.93 | 2.53 | 9.90E−21 |
| 92 | 19 | 45378144 | rs34278513 | T | 0.14 | 0.84 | 2.32 | 4.30E−17 |
| 93 | 19 | 45379516 | rs412776 | A | 0.14 | 0.91 | 2.49 | 3.30E−20 |
| 94 | 19 | 45380961 | rs3865427 | A | 0.13 | 0.87 | 2.4 | 3.40E−18 |
| 95 | 19 | 45380970 | rs11668861 | G | 0.2 | 0.59 | 1.81 | 1.70E−10 |
| 96 | 19 | 45382034 | rs6859 | A | 0.22 | 0.63 | 1.87 | 9.20E−12 |
| 97 | 19 | 45382966 | rs3852860 | C | 0.22 | 0.57 | 1.76 | 5.80E−10 |
| 98 | 19 | 45383061 | rs3852861 | G | 0.22 | 0.61 | 1.84 | 1.30E−11 |
| 99 | 19 | 45383079 | rs71352237 | C | 0.12 | 0.87 | 2.38 | 7.70E−18 |
| 100 | 19 | 45383115 | rs34224078 | G | 0.12 | 0.88 | 2.4 | 4.00E−18 |
| 101 | 19 | 45383139 | rs35879138 | A | 0.12 | 0.87 | 2.39 | 6.90E−18 |
| 102 | 19 | 45387459 | rs12972156 | G | 0.1 | 1.06 | 2.88 | 6.00E−23 |
| 103 | 19 | 45387596 | rs12972970 | A | 0.1 | 1.04 | 2.83 | 3.60E−22 |
| 104 | 19 | 45388130 | rs34342646 | A | 0.1 | 1.05 | 2.85 | 1.50E−22 |
| 105 | 19 | 45388500 | rs283811 | G | 0.18 | 0.72 | 2.05 | 3.60E−14 |
| 106 | 19 | 45388568 | rs283812 | C | 0.16 | 0.81 | 2.24 | 1.40E−17 |
| 107 | 19 | 45390333 | rs283815 | G | 0.19 | 0.66 | 1.93 | 5.10E−12 |
| 108 | 19 | 45392254 | rs6857 | T | 0.1 | 1.08 | 2.96 | 3.20E−24 |
| 109 | 19 | 45394336 | rs71352238 | C | 0.1 | 1.09 | 2.97 | 2.00E−24 |
| 110 | 19 | 45394969 | rs184017 | G | 0.19 | 0.73 | 2.07 | 1.10E−14 |
| 111 | 19 | 45395266 | rs157580 | A | 0.41 | 0.42 | 1.52 | 7.50E−07 |
| 112 | 19 | 45395619 | rs2075650 | G | 0.1 | 1.09 | 2.96 | 2.60E−24 |
| 113 | 19 | 45395714 | rs157581 | C | 0.21 | 0.74 | 2.09 | 8.40E−16 |
| 114 | 19 | 45395909 | rs34404554 | G | 0.1 | 1.09 | 2.97 | 1.60E−24 |
| 115 | 19 | 45396144 | rs11556505 | T | 0.1 | 1.09 | 2.97 | 1.80E−24 |
| 116 | 19 | 45396219 | rs157582 | T | 0.19 | 0.65 | 1.92 | 4.40E−12 |
| 117 | 19 | 45396665 | rs59007384 | T | 0.18 | 0.71 | 2.02 | 6.80E−14 |
| 118 | 19 | 45404691 | rs405697 | G | 0.39 | 0.51 | 1.66 | 1.80E−09 |
| 119 | 19 | 45406673 | rs10119 | A | 0.1 | 1.21 | 3.35 | 8.00E−31 |
| 120 | 19 | 45408836 | rs405509 | G | 0.28 | −0.32 | 0.73 | 1.10E−03 |
| 121 | 19 | 45409167 | rs440446 | G | 0.38 | 0.5 | 1.65 | 2.50E−09 |
| 122 | 19 | 45410002 | rs769449 | A | 0.09 | 1.16 | 3.21 | 3.20E−27 |
| 123 | 19 | 45411941 | rs429358 | C | 0.08 | 1.28 | 3.6 | 9.20E−34 |
| 124 | 19 | 45413576 | rs75627662 | T | 0.19 | 0.74 | 2.09 | 1.40E−15 |
| 125 | 19 | 45414451 | rs439401 | C | 0.41 | 0.52 | 1.68 | 1.10E−09 |
| 126 | 19 | 45415713 | rs10414043 | A | 0.11 | 1.1 | 3.01 | 3.70E−26 |
| 127 | 19 | 45415935 | rs7256200 | T | 0.11 | 1.09 | 2.99 | 1.00E−25 |
| 128 | 19 | 45416178 | rs483082 | T | 0.19 | 0.72 | 2.06 | 4.60E−15 |
| 129 | 19 | 45416478 | rs584007 | G | 0.4 | 0.52 | 1.68 | 1.20E−09 |
| 130 | 19 | 45416741 | rs438811 | T | 0.19 | 0.72 | 2.06 | 4.50E−15 |
| 131 | 19 | 45418790 | rs5117 | C | 0.18 | 0.65 | 1.91 | 2.80E−12 |
| 132 | 19 | 45418961 | rs3826688 | C | 0.4 | 0.5 | 1.65 | 3.10E−09 |
| 133 | 19 | 45420082 | rs73052335 | C | 0.11 | 1.11 | 3.05 | 7.80E−31 |
| 134 | 19 | 45421254 | rs12721046 | A | 0.11 | 1.2 | 3.32 | 3.40E−32 |
| 135 | 19 | 45421877 | rs484195 | G | 0.4 | 0.52 | 1.68 | 1.50E−09 |
| 136 | 19 | 45422160 | rs12721051 | G | 0.12 | 1.13 | 3.09 | 5.60E−29 |
| 137 | 19 | 45422846 | rs56131196 | A | 0.12 | 1.13 | 3.1 | 3.60E−29 |
| 138 | 19 | 45422946 | rs4420638 | G | 0.12 | 1.12 | 3.06 | 1.50E−28 |

TABLE 7-continued

The 147 candidate sites in the 8 AD susceptibility loci that are associated with AD

| # | CHR | BP (hg19) | rsID | EA | EAF | Beta | OR | P-value (adjusted for age) |
|---|---|---|---|---|---|---|---|---|
| 139 | 19 | 45425175 | rs157594 | G | 0.39 | 0.54 | 1.72 | 1.80E−10 |
| 140 | 19 | 45425460 | rs157595 | G | 0.4 | 0.54 | 1.71 | 3.30E−10 |
| 141 | 19 | 45427125 | rs111789331 | A | 0.11 | 1.02 | 2.76 | 9.50E−23 |
| 142 | 19 | 45428234 | rs66626994 | A | 0.11 | 1.03 | 2.79 | 4.10E−23 |
| 143 | 19 | 45429708 | rs60049679 | C | 0.11 | 0.82 | 2.28 | 6.70E−15 |
| 144 | 21 | 39634196 | rs2836255 | G | 0.15 | 0.46 | 1.58 | 1.20E−05 |
| 145 | 21 | 39636309 | rs7275784 | T | 0.15 | 0.46 | 1.58 | 1.10E−05 |
| 146 | 21 | 39663760 | rs928771 | G | 0.16 | 0.5 | 1.65 | 8.40E−07 |
| 147 | 21 | 39664976 | rs2836293 | A | 0.16 | 0.51 | 1.66 | 4.80E−07 |

CHR, chromosome; BP, hg19 coordinate in base pair; EA, effective alleles; EAF, effective allele frequency; OR, odds ratio. 147 variants were selected as including or in LD (pairwise $r^2 \geq 0.6$) with the identified 44 AD susceptibility sites for the refinement of genomic structure in those AD susceptibility loci. These sites can serve as inputs for the GRS modeling for AD prediction in the Chinese population.

To have a more comprehensive view for those identified with AD susceptibility, the aforementioned 147 variants were subjected to the PhenoScanner (Staley et al., 2016) for the batch query of association between genotype dosage and transcript level changes in specific human tissues or metabolite levels based on database evidence from previous studies. (Tables 8-9).

TABLE 8

Association of candidate sites/loci with the regulation of transcript levels

| Genes (loci) | rsID | Position (hg19) | Tissue | Target gene | EA | Beta | SE | P |
|---|---|---|---|---|---|---|---|---|
| KLF4-ACTL7B | rs9657651 | chr9:110869771 | Pancreas | IKBKAP | C | 0.26 | 0.09 | 4.5E−03 |
| KLF4-ACTL7B | rs10979217 | chr9:110875895 | Artery aorta | KLF4 | A | 0.27 | 0.09 | 3.3E−03 |
| KLF4-ACTL7B | rs10979217 | chr9:110875895 | Testis | RN7SL659P | A | 0.62 | 0.22 | 5.1E−03 |
| KLF4-ACTL7B | rs12339504 | chr9:110879938 | Colon transverse | RAD23B | G | −0.21 | 0.07 | 5.9E−03 |
| OPCML | rs73041479 | chr11:132736979 | Brain caudate basal ganglia | OPCML | C | −0.27 | 0.07 | 1.8E−04 |
| GCH1 | rs57875940 | chr14:55301494 | Skin sun exposed lower leg | FBXO34 | A | −0.17 | 0.06 | 3.2E−03 |
| GCH1 | rs57875940 | chr14:55301494 | Nerve tibial | KTN1 | A | −0.15 | 0.05 | 3.6E−03 |
| GCH1 | rs57875940 | chr14:55301494 | Cells EBV-transformed lymphocytes | LINC00520 | A | −0.34 | 0.12 | 7.2E−03 |
| GCH1 | rs150825385 | chr14:55330064 | Brain anterior cingulate cortex ba24 | CNIH1 | C | −0.38 | 0.12 | 3.2E−03 |
| GCH1 | rs55935131 | chr14:55331772 | Heart left ventricle | SAMD4A | A | 0.17 | 0.06 | 2.3E−03 |
| GCH1 | rs55935131 | chr14:55331772 | Brain caudate basal ganglia | SOCS4 | A | 0.28 | 0.09 | 2.4E−03 |
| GCH1 | rs2878170 | chr14:55335389 | Muscle skeletal | KTN1-AS1 | A | 0.21 | 0.06 | 3.7E−04 |
| GCH1 | rs2878170 | chr14:55335389 | Esophagus gastroesophageal junction | CDKN3 | A | −0.30 | 0.11 | 6.8E−03 |
| GCH1 | rs146123422 | chr14:55340311 | Small intestine terminal ileum | WDHD1 | A | 0.35 | 0.11 | 1.9E−03 |
| GCH1 | rs146123422 | chr14:55340311 | Brain hypothalamus | CHMP4BP1 | A | 0.56 | 0.18 | 3.7E−03 |
| GCH1 | rs17128052 | chr14:55356525 | Skin | GALIG | C | 0.06 | 0.02 | 8.9E−03 |
| GCH1 | rs57095876 | chr14:55357742 | Brain caudate basal ganglia | GMFB | A | −0.19 | 0.07 | 8.1E−03 |
| GCH1 | rs7147201 | chr14:55358877 | Skin sun exposed lower leg | ATG14 | A | 0.22 | 0.05 | 4.5E−06 |
| GCH1 | rs7147201 | chr14:55358877 | Ovary | BMP4 | A | 0.28 | 0.09 | 4.0E−03 |
| GCH1 | rs7147201 | chr14:55358877 | Brain cortex | CGRRF1 | A | −0.27 | 0.09 | 5.6E−03 |
| GCH1 | rs72713482 | chr14:55360836 | Esophagus muscularis | DLGAP5 | A | −0.29 | 0.10 | 3.6E−03 |
| GCH1 | rs8017210 | chr14:55361836 | Whole blood | MAPK1IP1L | NA | NA | NA | 5.7E−10 |
| GCH1 | rs8017210 | chr14:55361836 | Peripheral blood | GCH1 | NA | NA | NA | 1.0E−07 |
| GCH1 | rs8017210 | chr14:55361836 | Artery aorta | LGALS3 | A | −0.35 | 0.09 | 2.6E−04 |
| GCH1 | rs8017210 | chr14:55361836 | Prefrontal cortex | C14orf32 | NA | NA | NA | 6.9E−04 |
| FAM169B | rs11247317 | chr15:98926694 | Brain hypothalamus | TTC23 | G | −0.31 | 0.10 | 3.5E−03 |
| FAM169B | rs11247317 | chr15:98926694 | Spleen | FAM169B | G | −0.40 | 0.14 | 6.1E−03 |
| FAM169B | rs12442709 | chr15:98935519 | Skin not sun exposed suprapubic | ARRDC4 | A | −0.31 | 0.08 | 2.3E−04 |
| FAM169B | rs12442709 | chr15:98935519 | Skin not sun exposed suprapubic | SYNM | A | 0.25 | 0.07 | 2.5E−04 |
| FAM169B | rs12442709 | chr15:98935519 | Brain putamen basal ganglia | LRRC28 | A | −0.43 | 0.13 | 2.0E−03 |
| MYOM1 | rs12606254 | chr18:3187860 | Artery coronary | SMCHD1 | C | −0.33 | 0.10 | 1.3E−03 |
| MYOM1 | rs12606254 | chr18:3187860 | Adipose subcutaneous | DLGAP1-AS2 | C | 0.14 | 0.05 | 3.4E−03 |
| MYOM1 | rs1962519 | chr18:3188976 | Liver | LPIN2 | A | −0.32 | 0.10 | 1.4E−03 |
| MYOM1 | rs1962519 | chr18:3188976 | Lung | TGIF1 | A | 0.17 | 0.06 | 5.2E−03 |

TABLE 8-continued

Association of candidate sites/loci with the regulation of transcript levels

| Genes (loci) | rsID | Position (hg19) | Tissue | Target gene | EA | Beta | SE | P |
|---|---|---|---|---|---|---|---|---|
| MYOM1 | rs1962519 | chr18:3188976 | Stomach | CBX3P2 | A | −0.23 | 0.08 | 5.9E−03 |
| MYOM1 | rs4797101 | chr18:3191354 | Testis | DLGAP1-AS3 | C | 0.32 | 0.09 | 9.7E−04 |
| MYOM1 | rs4797101 | chr18:3191354 | Pancreas | NDC80 | C | −0.33 | 0.11 | 2.7E−03 |
| MYOM1 | rs4797101 | chr18:3191354 | Brain cerebellar hemisphere | DLGAP1-AS1 | C | 0.29 | 0.10 | 5.4E−03 |
| MYOM1 | rs4797101 | chr18:3191354 | Cells transformed fibroblasts | MYL12B | C | −0.09 | 0.03 | 7.5E−03 |
| NCLN | rs522941 | chr19:3184303 | Testis | PIP5K1C | A | −0.28 | 0.07 | 5.5E−05 |
| NCLN | rs556075 | chr19:3185636 | Brain hippocampus | GNG7 | C | 0.25 | 0.07 | 1.1E−03 |
| NCLN | rs510724 | chr19:3185874 | Brain frontal cortex ba9 | LMNB2 | C | 0.27 | 0.08 | 1.2E−03 |
| NCLN | rs11551095 | chr19:3186085 | Brain nucleus accumbens basal ganglia | CELF5 | G | −0.16 | 0.06 | 4.5E−03 |
| NCLN | rs537248 | chr19:3186493 | Thyroid | S1PR4 | C | −0.23 | 0.05 | 1.5E−05 |
| NCLN | rs537248 | chr19:3186493 | Colon transverse | ZBTB7A | C | −0.15 | 0.05 | 5.5E−03 |
| NCLN | rs566476 | chr19:3187386 | Small intestine terminal ileum | HMG20B | A | 0.27 | 0.07 | 5.4E−04 |
| NCLN | rs566476 | chr19:3187386 | Prostate | SLC39A3 | A | 0.32 | 0.10 | 2.1E−03 |
| NCLN | rs566476 | chr19:3187386 | Cells transformed fibroblasts | SGTA | A | 0.09 | 0.03 | 2.7E−03 |
| NCLN | rs518669 | chr19:3189652 | Small intestine terminal ileum | FZR1 | C | −0.33 | 0.11 | 5.0E−03 |
| NCLN | rs11669999 | chr19:3190737 | Brain nucleus accumbens basal ganglia | DAPK3 | C | 0.21 | 0.07 | 4.0E−03 |
| NCLN | rs475814 | chr19:3191032 | Artery tibial | ZNF57 | C | 0.14 | 0.05 | 1.8E−03 |
| NCLN | rs545850 | chr19:3191068 | Ovary | JSRP1 | C | 0.55 | 0.14 | 1.7E−04 |
| NCLN | rs545850 | chr19:3191068 | Prostate | ZNF77 | C | −0.35 | 0.12 | 4.0E−03 |
| NCLN | rs545850 | chr19:3191068 | Whole blood | LSM7 | C | −0.08 | 0.03 | 4.6E−03 |
| NCLN | rs545909 | chr19:3191089 | Thyroid | PLEKHJ1 | C | 0.15 | 0.04 | 9.7E−04 |
| NCLN | rs545909 | chr19:3191089 | Brain cerebellar hemisphere | DIRAS1 | C | −0.35 | 0.10 | 1.2E−03 |
| NCLN | rs545909 | chr19:3191089 | Brain hypothalamus | PIAS4 | C | −0.19 | 0.06 | 2.2E−03 |
| NCLN | rs545909 | chr19:3191089 | Cells EBV-transformed lymphocytes | GADD45B | C | 0.26 | 0.09 | 3.1E−03 |
| NCLN | rs545909 | chr19:3191089 | Thyroid | ATCAY | C | −0.29 | 0.10 | 3.2E−03 |
| NCLN | rs545909 | chr19:3191089 | Colon sigmoid | ZFR2 | C | −0.28 | 0.11 | 9.8E−03 |
| NCLN | rs477511 | chr19:3191187 | Nerve tibial | NCLN | C | −0.42 | 0.03 | 4.3E−29 |
| NCLN | rs507218 | chr19:3192116 | Brain cortex | MAP2K2 | A | 0.28 | 0.08 | 1.1E−03 |
| NCLN | rs529910 | chr19:3192277 | Brain hypothalamus | EEF2 | C | 0.38 | 0.11 | 9.3E−04 |
| NCLN | rs13382069 | chr19:3196790 | Esophagus mucosa | MATK | A | −0.88 | 0.27 | 1.1E−03 |
| NCLN | rs13382069 | chr19:3196790 | Artery tibial | MRPL54 | A | 0.44 | 0.17 | 9.7E−03 |
| NCLN | rs149256323 | chr19:3198405 | Thyroid | MFSD12 | C | −0.36 | 0.13 | 5.3E−03 |
| NCLN | rs4806915 | chr19:3198517 | Cells transformed fibroblasts | C19orf71 | A | −0.20 | 0.06 | 5.5E−04 |
| NCLN | rs4806915 | chr19:3198517 | Skin sun exposed lower leg | TLE6 | A | 0.20 | 0.06 | 7.7E−04 |
| NCLN | rs4806915 | chr19:3198517 | Lung | GNA15 | A | −0.14 | 0.05 | 1.8E−03 |
| NCLN | rs4806916 | chr19:3198532 | Whole blood | GIPC3 | A | 0.16 | 0.05 | 2.4E−03 |
| NCLN | rs311620 | chr19:3198695 | Skin sun exposed lower leg | APBA3 | C | −0.12 | 0.04 | 1.7E−03 |
| NCLN | rs311621 | chr19:3198777 | Brain cerebellar hemisphere | SIRT6 | A | 0.21 | 0.07 | 3.5E−03 |
| NCLN | rs2304249 | chr19:3199068 | Stomach | CACTIN-AS1 | A | 0.54 | 0.19 | 5.3E−03 |
| NCLN | rs2304249 | chr19:3199068 | Skin sun exposed lower leg | OAZ1 | A | −0.32 | 0.12 | 8.7E−03 |
| NCLN | rs519271 | chr19:3199945 | Prostate | C19orf77 | A | 0.40 | 0.11 | 4.5E−04 |
| NCLN | rs519271 | chr19:3199945 | Brain frontal cortex ba9 | MIR637 | A | −0.54 | 0.15 | 7.1E−04 |
| NCLN | rs519271 | chr19:3199945 | Brain cortex | TLE2 | A | 0.36 | 0.12 | 2.9E−03 |
| NCLN | rs519271 | chr19:3199945 | Thyroid | TMPRSS9 | A | −0.19 | 0.07 | 7.6E−03 |
| NCLN | rs311622 | chr19:3200790 | Adipose visceral omentum | ANKRD24 | A | −0.32 | 0.09 | 4.4E−04 |
| NCLN | rs311622 | chr19:3200790 | Adipose subcutaneous | TBXA2R | A | −0.03 | 0.01 | 1.8E−03 |
| NCLN | rs311622 | chr19:3200790 | Uterus | SF3A2 | A | 0.30 | 0.10 | 4.0E−03 |
| NCLN | rs311624 | chr19:3201323 | Pituitary | NMRK2 | C | −0.45 | 0.11 | 1.4E−04 |
| NCLN | rs311624 | chr19:3201323 | Skin not sun exposed suprapubic | ZNF555 | C | 0.29 | 0.09 | 7.3E−04 |
| NCLN | rs311624 | chr19:3201323 | Adipose subcutaneous | LINGO3 | C | 0.19 | 0.06 | 8.1E−04 |
| NCLN | rs28372911 | chr19:3204159 | Adipose subcutaneous | AMH | C | −0.56 | 0.17 | 9.4E−04 |
| NCLN | rs28372911 | chr19:3204159 | Skin sun exposed lower leg | DOHH | C | 0.27 | 0.08 | 1.6E−03 |
| NCLN | rs312072 | chr19:3208430 | Stomach | THOP1 | C | 0.22 | 0.06 | 2.8E−04 |
| NCLN | rs312072 | chr19:3208430 | Cells transformed fibroblasts | TIMM13 | C | −0.12 | 0.03 | 6.1E−04 |

TABLE 8-continued

Association of candidate sites/loci with the regulation of transcript levels

| Genes (loci) | rsID | Position (hg19) | Tissue | Target gene | EA | Beta | SE | P |
| --- | --- | --- | --- | --- | --- | --- | --- | --- |
| NCLN | rs312072 | chr19:3208430 | Lymphoblastoid cell lines | SPPL2B | C | 0.02 | 0.01 | 2.2E-03 |
| NCLN | rs312072 | chr19:3208430 | Heart left ventricle | AES | C | -0.17 | 0.06 | 3.8E-03 |
| NCLN | rs312074 | chr19:3208890 | Vagina | CACTIN | C | 0.36 | 0.10 | 5.3E-04 |
| NCLN | rs312074 | chr19:3208890 | Brain caudate basal ganglia | GNA11 | C | -0.25 | 0.08 | 1.7E-03 |
| NCLN | rs312074 | chr19:3208890 | Cells transformed fibroblasts | NFIC | C | -0.14 | 0.05 | 3.5E-03 |
| APOE_locus | rs395908 | chr19:45373565 | Liver | SFRS16 | NA | NA | NA | 3.1E-04 |
| APOE_locus | rs395908 | chr19:45373565 | Lymphoblastoid cell lines | ZNF284 | G | 0.02 | 0.01 | 5.1E-04 |
| APOE_locus | rs519113 | chr19:45376284 | Peripheral blood | PVRL2 | NA | NA | NA | 5.8E-58 |
| APOE_locus | rs519113 | chr19:45376284 | Peripheral blood monocytes | MFSD2 | NA | NA | NA | 4.0E-06 |
| APOE_locus | rs519113 | chr19:45376284 | Peripheral blood monocytes | ZNF764 | NA | NA | NA | 8.0E-06 |
| APOE_locus | rs519113 | chr19:45376284 | Brain cerebellum | PVR | G | -0.31 | 0.08 | 3.7E-04 |
| APOE_locus | rs519113 | chr19:45376284 | Esophagus mucosa | FBXO46 | G | 0.18 | 0.05 | 4.2E-04 |
| APOE_locus | rs519113 | chr19:45376284 | Brain cortex | PPM1N | G | -0.56 | 0.15 | 5.3E-04 |
| APOE_locus | rs34278513 | chr19:45378144 | Nerve tibial | CLPTM1 | C | 0.21 | 0.06 | 9.2E-04 |
| APOE_locus | rs34278513 | chr19:45378144 | Brain hypothalamus | ZNF155 | C | 0.76 | 0.22 | 1.2E-03 |
| APOE_locus | rs3865427 | chr19:45380961 | Thyroid | RSPH6A | A | -0.26 | 0.10 | 9.6E-03 |
| APOE_locus | rs11668861 | chr19:45380970 | Small intestine terminal ileum | CEACAM22P | G | -0.52 | 0.12 | 7.8E-05 |
| APOE_locus | rs11668861 | chr19:45380970 | Nerve tibial | ZNF226 | G | 0.12 | 0.04 | 1.9E-03 |
| APOE_locus | rs11668861 | chr19:45380970 | Colon transverse | IGSF23 | G | 0.24 | 0.08 | 3.6E-03 |
| APOE_locus | rs6859 | chr19:45382034 | Brain putamen basal ganglia | EML2 | A | 0.18 | 0.05 | 4.7E-04 |
| APOE_locus | rs6859 | chr19:45382034 | Brain putamen basal ganglia | BCAM | A | 0.23 | 0.07 | 8.4E-04 |
| APOE_locus | rs6859 | chr19:45382034 | Skin | ZNF404 | A | 0.02 | 0.01 | 9.9E-04 |
| APOE_locus | rs6859 | chr19:45382034 | Brain putamen basal ganglia | GPR4 | A | 0.25 | 0.07 | 1.2E-03 |
| APOE_locus | rs6859 | chr19:45382034 | Muscle skeletal | ZNF225 | A | 0.18 | 0.06 | 1.5E-03 |
| APOE_locus | rs71352237 | chr19:45383079 | Liver | ERCC1 | C | -0.42 | 0.15 | 6.9E-03 |
| APOE_locus | rs35879138 | chr19:45383139 | Cells transformed fibroblasts | KLC3 | A | 0.40 | 0.13 | 1.8E-03 |
| APOE_locus | rs283812 | chr19:45388568 | Small intestine terminal ileum | EIF5AP3 | T | -0.57 | 0.21 | 9.6E-03 |
| APOE_locus | rs6857 | chr19:45392254 | Brain frontal cortex ba9 | ZNF223 | T | -0.60 | 0.15 | 1.8E-04 |
| APOE_locus | rs6857 | chr19:45392254 | Brain anterior cingulate cortex ba24 | ZNF227 | T | -0.85 | 0.21 | 2.0E-04 |
| APOE_locus | rs6857 | chr19:45392254 | Adrenal gland | ZNF285 | T | -0.45 | 0.12 | 3.9E-04 |
| APOE_locus | rs6857 | chr19:45392254 | Heart left ventricle | BCL3 | T | -0.25 | 0.07 | 7.6E-04 |
| APOE_locus | rs184017 | chr19:45394969 | Lymphoblastoid cell lines | TOMM40 | NA | NA | NA | 5.9E-37 |
| APOE_locus | rs184017 | chr19:45394969 | Spleen | QPCTL | T | 0.35 | 0.09 | 4.0E-04 |
| APOE_locus | rs157580 | chr19:45395266 | Pituitary | FOSB | A | 0.39 | 0.09 | 5.4E-05 |
| APOE_locus | rs157580 | chr19:45395266 | Ovary | GIPR | A | 0.52 | 0.14 | 4.9E-04 |
| APOE_locus | rs157580 | chr19:45395266 | Brain hypothalamus | ZNF45 | A | 0.41 | 0.11 | 5.6E-04 |
| APOE_locus | rs157580 | chr19:45395266 | Brain nucleus accumbens basal ganglia | PPP1R37 | A | -0.18 | 0.05 | 9.1E-04 |
| APOE_locus | rs157580 | chr19:45395266 | Artery aorta | MARK4 | A | -0.13 | 0.04 | 1.6E-03 |
| APOE_locus | rs157580 | chr19:45395266 | Lymphoblastoid cell lines | ZNF285A | A | 0.06 | 0.02 | 2.4E-03 |
| APOE_locus | rs157580 | chr19:45395266 | Colon transverse | ZNF229 | A | -0.15 | 0.05 | 2.4E-03 |
| APOE_locus | rs2075650 | chr19:45395619 | Adipose subcutaneous | SIX5 | A | 0.20 | 0.06 | 6.4E-04 |
| APOE_locus | rs157582 | chr19:45396219 | Whole blood | EXOC3L2 | T | -0.27 | 0.08 | 5.4E-04 |
| APOE_locus | rs157582 | chr19:45396219 | Adipose subcutaneous | SYMPK | T | 0.04 | 0.01 | 8.2E-04 |
| APOE_locus | rs59007384 | chr19:45396665 | Skin not sun exposed suprapubic | DMWD | G | 0.30 | 0.08 | 1.2E-04 |
| APOE_locus | rs59007384 | chr19:45396665 | Whole blood | ZNF285B | G | 0.31 | 0.09 | 8.5E-04 |
| APOE_locus | rs59007384 | chr19:45396665 | Brain anterior cingulate cortex ba24 | ZNF180 | G | 0.40 | 0.12 | 1.4E-03 |
| APOE_locus | rs405697 | chr19:45404691 | Brain cerebellum | SNRPD2 | G | 0.43 | 0.12 | 3.1E-04 |
| APOE_locus | rs405697 | chr19:45404691 | Peripheral blood | GEMIN7 | NA | NA | NA | 4.2E-04 |
| APOE_locus | rs405697 | chr19:45404691 | Skin | RTN2 | G | -0.04 | 0.01 | 1.3E-03 |
| APOE_locus | rs10119 | chr19:45406673 | Vagina | NKPD1 | G | -0.29 | 0.07 | 6.2E-05 |
| APOE_locus | rs10119 | chr19:45406673 | Vagina | MYPOP | G | 0.35 | 0.12 | 4.2E-03 |
| APOE_locus | rs405509 | chr19:45408836 | Colon sigmoid | ZNF235 | T | -0.28 | 0.08 | 4.9E-04 |
| APOE_locus | rs405509 | chr19:45408836 | Adipose visceral omentum | ZNF230 | T | -0.23 | 0.07 | 7.9E-04 |

TABLE 8-continued

Association of candidate sites/loci with the regulation of transcript levels

| Genes (loci) | rsID | Position (hg19) | Tissue | Target gene | EA | Beta | SE | P |
|---|---|---|---|---|---|---|---|---|
| APOE_locus | rs405509 | chr19:45408836 | Heart left ventricle | ZNF233 | T | 0.17 | 0.06 | 6.5E−03 |
| APOE_locus | rs440446 | chr19:45409167 | Brain nucleus accumbens basal ganglia | ZNF234 | C | 0.32 | 0.11 | 4.2E−03 |
| APOE_locus | rs440446 | chr19:45409167 | Breast mammary tissue | IRF2BP1 | C | 0.14 | 0.05 | 6.0E−03 |
| APOE_locus | rs769449 | chr19:45410002 | Brain cerebellar hemisphere | ZNF296 | A | −0.49 | 0.14 | 6.6E−04 |
| APOE_locus | rs429358 | chr19:45411941 | Nerve tibial | CKM | C | 0.36 | 0.11 | 1.1E−03 |
| APOE_locus | rs429358 | chr19:45411941 | Cells EBV-transformed lymphocytes | NDUFA3P1 | C | −0.50 | 0.17 | 3.1E−03 |
| APOE_locus | rs439401 | chr19:45414451 | Skin sun exposed lower leg | APOE | C | −0.34 | 0.05 | 6.8E−12 |
| APOE_locus | rs439401 | chr19:45414451 | Liver | APOC4 | NA | NA | NA | 4.4E−08 |
| APOE_locus | rs439401 | chr19:45414451 | Adrenal gland | APOC1P1 | C | −0.54 | 0.10 | 1.1E−07 |
| APOE_locus | rs439401 | chr19:45414451 | Colon transverse | FOXA3 | C | −0.14 | 0.04 | 7.8E−04 |
| APOE_locus | rs439401 | chr19:45414451 | Adipose subcutaneous | PPP1R13L | C | −0.03 | 0.01 | 2.8E−03 |
| APOE_locus | rs439401 | chr19:45414451 | Lymphoblastoid cell lines | CEACAM20 | C | −0.02 | 0.01 | 3.0E−03 |
| APOE_locus | rs438811 | chr19:45416741 | Brain frontal cortex ba9 | RELB | C | 0.26 | 0.08 | 2.0E−03 |
| APOE_locus | rs5117 | chr19:45418790 | Pancreas | CEACAM19 | C | 0.33 | 0.10 | 1.5E−03 |
| APOE_locus | rs5117 | chr19:45418790 | Brain putamen basal ganglia | NANOS2 | C | −0.44 | 0.16 | 8.0E−03 |
| APOE_locus | rs3826688 | chr19:45418961 | Thyroid | ZNF221 | C | −0.22 | 0.07 | 2.8E−03 |
| APOE_locus | rs12721046 | chr19:45421254 | Brain cortex | ZNF224 | A | −0.32 | 0.10 | 1.7E−03 |
| APOE_locus | rs484195 | chr19:45421877 | Liver | APOC2 | A | −0.36 | 0.13 | 6.2E−03 |
| APOE_locus | rs4420638 | chr19:45422946 | Peripheral blood monocytes | CD81 | NA | NA | NA | 3.4E−06 |
| APOE_locus | rs4420638 | chr19:45422946 | Blood | MAD1L1 | NA | NA | NA | 3.5E−06 |
| APOE_locus | rs4420638 | chr19:45422946 | Small intestine terminal ileum | VASP | A | 0.56 | 0.14 | 2.1E−04 |
| APOE_locus | rs157594 | chr19:45425175 | Adrenal gland | APOC1 | T | 0.57 | 0.10 | 1.3E−07 |
| APOE_locus | rs157594 | chr19:45425175 | Colon sigmoid | DMPK | T | −0.20 | 0.06 | 1.7E−03 |
| APOE_locus | rs157594 | chr19:45425175 | Brain cerebellum | RN7SL53P | T | −0.43 | 0.16 | 8.9E−03 |
| APOE_locus | rs157595 | chr19:45425460 | Liver | OPA3 | G | 0.31 | 0.09 | 7.6E−04 |
| APOE_locus | rs157595 | chr19:45425460 | Adipose visceral omentum | CBLC | G | −0.32 | 0.10 | 1.3E−03 |
| APOE_locus | rs157595 | chr19:45425460 | Adipose visceral omentum | TRAPPC6A | G | 0.22 | 0.07 | 1.3E−03 |
| APOE_locus | rs157595 | chr19:45425460 | Adipose subcutaneous | ERCC2 | G | 0.18 | 0.06 | 2.1E−03 |
| APOE_locus | rs60049679 | chr19:45429708 | Pancreas | CLASRP | C | −0.47 | 0.11 | 4.7E−05 |
| APOE_locus | rs60049679 | chr19:45429708 | Thyroid | ZNF222 | C | −0.59 | 0.14 | 6.0E−05 |
| APOE_locus | rs60049679 | chr19:45429708 | Cells transformed fibroblasts | ZNF112 | C | 0.60 | 0.20 | 2.3E−03 |
| KCNJ15 | rs2836255 | chr21:39634196 | Brain caudate basal ganglia | KCNJ6 | A | 0.51 | 0.11 | 7.1E−06 |
| KCNJ15 | rs7275784 | chr21:39636309 | Peripheral blood | KCNJ15 | NA | NA | NA | 9.8E−198 |
| KCNJ15 | rs928771 | chr21:39663760 | Artery tibial | ERG | G | −0.12 | 0.04 | 8.1E−04 |
| KCNJ15 | rs928771 | chr21:39663760 | Thyroid | SPATA20P1 | G | −0.26 | 0.08 | 1.4E−03 |

With regard to Table 8, EA, effective allele; Beta, association between the trait and the SNP expressed per additional copy of the effect allele (odds ratios are given on the log-scale); SE, standard error of Beta; P, p-value. 147 candidate variants in the AD susceptibility loci were subjected to the PhenoScanner (Staley et al., 2016) to determine the association between genotype and the change of transcript levels. Table 8 shows the change of specific genes that correspond to the 147 variants, with a p-value cutoff of 0.01. Specific datasets were used for the association study (Consortium 2013; Grundberg et al., 2012; Leslie et al., 2014; Westra et al., 2013).

TABLE 9

Association of candidate sites/loci with changes in metabolite levels

| Genes (loci) | rsID | Pos (hg19) | Trait | EA | EAF | Beta | SE | P |
|---|---|---|---|---|---|---|---|---|
| KLF4-ACTL7B | rs10979217 | chr9:110875895 | Epiandrosterone sulfate | A | 0.94 | −0.04 | 0.01 | 8.6E−03 |
| KLF4-ACTL7B | rs12339504 | chr9:110879938 | Glucose | G | 0.07 | −0.05 | 0.02 | 6.7E−03 |
| OPCML | rs11223251 | chr11:132728786 | Ursodeoxycholate | A | 0.93 | 0.03 | 0.01 | 5.4E−03 |
| GCH1 | rs7147201 | chr14:55358877 | Cholate | A | 0.81 | 0.04 | 0.01 | 5.3E−03 |
| GCH1 | rs3783641 | chr14:55360139 | Pyroglutamine* | A | 0.19 | 0.01 | 0.00 | 8.0E−03 |
| MYOM1 | rs1962519 | chr18:3188976 | 1-arachidonoylglycerophosphoinositol* | A | 0.58 | −0.01 | 0.00 | 7.0E−03 |

TABLE 9-continued

Association of candidate sites/loci with changes in metabolite levels

| Genes (loci) | rsID | Pos (hg19) | Trait | EA | EAF | Beta | SE | P |
|---|---|---|---|---|---|---|---|---|
| NCLN | rs311621 | chr19:3198777 | ADSGEGDFXAEGGGVR* (SEQ ID NO: 246) | A | 0.56 | 0.01 | 0.00 | 3.1E−03 |
| NCLN | rs311621 | chr19:3198777 | Hyodeoxycholate | A | 0.60 | −0.02 | 0.01 | 5.3E−03 |
| NCLN | rs311621 | chr19:3198777 | Isobutyrylcarnitine | A | 0.59 | −0.01 | 0.00 | 8.1E−03 |
| APOE_locus | rs395908 | chr19:45373565 | CH2.DB.ratio | G | 0.91 | −0.08 | 0.02 | 2.7E−04 |
| APOE_locus | rs395908 | chr19:45373565 | Ratio of bisLallylic bonds to total fatty acids in lipids | G | 0.91 | 0.07 | 0.02 | 1.3E−03 |
| APOE_locus | rs395908 | chr19:45373565 | Double bonds in fatty acids | G | 0.90 | 0.06 | 0.02 | 1.6E−03 |
| APOE_locus | rs395908 | chr19:45373565 | Gamma-glutamylmethionine* | G | 0.84 | 0.02 | 0.01 | 3.8E−03 |
| APOE_locus | rs395908 | chr19:45373565 | N-acetylalanine | G | 0.84 | 0.00 | 0.00 | 7.6E−03 |
| APOE_locus | rs519113 | chr19:45376284 | Cholesterol | G | 0.23 | −0.01 | 0.00 | 2.4E−04 |
| APOE_locus | rs519113 | chr19:45376284 | Oleoylcarnitine | G | 0.23 | 0.01 | 0.00 | 4.7E−03 |
| APOE_locus | rs519113 | chr19:45376284 | 2-methylbutyroylcarnitine | G | 0.23 | 0.01 | 0.00 | 5.8E−03 |
| APOE_locus | rs6859 | chr19:45382034 | Isovalerate | A | 0.43 | 0.01 | 0.00 | 1.8E−04 |
| APOE_locus | rs6859 | chr19:45382034 | 1-stearoylglycerophosphoinositol | A | 0.42 | 0.01 | 0.00 | 4.7E−03 |
| APOE_locus | rs3852861 | chr19:45383061 | Stearate (18:0) | G | 0.61 | 0.01 | 0.00 | 4.9E−03 |
| APOE_locus | rs3852861 | chr19:45383061 | Indoleacetate | G | 0.61 | −0.01 | 0.00 | 9.1E−03 |
| APOE_locus | rs283812 | chr19:45388568 | Isoleucine | T | 0.80 | −0.03 | 0.01 | 7.9E−03 |
| APOE_locus | rs6857 | chr19:45392254 | Lathosterol | T | 0.13 | 0.02 | 0.01 | 7.1E−03 |
| APOE_locus | rs157580 | chr19:45395266 | 3-(4-hydroxyphenyl)lactate | A | 0.61 | −0.01 | 0.00 | 2.7E−03 |
| APOE_locus | rs157580 | chr19:45395266 | Cortisone | A | 0.61 | −0.01 | 0.00 | 2.7E−03 |
| APOE_locus | rs157580 | chr19:45395266 | Cortisol | A | 0.61 | −0.01 | 0.00 | 9.4E−03 |
| APOE_locus | rs2075650 | chr19:45395619 | 5-oxoproline | A | 0.86 | 0.01 | 0.00 | 1.7E−03 |
| APOE_locus | rs2075650 | chr19:45395619 | Glycocholate | A | 0.86 | 0.03 | 0.01 | 2.0E−03 |
| APOE_locus | rs2075650 | chr19:45395619 | Urea | A | 0.86 | 0.01 | 0.00 | 2.0E−03 |
| APOE_locus | rs2075650 | chr19:45395619 | Heptanoate (7:0) | A | 0.86 | −0.01 | 0.00 | 6.4E−03 |
| APOE_locus | rs2075650 | chr19:45395619 | Pelargonate (9:0) | A | 0.86 | −0.01 | 0.00 | 7.8E−03 |
| APOE_locus | rs157582 | chr19:45396219 | Dehydroisoandrosterone sulfate (DHEA-S) | T | 0.18 | −0.03 | 0.01 | 7.4E−04 |
| APOE_locus | rs10119 | chr19:45406673 | Uridine | G | 0.75 | 0.01 | 0.00 | 2.7E−03 |
| APOE_locus | rs405509 | chr19:45408836 | Sphingomyelins | T | 0.46 | 0.04 | 0.01 | 3.6E−04 |
| APOE_locus | rs405509 | chr19:45408836 | Palmitoyl sphingomyelin | T | 0.47 | 0.01 | 0.00 | 2.7E−03 |
| APOE_locus | rs769449 | chr19:45410002 | Other polyunsaturated fatty acids than 18:2 | A | 0.16 | 0.07 | 0.02 | 2.0E−05 |
| APOE_locus | rs769449 | chr19:45410002 | OmegaL3 fatty acids | A | 0.16 | 0.05 | 0.02 | 1.7E−03 |
| APOE_locus | rs429358 | chr19:45411941 | Total cholesterol in LDL | C | 0.17 | 0.23 | 0.01 | 2.6E−62 |
| APOE_locus | rs429358 | chr19:45411941 | Total cholesterol in small LDL | C | 0.17 | 0.22 | 0.01 | 1.2E−59 |
| APOE_locus | rs429358 | chr19:45411941 | M.LDL.C | C | 0.17 | 0.22 | 0.01 | 2.5E−59 |
| APOE_locus | rs429358 | chr19:45411941 | Total lipids in medium LDL | C | 0.17 | 0.23 | 0.01 | 3.3E−58 |
| APOE_locus | rs429358 | chr19:45411941 | Total lipids in small LDL | C | 0.17 | 0.22 | 0.01 | 2.1E−57 |
| APOE_locus | rs429358 | chr19:45411941 | Concentration of medium LDL particles | C | 0.17 | 0.22 | 0.01 | 1.1E−56 |
| APOE_locus | rs429358 | chr19:45411941 | Cholesterol esters in medium LDL | C | 0.17 | 0.22 | 0.01 | 5.5E−56 |
| APOE_locus | rs429358 | chr19:45411941 | Total lipids in large LDL | C | 0.17 | 0.22 | 0.01 | 1.7E−53 |
| APOE_locus | rs429358 | chr19:45411941 | Cholesterol esters in large LDL | C | 0.17 | 0.22 | 0.01 | 2.5E−53 |
| APOE_locus | rs429358 | chr19:45411941 | Total cholesterol in large LDL | C | 0.17 | 0.21 | 0.01 | 2.5E−53 |
| APOE_locus | rs429358 | chr19:45411941 | Phospholipids in medium LDL | C | 0.17 | 0.21 | 0.01 | 1.9E−52 |
| APOE_locus | rs429358 | chr19:45411941 | Concentration of small LDL particles | C | 0.17 | 0.21 | 0.01 | 2.1E−52 |
| APOE_locus | rs429358 | chr19:45411941 | Concentration of large LDL particles | C | 0.17 | 0.21 | 0.01 | 3.7E−52 |
| APOE_locus | rs429358 | chr19:45411941 | Free cholesterol in large LDL | C | 0.17 | 0.20 | 0.01 | 3.7E−51 |
| APOE_locus | rs429358 | chr19:45411941 | Phospholipids in large LDL | C | 0.17 | 0.20 | 0.01 | 2.7E−50 |
| APOE_locus | rs429358 | chr19:45411941 | ApoB | C | 0.17 | 0.19 | 0.01 | 2.8E−43 |
| APOE_locus | rs429358 | chr19:45411941 | Serum total cholesterol | C | 0.17 | 0.18 | 0.01 | 2.9E−40 |
| APOE_locus | rs429358 | chr19:45411941 | Phospholipids in IDL | C | 0.17 | 0.18 | 0.01 | 1.8E−39 |
| APOE_locus | rs429358 | chr19:45411941 | Total cholesterol in IDL | C | 0.17 | 0.18 | 0.01 | 5.9E−39 |
| APOE_locus | rs429358 | chr19:45411941 | Total lipids in IDL | C | 0.17 | 0.18 | 0.01 | 1.4E−37 |
| APOE_locus | rs429358 | chr19:45411941 | Concentration of IDL particles | C | 0.17 | 0.18 | 0.01 | 8.8E−36 |
| APOE_locus | rs429358 | chr19:45411941 | Free cholesterol in small VLDL | C | 0.17 | 0.14 | 0.01 | 1.2E−24 |
| APOE_locus | rs429358 | chr19:45411941 | Esterified cholesterol | C | 0.18 | 0.17 | 0.02 | 1.2E−24 |
| APOE_locus | rs429358 | chr19:45411941 | Total cholesterol in small VLDL | C | 0.17 | 0.14 | 0.01 | 2.2E−24 |
| APOE_locus | rs429358 | chr19:45411941 | 18:2 linoleic acid (LA) | C | 0.18 | 0.16 | 0.02 | 8.9E−23 |
| APOE_locus | rs429358 | chr19:45411941 | Total lipids in small VLDL | C | 0.17 | 0.13 | 0.01 | 2.1E−19 |
| APOE_locus | rs429358 | chr19:45411941 | OmegaL6 fatty acids | C | 0.18 | 0.14 | 0.02 | 1.0E−18 |
| APOE_locus | rs429358 | chr19:45411941 | Serum total triglycerides | C | 0.17 | 0.12 | 0.01 | 5.9E−18 |
| APOE_locus | rs429358 | chr19:45411941 | Free cholesterol | C | 0.18 | 0.14 | 0.02 | 1.6E−17 |
| APOE_locus | rs429358 | chr19:45411941 | Phospholipids in small VLDL | C | 0.17 | 0.12 | 0.01 | 1.9E−17 |
| APOE_locus | rs429358 | chr19:45411941 | Cholesterol esters in medium VLDL | C | 0.17 | 0.12 | 0.01 | 2.5E−17 |
| APOE_locus | rs429358 | chr19:45411941 | Concentration of small VLDL particles | C | 0.17 | 0.12 | 0.01 | 4.5E−17 |
| APOE_locus | rs429358 | chr19:45411941 | Triglycerides in small HDL | C | 0.17 | 0.10 | 0.01 | 1.5E−13 |
| APOE_locus | rs429358 | chr19:45411941 | Total cholesterol in large HDL | C | 0.17 | −0.09 | 0.01 | 1.5E−11 |
| APOE_locus | rs429358 | chr19:45411941 | Total fatty acids | C | 0.18 | 0.11 | 0.02 | 1.0E−10 |

TABLE 9-continued

Association of candidate sites/loci with changes in metabolite levels

| Genes (loci) | rsID | Pos (hg19) | Trait | EA | EAF | Beta | SE | P |
|---|---|---|---|---|---|---|---|---|
| APOE_locus | rs429358 | chr19:45411941 | Cholesterol esters in large HDL | C | 0.17 | −0.09 | 0.01 | 1.3E−10 |
| APOE_locus | rs429358 | chr19:45411941 | Total cholesterol in medium HDL | C | 0.17 | −0.08 | 0.01 | 7.3E−10 |
| APOE_locus | rs429358 | chr19:45411941 | Total lipids in large HDL | C | 0.17 | −0.08 | 0.01 | 3.5E−09 |
| APOE_locus | rs429358 | chr19:45411941 | Concentration of large HDL particles | C | 0.17 | −0.08 | 0.01 | 5.6E−09 |
| APOE_locus | rs429358 | chr19:45411941 | Cholesterol esters in medium HDL | C | 0.17 | −0.08 | 0.01 | 7.7E−09 |
| APOE_locus | rs429358 | chr19:45411941 | Phospholipids in large HDL | C | 0.17 | −0.08 | 0.01 | 1.5E−08 |
| APOE_locus | rs429358 | chr19:45411941 | Free cholesterol in large HDL | C | 0.17 | −0.07 | 0.01 | 4.5E−08 |
| APOE_locus | rs429358 | chr19:45411941 | HDL diameter | C | 0.17 | −0.07 | 0.01 | 3.4E−07 |
| APOE_locus | rs429358 | chr19:45411941 | MonoLunsaturated fatty acids | C | 0.18 | 0.08 | 0.02 | 4.3E−07 |
| APOE_locus | rs429358 | chr19:45411941 | OmegaL7 and L9 and saturated fatty acids | C | 0.18 | 0.08 | 0.02 | 1.2E−06 |
| APOE_locus | rs429358 | chr19:45411941 | Total phosphoglycerides | C | 0.18 | 0.08 | 0.02 | 4.0E−06 |
| APOE_locus | rs429358 | chr19:45411941 | Total lipids in small HDL | C | 0.17 | 0.06 | 0.01 | 1.8E−05 |
| APOE_locus | rs429358 | chr19:45411941 | Phosphatidylcholine and other cholines | C | 0.18 | 0.06 | 0.02 | 3.0E−04 |
| APOE_locus | rs429358 | chr19:45411941 | ApoA1 | C | 0.17 | 0.04 | 0.01 | 3.8E−03 |
| APOE_locus | rs429358 | chr19:45411941 | Concentration of small HDL particles | C | 0.17 | 0.04 | 0.01 | 4.0E−03 |
| APOE_locus | rs75627662 | chr19:45413576 | LDL diameter | C | 0.79 | 0.09 | 0.01 | 6.4E−11 |
| APOE_locus | rs75627662 | chr19:45413576 | Free cholesterol in medium HDL | C | 0.79 | 0.05 | 0.01 | 3.7E−05 |
| APOE_locus | rs75627662 | chr19:45413576 | Valine | C | 0.79 | 0.04 | 0.01 | 5.5E−04 |
| APOE_locus | rs75627662 | chr19:45413576 | Tyrosine | C | 0.79 | 0.03 | 0.01 | 3.9E−03 |
| APOE_locus | rs439401 | chr19:45414451 | Triglycerides in very large HDL | C | 0.69 | 0.09 | 0.01 | 1.3E−14 |
| APOE_locus | rs439401 | chr19:45414451 | Concentration of large VLDL particles | C | 0.69 | 0.08 | 0.01 | 3.0E−13 |
| APOE_locus | rs439401 | chr19:45414451 | Concentration of medium VLDL particles | C | 0.69 | 0.08 | 0.01 | 5.4E−13 |
| APOE_locus | rs439401 | chr19:45414451 | Triglycerides in medium VLDL | C | 0.69 | 0.08 | 0.01 | 1.2E−12 |
| APOE_locus | rs439401 | chr19:45414451 | 1-palmitoylglycerophosphoethanolamine | C | 0.65 | 0.01 | 0.00 | 8.6E−04 |
| APOE_locus | rs439401 | chr19:45414451 | 1-oleoylglycerophosphoethanolamine | C | 0.65 | 0.01 | 0.00 | 2.1E−03 |
| APOE_locus | rs439401 | chr19:45414451 | 1-arachidonoylglycerophosphoethanolamine* | C | 0.65 | 0.01 | 0.00 | 2.7E−03 |
| APOE_locus | rs439401 | chr19:45414451 | Levulinate (4-oxovalerate) | C | 0.65 | 0.01 | 0.00 | 2.7E−03 |
| APOE_locus | rs439401 | chr19:45414451 | Pyroglutamylglycine | C | 0.65 | 0.03 | 0.01 | 9.8E−03 |
| APOE_locus | rs10414043 | chr19:45415713 | Phospholipids in medium HDL | A | 0.15 | −0.06 | 0.01 | 6.7E−06 |
| APOE_locus | rs10414043 | chr19:45415713 | Concentration of medium HDL particles | A | 0.15 | −0.06 | 0.01 | 2.6E−05 |
| APOE_locus | rs483082 | chr19:45416178 | Triglycerides in chylomicrons and extremely large VLDL | T | 0.23 | 0.10 | 0.01 | 1.2E−15 |
| APOE_locus | rs483082 | chr19:45416178 | Cholesterol esters in large VLDL | T | 0.23 | 0.10 | 0.01 | 2.9E−14 |
| APOE_locus | rs483082 | chr19:45416178 | Phospholipids in chylomicrons and extremely large VLDL | T | 0.23 | 0.09 | 0.01 | 2.0E−13 |
| APOE_locus | rs483082 | chr19:45416178 | VLDL diameter | T | 0.23 | 0.09 | 0.01 | 4.5E−13 |
| APOE_locus | rs483082 | chr19:45416178 | Total lipids in large VLDL | T | 0.23 | 0.09 | 0.01 | 3.9E−12 |
| APOE_locus | rs483082 | chr19:45416178 | Total lipids in very large VLDL | T | 0.23 | 0.09 | 0.01 | 4.7E−12 |
| APOE_locus | rs483082 | chr19:45416178 | Total lipids in chylomicrons and extremely large VLDL | T | 0.23 | 0.09 | 0.01 | 8.8E−12 |
| APOE_locus | rs483082 | chr19:45416178 | Concentration of chylomicrons and extremely large VLDL particles | T | 0.23 | 0.08 | 0.01 | 4.4E−11 |
| APOE_locus | rs483082 | chr19:45416178 | Concentration of very large VLDL particles | T | 0.23 | 0.09 | 0.01 | 1.3E−09 |
| APOE_locus | rs483082 | chr19:45416178 | Glycoprotein acetyls mainly a1Lacid glycoprotein | T | 0.23 | 0.06 | 0.01 | 1.7E−06 |
| APOE_locus | rs483082 | chr19:45416178 | Ratio of bisLallylic bonds to double bonds in lipids | T | 0.23 | −0.04 | 0.02 | 3.9E−03 |
| APOE_locus | rs438811 | chr19:45416741 | Phospholipids in large VLDL | C | 0.77 | −0.09 | 0.01 | 1.1E−14 |
| APOE_locus | rs438811 | chr19:45416741 | Total cholesterol in large VLDL | C | 0.77 | −0.09 | 0.01 | 1.8E−14 |
| APOE_locus | rs438811 | chr19:45416741 | Free cholesterol in large VLDL | C | 0.77 | −0.09 | 0.01 | 4.9E−14 |
| APOE_locus | rs438811 | chr19:45416741 | Phospholipids in very large VLDL | C | 0.77 | −0.09 | 0.01 | 1.1E−13 |
| APOE_locus | rs438811 | chr19:45416741 | Triglycerides in large VLDL | C | 0.77 | −0.09 | 0.01 | 2.9E−13 |
| APOE_locus | rs438811 | chr19:45416741 | Triglycerides in very large VLDL | C | 0.77 | −0.08 | 0.01 | 5.0E−10 |
| APOE_locus | rs438811 | chr19:45416741 | Cholesterol esters in very large HDL | C | 0.77 | −0.04 | 0.01 | 4.0E−03 |
| APOE_locus | rs3826688 | chr19:45418961 | Total cholesterol in medium VLDL | C | 0.68 | 0.09 | 0.01 | 2.2E−16 |
| APOE_locus | rs3826688 | chr19:45418961 | Phospholipids in medium VLDL | C | 0.68 | 0.09 | 0.01 | 3.3E−16 |
| APOE_locus | rs3826688 | chr19:45418961 | Triglycerides in small VLDL | C | 0.68 | 0.09 | 0.01 | 1.4E−15 |
| APOE_locus | rs3826688 | chr19:45418961 | Free cholesterol in medium VLDL | C | 0.68 | 0.09 | 0.01 | 1.7E−15 |

TABLE 9-continued

Association of candidate sites/loci with changes in metabolite levels

| Genes (loci) | rsID | Pos (hg19) | Trait | EA | EAF | Beta | SE | P |
|---|---|---|---|---|---|---|---|---|
| APOE_locus | rs3826688 | chr19:45418961 | Total lipids in medium VLDL | C | 0.68 | 0.09 | 0.01 | 1.0E−13 |
| APOE_locus | rs3826688 | chr19:45418961 | Total cholesterol in HDL | C | 0.68 | −0.04 | 0.01 | 1.6E−04 |
| APOE_locus | rs484195 | chr19:45421877 | Phospholipids in very large HDL | A | 0.33 | 0.04 | 0.01 | 8.8E−04 |
| APOE_locus | rs484195 | chr19:45421877 | Free cholesterol in very large HDL | A | 0.33 | 0.03 | 0.01 | 3.0E−03 |
| APOE_locus | rs484195 | chr19:45421877 | Concentration of very large HDL particles | A | 0.33 | 0.03 | 0.01 | 3.6E−03 |
| APOE_locus | rs12721051 | chr19:45422160 | Free cholesterol in IDL | C | 0.76 | −0.16 | 0.01 | 2.0E−38 |
| APOE_locus | rs4420638 | chr19:45422946 | Glycochenodeoxycholate | A | 0.87 | 0.04 | 0.01 | 7.1E−03 |
| APOE_locus | rs157594 | chr19:45425175 | Phospholipids in very small VLDL | T | 0.41 | −0.13 | 0.01 | 4.0E−29 |
| APOE_locus | rs157594 | chr19:45425175 | Triglycerides in IDL | T | 0.41 | −0.13 | 0.01 | 4.3E−26 |
| APOE_locus | rs157594 | chr19:45425175 | Concentration of very small VLDL particles | T | 0.41 | −0.12 | 0.01 | 1.4E−24 |
| APOE_locus | rs157594 | chr19:45425175 | Total lipids in very small VLDL | T | 0.41 | −0.12 | 0.01 | 1.4E−23 |
| APOE_locus | rs157594 | chr19:45425175 | Triglycerides in very small VLDL | T | 0.41 | −0.11 | 0.01 | 1.1E−20 |
| APOE_locus | rs157594 | chr19:45425175 | 22:6 docosahexaenoic acid (DHA) | T | 0.40 | −0.04 | 0.01 | 2.7E−03 |
| APOE_locus | rs66626994 | chr19:45428234 | CH2 groups in fatty acids | A | 0.22 | −0.04 | 0.01 | 3.8E−03 |
| KCNJ15 | rs7275784 | chr21:39636309 | Pentadecanoate (15:0) | C | 0.50 | 0.01 | 0.00 | 4.6E−03 |
| KCNJ15 | rs928771 | chr21:39663760 | Glycerophosphorylcholine (GPC) | G | 0.50 | −0.01 | 0.00 | 6.1E−03 |
| KCNJ15 | rs2836293 | chr21:39664976 | Homocitrulline | A | 0.50 | 0.01 | 0.00 | 5.5E−03 |

With regard to Table 9, EA, effective alleles (or effect allele); EAF, effective allele frequencies; Beta, association between the trait and the SNP expressed per additional copy of the effect allele (odds ratios are given on the log-scale); SE, standard error of Beta; P, p-value. 147 candidate variants in AD susceptibility loci were subjected to the PhenoScanner to determine the association between genotype and levels of metabolites. Table 9 shows the change of metabolite levels that correspond to the specific genetic variants, with a p-value cutoff of 0.01. Specific datasets were included for the analysis (Shin et al., 2014; Kettunen et al., 2016).

Furthermore, a weighted-genetic risk score (GRS) combining all the genetic information from aforementioned 147 sites were calculated for each subject for the model construction to classify the phenotypes for each individual (see FIG. 1). Based on the information obtained in the pilot study, it was demonstrated that the GRS out-performed when compared with using dosage information in the APOE-ε4 variant, indicated by both the ROC (receiver operating characteristic) curve (which suggests a superior sensitivity and specificity for the AD prediction), and a higher value of AUC (Area Under the Curve), which indicates a superior overall performance in AD prediction (FIG. 2). Meanwhile, using a mixture of Gaussian models that fit individual GRS values, three categories of individuals were distinguished corresponding to low, medium, and high risk levels for AD. All the individuals in the pilot dataset were further classified using the aforementioned mixture of Gaussian models with Bayesian classifications, and confirmed the association between GRS values with AD and MCI, which is indicated by the odds ratio of 14.8 for AD and 5.2 for MCI when comparing the high risk categories with low risk categories (Table 10). Subjects displaying different phenotypes with pre-calculated GRS were classified into low, medium or high risk categories using a Bayesian model with pre-fitted multivariate Gaussian mixture models. Table 10 shows the relative risks of developing AD or MCI for subjects, classified into high, medium or low risk categories.

TABLE 10

Association of GRS with MCI and AD

| Category | NC (N = 442) | MCI (N = 253) | AD (N = 477) | For NC p | For NC OR | For MCI p | For MCI OR | For AD p | For AD OR |
|---|---|---|---|---|---|---|---|---|---|
| High | 7 (1.6%) | 9 (3.6%) | 36 (7.5%) | 1.7E−01 | 1.9 (0.7-5.2) | 5.5E−04 | 5.2 (1.9-13.1) | 1.3E−18 | 14.8 (7.6-30.3) |
| Medium | 131 (29.6%) | 99 (39.1%) | 238 (49.9%) | 4.9E−01 | 0.92 (0.7-1.2) | 8.7E−03 | 1.5 (1.1-1.9) | 3.0E−17 | 2.5 (2.0-3.1) |
| Low | 304 (68.8%) | 145 (57.3%) | 203 (42.6%) | NA | NA | NA | NA | NA | NA |

Through comprehensive analysis of a pilot cohort of Chinese AD subjects, novel AD susceptibility variants were identified, and through query of existing database for the known quantitative trait loci (QTL), possible outcomes both in transcript level as well as protein/biomarker level were associated with the newly identified loci. In addition, through combining the genetic information in the identified risk loci, a GRS model for AD predication was established, and strong associations between GRS and AD, together with the capability for AD prediction were demonstrated.

Example 2—APOE Loci as Biomarkers for Alzheimer's Disease

A low-coverage, whole-genome sequencing (WGS) study to identify AD-associated variants in the Chinese population was conducted. Analysis validated the APOE locus as one of the strongest risk factor for AD in the Chinese population (odds ratio of 3.06 for APOE-ε4 rs429358). Furthermore, a 55-kb AD-associated haplotype within the APOE locus in the Chinese population was identified. Particularly, various new loci that are involved in functional pathways associated with AD, including synaptic plasticity and the insulin-related pathway were identified. WGS data was also used to specifically examine the possible contribution of gene-gene interactions in the pathogenesis of AD. It was found that the effect of APOE-ε4 can be modulated by certain loci. This is the first WGS study of Chinese AD patients, demonstrating the capability of the low-pass sequencing strategy to study complex disease traits.

Study Cohort and Subject Recruitment

A cohort of Chinese subjects were recruited to this study from 2007 to 2016 at the Department of Neurology, Huashan Hospital, Fudan University, Shanghai, China. There were 1,654 subjects (mean age: 69.8 years): 662 with AD, 403 with MCI, and 589 age- and gender-matched NCs. AD patients were diagnosed on the basis of recommendations from the National Institute on Aging and the Alzheimer's Association workgroup (McKhann et al., 2011), and had an onset age ≥50 years. MCI patients were diagnosed according to the Peterson criteria (Petersen, 2004). Individuals with any significant neurologic disease or psychiatric disorder were excluded. 250 subjects of normal controls recruited from the community in Shanghai without subjective memory complaints. The other subjects were recruited from the Memory Clinic and underwent laboratory screening. All recruited samples were subjected to medical history assessment, neuropsychological assessment and imaging assessment including computed tomography (CT) or magnetic resonance imaging (MRI). Some participants further undertook positron emission tomography (PET) using Pittsburgh compound B (PiB). The study was approved by the Ethics Committee of Huashan Hospital, The Hong Kong University of Science and Technology (HKUST) and the HKUST Shenzhen Research Institute, and all subjects provided written informed consent for both study enrollment and sample collection. A total of 1,222 subjects (NC: 473, MCI: 260, AD: 489) passed the final quality control for the WGS library construction.

Sample Processing and APOE Genotyping

Whole blood was collected in non-EDTA tubes and centrifuged at 2000×g. Following removal of serum in the supernatant, the cell pellet was used for preparation of genomic DNA. The APOE-ε4 genotype of each subject was determined by TaqMan® SNP genotyping assays.

Whole Genome Sequencing

Low-coverage whole genome sequencing (5×) was performed by Novogene Co., Ltd. In brief, genomic DNA purity was checked by a NanoPhotometer® spectrophotometer, the concentration was measured using a Qubit® DNA Assay Kit with a Qubit® 2.0 Fluorometer, and fragment distribution was measured using the DNA Nano 6000 Assay Kit with the Agilent Bioanalyzer 2100 system. DNA (1.5 µg) of each sample was fragmented by sonication to 350 bp and used to generate a sequencing library with the Truseq Nano DNA HT Sample preparation Kit (Illumina). The genomic DNA libraries were sequenced on an Illumina Hiseq X Ten platform, and paired-end reads were generated. Adapter contamination and low-quality reads were filtered from the raw data to ensure data quality, producing clean data with base quality greater than Q20 for the majority of detected signals, and the fraction of Q30 was above 80%. The phenotypic labels were blinded for the researchers during the WGS process.

Specialized Variant Detection Protocol for Low-Pass WGS Cohort Data

A Gotcloud (Jun et al., 2015) pipeline was adapted to detect refine variants from the raw sequencing data of 1,348 samples (including 126 re-sequenced samples). An average of 15 GB Illumina sequencing data per subject was mapped to the GRCh37 reference genome containing the decoy fragments. A total of 24,742,555 SNPs were detected by glfmultiples after the initial calling steps. Hard-filter or SVM-based filtering methods were implemented in the Gotcloud pipeline using default settings of VcfCooker or Perl scripts (run_libsvm.pl) to filter low-confident calling of variants based on site information such as depth, allele balance, mapping quality, together with high-quality dataset derived from the 1000 genome project or Hapmap project. Variants with high-confident calls in the range of MAF≥5% (n=4,481,200; 18.1% of raw detected sites) were subjected to Beagle (Browning and Browning, 2007; Browning and Browning, 2009) for pre-phasing and pre-imputation. Phased variants were subsequently subjected to Thunder (Li et al., 2010) to refine the variants detected during our discovery phase. In the refinement step for each candidate loci, all raw variants in the 50-kb range near the candidate gene were extracted and submitted them to the same variant calling strategy with no additional filtering.

Haplotype Phasing and Imputation in the Refinement Stage

All genomic information in the 50-kb range around the candidate loci were extracted, subjected it to Beagle for pre-phasing and pre-imputation (phase-iteration: 50, impute-iteration: 15), and further to Thunder for the LD-based refinement of SNP calls (-r 30; --states 300; --weightedStates 300).

Haplotype Phasing and Estimation in the APOE Locus

Phased individual genomic information in 34 AD susceptibility sites in the APOE locus were subgrouped by phenotype, converted to the Plink ped format, and subjected to Haploview (Barrett, 2009) to estimate haplotype type and frequency in each phenotype group. Haplotype information at the individual level were calculated by Thunder and further subjected to R programming for data reformatting and statistical analysis.

Statistical Analysis and Data Visualization

Association tests including allelic or genotype tests using either Plink or R programming were performed. Pairwise linkage information (Both $r^2$ and D') between SNPs in candidate loci were generated using the Vcftools --hap-r2 command. All information were combined and subjected to LocusZoom (Pruim et al., 2010) for the regional visualization of each candidate locus. Linear regression analysis of cognitive performance in the APOE locus haplotype study in R was performed using the MMSE score as the outcome for the quantitative measure of cognitive performance. Epistasis analysis was conducted using the Plink --epistasis with --epi1 0.00001 command and reformatted, and the final result was plotted using R and the Bioconductor (Gentleman et al., 2004) package of OmicCircos (Hu et al., 2014) for data visualization. Genome-wide Complex Trait Analysis (GCTA) software (Yang et al., 2011) with user-specified prevalence of 10% for AD was adopted to estimate the proportion of phenotypic variance that could be explained by a particular group of variants. Power calculation was performed using the Quanto (Gauderman and Morrison, 2006), with user-specified prevalence of 10% and Type I error rate of 1E-05 for the estimation of statistical power.

Expression Quantitative Trait Loci (eQTL) Analysis for Candidate Sites

Genotype expression data was retrieved from the Genotype-Tissue Expression (GTEx) project (Consortium, 2015; Consortium, 2013) (www.gtexportal.org) to identify eQTLs in our novel AD susceptibility loci. In this database, 83.1% of the donations came from participants older than 40 years (40-49 years: 16.9%, 50-59 years: 34.6%, 60-69 years: 31.6%). The majority of donations were from Caucasians (84.3%). All statistical metrics were retrieved from the database.

Mouse Model

APP/PS1 (APPswe+PSEN1/dE9) double-transgenic mice were obtained, generated by incorporating a human/murine APP construct bearing the Swedish double mutation and the exon-9 deleted PSEN1 mutation from the Jackson Laboratory, together with corresponding wild-type (WT) mice for the transcript study of candidate genes. All mice were housed in the HKUST Animal and Plant Care Facility, and all animal experiments were approved by the HKUST Animal Ethics Committee. The experiments were conducted using randomly selected paired littermates, with no exclusion of samples during experiment and data analysis. All mice were female and the brain samples were collected at the age of 12-13 month old.

Droplet Digital PCR

For droplet digital PCR (ddPCR), RNA from mouse cortices was extracted using TRIzol (Invitrogen) and the RNeasy Mini Kit (Qiagen), and quantified using a BioDrop gLITE microvolume spectrophotometer. Reverse-transcribed equivalent amounts of RNA was obtained using the PrimeScript RT-PCR Kit (TaKaRa). ddPCR was performed according to the manufacturer's protocol (Bio-Rad). Next, the copy numbers for samples across duplicates were averaged. The copy numbers of target genes were normalized to those of β-actin. TaqMan probes used: TRPM8 (Mm01299593_m1), KCNJ15 (Mm02020346_s1), MYO1D (Mm01296373 m1), SHISA6 (Mm01329069_m1), SAMD4 (Mm01311175_m1) and Beta-actin (Mm02619580_g1) for the gene expression study in the APP/PS1 mouse model. Mouse brain collection was conducted by researchers who were blinded to the experimental groups. Sample sizes for the transcript study were chosen primarily on the basis of experience with similar types of experiments.

Availability of Data and Code

The ENCODE genome annotation data used in this study are available from UCSC genome browser "genome.ucsc.edu/". The GTEx eQTL data are available from GTEx Portal "www.gtexportal.org/".

SNP Detection

Any human or laboratory derived biomaterials that cover or include the target nucleotide sequences including genomic DNA, RNA, or cDNA derived from total RNA or mRNA, or bacterial plasmid/phagemid before or after amplification can be used as test materials. Any variation detection method including Taqman/SYBR green/PCR-based detection, Sanger sequencing, hybridization detection method or next/third generation sequencing method, or electrophoresis, mass-spectrometry based mass discrimination method can be used for the SNP detection.

Results

A total of 1,654 participants were recruited a: 589 normal controls (NC), 403 individuals with mild cognitive impairment (MCI), and 662 individuals with AD. The genomic DNA from 1,222 samples (NC: 473, MCI: 260, and AD: 489) passed the criteria for WGS library construction. A total of 24,742,555 SNPs were obtained after variant calling. As the discovery phase for the investigation of novel AD susceptibility loci, the variant pool was further restricted to the bi-allelic high-confidence calls that passed the filtering with a minor allele frequency (MAF)≥5% (n=4,481,200) for phasing and imputation. After finishing the variants refinement, high concordance rates among these sites were observed; the overall concordance rate was 99.3% when comparing 126 re-sequencing samples, and 99.2% when comparing 96 SNP array genotyping samples. Particularly, when comparing the WGS data with the genotyping results of APOE-ε2, ε3 and E4 (rs429358 and rs7412), the concordant rate reached 98.0%. To confirm the ethnicity of our Chinese AD cohort, we compared our data with the 1000 Genome Phase 3 data. The clustering results derived from fastStructure (Raj and Pritchard, 2014) demonstrated that the cohort perfectly clustered with the East Asian (EAS) population. Principal component analysis further demonstrated that the cohort was derived from the EAS super-population (Genome Project, 2015) i.e., closest to the Chinese Han Beijing (CHB) cohort with an overlap with the Southern Han Chinese (CHS), suggesting that the cohort is representative of the Han Chinese population, the major subgroup in China.

Various quality control steps were performed to assess sample quality, including the missing of gender information or inconsistency of gender record between sequencing data and clinical record, deviation from main population owing to sample quality or batch effects, and sample relatedness (see Methods). After finishing quality control, 50 samples (4%, see Methods for details) were excluded from the dataset together with 354,572 variants (7.9%) with a discordant call rate >1% when comparing 126 re-sequenced samples. Meanwhile, power calculation was conducted regarding the current study design for our case-control association test for AD, which highlighted the variant pools with MAF≥10% for the identification of AD-associated loci in our dataset. Thus, as the initial or discovery phase, the remaining 1,172 samples (NC: 442, MCI: 253, AD: 477) with 3,492,083 variants (92.1% of 3,792,458 sites with MAF≥10%) were subjected to the association study for the identification of AD susceptibility loci.

Figure 4:
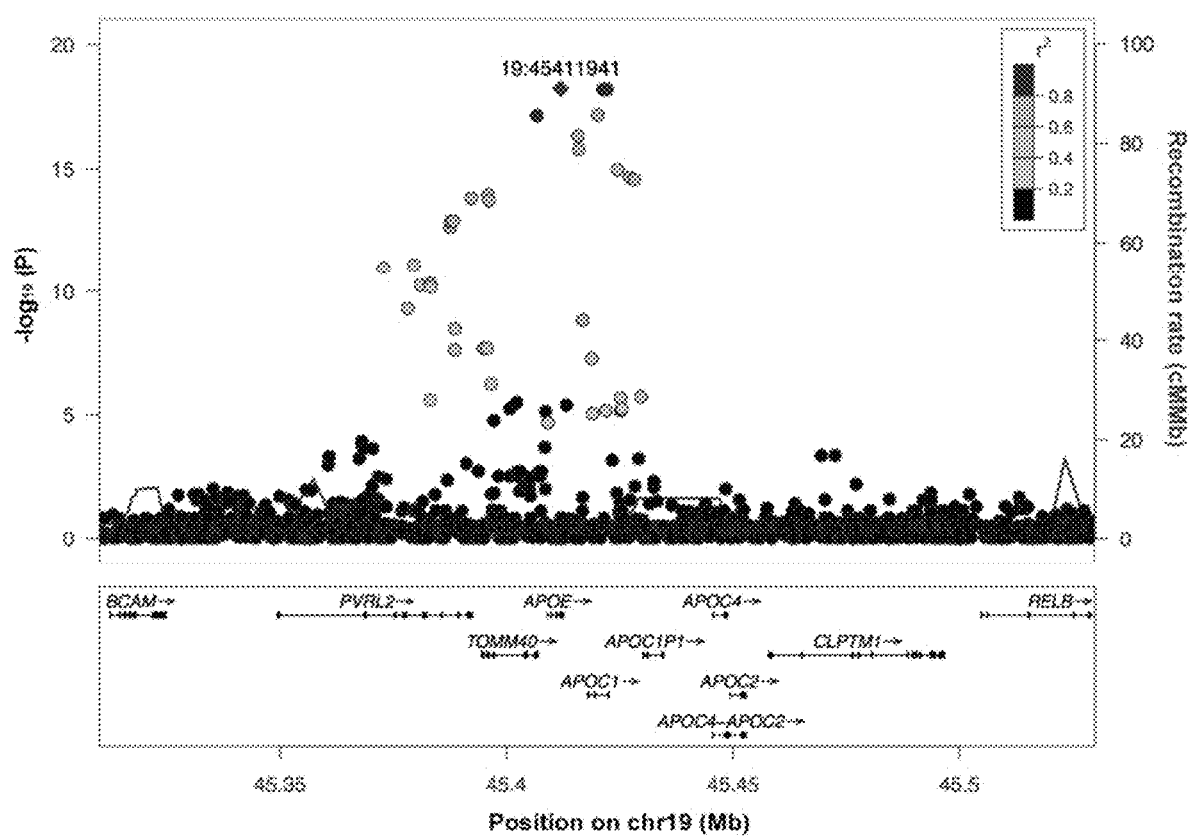
FIG. 4 depicts a regional plot for susceptibility variants located with the APOE locus.

On the basis of the allelic test for the identification of AD-associated loci, a total of 28 SNPs across the PVRL2, TOMM40, APOE, and APOC1 genes within the 55-kb range (chr19q13.32; chr19:45372794-45428234) passed the genome-wide threshold (unadjusted p=5E-08, allelic chi-square test) (FIG. 4, Table 11). Results in Table 11 were obtained from the association test between the AD (n=477) and NC (n=442) groups. The summary statistics of the 51 candidate sites located in chromosome 19 in or around APOE locus that passed the suggestive threshold (p=1E-05) are shown. If OR>1, then the risk allele is the minor allele. If OR<1, then the risk allele is the major allele (or the minor allele is having protective effect).

TABLE 11

AD susceptible SNPs discovered in Chinese AD cohort in APOE locus

| SNP APOE | SNP_ID | Major | Minor | Chi | P | OR |
|---|---|---|---|---|---|---|
| 19_45372794 | rs404935 | G | A | 47.3 | 6.10E−12 | 2.2 |
| 19_45378144 | rs34278513 | C | T | 40.1 | 2.50E−10 | 2.1 |
| 19_45379516 | rs412776 | G | A | 47.6 | 5.20E−12 | 2.3 |
| 19_45380961 | rs3865427 | C | A | 41.6 | 1.10E−10 | 2.2 |
| 19_45383061 | rs3852861 | T | G | 20.0 | 7.90E−06 | 1.6 |
| 19_45383079 | rs71352237 | T | C | 40.1 | 2.40E−10 | 2.2 |
| 19_45383115 | rs34224078 | A | G | 41.0 | 1.50E−10 | 2.2 |
| 19_45383139 | rs35879138 | T | A | 39.5 | 3.30E−10 | 2.1 |
| 19_45387459 | rs12972156 | C | G | 58.5 | 2.00E−14 | 2.7 |
| 19_45387596 | rs12972970 | G | A | 54.1 | 1.90E−13 | 2.6 |
| 19_45388130 | rs34342646 | G | A | 54.9 | 1.30E−13 | 2.6 |
| 19_45388500 | rs283811 | A | G | 32.5 | 1.20E−08 | 1.9 |
| 19_45388568 | rs283812 | T | C | 33.7 | 6.40E−09 | 1.9 |
| 19_45392254 | rs6857 | C | T | 59.4 | 1.30E−14 | 2.7 |
| 19_45394969 | rs184017 | T | G | 30.8 | 2.90E−08 | 1.8 |
| 19_45395714 | rs157581 | T | C | 30.8 | 2.90E−08 | 1.8 |
| 19_45395909 | rs34404554 | C | G | 60.5 | 7.50E−15 | 2.7 |
| 19_45396144 | rs11556505 | C | T | 60.5 | 7.50E−15 | 2.7 |
| 19_45396665 | rs59007384 | G | T | 25.0 | 5.70E−07 | 1.7 |
| 19_45406673 | rs10119 | G | A | 73.3 | 1.10E−17 | 2.9 |
| 19_45411941 | rs429358 | T | C | 78.2 | 9.50E−19 | 3.0 |
| 19_45415713 | rs10414043 | G | A | 71.2 | 3.20E−17 | 2.9 |
| 19_45415935 | rs7256200 | G | T | 68.8 | 1.10E−16 | 2.8 |
| 19_45416741 | rs438811 | C | T | 35.9 | 2.00E−09 | 1.9 |
| 19_45418790 | rs5117 | T | C | 27.1 | 2.00E−07 | 1.8 |
| 19_45420082 | rs73052335 | A | C | 48.6 | 3.10E−12 | 2.1 |
| 19_45421254 | rs12721046 | G | A | 81.4 | 1.80E−19 | 3.0 |
| 19_45422160 | rs12721051 | C | G | 78.9 | 6.50E−19 | 2.9 |
| 19_45424514 | rs157592 | A | C | 55.8 | 8.10E−14 | 2.6 |
| 19_45425175 | rs157594 | T | G | 19.7 | 9.00E−06 | 1.5 |
| 19_45425460 | rs157595 | A | G | 19.8 | 8.80E−06 | 1.5 |
| 19_45427125 | rs111789331 | T | A | 63.2 | 1.90E−15 | 2.7 |
| 19_45428234 | rs66626994 | G | A | 62.8 | 2.30E−15 | 2.7 |
| 19_45429708 | rs60049679 | G | C | 23.4 | 1.30E−06 | 1.8 |
| 19_45371168 | rs4803766 | G | A | 21.94 | 2.81E−06 | 1.563 |
| 19_45373565 | rs395908 | G | A | 41.52 | 1.17E−10 | 2.134 |
| 19_45376284 | rs519113 | C | G | 43.5 | 4.23E−11 | 2.115 |
| 19_45380970 | rs11668861 | G | T | 24.21 | 8.63E−07 | 0.5949 |
| 19_45382034 | rs6859 | A | G | 22.88 | 1.73E−06 | 0.6263 |
| 19_45382966 | rs3852860 | C | T | 20.66 | 5.49E−06 | 0.624 |
| 19_45390333 | rs283815 | A | G | 31.96 | 1.57E−08 | 1.842 |
| 19_45394336 | rs71352238 | T | C | 59.71 | 1.10E−14 | 2.698 |
| 19_45395619 | rs2075650 | A | G | 58.19 | 2.38E−14 | 2.668 |
| 19_45396219 | rs157582 | C | T | 32.91 | 9.67E−09 | 1.856 |
| 19_45410002 | rs769449 | G | A | 67.45 | 2.16E−16 | 2.894 |
| 19_45413576 | rs75627662 | C | T | 27.05 | 1.98E−07 | 1.762 |
| 19_45414451 | rs439401 | T | C | 21.48 | 3.57E−06 | 1.545 |
| 19_45416178 | rs483082 | G | T | 36.36 | 1.64E−09 | 1.906 |
| 19_45421877 | rs484195 | A | G | 21.55 | 3.44E−06 | 1.546 |
| 19_45422846 | rs56131196 | G | A | 78.55 | 7.82E−19 | 2.907 |
| 19_45422946 | rs4420638 | A | G | 75.27 | 4.10E−18 | 2.849 |

Existence of AD-Associated Haplotypes in the APOE Locus

Consistent with the previous meta-analysis data on APOE-ε4 allele frequency (Liu and Zhang, 2014; Bertman et al., 2007) the APOE-ε4 allele frequency in the Chinese population in the present study was significantly lower than that in the Caucasian population in both the NC and AD groups (unadjusted p=4.2E-09 in the AD group; unadjusted p=1.7E-02 in the NC group, data not shown). Regional visualization of association results in the APOE locus further revealed a strong association between the APOE locus and AD together with linkage disequilibrium (LD) between those AD susceptibility variants and APOE-ε4 (FIG. 4).

Haplotype analysis by Haploview (Barrett et al., 2009) further revealed the existence of AD-associated haplotypes in the APOE locus in the Chinese population, especially one mutant haplotype defined by all the minor alleles of 51 AD-associated sites in the APOE locus with a frequency of 5% in the NC group. This minor haplotype was significantly associated with AD (unadjusted p=8.3E-06, OR=2.48) and decreased cognitive performance indicated by Mini-Mental State Examination (MMSE) score (unadjusted p=1.5E-05, β=−2.58) (Table 12 and Table 13). This indicates a possible multi-gene effect in the APOE locus apart from the APOE-ε4 mutation, rs429358. Notably, APOE haplotypes with APOE-ε4 major allele (C at rs429358) were significantly associated with cognitive performance after adjusting for age, gender, and APOE-ε4 allele dosage (Table 13). These results suggest that these APOE haplotypes have residual effects on the cognitive system that are independent of APOE-ε4 status, corroborating the multi-gene effect in AD pathogenesis.

TABLE 12

APOE locus haplotypes associated with AD in the Chinese population

| Haplotypes | NC_AD genotype test Chi | unadj. P | NC_AD allelic test Chi | unadj. P | OR | Haplotype frequency NC | MCI | AD |
|---|---|---|---|---|---|---|---|---|
| SEQ ID No. 1-<br>gcgcttatcggatcttccggTggctagcatatgg | 25.8 | 3.8E-07 | 26.0 | 2.2E-06 | 0.61:<br>(0.50-0.74) | 0.44 | 0.45 | 0.33 |
| SEQ ID No. 2-<br>ataagcgagaagctgcgttaCattccagcggaac | 24.4 | 7.8E-07 | 23.4 | 8.3E-06 | 2.48<br>(1.69-3.68) | 0.05 | 0.07 | 0.11 |
| SEQ ID No. 3-<br>gcgcttatgaagctgcgttaCattccagcggaac | 5.8 | 1.6E-02 | 5.8 | 1.6E-02 | 8.06<br>(1.23-334) | 0.00 | 0.00 | 0.02 |

In Table 13, the APOE haplotypes identified in the Chinese WGS dataset (n=1,139) that are associated with cognitive performance are indicated. APOE-ε4 variant rs429358_T/C is shown in uppercase, the uppercase letter C denotes the minor allele and the uppercase letter T denotes the major allele. Specific APOE-ε4 mutant-free haplotype were identified to be associated with cognitive decline after adjusting for age, gender, and APOE-ε4 genotype. This suggests that there is residual effect of variants or haplotypes in the APOE locus besides APOE-ε4 rs429358.OE-ε4 genotype, suggesting the residual effects of variants or haplotypes in the APOE locus besides APOE-ε4 rs429358.

TABLE 13

Association of APOE locus haplotypes with cognitive performance

| Haplotypes | Unadjusted Wald P | Beta | Adjusted with age and gender Wald P | Beta | Adjusted with age, gender and APOE-E4 dosage Wald P | Beta |
|---|---|---|---|---|---|---|
| SEQ ID No: 4-<br>ataagcgagaagctgcgt<br>taCattccagcggaac | 18.9 1.5E-05 | -2.58:<br>(-3.74-1.42) | 18.8 1.6E-05 | -2.57:<br>(-3.73-1.4) | 0.8 3.7E-01 | -0.61:<br>(-1.93-0.71) |
| SEQ ID No: 5-<br>gcgcttatcggatcttcc<br>ggTggctagcatatgg | 17.6 3.0E-05 | 1.37:<br>(0.73-2) | 16.5 5.2E-05 | 1.33:<br>(0.69-1.97) | 2.4 1.2E-01 | 0.54:<br>(-0.14-1.22) |
| SEQ ID No: 6-<br>ataagcgagaagctgcgt<br>tgTggctagcaggtgg | 17.6 3.0E-05 | 1.37:<br>(0.73-2) | 16.5 5.2E-05 | 1.33:<br>(0.69-1.97) | 2.4 1.2E-01 | 0.54:<br>(-0.14-1.22) |
| SEQ ID No: 7-<br>ataagcgagaagctgcgt<br>tgTggtcagcaggtgg | 17.6 3.0E-05 | 1.37:<br>(0.73-2) | 16.5 5.2E-05 | 1.33:<br>(0.69-1.97) | 2.4 1.2E-01 | 0.54:<br>(-0.14-1.22) |
| SEQ ID No: 8-<br>gcgcttatcggatcttcc<br>tgTggctagcaggaag | 17.6 3.0E-05 | 1.37:<br>(0.73-2) | 16.5 5.2E-05 | 1.33:<br>(0.69-1.97) | 2.4 1.2E-01 | 0.54:<br>(-0.14-1.22) |
| SEQ ID No: 9-<br>ataagcgagaagctgcgt<br>taCattccagcggaag | 10.5 1.2E-03 | -4.71:<br>(-7.56-1.86) | 10.0 1.7E-03 | -4.59:<br>(-7.44-1.74) | 2.5 1.2E-01 | -2.31:<br>(-5.19-0.56) |
| SEQ ID No: 10-<br>ataagcgacggatcttcc<br>ggTattccagcggaag | 10.5 1.2E-03 | -5.27:<br>(-8.46-2.08) | 9.6 2.0E-03 | -5.05:<br>(-8.25-1.85) | 11.5 7.0E-04 | -5.42:<br>(-8.55-2.29) |
| SEQ ID No: 11-<br>ataagcgagaagctgcgt<br>taCattccgcatatgg | 8.3 4.1E-03 | -22.27:<br>(-37.44-7.1) | 8.8 3.1E-03 | -22.96:<br>(-38.13-7.8) | 6.0 1.5E-02 | -18.56:<br>(-33.47-3.66) |
| gcgcgtatcgggccgccc<br>tgTggtcagcaggtgg | 7.6 6.0E-03 | 2.85:<br>(0.82-4.88) | 8.0 4.8E-03 | 2.92:<br>(0.89-4.95) | 5.2 2.3E-02 | 2.32:<br>(0.33-4.31) |
| SEQ ID No: 12-<br>ataagcgagaagctgcgt<br>taCattccagcggtgg | 6.3 1.2E-02 | -13.77:<br>(-24.51-3.03) | 5.9 1.6E-02 | -13.3:<br>(-24.01-2.52) | 3.7 5.5E-02 | -10.33:<br>(-20.88-0.23) |
| SEQ ID No: 13-<br>gcgcttatcggatcttcc<br>ggTggctaagaggaac | 5.6 1.9E-02 | -18.26:<br>(-33.45-3.08) | 5.9 1.5E-02 | -18.8:<br>(-33.95-3.6) | 6.8 9.3E-03 | -19.73:<br>(-34.57-4.89) |

TABLE 13-continued

Association of APOE locus haplotypes with cognitive performance

| Haplotypes | Unadjusted | | Adjusted with age and gender | | Adjusted with age, gender and APOE-E4 dosage | |
|---|---|---|---|---|---|---|
| | Wald P | Beta | Wald P | Beta | Wald P | Beta |
| SEQ ID No: 14-<br>gcgcttatcggaccttcc<br>ggTggctagcaggtgg | 5.0 2.5E-02 | -6.17:<br>(-11.55-0.78) | 5.1 2.5E-02 | -6.2:<br>(-11.55-0.79) | 3.7 5.5E-02 | -5.16:<br>(-10.44-0.11) |
| SEQ ID No: 15-<br>ataagcgacggatcttcc<br>ggTggctagcaggtgc | 5.0 2.6E-02 | -71.26:<br>(-32.45-2.07) | 4.6 3.2E-02 | -16.7:<br>(-31.85-1.45) | 5.5 1.9E-02 | -17.77:<br>(-32.64-2.9) |
| SEQ ID No: 16-<br>gcgcttatcggatcttgt<br>taCattccagcggaac | 5.0 2.6E-02 | -17.26:<br>(-32.45-2.07) | 5.2 2.3E-02 | -17.7:<br>(-32.88-2.52) | 3.0 8.2E-02 | -13.25:<br>(-28.17-1.66) |
| SEQ ID No: 17-<br>ataagcgacggatcttcc<br>ggTggctagcaggaag | 4.4 3.6E-02 | -16.26:<br>(-31.46-1.07) | 4.2 4.1E-02 | -15.8:<br>(-31.01-0.63) | 5.0 2.6E-02 | -16.95:<br>(-31.8-2.09) |
| SEQ ID No: 18-<br>ataagcgacggatcttcc<br>taTggctagcatatgg | 3.9 4.9E-02 | -15.26:<br>(-30.46-0.06 | 4.1 4.4E-02 | -15.6:<br>(-30.81-0.41) | 4.8 2.9E-02 | -16.56:<br>(31.42-1.69) |
| SEQ ID No: 19-<br>gcgcgtatgaagctgcgt<br>taCagctagcatatgg | 3.9 4.9E-02 | -15.26:<br>(-30.46-0.06) | 4.0 4.5E-02 | -15.6:<br>(-30.8-0.39) | 3.3 6.9E-02 | -13.81:<br>(-28.69-1.08) |
| SEQ ID No: 20-<br>gcgcttatgaagctgcgt<br>taCagtccagcggaac | 3.9 4.9E-02 | -15.26:<br>(-30.46-0.06) | 4.2 4.1E-02 | -15.9:<br>(-31.06-0.68) | 2.2 1.3E-01 | -11.42:<br>(-26.34-3.51) |
| SEQ ID No: 21-<br>gtaagcgacgggccgccc<br>gaCggttcagcggaac | 3.9 4.9E-02 | -15.26:<br>(-30.46-0.06) | 4.1 4.2E-02 | -15.8:<br>(-30.97-0.59) | 3.4 6.5E-02 | -14.01:<br>(-28.88-0.86) |
| SEQ ID No: 22-<br>gtaagcgagaagctgcgt<br>taCattccagaggtgg | 3.9 4.9E-02 | -15.26:<br>(-30.46-0.06) | 3.6 5.8E-02 | -14.7:<br>(-29.9-0.5) | 3.0 8.5E-02 | -13.08:<br>(-27.96-1.8) |
| SEQ ID No: 23-<br>gcgcttatcggattgcgt<br>tgTggctcgcaggtgg | 3.9 5.0E-02 | -10.77:<br>(-21.52-0.02) | 3.6 5.7E-02 | -10.44:<br>(-21.2-0.31) | 3.6 5.8E-02 | -10.2:<br>(-20.72-0.32) |
| SEQ ID No: 24-<br>ataagcgagaagcttccc<br>ggTggctagcatatgg | 3.4 6.6E-02 | -14.26:<br>(-29.46-0.94) | 3.2 7.5E-02 | -13.83:<br>(-29.02-1.36) | 3.9 4.9E-02 | -14.96:<br>(-29.82-0.1) |
| SEQ ID No: 25-<br>gcgcttatcggatcttcc<br>tgTggctagcatatgg | 3.1 8.1E-02 | -5.14:<br>(-10.9-0.62) | 2.8 9.4E-02 | -4.93:<br>(-10.69-0.83) | 4.4 3.6E-02 | -6.02:<br>(-11.66-0.39) |

Contribution of Gene-Gene Interactions in the Pathogenesis of AD

The possible gene-gene interactions in AD was subsequently investigated by performing case-control epistasis analysis across the AD susceptibility variants against all high-confident variant calls with MAF≥10%, and the results presented as a global gene-gene interaction map. Potential cofactors for the APOE locus were identified. Interestingly, the risk effect of the APOE-ε4 variant rs429358 in AD could be masked by more than one variant located in IL-18. One of the top-ranked variants, rs7106524, was associated with a decreased transcript level of IL-18 with a simultaneous increase of the transcript level of BCO2 (IL-18 level: β=−0.25, p=6.4E-6, nerve, n=256; BCO2 level: β=0.63, p=8.2E-8, cortex, n=96). These results collectively suggest that the concurrence of specific variants might alter the genetic risk of AD-associated variants (Table 14). Epistasis analysis revealed variants with putative biological functions that may have a modification effect on APOE-ε4 variant. Novel sites (SNP2) exhibiting interaction effects with APOE-ε4 variant (SNP1), as indicated by p-values exceeding the suggestive threshold (INT_P<1E-5), are summarized. Putative biological significance is annotated as occupancy of transcription factor-binding or histone methylation regions. Variants with eQTL properties are also highlighted with the target genes that are being modulated.

TABLE 14

Novel AD susceptibility loci interact with variants that have putative functions in gene expression

| Gene_1 | SNP1 | Gene_2 | SNP2 | OR_INT | STAT | P | rsID (Annotation) | eQTL_target |
|---|---|---|---|---|---|---|---|---|
| APOE_locus | rs429358 | IL18 | rs360716 | 0.44 | 19.83 | 8.48E−06 | rs360716 | BCO2 |
| APOE_locus | rs429358 | IL18 | rs7106524 | 0.44 | 20.01 | 7.73E−06 | rs7106524 (Methylation) | BCO2, IL18 |
| APOE_locus | rs429358 | CATSPER1 | rs1783563 | 0.38 | 19.63 | 9.43E−06 | rs1783563(TF) | SF3B2, PACS1, CATSPER1 |
| APOE_locus | rs429358 | AX746604 | rs7951170 | 0.38 | 19.63 | 9.43E−06 | rs7951170 (UTR) | NA |
| APOE_locus | rs429358 | AX746604 | rs60462066 | 0.38 | 19.63 | 9.43E−06 | rs60462066 | NA |
| APOE_locus | rs429358 | AX746604 | rs7120611 | 0.38 | 19.63 | 9.43E−06 | rs7120611 | RAB1B, KLC2, RP11-755F10.1, BANF1, CNIH2, MAPK3K11, PACS1, SF3B2, YIF1A |
| APOE_locus | rs429358 | ABCF1 | rs1264436 | 0.32 | 22.39 | 2.23E−06 | rs1264436 | NA |
| APOE_locus | rs429358 | TUBB | rs56389899 | 0.34 | 21.35 | 3.83E−06 | rs56389899 (TF) | NA |

Example 3—IL33 and IL1RL1 as Biomarkers for Alzheimer's Disease

Cohort Information

A total of 1,251 (n=1,251) people were recruited for this study, including 662 (n=662) with Alzheimer's disease (AD) and 589 (n=589) corresponding normal controls (NC) of matched age and gender. Individuals with any significant neurologic disease or psychiatric disorder were excluded from this study. All participants were recruited from the Memory Clinic and underwent laboratory screening, medical history assessment, and neuropsychological assessment including memory, language, attention, executive function, and visuospatial ability. This study was approved by the ethic committee and subjects signed informed consent forms for both study enrollment and sample collection.

In the discrimination of phenotypes, AD patients were diagnosed based on the National Institute of Neurological and Communicative Disorders and Stroke and the Alzheimer's Disease and Related Disorders Association (NINCDS-ADRDA) criteria (McKhann, Drachman et al. 1984), together with onset age >=50. In the final analysis, normal controls were further restricted to participants with MMSE score ≥25, together with age ≥55 for all participants.

Sample Collection

Figure 5:
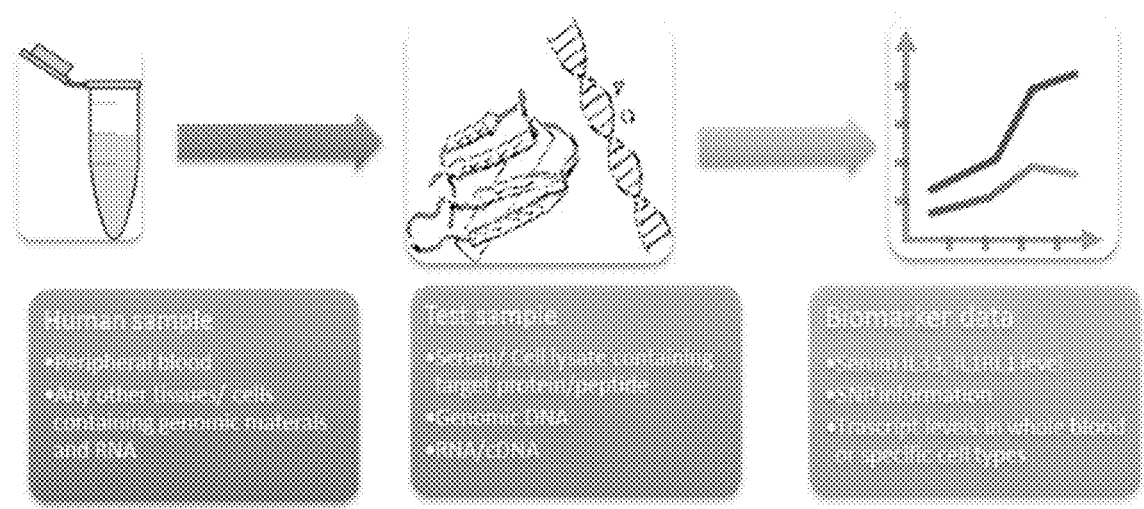
FIG. 5 depicts the basic work flow for sample collection and analysis.

The basic workflow of the study described herein for collection of samples and data analysis to identify potential AD biomarkers is shown in FIG. 5. Patient sample, such as whole blood, tissue, or cells from whole blood or other part of the human body, is collected and subjected to sample extraction. Genomic DNA, total or messenger RNA, protein extract, and/or serum plasma is collected from the samples for detection of biomarkers. Biomarker data is analyzed to determine the health status of the patient.

Figure 6:
FIG. 6 depicts a summary for the sample source, preparation and detection method.

A summary of the sample source, preparation, and detection method is shown in FIG. 6. Detailed specification/definitions for type/source of human samples collected for study, assays for biomarker collection, together with the analysis method for the biomarker data, are provided.

The EDTA tube and the PAXgene tube were used for sample collection. DNA was extracted from 2-3 ml whole-blood cell obtained from the pellets after centrifugation of the EDTA tube; RNA was extracted from the PAXgene tube with the PAXgene Blood RNA extraction kit (QIAGEN) according to the manufacturer's suggestion. Plasma was obtained from the supernatant after centrifugation of the EDTA tube (the separation step was strictly controlled within 2 hrs after blood sampling). After sample extraction, all the DNA and RNA samples were examined (quality and quantity) using the Bioanalyzer (Agilent) and the NanoDrop (Thermo Scientific) system.

To further study the potential functions of IL1RL variants, human lymphoblastoid cell lines with the target genotypes were purchased from the Coriell Institute.

Data Collection

For genotyping the candidate mutation site, 10 ng of genomic DNA was subjected to PCR using KAPA HiFi HotStart ReadyMix PCR Kit (KAPA) with pre-designed and tested primers for each reaction. Cycling conditions were as follows:

+95° C. 3 minutes; followed by 25 cycles of: 1. +98° C. 20 seconds, 2. +65° C. 15 seconds, 3. +72° C. 15 seconds; then +72° C. 1 minutes.

PCR final products were delivered to a $3^{rd}$ party company (Life Technologies) for PCR clearance and Sanger sequencing.

To detect transcript levels, 1 μg of total RNA was subjected to SuperScript II (Thermo Scientific) reverse transcription system according to the manufacturer's suggestion. cDNA with the amount derived from 50 ng total RNA was subjected to the SYBRgreen or Taqman system for real-time assay, according to the manufacturer's suggestion, to detect transcript levels. IL33 and IL1RL1 transcript levels were further normalized with the internal control, beta-actin.

To detect protein levels, 20 μg of protein was extracted from total cell lysate and underwent SDS-PAGE and Western-blot for detection of IL33 (Enzo Nessy-1, 1:2000:1:4000) and ST2L/ST2S (Millpore 06-1116, rabbit, 1:1500; 1:3000) protein levels.

Statistical Analysis

Chi-square analysis was conducted for the genotype results of the case-control study. Logistic regression model was adopted for the model selection and adjustment of age, gender, and APOE genotype. One-way ANOVA with post-hoc Tukey HSD Test was adopted for the comparison of the mean ST2S, ST2L, and IL33 protein levels in normal and mutation-harboring cells.

Results

A total of 1,251 (n=1,251) people were recruited for the study. See Table 15 for cohort information and Table 16 for SNP information. After the association test, IL33 SNP rs11791561 was shown to be associated with AD (AD: Chi-square value: 5.28, P-value: 0.02, odds ratio: 1.20 (95% CI: 1.02-1.43)). Meanwhile, the previously-known IL33 protective variant rs11792633 also showed a strong association with AD in this cohort (AD: Chi-square value: 7.35, P-value: 0.01, odds ratio: 0.80 (95% CI: 0.69-0.94). Moreover, the IL1RL1 missense variants rs4988956, rs10204137, rs10192157, and rs10206753 showed perfect linkage-disequilibrium in a range of around 400 bp, and were associated with AD together (AD: Chi-square value: 4.22, P-value: 0.04, odds ratio: 1.27 (95% CI: 1.00-1.61)) (Table 16).

In Table 15, a total of 1,251 participants (n=1,251), including 662 Alzheimer's disease patients (AD; n=662) and 589 corresponding age- and gender-matched normal controls (NC; n=589) were recruited from one medical center for the pilot study of human biomarkers related to the IL33/ST2 pathway. Individuals with any significant neurologic disease or psychiatric disorder were excluded from this study. Normal controls were further restricted to participants with MMSE score≥25, together with age ≥55 for all participants to further conduct the genetic analysis of disease-associated variants.

TABLE 15

| Cohort information | | |
|---|---|---|
| | NC<br>N = 589 | AD<br>N = 662 |
| Female (%) | 316 (53.6%) | 363 (54.8%) |
| Age/years (±SD) | 69.8 (±7.1) | 71.2 (±7.3) |

TABLE 15-continued

| Cohort information | | |
|---|---|---|
| | NC<br>N = 589 | AD<br>N = 662 |
| APOE-ε4 carriers (%) | 113 (19.2%) | 320 (48.3%) |
| APOE-ε4 Frequency<br>(Allele number/%) | 119 (10.1%) | 439 (32.1%) |
| APOE-ε2 Frequency<br>(Allele number/%) | 104 (88%) | 60 (4.4%) |
| MMSE score (±SD) | 28.4 (±1.5) | 15.1 (±6.3) |

Table 16 provides detailed information of IL33 and its receptor, IL1RL1, including the official gene symbol and corresponding genomic coordinate (UCSC GRCh37), gene transcript, protein ID, SNP ID, as well as the corresponding genomic sequence within the SNP region.

TABLE 16

Summary of gene, transcript, SNP and protein information

| Gene Symbol | Transcript ID | Protein ID | SNP ID | SNP region |
|---|---|---|---|---|
| IL33<br>(chr9: 6215786-6257983) | Full length:<br>NM_033439.3 | NP_254274.1 | rs11792633 | SEQ ID No: 26-<br>GAGTCCACACTCAGTATTAGGCATG[C/T]CTATCAC<br>GTTCCCATGTGATGCTGA |
| | | | rs1157505 | SEQ ID No: 27-<br>CCAATTCCTGGGCTCAAGCAATCAT[C/G]CCATCTC<br>AGCTTCCCAAGCAGCTGG |
| | | | rs7044343 | SEQ ID No: 28-<br>CATGCAGACAGGAAAGCTGATGCCC[C/T]GAGAAGT<br>AACCATTAGGGTCACAAC |
| | | | rs10975489 | SEQ ID No: 29-<br>GTCAGGAGATCGAGACCATCCTGGC[T/C]AACACAG<br>TGAAACCCCGTCTCTACT |
| | | | rs11791561 | SEQ ID No: 30-<br>TTGGGAGGCCGAGGTGGGTGAATCG[C/G]CTGAGGT<br>CAGGAGTTTGCAGCCAGC |
| | | | rs149023172 | SEQ ID No: 31-<br>GCCACTGCACTCCAGCCTGGGCGAC[A/G]GAGCGAG<br>ACTCCATCTCAAAATAAA |
| IL1RL1<br>(chr2: 102927962-102968497) | Full length:<br>NM_016232.4<br>Decoy receptor:<br>NM_003856.2 | NP_057316.3<br>NP_003847.2 | rs10204137 | SEQ ID No: 32-<br>GCTGAGGCGCTTCAGGACTCCCTCC[A/G]GCATCTT<br>ATGAAAGTACAGGGGACC |
| | | | rs4988956 | SEQ ID No: 33-<br>TCTTGTATGACTAGATGTAGTCACT[A/G]CAGTGGA<br>AACCAACATACGAAAGAG |
| | | | rs10192157 | SEQ ID No: 34-<br>ATTCCCAGAAAGGCCTCTAGTTTGA[C/T]TCCCTTG<br>GCTGCCCAGAAGCAATAG |
| | | | rs10206753 | SEQ ID No: 35-<br>AGAAAGGCCTCTAGTTTGACTCCCT[C/T]GGCTGCC<br>CAGAAGCAATAGTGCCTG |
| IL33<br>(chr9: 6215786-6257983) | Full length:<br>NM_033439.3 | NP_254274.1 | rs11792633 | SEQ ID No: 36-<br>GAGTCCACACTCAGTATTAGGCATG[C/T]CTATCAC<br>GTTCCCATGTGATGCTGA |
| | | | rs1157505 | SEQ ID No: 37-<br>CCAATTCCTGGGCTCAAGCAATCAT[C/G]CCATCTC<br>AGCTTCCCAAGCAGCTGG |
| | | | rs7044343 | SEQ ID No: 38-<br>CATGCAGACAGGAAAGCTGATGCCC[C/T]GAGAAGT<br>AACCATTAGGGTCACAAC |
| | | | rs10975489 | SEQ ID No: 39-<br>GTCAGGAGATCGAGACCATCCTGGC[T/C]AACACAG<br>TGAAACCCCGTCTCTACT |
| | | | rs11791561 | SEQ ID No: 40-<br>TTGGGAGGCCGAGGTGGGTGAATCG[C/G]CTGAGGT<br>CAGGAGTTTGCAGCCAGC |

TABLE 16-continued

Summary of gene, transcript, SNP and protein information

| Gene Symbol | Transcript ID | Protein ID | SNP ID | SNP region |
|---|---|---|---|---|
| | | | rs149023172 | SEQ ID No: 41-<br>GCCACTGCACTCCAGCCTGGGCGAC[A/G]GAGCGAG<br>ACTCCATCTCAAAATAAA |
| IL1RL1<br>(chr2: 102927962-<br>102968497) | Full length:<br>NM_016232.4<br>Decoy receptor:<br>NM_003856.2 | NP_057316.3<br>NP_003847.2 | rs10204137 | SEQ ID NO: 42-<br>GCTGAGGCGCTTCAGGACTCCCTCC[A/G]GCATCTT<br>ATGAAAGTACAGGGGACC |
| | | | rs4988956 | SEQ ID No: 43-<br>TCTTGTATGACTAGATGTAGTCACT[A/G]CAGTGGA<br>AACCAACATACGAAAGAG |
| | | | rs10192157 | SEQ ID No: 44-<br>ATTCCCAGAAAGGCCTCTAGTTTGA[C/T]TCCCTTG<br>GCTGCCCAGAAGCAATAG |
| | | | rs10206753 | SEQ ID No: 45-<br>AGAAAGGCCTCTAGTTTGACTCCCT[C/T]GGCTGCC<br>CAGAAGCAATAGTGCCTG |

Genetic association results for the IL33/IL1RL1 genetic variants are shown in Table 17, which include detailed genetic association results for the candidate SNPs in IL33/ST2 regions. Genomic DNA was obtained from whole blood samples and further subjected to the Sanger genotyping assays for the identification of individual genotypes at target sites. Data was recorded as numeric values to indicate the dosage of mutation across each site. Statistical analysis in both the allelic and the genotype tests were conducted using the chi-square test adopted from R packages for the comparison of genotype-phenotype difference in NC against AD. Statistical values (Chi-square values) together with the corresponding unadjusted P-value are listed for each site. Significant level alpha was set at 0.05, and P-values lower than alpha are marked with an asterisk (*) and highlighted in red.

TABLE 17

Association results for the IL33/IL1RL1 genetic variants

| | | AD_NC | | | |
|---|---|---|---|---|---|
| | | Allele | | Genotype | |
| Gene | SNP ID | Chi | P-value | Chi | P-value |
| IL33 | rs11792633_C/T | 7.35 | 0.01* | 6.77 | 0.03* |
| | rs1157505_C/G | 1.70 | 0.19 | 1.72 | 0.42 |
| | rs7044343_C/T | 1.33 | 0.25 | 1.25 | 0.53 |
| | rs10975489_T/C | 2.79 | 0.10 | 4.69 | 0.10 |
| | rs11791561_C/G | 5.28 | 0.02* | 5.15 | 0.08 |
| | rs149023172_G/A | 0.02 | 0.88 | 0.03 | 0.99 |

TABLE 17-continued

Association results for the IL33/IL1RL1 genetic variants

| | | AD_NC | | | |
|---|---|---|---|---|---|
| | | Allele | | Genotype | |
| Gene | SNP ID | Chi | P-value | Chi | P-value |
| IL1RL1 | rs10204137_A/G | 4.22 | 0.04* | 4.50 | 0.11 |
| | rs4988956_A/G | 4.22 | 0.04* | 4.50 | 0.11 |
| | rs10192157_C/T | 4.22 | 0.04* | 4.50 | 0.11 |
| | rs10206753_C/T | 4.22 | 0.04* | 4.50 | 0.11 |

Detailed genetic association results for the candidate SNPs in IL33/ST2 regions. Genomic DNA was obtained from whole blood samples and further subjected to the Sanger genotyping assays for the identification of individual genotypes at target sites. Data was recorded as numeric values to indicate the dosage of mutation across each site. Statistical analysis in both the allelic and the genotype tests were conducted using the chi-square test adopted from R packages for the comparison of genotype-phenotype difference in NC against AD. Statistical values (Chi-square values) together with the corresponding unadjusted P-value are listed for each site. Significant level alpha was set at 0.05, and P-values lower than alpha are marked with an asterisk (*) and highlighted in red.

Table 18 shows a list of primers used for amplification of the genetic variants discussed herein.

TABLE 18

List of primers used for genotyping

| Primers for genotyping | SNP ID | Forward primer | Reverse Primer |
|---|---|---|---|
| IL33 | rs11792633 | SEQ ID NO: 46-<br>ACTTCCACATCTTCAGTACTTCC | SEQ ID NO: 47-<br>TGTCTTTTCAGAGCTAAAAGGC |
| | rs1157505 | SEQ ID NO: 48-<br>GGAACCATGGAGAACTGTGT | SEQ ID NO: 49-<br>GGCTTGAACCACCACACTTA |
| | rs7044343 | SEQ ID NO: 50-<br>GTTGCACCTAACACTTCCTCT | SEQ ID NO: 51-<br>TACCATCAACACCGTCACCT |
| | rs10975489 | SEQ ID NO: 52-<br>AGCTGTGGTTTTAGCAGCCT | SEQ ID NO: 53-<br>ATTTGTCTTTGAACTGGAACATCT |
| | rs11791561 | SEQ ID NO: 54-<br>CCATCTCAGCTTCCCAAGCA | SEQ ID NO: 55-<br>ACATTTAGCTCTTGTTACCCAGG |

TABLE 18-continued

List of primers used for genotyping

| Primers for genotyping | SNP ID | Forward primer | Reverse Primer |
|---|---|---|---|
| | rs149023172 | SEQ ID NO: 56-<br>AGCTGTGGTTTTAGCAGCCT | SEQ ID NO: 57-<br>ATTTGTCTTTGAACTGGAACATCT |
| IL1RL1 | rs10204137 | SEQ ID NO: 58-<br>GCAGTGGAAACCAACATACGAA | SEQ ID NO: 59-<br>CTCAGATGCCTTTGCACATCA |
| | rs4988945<br>rs10192157<br>rs10206753 | Tagged by rs10204137 | |

Table 19 shows a list of primers used for real-time assays discussed herein.

TABLE 19

List of primers used for real-time assay

| Primers for Real-time assay Gene | Isoform | Forward primer | Reverse primer |
|---|---|---|---|
| IL33 | Full length | SEQ ID NO: 60-<br>GTGACGGTGTTGATGGTAAGAT | SEQ ID NO: 61-<br>AGCTCCACAGAGTGTTCCTTG |
| IL1RL1 | Long form | SEQ ID NO: 62-<br>CTGACCCCTCAGATCACTCAC | SEQ ID NO: 63-<br>CACTTGATGGTCCCCTGTACT |
| | Short form | SEQ ID NO: 64-<br>CTGTTTGCTGGGAGCTTCTCT | SEQ ID NO: 65-<br>CAGTTTACGGTTGTTGGTGCAT |

To further evaluate the functions of the IL1RL1 variants, 3 human B lymphoblastoid cell lines carrying mutations with different doses of candidate mutations were purchased and cultured in RPMI medium with 15% FBS and 1× glutamax. Cells were collected for examination of IL1RL1 and IL33 transcript levels at basal conditions. Dose-dependent reduction of IL1RL1 and IL33 transcript levels were observed, together with an alteration of IL33/ST2L/ST2S protein levels in the cell lysate, indicating a possible function in the regulation of IL1RL1 and IL33 levels during the ageing process (FIGS. 7-9).

FIG. 7 shows that all cell lines were originally collected from participants in a genome study with high-coverage whole genome sequencing (WGS) data available for identification of the genomic background. Cell lines were pre-screened to exclude those harboring possible disease-causing or deleterious mutations, as less than 2 high-risk SNPs defined as 1. The minor allele frequency was below 0.05; 2. For the ST2 mutation study, 3 female B lymphoblastoid cell lines with different mutation dosage (0,1,2) were obtained and cultured in RPMI 1640 (sigma) with 15% FBS and 1× glutamax. 1 μg total RNA was collected for the reverse transcription and an equal amount of cDNA obtained from 12.5 ng total RNA was subjected to SYBR green assay to determine the transcript level of IL33 (FIG. 7A), full-length ST2 (ST2L) (FIG. 7B), and ST2S (FIG. 7C), the decoy form of ST2. Data was normalized with the internal control beta-actin, and further normalized with normal cell lines. Data shown were collected from 3 batches of independent experiments, with a trend of elevation of transcript levels in mutant cell lines at an allele dosage-dependent manner.

FIG. 8 shows that in order to further investigate the possible effects of ST2 missense mutations on protein expression, 20 μg of total protein obtained from the ST2 mutation-harboring human B lymphoblastoid cell lines was subjected to western blotting analysis for quantification of ST2 and IL33 levels. Data shown is from 3 batches of independent experiments (n=3), with a trend of elevation in ST2L protein levels, together with a reduction of mature IL33 levels in mutant cell lines at an allele dose-dependent manner. Expression levels of both IL33 and ST2L were first normalized with loading control beta-actin, and then normalized with normal cell lines. FIG. 8A shows ST2 expression levels in wild type and mutant. FIG. 8B shows normalized ST2 expression levels in wild type and mutant. FIG. 8C shows IL33 expression levels in wild type and mutant. FIG. 8D shows normalized IL33 expression levels in wild type and mutant.

FIG. 9 shows that 20 μg total protein obtained from the ST2 mutation-harboring human B lymphoblastoid cell lines was subjected to western blotting analysis for quantification of soluble ST2 (ST2S) levels to further investigate the possible effects of ST2 missense mutations on protein expression. Data shown is from one experiment on 6 biological replicates for each genotype, with a trend of elevation in ST2S protein levels in mutant cell lines at an allele dose-dependent manner. Expression levels of ST2S protein were first normalized with loading control beta-tubulin, and then normalized with normal control cell lines. FIG. 9A shows expression level of ST2 in wild type and mutant. FIG. 9B shows normalized expression of ST2 in wild type and mutant.

Example 4—Brain Imaging and Prediction of AD

Brain imaging techniques have played a vital role in the characterization of AD pathology and clinical assessments of AD patients over the past decades. From computed tomography (CT) to magnetic resonance imaging (MRI), followed by functional MRI (fMRI) and positron emission tomography (PET) for amyloid imaging, the usage of such techniques is under rapid development, from ruling out other sources of dementia to providing a more precise diagnosis of AD in a quantitative manner. As an example for this study, by leveraging the benefits of MRI, a quantitative measurement of brain atrophy in a Chinese AD cohort can be achieved to obtain spatio-temporal pattern which is AD-specific. That information can aid to optimize the current model for AD prediction by further adjusting the variant pool through the identification of other novel variants that have better associations with the endophenotypes (volumetric data or the progression speed of atrophy in certain brain regions), or re-weighting the current variants according to the associations between genomic information and endophenotypes data. Imaging data can aid evaluate a model performance, as well as provide a deeper look into human subjects for the elucidation of possible disease mechanisms.

Example 5—Genotyping

A sample containing nucleic acids can be obtained from a subject. Genotyping can be performed on a Sequenom MassArray iPLEX platform. Primer sequence for use can be found as disclosed herein and can be at least 70%, 80%, 90% or 100% homologous to a sequence disclosed herein. Positive control DNA can be included for each variant; where positive genomic control DNA is unavailable, a synthetic positive control DNA sequence can be generated by a mismatch primer PCR method. Direct DNA sequencing can be employed to confirm genotyping for all variants.

Example 6—Clinical Information and Assessing Risk of AD

Studies including 550 subjects, (AD: 397, NC: 153), showed that the presence of smoking was positively correlated with AD (p-value=0.00144). Strong correlation of cholesterol abnormalities was also observed (p-value=1.02× 10-7). For diabetes and hypertension, trends of association have been observed, while suggestive associations between the indications and AD have been observed in the current cohort (odds ratio for AD=0.74 and 1.14, respectively, for diabetes and hypertension). Further including of education level indicates a strong negative association between years of education and AD (p<2.2E-16).

For disease history, the data indicates that a positive correlation exists between AD and the number of years of smoking (p=0.007547), and negative correlation for number of years with cholesterol abnormalities (p=0.000492). For diabetes and hypertension, trends of negative correlations have been observed for AD risk and number of years the subject has been suffering from those two diseases.

What is claimed is:

1. A method for lessening a symptom of Alzheimer's disease (AD) in a subject, said method comprising:
   a. obtaining genomic DNA in a biological sample from said subject;
   b. determining the genomic DNA sequence at single nucleotide polymorphisms (SNP) sites rs6857, rs6859, rs12721046, rs56131196, and rs4420638, and detecting presence of a T allele at SNP site rs6857, an A allele at SNP site rs6859, an A allele at SNP site rs12721046, an A allele at SNP site rs56131196, or a G allele at SNP site rs4420638; and
   c. administering an acetylcholinesterase inhibitor, a glutamate receptor blocker, tricyclic antidepressant, benzodiazepine, citalopram, fluoxetine, paroxetine, sertraline, trazodone, aripiprazole, clozapine, haloperidol, olanzapine, quetiapine, risperidone, ziprasidone, zolpidem, zaleplon, chloral hydrate or a combination thereof to the subject who is determined in step b as having a T allele at SNP site rs6857, an A allele at SNP site rs6859, an A allele at SNP site rs12721046, an A allele at SNP site rs56131196, or a G allele at SNP site rs4420638; thereby lessening a symptom of AD.

2. The method of claim 1, further comprising determining the genomic DNA sequence at SNP sites rs928771, rs72713460, and rs17737822.

3. The method of claim 1, wherein said subject is asymptomatic of AD.

4. The method of claim 1, wherein said subject has a symptom of AD.

5. The method of claim 1, further comprising assessing AD status in said subject based on a clinical information, wherein said clinical information comprises age, gender, education level, cognitive performance score, smoking, diabetes, hypertension, abnormal cholesterol levels, said subject having a family history of one or more of AD, dementia, abnormal cholesterol levels, stroke, cerebral infarction, diabetes, hypertension, or a combination thereof.

6. The method of claim 1, further comprising assessing AD status in said subject based on an assessment by a medical doctor, a psychologist, a neurologist, a psychiatrist, or other professionals who can screen said subject for AD.

7. The method of claim 6, wherein said assessment comprises an evaluation of said subject's motor skills, autonomic function, neuropsychiatry, mood, cognition, behavior, thoughts, ability to sense, past medical history, or a combination thereof.

8. The method of claim 1, further comprising evaluating a brain image data of said subject.

9. The method of claim 1, further comprising generating a genetic risk score (GRS) based on the presence of a T allele at SNP site rs6857, an A allele at SNP site rs6859, an A allele at SNP site rs12721046, an A allele at SNP site rs56131196, or a G allele at SNP site rs4420638.

10. The method of claim 1, further comprising committing said subject to a course of action of further diagnosis, drug discovery, or drug evaluation.

11. The method of claim 1, wherein step (b) comprises contacting the genomic DNA with a probe that specifically binds an allele of one of the SNPs and detecting binding between the probe and the genomic DNA.

12. The method of claim 1, wherein step (b) comprises sequencing of the genomic DNA sequence, optionally following amplification of the genomic DNA sequence.

13. The method of claim 1, wherein the acetylcholinesterase inhibitor is donepezil, galantamine or rivastigmine.

14. The method of claim 1, wherein the glutamate receptor blocker is memantine.

15. The method of claim 1, wherein the tricyclic antidepressant is nortriptyline.

16. The method of claim 1, wherein the benzodiazepine is lorazepam, oxazepam, or temazepam.

* * * * *

SEQUENCE LISTING

```
<160> NUMBER OF SEQ ID NOS: 246

<210> SEQ ID NO 1
<211> LENGTH: 34
<212> TYPE: DNA
<213> ORGANISM: Homo sapiens

<400> SEQUENCE: 1
gcgcttatcg gatcttccgg tggctagcat atgg                              34

<210> SEQ ID NO 2
<211> LENGTH: 34
<212> TYPE: DNA
<213> ORGANISM: Homo sapiens

<400> SEQUENCE: 2
ataagcgaga agctgcgtta cattccagcg gaac                              34

<210> SEQ ID NO 3
<211> LENGTH: 34
<212> TYPE: DNA
<213> ORGANISM: Homo sapiens

<400> SEQUENCE: 3
gcgcttatga agctgcgtta cattccagcg gaac                              34

<210> SEQ ID NO 4
<211> LENGTH: 34
<212> TYPE: DNA
<213> ORGANISM: Homo sapiens

<400> SEQUENCE: 4
ataagcgaga agctgcgtta cattccagcg gaac                              34

<210> SEQ ID NO 5
<211> LENGTH: 34
<212> TYPE: DNA
<213> ORGANISM: Homo sapiens
```

```
<400> SEQUENCE: 5
gcgcttatcg gatcttccgg tggctagcat atgg                                34

<210> SEQ ID NO 6
<211> LENGTH: 34
<212> TYPE: DNA
<213> ORGANISM: Homo sapiens

<400> SEQUENCE: 6
ataagcgaga agctgcgttg tggctagcag gtgg                                34

<210> SEQ ID NO 7
<211> LENGTH: 34
<212> TYPE: DNA
<213> ORGANISM: Homo sapiens

<400> SEQUENCE: 7
ataagcgaga agctgcgttg tggtcagcag gtgg                                34

<210> SEQ ID NO 8
<211> LENGTH: 34
<212> TYPE: DNA
<213> ORGANISM: Homo sapiens

<400> SEQUENCE: 8
gcgcttatcg gatcttcctg tggctagcag gaag                                34

<210> SEQ ID NO 9
<211> LENGTH: 34
<212> TYPE: DNA
<213> ORGANISM: Homo sapiens

<400> SEQUENCE: 9
ataagcgaga agctgcgtta cattccagcg gaag                                34

<210> SEQ ID NO 10
<211> LENGTH: 34
<212> TYPE: DNA
<213> ORGANISM: Homo sapiens

<400> SEQUENCE: 10
ataagcgacg gatcttccgg tattccagcg gaag                                34

<210> SEQ ID NO 11
<211> LENGTH: 34
<212> TYPE: DNA
<213> ORGANISM: Homo sapiens

<400> SEQUENCE: 11
ataagcgaga agctgcgtta cattccgcat atgg                                34

<210> SEQ ID NO 12
<211> LENGTH: 34
<212> TYPE: DNA
<213> ORGANISM: Homo sapiens

<400> SEQUENCE: 12
ataagcgaga agctgcgtta cattccagcg gtgg                                34

<210> SEQ ID NO 13
<211> LENGTH: 34
<212> TYPE: DNA
```

```
<213> ORGANISM: Homo sapiens

<400> SEQUENCE: 13
gcgcttatcg gatcttccgg tggctaagag gaac                         34

<210> SEQ ID NO 14
<211> LENGTH: 34
<212> TYPE: DNA
<213> ORGANISM: Homo sapiens

<400> SEQUENCE: 14
gcgcttatcg gaccttccgg tggctagcag gtgg                         34

<210> SEQ ID NO 15
<211> LENGTH: 34
<212> TYPE: DNA
<213> ORGANISM: Homo sapiens

<400> SEQUENCE: 15
ataagcgacg gatcttccgg tggctagcag gtgc                         34

<210> SEQ ID NO 16
<211> LENGTH: 34
<212> TYPE: DNA
<213> ORGANISM: Homo sapiens

<400> SEQUENCE: 16
gcgcttatcg gatcttgtta cattccagcg gaac                         34

<210> SEQ ID NO 17
<211> LENGTH: 34
<212> TYPE: DNA
<213> ORGANISM: Homo sapiens

<400> SEQUENCE: 17
ataagcgacg gatcttccgg tggctagcag gaag                         34

<210> SEQ ID NO 18
<211> LENGTH: 34
<212> TYPE: DNA
<213> ORGANISM: Homo sapiens

<400> SEQUENCE: 18
ataagcgacg gatcttccta tggctagcat atgg                         34

<210> SEQ ID NO 19
<211> LENGTH: 34
<212> TYPE: DNA
<213> ORGANISM: Homo sapiens

<400> SEQUENCE: 19
gcgcgtatga agctgcgtta cagctagcat atgg                         34

<210> SEQ ID NO 20
<211> LENGTH: 34
<212> TYPE: DNA
<213> ORGANISM: Homo sapiens

<400> SEQUENCE: 20
gcgcttatga agctgcgtta cagtccagcg gaac                         34

<210> SEQ ID NO 21
<211> LENGTH: 34
```

```
<212> TYPE: DNA
<213> ORGANISM: Homo sapiens

<400> SEQUENCE: 21
gtaagcgacg ggccgcccga cggttcagcg gaac                                34

<210> SEQ ID NO 22
<211> LENGTH: 34
<212> TYPE: DNA
<213> ORGANISM: Homo sapiens

<400> SEQUENCE: 22
gtaagcgaga agctgcgtta cattccagag gtgg                                34

<210> SEQ ID NO 23
<211> LENGTH: 34
<212> TYPE: DNA
<213> ORGANISM: Homo sapiens

<400> SEQUENCE: 23
gcgcttatcg gattgcgttg tggctcgcag gtgg                                34

<210> SEQ ID NO 24
<211> LENGTH: 34
<212> TYPE: DNA
<213> ORGANISM: Homo sapiens

<400> SEQUENCE: 24
ataagcgaga agcttcccgg tggctagcat atgg                                34

<210> SEQ ID NO 25
<211> LENGTH: 34
<212> TYPE: DNA
<213> ORGANISM: Homo sapiens

<400> SEQUENCE: 25
gcgcttatcg gatcttcctg tggctagcat atgg                                34

<210> SEQ ID NO 26
<211> LENGTH: 51
<212> TYPE: DNA
<213> ORGANISM: Homo sapiens

<400> SEQUENCE: 26
gagtccacac tcagtattag gcatgyctat cacgttccca tgtgatgctg a             51

<210> SEQ ID NO 27
<211> LENGTH: 51
<212> TYPE: DNA
<213> ORGANISM: Homo sapiens

<400> SEQUENCE: 27
ccaattcctg ggctcaagca atcatsccat ctcagcttcc caagcagctg g             51

<210> SEQ ID NO 28
<211> LENGTH: 51
<212> TYPE: DNA
<213> ORGANISM: Homo sapiens

<400> SEQUENCE: 28
catgcagaca ggaaagctga tgcccygaga agtaaccatt agggtcacaa c             51

<210> SEQ ID NO 29
```

-continued

<210> SEQ ID NO 29
<211> LENGTH: 51
<212> TYPE: DNA
<213> ORGANISM: Homo sapiens

<400> SEQUENCE: 29
gtcaggagat cgagaccatc ctggcyaaca cagtgaaacc ccgtctctac t        51

<210> SEQ ID NO 30
<211> LENGTH: 51
<212> TYPE: DNA
<213> ORGANISM: Homo sapiens

<400> SEQUENCE: 30
ttgggaggcc gaggtgggtg aatcgsctga ggtcaggagt ttgcagccag c        51

<210> SEQ ID NO 31
<211> LENGTH: 51
<212> TYPE: DNA
<213> ORGANISM: Homo sapiens

<400> SEQUENCE: 31
gccactgcac tccagcctgg gcgacrgagc gagactccat ctcaaaataa a        51

<210> SEQ ID NO 32
<211> LENGTH: 51
<212> TYPE: DNA
<213> ORGANISM: Homo sapiens

<400> SEQUENCE: 32
gctgaggcgc ttcaggactc cctccrgcat cttatgaaag tacaggggac c        51

<210> SEQ ID NO 33
<211> LENGTH: 51
<212> TYPE: DNA
<213> ORGANISM: Homo sapiens

<400> SEQUENCE: 33
tcttgtatga ctagatgtag tcactrcagt ggaaaccaac atacgaaaga g        51

<210> SEQ ID NO 34
<211> LENGTH: 51
<212> TYPE: DNA
<213> ORGANISM: Homo sapiens

<400> SEQUENCE: 34
attcccagaa aggcctctag tttgaytccc ttggctgccc agaagcaata g        51

<210> SEQ ID NO 35
<211> LENGTH: 51
<212> TYPE: DNA
<213> ORGANISM: Homo sapiens

<400> SEQUENCE: 35
agaaaggcct ctagtttgac tccctyggct gcccagaagc aatagtgcct g        51

<210> SEQ ID NO 36
<211> LENGTH: 51
<212> TYPE: DNA
<213> ORGANISM: Homo sapiens

<400> SEQUENCE: 36
gagtccacac tcagtattag gcatgyctat cacgttccca tgtgatgctg a        51

<210> SEQ ID NO 37
<211> LENGTH: 51
<212> TYPE: DNA
<213> ORGANISM: Homo sapiens

<400> SEQUENCE: 37
ccaattcctg ggctcaagca atcatsccat ctcagcttcc caagcagctg g         51

<210> SEQ ID NO 38
<211> LENGTH: 51
<212> TYPE: DNA
<213> ORGANISM: Homo sapiens

<400> SEQUENCE: 38
catgcagaca ggaaagctga tgcccygaga agtaaccatt agggtcacaa c         51

<210> SEQ ID NO 39
<211> LENGTH: 51
<212> TYPE: DNA
<213> ORGANISM: Homo sapiens

<400> SEQUENCE: 39
gtcaggagat cgagaccatc ctggcyaaca cagtgaaacc ccgtctctac t         51

<210> SEQ ID NO 40
<211> LENGTH: 51
<212> TYPE: DNA
<213> ORGANISM: Homo sapiens

<400> SEQUENCE: 40
ttgggaggcc gaggtgggtg aatcgsctga ggtcaggagt ttgcagccag c         51

<210> SEQ ID NO 41
<211> LENGTH: 51
<212> TYPE: DNA
<213> ORGANISM: Homo sapiens

<400> SEQUENCE: 41
gccactgcac tccagcctgg gcgacrgagc gagactccat ctcaaaataa a         51

<210> SEQ ID NO 42
<211> LENGTH: 51
<212> TYPE: DNA
<213> ORGANISM: Homo sapiens

<400> SEQUENCE: 42
gctgaggcgc ttcaggactc cctccrgcat cttatgaaag tacaggggac c         51

<210> SEQ ID NO 43
<211> LENGTH: 51
<212> TYPE: DNA
<213> ORGANISM: Homo sapiens

<400> SEQUENCE: 43
tcttgtatga ctagatgtag tcactrcagt ggaaaccaac atacgaaaga g         51

<210> SEQ ID NO 44
<211> LENGTH: 51
<212> TYPE: DNA
<213> ORGANISM: Homo sapiens

<400> SEQUENCE: 44
attcccagaa aggcctctag tttgaytccc ttggctgccc agaagcaata g         51

<210> SEQ ID NO 45
<211> LENGTH: 51
<212> TYPE: DNA
<213> ORGANISM: Homo sapiens

<400> SEQUENCE: 45
agaaaggcct ctagtttgac tccctyggct gcccagaagc aatagtgcct g          51

<210> SEQ ID NO 46
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
acttccacat cttcagtact tcc                                         23

<210> SEQ ID NO 47
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
tgtcttttca gagctaaaag gc                                          22

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
ggaaccatgg agaactgtgt                                             20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
ggcttgaacc accacactta                                             20

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
gttgcaccta acacttcctc t                                           21

<210> SEQ ID NO 51
<211> LENGTH: 20
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 51
taccatcaac accgtcacct                                               20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
agctgtggtt ttagcagcct                                               20

<210> SEQ ID NO 53
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
atttgtcttt gaactggaac atct                                          24

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ccatctcagc ttcccaagca                                               20

<210> SEQ ID NO 55
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
acatttagct cttgttaccc agg                                           23

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
agctgtggtt ttagcagcct                                               20

<210> SEQ ID NO 57
<211> LENGTH: 24
<212> TYPE: DNA
<213> ORGANISM: Artificial Sequence
```

<220> FEATURE:
<223> OTHER INFORMATION: Description of Artificial Sequence: Synthetic
      primer

<400> SEQUENCE: 57
atttgtcttt gaactggaac atct                                          24

<210> SEQ ID NO 58
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
gcagtggaaa ccaacatacg aa                                            22

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
ctcagatgcc tttgcacatc a                                             21

<210> SEQ ID NO 60
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
gtgacggtgt tgatggtaag at                                            22

<210> SEQ ID NO 61
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
agctccacag agtgttcctt g                                             21

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
ctgacccctc agatcactca c                                             21

<210> SEQ ID NO 63
<211> LENGTH: 21
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 63
cacttgatgg tcccctgtac t                                             21

<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
ctgtttgctg ggagcttctc t                                             21

<210> SEQ ID NO 65
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
cagtttacgg ttgttggtgc at                                            22

<210> SEQ ID NO 66
<211> LENGTH: 51
<212> TYPE: DNA
<213> ORGANISM: Homo sapiens

<400> SEQUENCE: 66
gctcaagcag tcctcagcat cctgartagt tctacaggca tgcaccaaca c            51

<210> SEQ ID NO 67
<211> LENGTH: 51
<212> TYPE: DNA
<213> ORGANISM: Homo sapiens

<400> SEQUENCE: 67
gggcccagcc ttccccgacc ttacaycctc gcccctccag ggccttctcg g            51

<210> SEQ ID NO 68
<211> LENGTH: 51
<212> TYPE: DNA
<213> ORGANISM: Homo sapiens

<400> SEQUENCE: 68
attagacctt cttgacttac tgaatrctgt caacccaatg cttttattat c            51

<210> SEQ ID NO 69
<211> LENGTH: 53
<212> TYPE: DNA
<213> ORGANISM: Homo sapiens
<220> FEATURE:
<221> NAME/KEY: misc_feature
<222> LOCATION: (26)..(28)
<223> OTHER INFORMATION: This region may be absent

<400> SEQUENCE: 69
tgtttgtttg tttgtttgtt ttttttttgc ttttgttttt tcttattgag atg          53

<210> SEQ ID NO 70

```
<211> LENGTH: 51
<212> TYPE: DNA
<213> ORGANISM: Homo sapiens

<400> SEQUENCE: 70
ggcacgcacc accatgccca gctaaytttt gtatttttag tagcaacagg g         51

<210> SEQ ID NO 71
<211> LENGTH: 51
<212> TYPE: DNA
<213> ORGANISM: Homo sapiens

<400> SEQUENCE: 71
ccaaagagtt gggattatag gcgtgrgcca ccacgccagg ccaattttt t          51

<210> SEQ ID NO 72
<211> LENGTH: 51
<212> TYPE: DNA
<213> ORGANISM: Homo sapiens

<400> SEQUENCE: 72
caaagcgaga accgaaggtg tttggrctag gaaaatgtta ttcttgatgt t         51

<210> SEQ ID NO 73
<211> LENGTH: 51
<212> TYPE: DNA
<213> ORGANISM: Homo sapiens

<400> SEQUENCE: 73
tatggctggt tttgttgttt tttttktttt tttttttcac aagaaagagg a         51

<210> SEQ ID NO 74
<211> LENGTH: 51
<212> TYPE: DNA
<213> ORGANISM: Homo sapiens

<400> SEQUENCE: 74
agactccatc tcaaataaaa aaaaamaaaa aaaacaaaaa ctgtttttt a          51

<210> SEQ ID NO 75
<211> LENGTH: 51
<212> TYPE: DNA
<213> ORGANISM: Homo sapiens

<400> SEQUENCE: 75
gtggatcaga atctgatcta cctaakttgg gtgcagtggt gcatgcctgt g         51

<210> SEQ ID NO 76
<211> LENGTH: 51
<212> TYPE: DNA
<213> ORGANISM: Homo sapiens

<400> SEQUENCE: 76
tgtaatccca gcactttggg aggccraggc gggcggatca cgaggtcagg a         51

<210> SEQ ID NO 77
<211> LENGTH: 51
<212> TYPE: DNA
<213> ORGANISM: Homo sapiens

<400> SEQUENCE: 77
aacatctttg atttcttttt ctttyttttt tttttttttt tggcccggac t         51
```

```
<210> SEQ ID NO 78
<211> LENGTH: 51
<212> TYPE: DNA
<213> ORGANISM: Homo sapiens

<400> SEQUENCE: 78
gagattccgt ctcaaaaaaa aaaamaaaa cacaaacaaa aaaaaaaaac t            51

<210> SEQ ID NO 79
<211> LENGTH: 51
<212> TYPE: DNA
<213> ORGANISM: Homo sapiens

<400> SEQUENCE: 79
actctgtctc aaaaaaaaaa aaaamaaaa aaaaaacaag atggtcttgc c            51

<210> SEQ ID NO 80
<211> LENGTH: 51
<212> TYPE: DNA
<213> ORGANISM: Homo sapiens

<400> SEQUENCE: 80
ttttaggtca ggcatataat cctaarataa aaaaatatgt attaatcgtg a            51

<210> SEQ ID NO 81
<211> LENGTH: 51
<212> TYPE: DNA
<213> ORGANISM: Homo sapiens

<400> SEQUENCE: 81
ggagtgcagt gatgcgatct cggctyactg caagctccgc ctcctgggtt c            51

<210> SEQ ID NO 82
<211> LENGTH: 51
<212> TYPE: DNA
<213> ORGANISM: Homo sapiens

<400> SEQUENCE: 82
gttttcaaag tgtgacctgc agaccycatg gggtccctga gatttttcag a            51

<210> SEQ ID NO 83
<211> LENGTH: 51
<212> TYPE: DNA
<213> ORGANISM: Homo sapiens

<400> SEQUENCE: 83
tatttttatg taacgcctgt tcacaygaaa gaacgcgatg tgagggaaga a            51

<210> SEQ ID NO 84
<211> LENGTH: 51
<212> TYPE: DNA
<213> ORGANISM: Homo sapiens

<400> SEQUENCE: 84
agtaactgag taatgccact atgaamaatt gcatgtaagt ctttgtggga c            51

<210> SEQ ID NO 85
<211> LENGTH: 51
<212> TYPE: DNA
<213> ORGANISM: Homo sapiens

<400> SEQUENCE: 85
tccaggaatg tcaggtgtct atcagrtgat ggtcatgcag ttgttaaact g            51
```

<210> SEQ ID NO 86
<211> LENGTH: 51
<212> TYPE: DNA
<213> ORGANISM: Homo sapiens

<400> SEQUENCE: 86
ggtcacagcc agcaccaggg aaagasagtc tcccaattga tagaaaacag c        51

<210> SEQ ID NO 87
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t or g

<400> SEQUENCE: 87
ctcccaggtt ccctcctctt tgaccnggcc tgccagggtg cctccttcct c        51

<210> SEQ ID NO 88
<211> LENGTH: 51
<212> TYPE: DNA
<213> ORGANISM: Homo sapiens

<400> SEQUENCE: 88
tatgaggtaa cgcagcagaa atgcaraaga tctaagtagc attgtttata c        51

<210> SEQ ID NO 89
<211> LENGTH: 51
<212> TYPE: DNA
<213> ORGANISM: Homo sapiens

<400> SEQUENCE: 89
ccctggctgc cacagagggc gatagrgccg gcacttgggc attagctccg c        51

<210> SEQ ID NO 90
<211> LENGTH: 51
<212> TYPE: DNA
<213> ORGANISM: Homo sapiens

<400> SEQUENCE: 90
ataggagaaa tgaaatcata cgctcrgccc aacagaggaa acacggctcc t        51

<210> SEQ ID NO 91
<211> LENGTH: 51
<212> TYPE: DNA
<213> ORGANISM: Homo sapiens

<400> SEQUENCE: 91
tcaggtaaat tctttgtgaa gctagrgatt ctgccacacc aaggggatgc t        51

<210> SEQ ID NO 92
<211> LENGTH: 51
<212> TYPE: DNA
<213> ORGANISM: Homo sapiens

<400> SEQUENCE: 92
tgcttggatg ccgtggactg tttagrtgtt gtgattcctt cctcactagc a        51

<210> SEQ ID NO 93
<211> LENGTH: 51
<212> TYPE: DNA

<400> SEQUENCE: 93
tccactgcat tcgccaggcc tacgtsggac tttcaattct ttacctccca g            51

<210> SEQ ID NO 94
<211> LENGTH: 51
<212> TYPE: DNA
<213> ORGANISM: Homo sapiens

<400> SEQUENCE: 94
ttccctgtga aggagtcccg tccgcwtgtt ctcctggccc ccttagttcc c            51

<210> SEQ ID NO 95
<211> LENGTH: 51
<212> TYPE: DNA
<213> ORGANISM: Homo sapiens

<400> SEQUENCE: 95
cctccatggc gtccaccaca agtggyctca gcccattcag acgcgggtct g            51

<210> SEQ ID NO 96
<211> LENGTH: 51
<212> TYPE: DNA
<213> ORGANISM: Homo sapiens

<400> SEQUENCE: 96
caagtggtct cagcccattc agacgygggt ctgagggagt tggtgctggt t            51

<210> SEQ ID NO 97
<211> LENGTH: 51
<212> TYPE: DNA
<213> ORGANISM: Homo sapiens

<400> SEQUENCE: 97
cgggaggctc cggggcccgc ccccgscccc cctgcgtcag gcctgtaccc g            51

<210> SEQ ID NO 98
<211> LENGTH: 51
<212> TYPE: DNA
<213> ORGANISM: Homo sapiens

<400> SEQUENCE: 98
ggtgtgtggc gggcagcagg gagatbgtcg cggtgcgtgg cgggcagcag g            51

<210> SEQ ID NO 99
<211> LENGTH: 51
<212> TYPE: DNA
<213> ORGANISM: Homo sapiens

<400> SEQUENCE: 99 gggggggtccg tgtgcagctc aggtgygcgg agcagggacc cctgagctgc g            51

<210> SEQ ID NO 100
<211> LENGTH: 51
<212> TYPE: DNA
<213> ORGANISM: Homo sapiens

<400> SEQUENCE: 100
caggagaata gattgaaccc gggagrtgga ggctgcagtg agccgagatt g            51

<210> SEQ ID NO 101
<211> LENGTH: 51
<212> TYPE: DNA

<213> ORGANISM: Homo sapiens

<400> SEQUENCE: 101
ctgtgggcat ggacccggca cgcgtycatg gcccctgtga cccgttatgt c    51

<210> SEQ ID NO 102
<211> LENGTH: 51
<212> TYPE: DNA
<213> ORGANISM: Homo sapiens

<400> SEQUENCE: 102
tgggcatgga cccggcacgc gttcayggcc cctgtgaccc gttatgtcgg g    51

<210> SEQ ID NO 103
<211> LENGTH: 51
<212> TYPE: DNA
<213> ORGANISM: Homo sapiens

<400> SEQUENCE: 103
cttcccccag tgatcatatc tttttktttt gttttgtttt gttttttga g    51

<210> SEQ ID NO 104
<211> LENGTH: 51
<212> TYPE: DNA
<213> ORGANISM: Homo sapiens

<400> SEQUENCE: 104
gacccactgc aaatccccgt tccccygcac tcctcttctc ccagcccatc c    51

<210> SEQ ID NO 105
<211> LENGTH: 51
<212> TYPE: DNA
<213> ORGANISM: Homo sapiens

<400> SEQUENCE: 105
tgtgaagggg ctgagggtga gtggtrtggt tatagtaagg caacgcgata g    51

<210> SEQ ID NO 106
<211> LENGTH: 51
<212> TYPE: DNA
<213> ORGANISM: Homo sapiens

<400> SEQUENCE: 106
ctgaggtgag agaatggcgt gaaccyggga ggtggagctt gcagtgagcc g    51

<210> SEQ ID NO 107
<211> LENGTH: 51
<212> TYPE: DNA
<213> ORGANISM: Homo sapiens

<400> SEQUENCE: 107
cctgtagtag ctacaaaaaa aaaaaragag agagagagat gctacttaaa c    51

<210> SEQ ID NO 108
<211> LENGTH: 51
<212> TYPE: DNA
<213> ORGANISM: Homo sapiens

<400> SEQUENCE: 108
ggctggagtg cagtggcatg atctcrgctc actgcaagct ctgcctccca g    51

<210> SEQ ID NO 109
<211> LENGTH: 51

<212> TYPE: DNA
<213> ORGANISM: Homo sapiens

<400> SEQUENCE: 109
attgagagaa aaaggcttca gacgarcaaa ctactccaag ctaaaggagg a          51

<210> SEQ ID NO 110
<211> LENGTH: 51
<212> TYPE: DNA
<213> ORGANISM: Homo sapiens

<400> SEQUENCE: 110
ttaaaaaaat tagacgaatg gctaaytaga ataaccaatg cagagaagtc c          51

<210> SEQ ID NO 111
<211> LENGTH: 51
<212> TYPE: DNA
<213> ORGANISM: Homo sapiens

<400> SEQUENCE: 111
tgctgtattc aggaaaccca tctcaygtgc agagacacac ataggctcaa a          51

<210> SEQ ID NO 112
<211> LENGTH: 51
<212> TYPE: DNA
<213> ORGANISM: Homo sapiens

<400> SEQUENCE: 112
aaaagatcaa taaaattgat agaccrctag caagactaat aaagaagaaa a          51

<210> SEQ ID NO 113
<211> LENGTH: 51
<212> TYPE: DNA
<213> ORGANISM: Homo sapiens

<400> SEQUENCE: 113
gatagcatta ggagatatac ctaatrttaa atgacgagtt aatgggtgca g          51

<210> SEQ ID NO 114
<211> LENGTH: 51
<212> TYPE: DNA
<213> ORGANISM: Homo sapiens

<400> SEQUENCE: 114
ctgcagtgag ctatgattac accackgcat tccagcctgg gtgacagaac a          51

<210> SEQ ID NO 115
<211> LENGTH: 51
<212> TYPE: DNA
<213> ORGANISM: Homo sapiens

<400> SEQUENCE: 115
actccagcct gggcaacaga gcaagkccct gtctcaaaaa aaaaaaaaaa a          51

<210> SEQ ID NO 116
<211> LENGTH: 51
<212> TYPE: DNA
<213> ORGANISM: Homo sapiens

<400> SEQUENCE: 116
ttgaactccc agcctcaggt gatccrccct cctcagcctc tcaaagtgct g          51

<210> SEQ ID NO 117

```
<211> LENGTH: 51
<212> TYPE: DNA
<213> ORGANISM: Homo sapiens

<400> SEQUENCE: 117
gctattctca tcctctcagc cagccytgtc acaaacacta cgtttcttgg t          51

<210> SEQ ID NO 118
<211> LENGTH: 51
<212> TYPE: DNA
<213> ORGANISM: Homo sapiens

<400> SEQUENCE: 118
catccaagta agtaccatca gagtgygcaa gccaccatca ttagtgacag a          51

<210> SEQ ID NO 119
<211> LENGTH: 51
<212> TYPE: DNA
<213> ORGANISM: Homo sapiens

<400> SEQUENCE: 119
actttgggag gccaaggcag gcgtaycatt tgaggtcagg agttcgagac c          51

<210> SEQ ID NO 120
<211> LENGTH: 51
<212> TYPE: DNA
<213> ORGANISM: Homo sapiens

<400> SEQUENCE: 120
cctctccctg ccttgcagtt gcttgsagat tttgtacgct agccccagga a          51

<210> SEQ ID NO 121
<211> LENGTH: 51
<212> TYPE: DNA
<213> ORGANISM: Homo sapiens

<400> SEQUENCE: 121
gacagtgatt tgtacctctt ttcagygaac cagtcaagat ccacattgct c          51

<210> SEQ ID NO 122
<211> LENGTH: 51
<212> TYPE: DNA
<213> ORGANISM: Homo sapiens

<400> SEQUENCE: 122
acaaaaaaaa caccagttat tgtccygact ttacagatga ggacacagat a          51

<210> SEQ ID NO 123
<211> LENGTH: 51
<212> TYPE: DNA
<213> ORGANISM: Homo sapiens

<400> SEQUENCE: 123
agctccagca aggaaatgag acagastggt ttctcagatt aactgtgcac t          51

<210> SEQ ID NO 124
<211> LENGTH: 51
<212> TYPE: DNA
<213> ORGANISM: Homo sapiens

<400> SEQUENCE: 124
ataatctcta aaccagcatg gacacrttct gcaaaaaaca aacaacccaa a          51
```

```
<210> SEQ ID NO 125
<211> LENGTH: 51
<212> TYPE: DNA
<213> ORGANISM: Homo sapiens

<400> SEQUENCE: 125
gaccatctac agttccactt ttcacrgttt cagttaccct tggtcaaaca t            51

<210> SEQ ID NO 126
<211> LENGTH: 51
<212> TYPE: DNA
<213> ORGANISM: Homo sapiens

<400> SEQUENCE: 126
agactgcaaa agctatggcc acagcrcatg gtaagtgctt agttaagatg g            51

<210> SEQ ID NO 127
<211> LENGTH: 51
<212> TYPE: DNA
<213> ORGANISM: Homo sapiens

<400> SEQUENCE: 127
attacagtcc tcatatagaa atcachggca aatgagtcag gtggggaatg c            51

<210> SEQ ID NO 128
<211> LENGTH: 51
<212> TYPE: DNA
<213> ORGANISM: Homo sapiens

<400> SEQUENCE: 128
gtatttagta ctaatacaag ttgaawtgtg ccattcgcca aaaagatat g             51

<210> SEQ ID NO 129
<211> LENGTH: 51
<212> TYPE: DNA
<213> ORGANISM: Homo sapiens

<400> SEQUENCE: 129 aacctttgt gattgctaca tttcartatg aagtgtctaa gatgcatttt t             51

<210> SEQ ID NO 130
<211> LENGTH: 51
<212> TYPE: DNA
<213> ORGANISM: Homo sapiens

<400> SEQUENCE: 130
caaagcttcg cttgggggaa aaactkaaac ctagagttgg gactaaagtg g            51

<210> SEQ ID NO 131
<211> LENGTH: 51
<212> TYPE: DNA
<213> ORGANISM: Homo sapiens

<400> SEQUENCE: 131
gcccatctcc ttccttccat catggrcccc cacacaccaa gccgctgcct c            51

<210> SEQ ID NO 132
<211> LENGTH: 51
<212> TYPE: DNA
<213> ORGANISM: Homo sapiens

<400> SEQUENCE: 132
agatccagag ggtgaagcct gtgtcrctgc tgctgcagca ctggcagggg c            51
```

<210> SEQ ID NO 133
<211> LENGTH: 51
<212> TYPE: DNA
<213> ORGANISM: Homo sapiens

<400> SEQUENCE: 133 tgggggtgc ccgagtggaa aagcascggc ttaggccggg gtggggaaag t        51

<210> SEQ ID NO 134
<211> LENGTH: 51
<212> TYPE: DNA
<213> ORGANISM: Homo sapiens

<400> SEQUENCE: 134
ctgtagtccc aactactctg gaggchgagg caggagaatg gcgtgaaccc g        51

<210> SEQ ID NO 135
<211> LENGTH: 51
<212> TYPE: DNA
<213> ORGANISM: Homo sapiens

<400> SEQUENCE: 135
aaaaaaaaaa aaaacacaa acaaamaaaa aaaacttatt ctcctgctct c         51

<210> SEQ ID NO 136
<211> LENGTH: 51
<212> TYPE: DNA
<213> ORGANISM: Homo sapiens

<400> SEQUENCE: 136
cctcctgtgg tcctcagtgc tgaggscgat gctggcaccc agcggacggg c        51

<210> SEQ ID NO 137
<211> LENGTH: 51
<212> TYPE: DNA
<213> ORGANISM: Homo sapiens

<400> SEQUENCE: 137
gccccacaca cgggtcacct gccccrggaa cagccaggcc attcccctgc t        51

<210> SEQ ID NO 138
<211> LENGTH: 51
<212> TYPE: DNA
<213> ORGANISM: Homo sapiens

<400> SEQUENCE: 138
gagggcctca gggtgggtgt cgtggrgctg aaacaggccc ggctcttgcc c        51

<210> SEQ ID NO 139
<211> LENGTH: 51
<212> TYPE: DNA
<213> ORGANISM: Homo sapiens

<400> SEQUENCE: 139
gcggaggtca tggggtgcgg gagccrggcg ggggtgactg tggccttgcc t        51

<210> SEQ ID NO 140
<211> LENGTH: 51
<212> TYPE: DNA
<213> ORGANISM: Homo sapiens

<400> SEQUENCE: 140
gatcacctgt caggagttcg agaccygcct aacgtgttga aaccctgtct c        51

<210> SEQ ID NO 141
<211> LENGTH: 51
<212> TYPE: DNA
<213> ORGANISM: Homo sapiens

<400> SEQUENCE: 141
ctggagacgg tgggtgcccc tttcayggat gggtccggrg ctctgcggag c        51

<210> SEQ ID NO 142
<211> LENGTH: 51
<212> TYPE: DNA
<213> ORGANISM: Homo sapiens

<400> SEQUENCE: 142
atatctgcta ggaggtaaag aaaatrtaat gaatcctgga gcacctggct g        51

<210> SEQ ID NO 143
<211> LENGTH: 51
<212> TYPE: DNA
<213> ORGANISM: Homo sapiens

<400> SEQUENCE: 143
agacacagtg ttgagatcag aagcakggac tatggattcc aacatacctt g        51

<210> SEQ ID NO 144
<211> LENGTH: 51
<212> TYPE: DNA
<213> ORGANISM: Homo sapiens

<400> SEQUENCE: 144
gtcaggagat cgagaccatc ctggcyaaca cagtgaaacc ccgtctctac t        51

<210> SEQ ID NO 145
<211> LENGTH: 51
<212> TYPE: DNA
<213> ORGANISM: Homo sapiens

<400> SEQUENCE: 145
ttgggaggcc gaggtgggtg aatcgsctga ggtcaggagt ttgcagccag c        51

<210> SEQ ID NO 146
<211> LENGTH: 51
<212> TYPE: DNA
<213> ORGANISM: Homo sapiens

<400> SEQUENCE: 146
agattaagac catcctgggt aacacdgtga aacccgtct ctactaaaaa a         51

<210> SEQ ID NO 147
<211> LENGTH: 51
<212> TYPE: DNA
<213> ORGANISM: Homo sapiens

<400> SEQUENCE: 147
tcaggaggct gaggcaggag aatggygtga gcccgggagg cggagcttgc a        51

<210> SEQ ID NO 148
<211> LENGTH: 51
<212> TYPE: DNA
<213> ORGANISM: Homo sapiens

<400> SEQUENCE: 148

```
atcttcataa aggtatcttc aagttrtcag tctccccagt ctgtgcagag t         51
```

<210> SEQ ID NO 149
<211> LENGTH: 51
<212> TYPE: DNA
<213> ORGANISM: Homo sapiens

<400> SEQUENCE: 149

```
agctctgtta aacaggtaa taattygagc tcacttagag aaaaatctca a          51
```

<210> SEQ ID NO 150
<211> LENGTH: 51
<212> TYPE: DNA
<213> ORGANISM: Homo sapiens

<400> SEQUENCE: 150

```
ctcttttaga gcattgtttt cttttyttct tttttgtaa gattacacag t          51
```

<210> SEQ ID NO 151
<211> LENGTH: 51
<212> TYPE: DNA
<213> ORGANISM: Homo sapiens

<400> SEQUENCE: 151

```
acagctctgc tttatactgg gcacarcttt ccctctttct tcactcatct g         51
```

<210> SEQ ID NO 152
<211> LENGTH: 51
<212> TYPE: DNA
<213> ORGANISM: Homo sapiens

<400> SEQUENCE: 152

```
tgtccccacc tttcgcccct cacccyagct cccccaacgc caaagacaag g         51
```

<210> SEQ ID NO 153
<211> LENGTH: 51
<212> TYPE: DNA
<213> ORGANISM: Homo sapiens

<400> SEQUENCE: 153

```
cagcgcggct ggcgggcgg ttcgcsgcgg tgcccacagg acctcagggc g          51
```

<210> SEQ ID NO 154
<211> LENGTH: 51
<212> TYPE: DNA
<213> ORGANISM: Homo sapiens

<400> SEQUENCE: 154

```
acatgctgaa ggcgtcttgt ctgcckctcg gcttcatcgt cttcctgccc g         51
```

<210> SEQ ID NO 155
<211> LENGTH: 51
<212> TYPE: DNA
<213> ORGANISM: Homo sapiens

<400> SEQUENCE: 155

```
ccatggccgg gccaagcgtc ccgcgyccct ggagccctaa gtcccctctc t         51
```

<210> SEQ ID NO 156
<211> LENGTH: 51
<212> TYPE: DNA
<213> ORGANISM: Homo sapiens

<400> SEQUENCE: 156
gtggcgggca gcagggagat cgtcgyggtg cgtggcgggc agcagggaga t    51

<210> SEQ ID NO 157
<211> LENGTH: 51
<212> TYPE: DNA
<213> ORGANISM: Homo sapiens

<400> SEQUENCE: 157
gggcagcagg gagatcgtcg cggtgygtgg cgggcagcag ggagatcgtc g    51

<210> SEQ ID NO 158
<211> LENGTH: 51
<212> TYPE: DNA
<213> ORGANISM: Homo sapiens

<400> SEQUENCE: 158
ggcctgcgtc actccacagt ggcacrggcg ctgggctccg catcccatgg g    51

<210> SEQ ID NO 159
<211> LENGTH: 51
<212> TYPE: DNA
<213> ORGANISM: Homo sapiens

<400> SEQUENCE: 159
gatctcctga cctcatgatt tgcccwcctc agcctcccaa agtgctcgga t    51

<210> SEQ ID NO 160
<211> LENGTH: 51
<212> TYPE: DNA
<213> ORGANISM: Homo sapiens

<400> SEQUENCE: 160
gtcccctccc cagccccaga acccrgcat gtgcgcatcc gtcccagtgc c    51

<210> SEQ ID NO 161
<211> LENGTH: 51
<212> TYPE: DNA
<213> ORGANISM: Homo sapiens

<400> SEQUENCE: 161
gaacagatcc tacactgtgg acaaastctt ttggatctgg cttctctcac t    51

<210> SEQ ID NO 162
<211> LENGTH: 51
<212> TYPE: DNA
<213> ORGANISM: Homo sapiens

<400> SEQUENCE: 162
gggattgaat acaggagggg agcgaycaca gctgcccact ggacgtggca g    51

<210> SEQ ID NO 163
<211> LENGTH: 51
<212> TYPE: DNA
<213> ORGANISM: Homo sapiens
<220> FEATURE:
<221> NAME/KEY: modified_base
<222> LOCATION: (26)..(26)
<223> OTHER INFORMATION: a, c, t or g

<400> SEQUENCE: 163
aaccctccac cccgcagacc aggcgncgtg tgtgtgtggg agagaaggag g    51

<210> SEQ ID NO 164

<211> LENGTH: 51
<212> TYPE: DNA
<213> ORGANISM: Homo sapiens

<400> SEQUENCE: 164
ctctgtggga ttccctcccc attccyggag atagctggtt cgccctgctt g        51

<210> SEQ ID NO 165
<211> LENGTH: 513
<212> TYPE: PRT
<213> ORGANISM: Homo sapiens

<400> SEQUENCE: 165

Met Arg Gln Pro Pro Gly Glu Ser Asp Met Ala Val Ser Asp Ala Leu
1               5                   10                  15

Leu Pro Ser Phe Ser Thr Phe Ala Ser Gly Pro Ala Gly Arg Glu Lys
            20                  25                  30

Thr Leu Arg Gln Ala Gly Ala Pro Asn Asn Arg Trp Arg Glu Glu Leu
        35                  40                  45

Ser His Met Lys Arg Leu Pro Pro Val Leu Pro Gly Arg Pro Tyr Asp
    50                  55                  60

Leu Ala Ala Ala Thr Val Ala Thr Asp Leu Glu Ser Gly Gly Ala Gly
65                  70                  75                  80

Ala Ala Cys Gly Gly Ser Asn Leu Ala Pro Leu Pro Arg Arg Glu Thr
                85                  90                  95

Glu Glu Phe Asn Asp Leu Leu Asp Leu Asp Phe Ile Leu Ser Asn Ser
            100                 105                 110

Leu Thr His Pro Pro Glu Ser Val Ala Ala Thr Val Ser Ser Ser Ala
        115                 120                 125

Ser Ala Ser Ser Ser Ser Ser Pro Ser Ser Gly Pro Ala Ser Ala
    130                 135                 140

Pro Ser Thr Cys Ser Phe Thr Tyr Pro Ile Arg Ala Gly Asn Asp Pro
145                 150                 155                 160

Gly Val Ala Pro Gly Gly Thr Gly Gly Gly Leu Leu Tyr Gly Arg Glu
                165                 170                 175

Ser Ala Pro Pro Pro Thr Ala Pro Phe Asn Leu Ala Asp Ile Asn Asp
            180                 185                 190

Val Ser Pro Ser Gly Gly Phe Val Ala Glu Leu Leu Arg Pro Glu Leu
        195                 200                 205

Asp Pro Val Tyr Ile Pro Pro Gln Gln Pro Gln Pro Pro Gly Gly Gly
    210                 215                 220

Leu Met Gly Lys Phe Val Leu Lys Ala Ser Leu Ser Ala Pro Gly Ser
225                 230                 235                 240

Glu Tyr Gly Ser Pro Ser Val Ile Ser Val Ser Lys Gly Ser Pro Asp
                245                 250                 255

Gly Ser His Pro Val Val Val Ala Pro Tyr Asn Gly Gly Pro Pro Arg
            260                 265                 270

Thr Cys Pro Lys Ile Lys Gln Glu Ala Val Ser Ser Cys Thr His Leu
        275                 280                 285

Gly Ala Gly Pro Pro Leu Ser Asn Gly His Arg Pro Ala Ala His Asp
    290                 295                 300

Phe Pro Leu Gly Arg Gln Leu Pro Ser Arg Thr Thr Pro Thr Leu Gly
305                 310                 315                 320

Leu Glu Glu Val Leu Ser Ser Arg Asp Cys His Pro Ala Leu Pro Leu
                325                 330                 335

-continued

```
Pro Pro Gly Phe His Pro His Pro Gly Pro Asn Tyr Pro Ser Phe Leu
            340             345                 350

Pro Asp Gln Met Gln Pro Gln Val Pro Pro Leu His Tyr Gln Gly Gln
        355                 360                 365

Ser Arg Gly Phe Val Ala Arg Ala Gly Glu Pro Cys Val Cys Trp Pro
    370                 375                 380

His Phe Gly Thr His Gly Met Met Leu Thr Pro Ser Ser Pro Leu
385                 390                 395                 400

Glu Leu Met Pro Pro Gly Ser Cys Met Pro Glu Glu Pro Lys Pro Lys
                405                 410                 415

Arg Gly Arg Arg Ser Trp Pro Arg Lys Arg Thr Ala Thr His Thr Cys
            420                 425                 430

Asp Tyr Ala Gly Cys Gly Lys Thr Tyr Thr Lys Ser Ser His Leu Lys
        435                 440                 445

Ala His Leu Arg Thr His Thr Gly Glu Lys Pro Tyr His Cys Asp Trp
    450                 455                 460

Asp Gly Cys Gly Trp Lys Phe Ala Arg Ser Asp Glu Leu Thr Arg His
465                 470                 475                 480

Tyr Arg Lys His Thr Gly His Arg Pro Phe Gln Cys Gln Lys Cys Asp
                485                 490                 495

Arg Ala Phe Ser Arg Ser Asp His Leu Ala Leu His Met Lys Arg His
            500                 505                 510

Phe

<210> SEQ ID NO 166
<211> LENGTH: 415
<212> TYPE: PRT
<213> ORGANISM: Homo sapiens

<400> SEQUENCE: 166

Met Ala Thr Arg Asn Ser Pro Met Pro Leu Gly Thr Ala Gln Gly Asp
1               5                   10                  15

Pro Gly Glu Ala Gly Thr Arg Pro Gly Pro Asp Ala Ser Leu Arg Asp
            20                  25                  30

Thr Gly Ala Ala Thr Gln Leu Lys Met Lys Pro Arg Lys Val His Lys
        35                  40                  45

Ile Lys Ala Val Ile Ile Asp Leu Gly Ser Gln Tyr Cys Lys Cys Gly
    50                  55                  60

Tyr Ala Gly Glu Pro Arg Pro Thr Tyr Phe Ile Ser Ser Thr Val Gly
65                  70                  75                  80

Lys Arg Cys Pro Glu Ala Ala Asp Ala Gly Asp Thr Arg Lys Trp Thr
                85                  90                  95

Leu Val Gly His Glu Leu Leu Asn Thr Glu Ala Pro Leu Lys Leu Val
            100                 105                 110

Asn Pro Leu Lys His Gly Ile Val Val Asp Trp Asp Cys Val Gln Asp
        115                 120                 125

Ile Trp Glu Tyr Ile Phe Arg Thr Ala Met Lys Ile Leu Pro Glu Glu
    130                 135                 140

His Ala Val Leu Val Ser Asp Pro Pro Leu Ser Pro Ser Ser Asn Arg
145                 150                 155                 160

Glu Lys Tyr Ala Glu Leu Met Phe Glu Thr Phe Gly Ile Pro Ala Met
                165                 170                 175

His Val Thr Ser Gln Ser Leu Leu Ser Ile Tyr Ser Tyr Gly Lys Thr
            180                 185                 190
```

```
Ser Gly Leu Val Val Glu Ser Gly His Gly Val Ser His Val Val Pro
            195                 200                 205

Ile Ser Glu Gly Asp Val Leu Pro Gly Leu Thr Ser Arg Ala Asp Tyr
    210                 215                 220

Ala Gly Gly Asp Leu Thr Asn Tyr Leu Met Gln Leu Leu Asn Glu Ala
225                 230                 235                 240

Gly His Ala Phe Thr Asp Asp His Leu His Ile Ile Glu His Ile Lys
                245                 250                 255

Lys Lys Cys Cys Tyr Ala Ala Phe Leu Pro Glu Glu Leu Gly Leu
                260                 265                 270

Val Pro Glu Glu Leu Arg Val Asp Tyr Glu Leu Pro Asp Gly Lys Leu
    275                 280                 285

Ile Thr Ile Gly Gln Glu Arg Phe Arg Cys Ser Glu Met Leu Phe Gln
    290                 295                 300

Pro Ser Leu Ala Gly Ser Thr Gln Pro Gly Leu Pro Glu Leu Thr Ala
305                 310                 315                 320

Ala Cys Leu Gly Arg Cys Gln Asp Thr Gly Phe Lys Glu Glu Met Ala
                325                 330                 335

Ala Asn Val Leu Leu Cys Gly Gly Cys Thr Met Leu Asp Gly Phe Pro
                340                 345                 350

Glu Arg Phe Gln Arg Glu Leu Ser Leu Leu Cys Pro Gly Asp Ser Pro
                355                 360                 365

Ala Val Ala Ala Ala Pro Glu Arg Lys Thr Ser Val Trp Thr Gly Gly
            370                 375                 380

Ser Ile Leu Ala Ser Leu Gln Ala Phe Gln Gln Leu Trp Val Ser Lys
385                 390                 395                 400

Glu Glu Phe Glu Glu Arg Gly Ser Val Ala Ile Tyr Ser Lys Cys
                405                 410                 415

<210> SEQ ID NO 167
<211> LENGTH: 345
<212> TYPE: PRT
<213> ORGANISM: Homo sapiens

<400> SEQUENCE: 167

Met Gly Val Cys Gly Tyr Leu Phe Leu Pro Trp Lys Cys Leu Val Val
1               5                   10                  15

Val Ser Leu Arg Leu Leu Phe Leu Val Pro Thr Gly Val Pro Val Arg
            20                  25                  30

Ser Gly Asp Ala Thr Phe Pro Lys Ala Met Asp Asn Val Thr Val Arg
        35                  40                  45

Gln Gly Glu Ser Ala Thr Leu Arg Cys Thr Ile Asp Asp Arg Val Thr
    50                  55                  60

Arg Val Ala Trp Leu Asn Arg Ser Thr Ile Leu Tyr Ala Gly Asn Asp
65                  70                  75                  80

Lys Trp Ser Ile Asp Pro Arg Val Ile Ile Leu Val Asn Thr Pro Thr
                85                  90                  95

Gln Tyr Ser Ile Met Ile Gln Asn Val Asp Val Tyr Asp Glu Gly Pro
            100                 105                 110

Tyr Thr Cys Ser Val Gln Thr Asp Asn His Pro Lys Thr Ser Arg Val
        115                 120                 125

His Leu Ile Val Gln Val Pro Pro Gln Ile Met Asn Ile Ser Ser Asp
    130                 135                 140

Ile Thr Val Asn Glu Gly Ser Ser Val Thr Leu Leu Cys Leu Ala Ile
145                 150                 155                 160
```

```
Gly Arg Pro Glu Pro Thr Val Thr Trp Arg His Leu Ser Val Lys Glu
                165                 170                 175

Gly Gln Gly Phe Val Ser Glu Asp Glu Tyr Leu Glu Ile Ser Asp Ile
            180                 185                 190

Lys Arg Asp Gln Ser Gly Glu Tyr Glu Cys Ser Ala Leu Asn Asp Val
        195                 200                 205

Ala Ala Pro Asp Val Arg Lys Val Lys Ile Thr Val Asn Tyr Pro Pro
    210                 215                 220

Tyr Ile Ser Lys Ala Lys Asn Thr Gly Val Ser Val Gly Gln Lys Gly
225                 230                 235                 240

Ile Leu Ser Cys Glu Ala Ser Ala Val Pro Met Ala Glu Phe Gln Trp
                245                 250                 255

Phe Lys Glu Glu Thr Arg Leu Ala Thr Gly Leu Asp Gly Met Arg Ile
            260                 265                 270

Glu Asn Lys Gly Arg Met Ser Thr Leu Thr Phe Phe Asn Val Ser Glu
        275                 280                 285

Lys Asp Tyr Gly Asn Tyr Thr Cys Val Ala Thr Asn Lys Leu Gly Asn
    290                 295                 300

Thr Asn Ala Ser Ile Thr Leu Tyr Gly Pro Gly Ala Val Ile Asp Gly
305                 310                 315                 320

Val Asn Ser Ala Ser Arg Ala Leu Ala Cys Leu Trp Leu Ser Gly Thr
                325                 330                 335

Leu Leu Ala His Phe Phe Ile Lys Phe
            340                 345

<210> SEQ ID NO 168
<211> LENGTH: 718
<212> TYPE: PRT
<213> ORGANISM: Homo sapiens

<400> SEQUENCE: 168

Met Met Phe Arg Asp Gln Val Gly Val Leu Ala Gly Trp Phe Lys Gly
1               5                   10                  15

Trp Asn Glu Cys Glu Gln Thr Val Ala Leu Leu Ser Leu Leu Lys Arg
                20                  25                  30

Val Ser Gln Thr Gln Ala Arg Phe Leu Gln Leu Cys Leu Glu His Ser
            35                  40                  45

Leu Ala Asp Cys Ala Glu Leu His Val Leu Glu Arg Glu Ala Asn Ser
        50                  55                  60

Pro Gly Ile Ile Asn Gln Trp Gln Gln Glu Ser Lys Asp Lys Val Ile
65                  70                  75                  80

Ser Leu Leu Leu Thr His Leu Pro Leu Leu Pro Gly Asn Leu Asp
                85                  90                  95

Ala Lys Val Glu Tyr Met Lys Leu Leu Pro Lys Ile Leu Ala His Ser
            100                 105                 110

Ile Glu His Asn Gln His Ile Glu Glu Ser Arg Gln Leu Leu Ser Tyr
        115                 120                 125

Ala Leu Ile His Pro Ala Thr Ser Leu Glu Asp Arg Ser Ala Leu Ala
    130                 135                 140

Met Trp Leu Asn His Leu Glu Asp Arg Thr Ser Thr Ser Phe Gly Gly
145                 150                 155                 160

Gln Asn Arg Gly Arg Ser Asp Ser Val Asp Tyr Gly Gln Thr His Tyr
                165                 170                 175

Tyr His Gln Arg Gln Asn Ser Asp Asp Lys Leu Asn Gly Trp Gln Asn
```

-continued

```
                180                 185                 190
Ser Arg Asp Ser Gly Ile Cys Ile Asn Ala Ser Asn Trp Gln Asp Lys
            195                 200                 205

Ser Met Gly Cys Glu Asn Gly His Val Pro Leu Tyr Ser Ser Ser Ser
            210                 215                 220

Val Pro Thr Thr Ile Asn Thr Ile Gly Thr Ser Thr Ser Thr Ile Leu
225                 230                 235                 240

Ser Gly Gln Ala His His Ser Pro Leu Lys Arg Ser Val Ser Leu Thr
            245                 250                 255

Pro Pro Met Asn Val Pro Asn Gln Pro Leu Gly His Gly Trp Met Ser
            260                 265                 270

His Glu Asp Leu Arg Ala Arg Gly Pro Gln Cys Leu Pro Ser Asp His
            275                 280                 285

Ala Pro Leu Ser Pro Gln Ser Ser Val Ala Ser Ser Gly Ser Gly Gly
            290                 295                 300

Ser Glu His Leu Glu Asp Gln Thr Thr Ala Arg Asn Thr Phe Gln Glu
305                 310                 315                 320

Glu Gly Ser Gly Met Lys Asp Val Pro Ala Trp Leu Lys Ser Leu Arg
            325                 330                 335

Leu His Lys Tyr Ala Ala Leu Phe Ser Gln Met Thr Tyr Glu Glu Met
            340                 345                 350

Met Ala Leu Thr Glu Cys Gln Leu Glu Ala Gln Asn Val Thr Lys Gly
            355                 360                 365

Ala Arg His Lys Ile Val Ile Ser Ile Gln Lys Leu Lys Glu Arg Gln
            370                 375                 380

Asn Leu Leu Lys Ser Leu Glu Arg Asp Ile Ile Glu Gly Gly Ser Leu
385                 390                 395                 400

Arg Ile Pro Leu Gln Glu Leu His Gln Met Ile Leu Thr Pro Ile Lys
            405                 410                 415

Ala Tyr Ser Ser Pro Ser Thr Thr Pro Glu Ala Arg Arg Glu Pro
            420                 425                 430

Gln Ala Pro Arg Gln Pro Ser Leu Met Gly Pro Glu Ser Gln Ser Pro
            435                 440                 445

Asp Cys Lys Asp Gly Ala Ala Ala Thr Gly Ala Thr Ala Thr Pro Ser
450                 455                 460

Ala Gly Ala Ser Gly Gly Leu Gln Pro His Gln Leu Ser Ser Cys Asp
465                 470                 475                 480

Gly Glu Leu Ala Val Ala Pro Leu Pro Glu Gly Asp Leu Pro Gly Gln
            485                 490                 495

Phe Thr Arg Val Met Gly Lys Val Cys Thr Gln Leu Leu Val Ser Arg
            500                 505                 510

Pro Asp Glu Glu Asn Ile Ser Ser Tyr Leu Gln Leu Ile Asp Lys Cys
            515                 520                 525

Leu Ile His Glu Ala Phe Thr Glu Thr Gln Lys Lys Arg Leu Leu Ser
            530                 535                 540

Trp Lys Gln Gln Val Gln Lys Leu Phe Arg Ser Phe Pro Arg Lys Thr
545                 550                 555                 560

Leu Leu Asp Ile Ser Gly Tyr Arg Gln Gln Arg Asn Arg Gly Phe Gly
            565                 570                 575

Gln Ser Asn Ser Leu Pro Thr Ala Gly Ser Val Gly Gly Gly Met Gly
            580                 585                 590

Arg Arg Asn Pro Arg Gln Tyr Gln Ile Pro Ser Arg Asn Val Pro Ser
            595                 600                 605
```

```
Ala Arg Leu Gly Leu Leu Gly Thr Ser Gly Phe Val Ser Ser Asn Gln
        610                 615                 620

Arg Asn Thr Thr Ala Thr Pro Thr Ile Met Lys Gln Gly Arg Gln Asn
625                 630                 635                 640

Leu Trp Phe Ala Asn Pro Gly Gly Ser Asn Ser Met Pro Ser Arg Thr
                645                 650                 655

His Ser Ser Val Gln Arg Thr Arg Ser Leu Pro Val His Thr Ser Pro
            660                 665                 670

Gln Asn Met Leu Met Phe Gln Gln Pro Glu Phe Gln Leu Pro Val Thr
        675                 680                 685

Glu Pro Asp Ile Asn Asn Arg Leu Glu Ser Leu Cys Leu Ser Met Thr
690                 695                 700

Glu His Ala Leu Gly Asp Gly Val Asp Arg Thr Ser Thr Ile
705                 710                 715

<210> SEQ ID NO 169
<211> LENGTH: 250
<212> TYPE: PRT
<213> ORGANISM: Homo sapiens

<400> SEQUENCE: 169

Met Glu Lys Gly Pro Val Arg Ala Pro Ala Glu Lys Pro Arg Gly Ala
1               5                   10                  15

Arg Cys Ser Asn Gly Phe Pro Glu Arg Asp Pro Pro Arg Pro Gly Pro
            20                  25                  30

Ser Arg Pro Ala Glu Lys Pro Pro Arg Pro Glu Ala Lys Ser Ala Gln
        35                  40                  45

Pro Ala Asp Gly Trp Lys Gly Glu Arg Pro Arg Ser Glu Glu Asp Asn
50                  55                  60

Glu Leu Asn Leu Pro Asn Leu Ala Ala Ala Tyr Ser Ser Ile Leu Ser
65                  70                  75                  80

Ser Leu Gly Glu Asn Pro Gln Arg Gln Gly Leu Leu Lys Thr Pro Trp
                85                  90                  95

Arg Ala Ala Ser Ala Met Gln Phe Phe Thr Lys Gly Tyr Gln Glu Thr
            100                 105                 110

Ile Ser Asp Val Leu Asn Asp Ala Ile Phe Asp Glu Asp His Asp Glu
        115                 120                 125

Met Val Ile Val Lys Asp Ile Asp Met Phe Ser Met Cys Glu His His
130                 135                 140

Leu Val Pro Phe Val Gly Lys Val His Ile Gly Tyr Leu Pro Asn Lys
145                 150                 155                 160

Gln Val Leu Gly Leu Ser Lys Leu Ala Arg Ile Val Glu Ile Tyr Ser
                165                 170                 175

Arg Arg Leu Gln Val Gln Glu Arg Leu Thr Lys Gln Ile Ala Val Ala
            180                 185                 190

Ile Thr Glu Ala Leu Arg Pro Ala Gly Val Gly Val Val Val Glu Ala
        195                 200                 205

Thr His Met Cys Met Val Met Arg Gly Val Gln Lys Met Asn Ser Lys
210                 215                 220

Thr Val Thr Ser Thr Met Leu Gly Val Phe Arg Glu Asp Pro Lys Thr
225                 230                 235                 240

Arg Glu Glu Phe Leu Thr Leu Ile Arg Ser
                245                 250
```

```
<210> SEQ ID NO 170
<211> LENGTH: 192
<212> TYPE: PRT
<213> ORGANISM: Homo sapiens

<400> SEQUENCE: 170

Met Lys Val Gln Ser Phe Gly Glu Arg Val Val Leu Phe Ile Leu Asn
1               5                   10                  15

Ala Ile Ile Phe Gly Arg Leu Glu Arg Asn Leu Asp Asp Asp Asp Met
            20                  25                  30

Phe Phe Leu Pro His Ser Val Lys Glu Gln Ala Lys Ile Leu Trp Arg
        35                  40                  45

Arg Gly Ala Ala Val Gly Phe Tyr Thr Thr Lys Met Lys Gly Arg Leu
    50                  55                  60

Cys Gly Asp Gly Thr Gly Ala Cys Tyr Leu Leu Pro Val Phe Asp Thr
65                  70                  75                  80

Val Phe Ile Arg Arg Lys His Trp His Arg Gly Leu Gly Thr Ala Met
                85                  90                  95

Leu Arg Asp Phe Cys Glu Thr Phe Pro Glu Asp Glu Ala Leu Gly Val
            100                 105                 110

Ser Cys Ser Met Ser Pro Ala Met Tyr Gln Ala His Pro Gly Asn Ser
        115                 120                 125

Glu Asp Val Ser Arg His Ala Arg Thr Ser Gln Asn Asp Arg Pro Arg
    130                 135                 140

Gln Pro Ala Pro Gly Asp Gly Ser Lys Glu Arg Met Cys Gly Glu Glu
145                 150                 155                 160

Leu Glu Asp Thr Lys Asp Asp Pro Glu Cys Gly Val Glu Glu Glu Asp
                165                 170                 175

Ala Gly Leu Ala Gly Gln Pro Pro Gly Lys Leu Thr Arg Ser Ser Pro
            180                 185                 190

<210> SEQ ID NO 171
<211> LENGTH: 1685
<212> TYPE: PRT
<213> ORGANISM: Homo sapiens

<400> SEQUENCE: 171

Met Ser Leu Pro Phe Tyr Gln Arg Cys His Gln His Tyr Asp Leu Ser
1               5                   10                  15

Tyr Arg Asn Lys Asp Val Arg Ser Thr Val Ser His Tyr Gln Arg Glu
            20                  25                  30

Lys Lys Arg Ser Ala Val Tyr Thr Gln Gly Ser Thr Ala Tyr Ser Ser
        35                  40                  45

Arg Ser Ser Ala Ala His Arg Arg Glu Ser Glu Ala Phe Arg Arg Ala
    50                  55                  60

Ser Ala Ser Ser Gln Gln Ala Ser Gln His Ala Leu Ser Ser
65                  70                  75                  80

Glu Val Ser Arg Lys Ala Ala Ser Ala Tyr Asp Tyr Gly Ser Ser His
                85                  90                  95

Gly Leu Thr Asp Ser Ser Leu Leu Asp Asp Tyr Ser Ser Lys Leu
            100                 105                 110

Ser Pro Lys Pro Lys Arg Ala Lys His Ser Leu Leu Ser Gly Glu Glu
        115                 120                 125

Lys Glu Asn Leu Pro Ser Asp Tyr Met Val Pro Ile Phe Ser Gly Arg
    130                 135                 140

Gln Lys His Val Ser Gly Ile Thr Asp Thr Glu Glu Arg Ile Lys
```

```
            145                 150                 155                 160
        Glu Ala Ala Ala Tyr Ile Ala Gln Arg Asn Leu Leu Ala Ser Glu Glu
                        165                 170                 175
        Gly Ile Thr Thr Ser Lys Gln Ser Thr Ala Ser Lys Gln Thr Thr Ala
                        180                 185                 190
        Ser Lys Gln Ser Thr Ala Ser Lys Gln Ser Thr Ala Ser Lys Gln Ser
                        195                 200                 205
        Thr Ala Ser Arg Gln Ser Thr Ala Ser Arg Gln Ser Val Val Ser Lys
                        210                 215                 220
        Gln Ala Thr Ser Ala Leu Gln Gln Glu Thr Ser Glu Lys Lys Ser
        225                 230                 235                 240
        Arg Lys Val Val Ile Arg Glu Lys Ala Glu Arg Leu Ser Leu Arg Lys
                        245                 250                 255
        Thr Leu Glu Glu Thr Glu Thr Tyr His Ala Lys Leu Asn Glu Asp His
                        260                 265                 270
        Leu Leu His Ala Pro Glu Phe Ile Ile Lys Pro Arg Ser His Thr Val
                        275                 280                 285
        Trp Glu Lys Glu Asn Val Lys Leu His Cys Ser Ile Ala Gly Trp Pro
                        290                 295                 300
        Glu Pro Arg Val Thr Trp Tyr Lys Asn Gln Val Pro Ile Asn Val His
        305                 310                 315                 320
        Ala Asn Pro Gly Lys Tyr Ile Ile Glu Ser Arg Tyr Gly Met His Thr
                        325                 330                 335
        Leu Glu Ile Asn Gly Cys Asp Phe Glu Asp Thr Ala Gln Tyr Arg Ala
                        340                 345                 350
        Ser Ala Met Asn Val Lys Gly Glu Leu Ser Ala Tyr Ala Ser Val Val
                        355                 360                 365
        Val Lys Arg Tyr Lys Gly Glu Phe Asp Glu Thr Arg Phe His Ala Gly
                        370                 375                 380
        Ala Ser Thr Met Pro Leu Ser Phe Gly Val Thr Pro Tyr Gly Tyr Ala
        385                 390                 395                 400
        Ser Arg Phe Glu Ile His Phe Asp Asp Lys Phe Asp Val Ser Phe Gly
                        405                 410                 415
        Arg Glu Gly Glu Thr Met Ser Leu Gly Cys Arg Val Val Ile Thr Pro
                        420                 425                 430
        Glu Ile Lys His Phe Gln Pro Glu Ile Gln Trp Tyr Arg Asn Gly Val
                        435                 440                 445
        Pro Leu Ser Pro Ser Lys Trp Val Gln Thr Leu Trp Ser Gly Glu Arg
                        450                 455                 460
        Ala Thr Leu Thr Phe Ser His Leu Asn Lys Glu Asp Glu Gly Leu Tyr
        465                 470                 475                 480
        Thr Ile Arg Val Arg Met Gly Glu Tyr Tyr Glu Gln Tyr Ser Ala Tyr
                        485                 490                 495
        Val Phe Val Arg Asp Ala Asp Ala Glu Ile Glu Gly Ala Pro Ala Ala
                        500                 505                 510
        Pro Leu Asp Val Lys Cys Leu Glu Ala Asn Lys Asp Tyr Ile Ile Ile
                        515                 520                 525
        Ser Trp Lys Gln Pro Ala Val Asp Gly Gly Ser Pro Ile Leu Gly Tyr
                        530                 535                 540
        Phe Ile Asp Lys Cys Glu Val Gly Thr Asp Ser Trp Ser Gln Cys Asn
        545                 550                 555                 560
        Asp Thr Pro Val Lys Phe Ala Arg Phe Pro Val Thr Gly Leu Ile Glu
                        565                 570                 575
```

-continued

```
Gly Arg Ser Tyr Ile Phe Arg Val Arg Ala Val Asn Lys Met Gly Ile
                580                 585                 590

Gly Phe Pro Ser Arg Val Ser Glu Pro Val Ala Ala Leu Asp Pro Ala
            595                 600                 605

Glu Lys Ala Arg Leu Lys Ser Arg Pro Ser Ala Pro Trp Thr Gly Gln
610                 615                 620

Ile Ile Val Thr Glu Glu Pro Ser Glu Gly Ile Val Pro Gly Pro
625                 630                 635                 640

Pro Thr Asp Leu Ser Val Thr Glu Ala Thr Arg Ser Tyr Val Val Leu
                645                 650                 655

Ser Trp Lys Pro Pro Gly Gln Arg Gly His Glu Gly Ile Met Tyr Phe
            660                 665                 670

Val Glu Lys Cys Glu Ala Gly Thr Glu Asn Trp Gln Arg Val Asn Thr
        675                 680                 685

Glu Leu Pro Val Lys Ser Pro Arg Phe Ala Leu Phe Asp Leu Ala Glu
    690                 695                 700

Gly Lys Ser Tyr Cys Phe Arg Val Arg Cys Ser Asn Ser Ala Gly Val
705                 710                 715                 720

Gly Glu Pro Ser Glu Ala Thr Glu Val Thr Val Val Gly Asp Lys Leu
                725                 730                 735

Asp Ile Pro Lys Ala Pro Gly Lys Ile Ile Pro Ser Arg Asn Thr Asp
            740                 745                 750

Thr Ser Val Val Val Ser Trp Glu Glu Ser Lys Asp Ala Lys Glu Leu
        755                 760                 765

Val Gly Tyr Tyr Ile Glu Ala Ser Val Ala Gly Ser Gly Lys Trp Glu
    770                 775                 780

Pro Cys Asn Asn Asn Pro Val Lys Gly Ser Arg Phe Thr Cys His Gly
785                 790                 795                 800

Leu Val Thr Gly Gln Ser Tyr Ile Phe Arg Val Arg Ala Val Asn Ala
                805                 810                 815

Ala Gly Leu Ser Glu Tyr Ser Gln Asp Ser Glu Ala Ile Glu Val Lys
            820                 825                 830

Ala Ala Ile Gly Gly Val Ser Pro Asp Val Cys Pro Ala Leu Ser
        835                 840                 845

Asp Glu Pro Gly Gly Leu Thr Ala Ser Arg Gly Arg Val His Glu Ala
    850                 855                 860

Ser Pro Pro Thr Phe Gln Lys Asp Ala Leu Leu Gly Ser Lys Pro Asn
865                 870                 875                 880

Lys Pro Ser Leu Pro Ser Ser Gln Asn Leu Gly Gln Thr Glu Val
                885                 890                 895

Ser Lys Val Ser Glu Thr Val Gln Glu Leu Thr Pro Pro Gln
            900                 905                 910

Lys Ala Ala Pro Gln Gly Lys Ser Lys Ser Asp Pro Leu Lys Lys Lys
        915                 920                 925

Thr Asp Arg Ala Pro Pro Ser Pro Pro Cys Asp Ile Thr Cys Leu Glu
    930                 935                 940

Ser Phe Arg Asp Ser Met Val Leu Gly Trp Lys Gln Pro Asp Lys Ile
945                 950                 955                 960

Gly Gly Ala Glu Ile Thr Gly Tyr Tyr Val Asn Tyr Arg Glu Val Ile
                965                 970                 975

Asp Gly Val Pro Gly Lys Trp Arg Glu Ala Asn Val Lys Ala Val Ser
            980                 985                 990
```

```
Glu Glu Ala Tyr Lys Ile Ser Asn Leu Lys Glu Asn Met Val Tyr Gln
            995                 1000                1005

Phe Gln Val Ala Ala Met Asn Met Ala Gly Leu Gly Ala Pro Ser
    1010                1015                1020

Ala Val Ser Glu Cys Phe Lys Cys Glu Glu Trp Thr Ile Ala Val
    1025                1030                1035

Pro Gly Pro Pro His Ser Leu Lys Cys Ser Glu Val Arg Lys Asp
    1040                1045                1050

Ser Leu Val Leu Gln Trp Lys Pro Pro Val His Ser Gly Arg Thr
    1055                1060                1065

Pro Val Thr Gly Tyr Phe Val Asp Leu Lys Glu Ala Lys Ala Lys
    1070                1075                1080

Glu Asp Gln Trp Arg Gly Leu Asn Glu Ala Ala Ile Lys Asn Val
    1085                1090                1095

Tyr Leu Lys Val Arg Gly Leu Lys Glu Gly Val Ser Tyr Val Phe
    1100                1105                1110

Arg Val Arg Ala Ile Asn Gln Ala Gly Val Gly Lys Pro Ser Asp
    1115                1120                1125

Leu Ala Gly Pro Val Val Ala Glu Thr Arg Pro Gly Thr Lys Glu
    1130                1135                1140

Val Val Val Asn Val Asp Asp Gly Val Ile Ser Leu Asn Phe
    1145                1150                1155

Glu Cys Asp Lys Met Thr Pro Lys Ser Glu Phe Ser Trp Ser Lys
    1160                1165                1170

Asp Tyr Val Ser Thr Glu Asp Ser Pro Arg Leu Glu Val Glu Ser
    1175                1180                1185

Lys Gly Asn Lys Thr Lys Met Thr Phe Lys Asp Leu Gly Met Asp
    1190                1195                1200

Asp Leu Gly Ile Tyr Ser Cys Asp Val Thr Asp Thr Asp Gly Ile
    1205                1210                1215

Ala Ser Ser Tyr Leu Ile Asp Glu Glu Glu Leu Lys Arg Leu Leu
    1220                1225                1230

Ala Leu Ser His Glu His Lys Phe Pro Thr Val Pro Val Lys Ser
    1235                1240                1245

Glu Leu Ala Val Glu Ile Leu Glu Lys Gly Gln Val Arg Phe Trp
    1250                1255                1260

Met Gln Ala Glu Lys Leu Ser Gly Asn Ala Lys Val Asn Tyr Ile
    1265                1270                1275

Phe Asn Glu Lys Glu Ile Phe Glu Gly Pro Lys Tyr Lys Met His
    1280                1285                1290

Ile Asp Arg Asn Thr Gly Ile Ile Glu Met Phe Met Glu Lys Leu
    1295                1300                1305

Gln Asp Glu Asp Glu Gly Thr Tyr Thr Phe Gln Leu Gln Asp Gly
    1310                1315                1320

Lys Ala Thr Asn His Ser Thr Val Val Leu Val Gly Asp Val Phe
    1325                1330                1335

Lys Lys Leu Gln Lys Glu Ala Glu Phe Gln Arg Gln Glu Trp Ile
    1340                1345                1350

Arg Lys Gln Gly Pro His Phe Val Glu Tyr Leu Ser Trp Glu Val
    1355                1360                1365

Thr Gly Glu Cys Asn Val Leu Leu Lys Cys Lys Val Ala Asn Ile
    1370                1375                1380

Lys Lys Glu Thr His Ile Val Trp Tyr Lys Asp Glu Arg Glu Ile
```

```
              1385                1390                1395

Ser Val Asp Glu Lys His Asp Phe Lys Asp Gly Ile Cys Thr Leu
        1400                1405                1410

Leu Ile Thr Glu Phe Ser Lys Lys Asp Ala Gly Ile Tyr Glu Val
        1415                1420                1425

Ile Leu Lys Asp Asp Arg Gly Lys Asp Lys Ser Arg Leu Lys Leu
        1430                1435                1440

Val Asp Glu Ala Phe Lys Glu Leu Met Met Glu Val Cys Lys Lys
        1445                1450                1455

Ile Ala Leu Ser Ala Thr Asp Leu Lys Ile Gln Ser Thr Ala Glu
        1460                1465                1470

Gly Ile Gln Leu Tyr Ser Phe Val Thr Tyr Tyr Val Glu Asp Leu
        1475                1480                1485

Lys Val Asn Trp Ser His Asn Gly Ser Ala Ile Arg Tyr Ser Asp
        1490                1495                1500

Arg Val Lys Thr Gly Val Thr Gly Glu Gln Ile Trp Leu Gln Ile
        1505                1510                1515

Asn Glu Pro Thr Pro Asn Asp Lys Gly Lys Tyr Val Met Glu Leu
        1520                1525                1530

Phe Asp Gly Lys Thr Gly His Gln Lys Thr Val Asp Leu Ser Gly
        1535                1540                1545

Gln Ala Tyr Asp Glu Ala Tyr Ala Glu Phe Gln Arg Leu Lys Gln
        1550                1555                1560

Ala Ala Ile Ala Glu Lys Asn Arg Ala Arg Val Leu Gly Gly Leu
        1565                1570                1575

Pro Asp Val Val Thr Ile Gln Glu Gly Lys Ala Leu Asn Leu Thr
        1580                1585                1590

Cys Asn Val Trp Gly Asp Pro Pro Glu Val Ser Trp Leu Lys
        1595                1600                1605

Asn Glu Lys Ala Leu Ala Ser Asp Asp His Cys Asn Leu Lys Phe
        1610                1615                1620

Glu Ala Gly Arg Thr Ala Tyr Phe Thr Ile Asn Gly Val Ser Thr
        1625                1630                1635

Ala Asp Ser Gly Lys Tyr Gly Leu Val Val Lys Asn Lys Tyr Gly
        1640                1645                1650

Ser Glu Thr Ser Asp Phe Thr Val Ser Val Phe Ile Pro Glu Glu
        1655                1660                1665

Glu Ala Arg Met Ala Ala Leu Glu Ser Leu Lys Gly Gly Lys Lys
        1670                1675                1680

Ala Lys
    1685

<210> SEQ ID NO 172
<211> LENGTH: 563
<212> TYPE: PRT
<213> ORGANISM: Homo sapiens

<400> SEQUENCE: 172

Met Leu Glu Glu Ala Gly Glu Val Leu Glu Asn Met Leu Lys Ala Ser
1               5                  10                  15

Cys Leu Pro Leu Gly Phe Ile Val Phe Leu Pro Ala Val Leu Leu Leu
                20                  25                  30

Val Ala Pro Pro Leu Pro Ala Ala Asp Ala Ala His Glu Phe Thr Val
            35                  40                  45
```

```
Tyr Arg Met Gln Gln Tyr Asp Leu Gln Gly Gln Pro Tyr Gly Thr Arg
    50                  55                  60

Asn Ala Val Leu Asn Thr Glu Ala Arg Thr Met Ala Ala Glu Val Leu
 65                  70                  75                  80

Ser Arg Arg Cys Val Leu Met Arg Leu Leu Asp Phe Ser Tyr Glu Gln
                 85                  90                  95

Tyr Gln Lys Ala Leu Arg Gln Ser Ala Gly Ala Val Val Ile Ile Leu
            100                 105                 110

Pro Arg Ala Met Ala Ala Val Pro Gln Asp Val Val Arg Gln Phe Met
            115                 120                 125

Glu Ile Glu Pro Glu Met Leu Ala Met Glu Thr Ala Val Pro Val Tyr
130                 135                 140

Phe Ala Val Glu Asp Glu Ala Leu Leu Ser Ile Tyr Lys Gln Thr Gln
145                 150                 155                 160

Ala Ala Ser Ala Ser Gln Gly Ser Ala Ser Ala Ala Glu Val Leu Leu
                165                 170                 175

Arg Thr Ala Thr Ala Asn Gly Phe Gln Met Val Thr Ser Gly Val Gln
                180                 185                 190

Ser Lys Ala Val Ser Asp Trp Leu Ile Ala Ser Val Glu Gly Arg Leu
            195                 200                 205

Thr Gly Leu Gly Gly Glu Asp Leu Pro Thr Ile Val Ile Val Ala His
210                 215                 220

Tyr Asp Ala Phe Gly Val Ala Pro Trp Leu Ser Leu Gly Ala Asp Ser
225                 230                 235                 240

Asn Gly Ser Gly Val Ser Val Leu Leu Glu Leu Ala Arg Leu Phe Ser
                245                 250                 255

Arg Leu Tyr Thr Tyr Lys Arg Thr His Ala Ala Tyr Asn Leu Leu Phe
                260                 265                 270

Phe Ala Ser Gly Gly Lys Phe Asn Tyr Gln Gly Thr Lys Arg Trp
            275                 280                 285

Leu Glu Asp Asn Leu Asp His Thr Asp Ser Ser Leu Leu Gln Asp Asn
            290                 295                 300

Val Ala Phe Val Leu Cys Leu Asp Thr Val Gly Arg Gly Ser Ser Leu
305                 310                 315                 320

His Leu His Val Ser Lys Pro Pro Arg Glu Gly Thr Leu Gln His Ala
                325                 330                 335

Phe Leu Arg Glu Leu Glu Thr Val Ala Ala His Gln Phe Pro Glu Val
                340                 345                 350

Arg Phe Ser Met Val His Lys Arg Ile Asn Leu Ala Glu Asp Val Leu
            355                 360                 365

Ala Trp Glu His Glu Arg Phe Ala Ile Arg Arg Leu Pro Ala Phe Thr
370                 375                 380

Leu Ser His Leu Glu Ser His Arg Asp Gly Gln Arg Ser Ser Ile Met
385                 390                 395                 400

Asp Val Arg Ser Arg Val Asp Ser Lys Thr Leu Thr Arg Asn Thr Arg
                405                 410                 415

Ile Ile Ala Glu Ala Leu Thr Arg Val Ile Tyr Asn Leu Thr Glu Lys
                420                 425                 430

Gly Thr Pro Pro Asp Met Pro Val Phe Thr Glu Gln Met Gln Ile Gln
            435                 440                 445

Gln Glu Gln Leu Asp Ser Val Met Asp Trp Leu Thr Asn Gln Pro Arg
450                 455                 460

Ala Ala Gln Leu Val Asp Lys Asp Ser Thr Phe Leu Ser Thr Leu Glu
```

```
                    465                 470                 475                 480
His His Leu Ser Arg Tyr Leu Lys Asp Val Lys Gln His His Val Lys
                    485                 490                 495

Ala Asp Lys Arg Asp Pro Glu Phe Val Phe Tyr Asp Gln Leu Lys Gln
                    500                 505                 510

Val Met Asn Ala Tyr Arg Val Lys Pro Ala Val Phe Asp Leu Leu Leu
                    515                 520                 525

Ala Val Gly Ile Ala Ala Tyr Leu Gly Met Ala Tyr Val Ala Val Gln
                    530                 535                 540

His Phe Ser Leu Leu Tyr Lys Thr Val Gln Arg Leu Leu Val Lys Ala
545                 550                 555                 560

Lys Thr Gln

<210> SEQ ID NO 173
<211> LENGTH: 375
<212> TYPE: PRT
<213> ORGANISM: Homo sapiens

<400> SEQUENCE: 173

Met Asp Ala Ile His Ile Gly Met Ser Ser Thr Pro Leu Val Lys His
1               5                   10                  15

Thr Ala Gly Ala Gly Leu Lys Ala Asn Arg Pro Arg Val Met Ser Lys
                20                  25                  30

Ser Gly His Ser Asn Val Arg Ile Asp Lys Val Asp Gly Ile Tyr Leu
            35                  40                  45

Leu Tyr Leu Gln Asp Leu Trp Thr Thr Val Ile Asp Met Lys Trp Arg
        50                  55                  60

Tyr Lys Leu Thr Leu Phe Ala Ala Thr Phe Val Met Thr Trp Phe Leu
65                  70                  75                  80

Phe Gly Val Ile Tyr Tyr Ala Ile Ala Phe Ile His Gly Asp Leu Glu
                85                  90                  95

Pro Gly Glu Pro Ile Ser Asn His Thr Pro Cys Ile Met Lys Val Asp
            100                 105                 110

Ser Leu Thr Gly Ala Phe Leu Phe Ser Leu Glu Ser Gln Thr Thr Ile
        115                 120                 125

Gly Tyr Gly Val Arg Ser Ile Thr Glu Glu Cys Pro His Ala Ile Phe
    130                 135                 140

Leu Leu Val Ala Gln Leu Val Ile Thr Thr Leu Ile Glu Ile Phe Ile
145                 150                 155                 160

Thr Gly Thr Phe Leu Ala Lys Ile Ala Arg Pro Lys Lys Arg Ala Glu
                165                 170                 175

Thr Ile Lys Phe Ser His Cys Ala Val Ile Thr Lys Gln Asn Gly Lys
            180                 185                 190

Leu Cys Leu Val Ile Gln Val Ala Asn Met Arg Lys Ser Leu Leu Ile
        195                 200                 205

Gln Cys Gln Leu Ser Gly Lys Leu Leu Gln Thr His Val Thr Lys Glu
    210                 215                 220

Gly Glu Arg Ile Leu Leu Asn Gln Ala Thr Val Lys Phe His Val Asp
225                 230                 235                 240

Ser Ser Ser Glu Ser Pro Phe Leu Ile Leu Pro Met Thr Phe Tyr His
                245                 250                 255

Val Leu Asp Glu Thr Ser Pro Leu Arg Asp Leu Thr Pro Gln Asn Leu
            260                 265                 270

Lys Glu Lys Glu Phe Glu Leu Val Val Leu Leu Asn Ala Thr Val Glu
```

```
            275                 280                 285
Ser Thr Ser Ala Val Cys Gln Ser Arg Thr Ser Tyr Ile Pro Glu Glu
        290                 295                 300
Ile Tyr Trp Gly Phe Glu Phe Val Pro Val Val Ser Leu Ser Lys Asn
305                 310                 315                 320
Gly Lys Tyr Val Ala Asp Phe Ser Gln Phe Glu Gln Ile Arg Lys Ser
                325                 330                 335
Pro Asp Cys Thr Phe Tyr Cys Ala Asp Ser Glu Lys Gln Gln Leu Glu
                340                 345                 350
Glu Lys Tyr Arg Gln Glu Asp Gln Arg Glu Arg Glu Leu Arg Thr Leu
                355                 360                 365
Leu Leu Gln Gln Ser Asn Val
                370                 375

<210> SEQ ID NO 174
<211> LENGTH: 538
<212> TYPE: PRT
<213> ORGANISM: Homo sapiens

<400> SEQUENCE: 174

Met Ala Arg Ala Ala Leu Leu Pro Ser Arg Ser Pro Pro Thr Pro
1               5                   10                  15
Leu Leu Trp Pro Leu Leu Leu Leu Leu Leu Glu Thr Gly Ala Gln
                20                  25                  30
Asp Val Arg Val Gln Val Leu Pro Glu Val Arg Gly Gln Leu Gly Gly
            35                  40                  45
Thr Val Glu Leu Pro Cys His Leu Leu Pro Pro Val Pro Gly Leu Tyr
        50                  55                  60
Ile Ser Leu Val Thr Trp Gln Arg Pro Asp Ala Pro Ala Asn His Gln
65                  70                  75                  80
Asn Val Ala Ala Phe His Pro Lys Met Gly Pro Ser Phe Pro Ser Pro
                85                  90                  95
Lys Pro Gly Ser Glu Arg Leu Ser Phe Val Ser Ala Lys Gln Ser Thr
                100                 105                 110
Gly Gln Asp Thr Glu Ala Glu Leu Gln Asp Ala Thr Leu Ala Leu His
                115                 120                 125
Gly Leu Thr Val Glu Asp Glu Gly Asn Tyr Thr Cys Glu Phe Ala Thr
                130                 135                 140
Phe Pro Lys Gly Ser Val Arg Gly Met Thr Trp Leu Arg Val Ile Ala
145                 150                 155                 160
Lys Pro Lys Asn Gln Ala Glu Ala Gln Lys Val Thr Phe Ser Gln Asp
                165                 170                 175
Pro Thr Thr Val Ala Leu Cys Ile Ser Lys Glu Gly Arg Pro Pro Ala
                180                 185                 190
Arg Ile Ser Trp Leu Ser Ser Leu Asp Trp Glu Ala Lys Glu Thr Gln
                195                 200                 205
Val Ser Gly Thr Leu Ala Gly Thr Val Thr Val Thr Ser Arg Phe Thr
                210                 215                 220
Leu Val Pro Ser Gly Arg Ala Asp Gly Val Thr Val Thr Cys Lys Val
225                 230                 235                 240
Glu His Glu Ser Phe Glu Glu Pro Ala Leu Ile Pro Val Thr Leu Ser
                245                 250                 255
Val Arg Tyr Pro Pro Glu Val Ser Ile Ser Gly Tyr Asp Asp Asn Trp
                260                 265                 270
```

```
Tyr Leu Gly Arg Thr Asp Ala Thr Leu Ser Cys Asp Val Arg Ser Asn
            275                 280                 285

Pro Glu Pro Thr Gly Tyr Asp Trp Ser Thr Thr Ser Gly Thr Phe Pro
        290                 295                 300

Thr Ser Ala Val Ala Gln Gly Ser Gln Leu Val Ile His Ala Val Asp
305                 310                 315                 320

Ser Leu Phe Asn Thr Thr Phe Val Cys Thr Val Thr Asn Ala Val Gly
                325                 330                 335

Met Gly Arg Ala Glu Gln Val Ile Phe Val Arg Glu Thr Pro Asn Thr
            340                 345                 350

Ala Gly Ala Gly Ala Thr Gly Gly Ile Ile Gly Gly Ile Ile Ala Ala
        355                 360                 365

Ile Ile Ala Thr Ala Val Ala Ala Thr Gly Ile Leu Ile Cys Arg Gln
    370                 375                 380

Gln Arg Lys Glu Gln Thr Leu Gln Gly Ala Glu Asp Glu Asp Leu
385                 390                 395                 400

Glu Gly Pro Pro Ser Tyr Lys Pro Pro Thr Pro Lys Ala Lys Leu Glu
                405                 410                 415

Ala Gln Glu Met Pro Ser Gln Leu Phe Thr Leu Gly Ala Ser Glu His
            420                 425                 430

Ser Pro Leu Lys Thr Pro Tyr Phe Asp Ala Gly Ala Ser Cys Thr Glu
        435                 440                 445

Gln Glu Met Pro Arg Tyr His Glu Leu Pro Thr Leu Glu Glu Arg Ser
    450                 455                 460

Gly Pro Leu His Pro Gly Ala Thr Ser Leu Gly Ser Pro Ile Pro Val
465                 470                 475                 480

Pro Pro Gly Pro Pro Ala Val Glu Asp Val Ser Leu Asp Leu Glu Asp
                485                 490                 495

Glu Glu Gly Glu Glu Glu Glu Tyr Leu Asp Lys Ile Asn Pro Ile
            500                 505                 510

Tyr Asp Ala Leu Ser Tyr Ser Ser Pro Ser Asp Ser Tyr Gln Gly Lys
        515                 520                 525

Gly Phe Val Met Ser Arg Ala Met Tyr Val
    530                 535

<210> SEQ ID NO 175
<211> LENGTH: 360
<212> TYPE: PRT
<213> ORGANISM: Homo sapiens

<400> SEQUENCE: 175

Met Gly Asn Val Leu Ala Ala Ser Ser Pro Ala Gly Pro Pro Pro
1               5                   10                  15

Pro Pro Ala Pro Ala Leu Val Gly Leu Pro Pro Pro Pro Ser Pro
            20                  25                  30

Pro Gly Phe Thr Leu Pro Pro Leu Gly Gly Ser Leu Gly Ala Gly Thr
        35                  40                  45

Ser Thr Ser Arg Ser Ser Glu Arg Thr Pro Gly Ala Ala Thr Ala Ser
    50                  55                  60

Ala Ser Gly Ala Ala Glu Asp Gly Ala Cys Gly Cys Leu Pro Asn Pro
65                  70                  75                  80

Gly Thr Phe Glu Glu Cys His Arg Lys Cys Lys Glu Leu Phe Pro Ile
                85                  90                  95

Gln Met Glu Gly Val Lys Leu Thr Val Asn Lys Gly Leu Ser Asn His
            100                 105                 110
```

```
Phe Gln Val Asn His Thr Val Ala Leu Ser Thr Ile Gly Glu Ser Asn
            115                 120                 125

Tyr His Phe Gly Val Thr Tyr Val Gly Thr Lys Gln Leu Ser Pro Thr
    130                 135                 140

Glu Ala Phe Pro Val Leu Val Gly Asp Met Asp Asn Ser Gly Ser Leu
145                 150                 155                 160

Asn Ala Gln Val Ile His Gln Leu Gly Pro Gly Leu Arg Ser Lys Met
                165                 170                 175

Ala Ile Gln Thr Gln Gln Ser Lys Phe Val Asn Trp Gln Val Asp Gly
            180                 185                 190

Glu Tyr Arg Gly Ser Asp Phe Thr Ala Ala Val Thr Leu Gly Asn Pro
    195                 200                 205

Asp Val Leu Val Gly Ser Gly Ile Leu Val Ala His Tyr Leu Gln Ser
210                 215                 220

Ile Thr Pro Cys Leu Ala Leu Gly Gly Glu Leu Val Tyr His Arg Arg
225                 230                 235                 240

Pro Gly Glu Glu Gly Thr Val Met Ser Leu Ala Gly Lys Tyr Thr Leu
                245                 250                 255

Asn Asn Trp Leu Ala Thr Val Thr Leu Gly Gln Ala Gly Met His Ala
            260                 265                 270

Thr Tyr Tyr His Lys Ala Ser Asp Gln Leu Gln Val Gly Val Glu Phe
    275                 280                 285

Glu Ala Ser Thr Arg Met Gln Asp Thr Ser Val Ser Phe Gly Tyr Gln
290                 295                 300

Leu Asp Leu Pro Lys Ala Asn Leu Leu Phe Lys Gly Ser Val Asp Ser
305                 310                 315                 320

Asn Trp Ile Val Gly Ala Thr Leu Glu Lys Lys Leu Pro Pro Leu Pro
                325                 330                 335

Leu Thr Leu Ala Leu Gly Ala Phe Leu Asn His Arg Lys Asn Lys Phe
            340                 345                 350

Gln Cys Gly Phe Gly Leu Ile Gly
            355                 360

<210> SEQ ID NO 176
<211> LENGTH: 317
<212> TYPE: PRT
<213> ORGANISM: Homo sapiens

<400> SEQUENCE: 176

Met Lys Val Leu Trp Ala Ala Leu Leu Val Thr Phe Leu Ala Gly Cys
1               5                   10                  15

Gln Ala Lys Val Glu Gln Ala Val Glu Thr Glu Pro Glu Pro Glu Leu
            20                  25                  30

Arg Gln Gln Thr Glu Trp Gln Ser Gly Gln Arg Trp Glu Leu Ala Leu
        35                  40                  45

Gly Arg Phe Trp Asp Tyr Leu Arg Trp Val Gln Thr Leu Ser Glu Gln
    50                  55                  60

Val Gln Glu Glu Leu Leu Ser Ser Gln Val Thr Gln Glu Leu Arg Ala
65                  70                  75                  80

Leu Met Asp Glu Thr Met Lys Glu Leu Lys Ala Tyr Lys Ser Glu Leu
                85                  90                  95

Glu Glu Gln Leu Thr Pro Val Ala Glu Glu Thr Arg Ala Arg Leu Ser
            100                 105                 110

Lys Glu Leu Gln Ala Ala Gln Ala Arg Leu Gly Ala Asp Met Glu Asp
```

```
            115                 120                 125
Val Cys Gly Arg Leu Val Gln Tyr Arg Gly Glu Val Gln Ala Met Leu
130                 135                 140

Gly Gln Ser Thr Glu Glu Leu Arg Val Arg Leu Ala Ser His Leu Arg
145                 150                 155                 160

Lys Leu Arg Lys Arg Leu Leu Arg Asp Ala Asp Leu Gln Lys Arg
                165                 170                 175

Leu Ala Val Tyr Gln Ala Gly Ala Arg Glu Gly Ala Glu Arg Gly Leu
                180                 185                 190

Ser Ala Ile Arg Glu Arg Leu Gly Pro Leu Val Glu Gln Gly Arg Val
                195                 200                 205

Arg Ala Ala Thr Val Gly Ser Leu Ala Gly Gln Pro Leu Gln Glu Arg
210                 215                 220

Ala Gln Ala Trp Gly Arg Leu Arg Ala Arg Met Glu Glu Met Gly
225                 230                 235                 240

Ser Arg Thr Arg Asp Arg Leu Asp Glu Val Lys Glu Gln Val Ala Glu
                245                 250                 255

Val Arg Ala Lys Leu Glu Glu Gln Ala Gln Gln Ile Arg Leu Gln Ala
                260                 265                 270

Glu Ala Phe Gln Ala Arg Leu Lys Ser Trp Phe Glu Pro Leu Val Glu
                275                 280                 285

Asp Met Gln Arg Gln Trp Ala Gly Leu Val Glu Lys Val Gln Ala Ala
                290                 295                 300

Val Gly Thr Ser Ala Ala Pro Val Pro Ser Asp Asn His
305                 310                 315

<210> SEQ ID NO 177
<211> LENGTH: 83
<212> TYPE: PRT
<213> ORGANISM: Homo sapiens

<400> SEQUENCE: 177

Met Arg Leu Phe Leu Ser Leu Pro Val Leu Val Val Leu Ser Ile
1               5                   10                  15

Val Leu Glu Gly Pro Ala Pro Ala Gln Gly Thr Pro Asp Val Ser Ser
                20                  25                  30

Ala Leu Asp Lys Leu Lys Glu Phe Gly Asn Thr Leu Glu Asp Lys Ala
                35                  40                  45

Arg Glu Leu Ile Ser Arg Ile Lys Gln Ser Glu Leu Ser Ala Lys Met
            50                  55                  60

Arg Glu Trp Phe Ser Glu Thr Phe Gln Lys Val Lys Glu Lys Leu Lys
65                  70                  75                  80

Ile Asp Ser

<210> SEQ ID NO 178
<211> LENGTH: 270
<212> TYPE: PRT
<213> ORGANISM: Homo sapiens

<400> SEQUENCE: 178

Met Lys Pro Lys Met Lys Tyr Ser Thr Asn Lys Ile Ser Thr Ala Lys
1               5                   10                  15

Trp Lys Asn Thr Ala Ser Lys Ala Leu Cys Phe Lys Leu Gly Lys Ser
                20                  25                  30

Gln Gln Lys Ala Lys Glu Val Cys Pro Met Tyr Phe Met Lys Leu Arg
                35                  40                  45
```

```
Ser Gly Leu Met Ile Lys Lys Glu Ala Cys Tyr Phe Arg Arg Glu Thr
    50                  55                  60

Thr Lys Arg Pro Ser Leu Lys Thr Gly Arg Lys His Lys Arg His Leu
65                  70                  75                  80

Val Leu Ala Ala Cys Gln Gln Gln Ser Thr Val Glu Cys Phe Ala Phe
                85                  90                  95

Gly Ile Ser Gly Val Gln Lys Tyr Thr Arg Ala Leu His Asp Ser Ser
                100                 105                 110

Ile Thr Gly Ile Ser Pro Ile Thr Glu Tyr Leu Ala Ser Leu Ser Thr
            115                 120                 125

Tyr Asn Asp Gln Ser Ile Thr Phe Ala Leu Glu Asp Glu Ser Tyr Glu
    130                 135                 140

Ile Tyr Val Glu Asp Leu Lys Lys Asp Glu Lys Lys Asp Lys Val Leu
145                 150                 155                 160

Leu Ser Tyr Tyr Glu Ser Gln His Pro Ser Asn Glu Ser Gly Asp Gly
                165                 170                 175

Val Asp Gly Lys Met Leu Met Val Thr Leu Ser Pro Thr Lys Asp Phe
                180                 185                 190

Trp Leu His Ala Asn Asn Lys Glu His Ser Val Glu Leu His Lys Cys
            195                 200                 205

Glu Lys Pro Leu Pro Asp Gln Ala Phe Phe Val Leu His Asn Met His
    210                 215                 220

Ser Asn Cys Val Ser Phe Glu Cys Lys Thr Asp Pro Gly Val Phe Ile
225                 230                 235                 240

Gly Val Lys Asp Asn His Leu Ala Leu Ile Lys Val Asp Ser Ser Glu
                245                 250                 255

Asn Leu Cys Thr Glu Asn Ile Leu Phe Lys Leu Ser Glu Thr
            260                 265                 270

<210> SEQ ID NO 179
<211> LENGTH: 556
<212> TYPE: PRT
<213> ORGANISM: Homo sapiens

<400> SEQUENCE: 179

Met Gly Phe Trp Ile Leu Ala Ile Leu Thr Ile Leu Met Tyr Ser Thr
1                   5                   10                  15

Ala Ala Lys Phe Ser Lys Gln Ser Trp Gly Leu Glu Asn Glu Ala Leu
                20                  25                  30

Ile Val Arg Cys Pro Arg Gln Gly Lys Pro Ser Tyr Thr Val Asp Trp
            35                  40                  45

Tyr Tyr Ser Gln Thr Asn Lys Ser Ile Pro Thr Gln Glu Arg Asn Arg
    50                  55                  60

Val Phe Ala Ser Gly Gln Leu Leu Lys Phe Leu Pro Ala Ala Val Ala
65                  70                  75                  80

Asp Ser Gly Ile Tyr Thr Cys Ile Val Arg Ser Pro Thr Phe Asn Arg
                85                  90                  95

Thr Gly Tyr Ala Asn Val Thr Ile Tyr Lys Lys Gln Ser Asp Cys Asn
                100                 105                 110

Val Pro Asp Tyr Leu Met Tyr Ser Thr Val Ser Gly Ser Glu Lys Asn
            115                 120                 125

Ser Lys Ile Tyr Cys Pro Thr Ile Asp Leu Tyr Asn Trp Thr Ala Pro
    130                 135                 140

Leu Glu Trp Phe Lys Asn Cys Gln Ala Leu Gln Gly Ser Arg Tyr Arg
```

```
                145                 150                 155                 160
Ala His Lys Ser Phe Leu Val Ile Asp Asn Val Met Thr Glu Asp Ala
                    165                 170                 175

Gly Asp Tyr Thr Cys Lys Phe Ile His Asn Glu Asn Gly Ala Asn Tyr
                180                 185                 190

Ser Val Thr Ala Thr Arg Ser Phe Thr Val Lys Asp Glu Gln Gly Phe
            195                 200                 205

Ser Leu Phe Pro Val Ile Gly Ala Pro Ala Gln Asn Glu Ile Lys Glu
        210                 215                 220

Val Glu Ile Gly Lys Asn Ala Asn Leu Thr Cys Ser Ala Cys Phe Gly
225                 230                 235                 240

Lys Gly Thr Gln Phe Leu Ala Ala Val Leu Trp Gln Leu Asn Gly Thr
                245                 250                 255

Lys Ile Thr Asp Phe Gly Glu Pro Arg Ile Gln Gln Glu Glu Gly Gln
                    260                 265                 270

Asn Gln Ser Phe Ser Asn Gly Leu Ala Cys Leu Asp Met Val Leu Arg
                275                 280                 285

Ile Ala Asp Val Lys Glu Glu Asp Leu Leu Leu Gln Tyr Asp Cys Leu
        290                 295                 300

Ala Leu Asn Leu His Gly Leu Arg Arg His Thr Val Arg Leu Ser Arg
305                 310                 315                 320

Lys Asn Pro Ile Asp His His Ser Ile Tyr Cys Ile Ile Ala Val Cys
                    325                 330                 335

Ser Val Phe Leu Met Leu Ile Asn Val Leu Val Ile Ile Leu Lys Met
                340                 345                 350

Phe Trp Ile Glu Ala Thr Leu Leu Trp Arg Asp Ile Ala Lys Pro Tyr
            355                 360                 365

Lys Thr Arg Asn Asp Gly Lys Leu Tyr Asp Ala Tyr Val Val Tyr Pro
        370                 375                 380

Arg Asn Tyr Lys Ser Ser Thr Asp Gly Ala Ser Arg Val Glu His Phe
385                 390                 395                 400

Val His Gln Ile Leu Pro Asp Val Leu Glu Asn Lys Cys Gly Tyr Thr
                    405                 410                 415

Leu Cys Ile Tyr Gly Arg Asp Met Leu Pro Gly Glu Asp Val Val Thr
                420                 425                 430

Ala Val Glu Thr Asn Ile Arg Lys Ser Arg Arg His Ile Phe Ile Leu
            435                 440                 445

Thr Pro Gln Ile Thr His Asn Lys Glu Phe Ala Tyr Glu Gln Glu Val
        450                 455                 460

Ala Leu His Cys Ala Leu Ile Gln Asn Asp Ala Lys Val Ile Leu Ile
465                 470                 475                 480

Glu Met Glu Ala Leu Ser Glu Leu Asp Met Leu Gln Ala Glu Ala Leu
                    485                 490                 495

Gln Asp Ser Leu Gln His Leu Met Lys Val Gln Gly Thr Ile Lys Trp
                500                 505                 510

Arg Glu Asp His Ile Ala Asn Lys Arg Ser Leu Asn Ser Lys Phe Trp
            515                 520                 525

Lys His Val Arg Tyr Gln Met Pro Val Pro Ser Lys Ile Pro Arg Lys
        530                 535                 540

Ala Ser Ser Leu Thr Pro Leu Ala Ala Gln Lys Gln
545                 550                 555

<210> SEQ ID NO 180
```

```
<211> LENGTH: 51
<212> TYPE: DNA
<213> ORGANISM: Homo sapiens

<400> SEQUENCE: 180
ggagtgcagt gatgcgatct cggctyactg caagctccgc tcctgggtt c              51

<210> SEQ ID NO 181
<211> LENGTH: 51
<212> TYPE: DNA
<213> ORGANISM: Homo sapiens

<400> SEQUENCE: 181
acaagcctcc ccacatcctc ctggcygccc tccaagctgt tagaatagtg a             51

<210> SEQ ID NO 182
<211> LENGTH: 51
<212> TYPE: DNA
<213> ORGANISM: Homo sapiens

<400> SEQUENCE: 182
gggtggcctc tctgggtaac attacsaggt gtgagtatag gcagtttctg g             51

<210> SEQ ID NO 183
<211> LENGTH: 51
<212> TYPE: DNA
<213> ORGANISM: Homo sapiens

<400> SEQUENCE: 183
agaaacacaa tccggcccca aggcayggag ccaaagagga aaagcacaaa g             51

<210> SEQ ID NO 184
<211> LENGTH: 51
<212> TYPE: DNA
<213> ORGANISM: Homo sapiens

<400> SEQUENCE: 184
atttccagtt cggtgtctgt ctgggbgggt ggagctgacc ctcccctggg t             51

<210> SEQ ID NO 185
<211> LENGTH: 51
<212> TYPE: DNA
<213> ORGANISM: Homo sapiens

<400> SEQUENCE: 185
gggggtgtgg cccccaagct catagmtttg tgaggacccc acagcacatt c             51

<210> SEQ ID NO 186
<211> LENGTH: 51
<212> TYPE: DNA
<213> ORGANISM: Homo sapiens

<400> SEQUENCE: 186
gcccccaagc tcatagcttt gtgagkaccc cacagcacat tcagggaggg c             51

<210> SEQ ID NO 187
<211> LENGTH: 51
<212> TYPE: DNA
<213> ORGANISM: Homo sapiens

<400> SEQUENCE: 187
cttgggactt ggagggaggt ggaacrgcac actggacttc tcccgtctct a             51
```

-continued

```
<210> SEQ ID NO 188
<211> LENGTH: 51
<212> TYPE: DNA
<213> ORGANISM: Homo sapiens

<400> SEQUENCE: 188 ggttttacc cgcgtcacct ctgctytccc aagcctccat gcctcctctg t          51

<210> SEQ ID NO 189
<211> LENGTH: 51
<212> TYPE: DNA
<213> ORGANISM: Homo sapiens

<400> SEQUENCE: 189
gacccagtaa ggacatgccc gtgatkccct catgcagcct cattgacctc c          51

<210> SEQ ID NO 190
<211> LENGTH: 51
<212> TYPE: DNA
<213> ORGANISM: Homo sapiens

<400> SEQUENCE: 190
ccgtgatgcc ctcatgcagc ctcatygacc tccacagacc ccaccaagcc c          51

<210> SEQ ID NO 191
<211> LENGTH: 51
<212> TYPE: DNA
<213> ORGANISM: Homo sapiens

<400> SEQUENCE: 191
gaccccacca agccctgtgc caggcrgtgc tggggctgca gctgtggcct g          51

<210> SEQ ID NO 192
<211> LENGTH: 51
<212> TYPE: DNA
<213> ORGANISM: Homo sapiens

<400> SEQUENCE: 192
cagtgctggg gctgcagctg tggccwgcac agacccagtg ccgtcctccg g          51

<210> SEQ ID NO 193
<211> LENGTH: 51
<212> TYPE: DNA
<213> ORGANISM: Homo sapiens

<400> SEQUENCE: 193
tttgagacag gatctcactc tgtccstcag gctagagttc agtggtataa t          51

<210> SEQ ID NO 194
<211> LENGTH: 51
<212> TYPE: DNA
<213> ORGANISM: Homo sapiens

<400> SEQUENCE: 194
cctagctagt ttttgtattt ttgtaragac agggttttgc catgttgccc a          51

<210> SEQ ID NO 195
<211> LENGTH: 51
<212> TYPE: DNA
<213> ORGANISM: Homo sapiens

<400> SEQUENCE: 195
acaggaactt taacctaatt tgaggracag gaaggcactt catttattca t          51
```

```
<210> SEQ ID NO 196
<211> LENGTH: 51
<212> TYPE: DNA
<213> ORGANISM: Homo sapiens

<400> SEQUENCE: 196
atcccagcac tttgggaggc cgaggygggc agatcacctg aggtcaggag t          51

<210> SEQ ID NO 197
<211> LENGTH: 51
<212> TYPE: DNA
<213> ORGANISM: Homo sapiens

<400> SEQUENCE: 197
tcaaattaaa aaaaaaaaaa aaaaaraaag aaagaaagat cagccaggcg t          51

<210> SEQ ID NO 198
<211> LENGTH: 51
<212> TYPE: DNA
<213> ORGANISM: Homo sapiens

<400> SEQUENCE: 198
ctgggattac aggtgtgagc caccaygcct gaccagataa tcaattttca t          51

<210> SEQ ID NO 199
<211> LENGTH: 51
<212> TYPE: DNA
<213> ORGANISM: Homo sapiens

<400> SEQUENCE: 199
atgaggctca ccctgtctga ccctargctg gggctgcttg cttggtaggc a          51

<210> SEQ ID NO 200
<211> LENGTH: 51
<212> TYPE: DNA
<213> ORGANISM: Homo sapiens

<400> SEQUENCE: 200
ggaagggtgg gaggggcgcc gtggcyaccc tgcgagtgag aaccaataca a          51

<210> SEQ ID NO 201
<211> LENGTH: 51
<212> TYPE: DNA
<213> ORGANISM: Homo sapiens

<400> SEQUENCE: 201
cccgagatcc aggccatcgc agcccmgcgg gggcccctcg cccctcaccc t          51

<210> SEQ ID NO 202
<211> LENGTH: 51
<212> TYPE: DNA
<213> ORGANISM: Homo sapiens

<400> SEQUENCE: 202
gtcacggtgt cagcaaggtg tcagcraggt tccttgggta tgggacccaa a          51

<210> SEQ ID NO 203
<211> LENGTH: 51
<212> TYPE: DNA
<213> ORGANISM: Homo sapiens

<400> SEQUENCE: 203
gagatgagag ttggtgtggg gttggrgtgg agtgtgacag cgtttctctt c          51
```

<210> SEQ ID NO 204
<211> LENGTH: 51
<212> TYPE: DNA
<213> ORGANISM: Homo sapiens

<400> SEQUENCE: 204
taaggacacc aggaaggctc acctgraaat ggttactcaa cccttgttg a    51

<210> SEQ ID NO 205
<211> LENGTH: 51
<212> TYPE: DNA
<213> ORGANISM: Homo sapiens

<400> SEQUENCE: 205
atccagaggt actgtctccc catagsagct aggctggagt gaaggaacag g    51

<210> SEQ ID NO 206
<211> LENGTH: 51
<212> TYPE: DNA
<213> ORGANISM: Homo sapiens

<400> SEQUENCE: 206
caatcgggga gtccaactac cacttyggg tcacatatgt ggggacaaag c    51

<210> SEQ ID NO 207
<211> LENGTH: 51
<212> TYPE: DNA
<213> ORGANISM: Homo sapiens

<400> SEQUENCE: 207
tttggctaca aatttgttat tagaargata caatgaatgg atgaaaaagg a    51

<210> SEQ ID NO 208
<211> LENGTH: 51
<212> TYPE: DNA
<213> ORGANISM: Homo sapiens

<400> SEQUENCE: 208
gggcaaaact ggaggcccag acaggkttgg ggggactgaa tgaggtctct g    51

<210> SEQ ID NO 209
<211> LENGTH: 51
<212> TYPE: DNA
<213> ORGANISM: Homo sapiens

<400> SEQUENCE: 209
cacctacctt ttaacaagtg ttcccyggta atgtggaggc ccacagggtg g    51

<210> SEQ ID NO 210
<211> LENGTH: 51
<212> TYPE: DNA
<213> ORGANISM: Homo sapiens

<400> SEQUENCE: 210
cagaatcctg cgtgcccctc aattcyggaa tccctcccgg gaccccaggc c    51

<210> SEQ ID NO 211
<211> LENGTH: 51
<212> TYPE: DNA
<213> ORGANISM: Homo sapiens

<400> SEQUENCE: 211
aagggaggac acctcgccca gtaatmcaga caccctcctc cattctgggg g    51

<210> SEQ ID NO 212
<211> LENGTH: 51
<212> TYPE: DNA
<213> ORGANISM: Homo sapiens

<400> SEQUENCE: 212
ctagaaagag ctgggaccct gggaasccct ggcctccagg tagtctcagg a    51

<210> SEQ ID NO 213
<211> LENGTH: 51
<212> TYPE: DNA
<213> ORGANISM: Homo sapiens

<400> SEQUENCE: 213
acctcaacct cctggcccca ttcagrcaga ccctgggccc cctcttctga g    51

<210> SEQ ID NO 214
<211> LENGTH: 51
<212> TYPE: DNA
<213> ORGANISM: Homo sapiens

<400> SEQUENCE: 214
gctgggcgcg gacatggagg acgtgygcgg ccgcctggtg cagtaccgcg g    51

<210> SEQ ID NO 215
<211> LENGTH: 51
<212> TYPE: DNA
<213> ORGANISM: Homo sapiens

<400> SEQUENCE: 215
tggtgccttt attctaagct attttyattt tttttctgct gtcattattc t    51

<210> SEQ ID NO 216
<211> LENGTH: 51
<212> TYPE: DNA
<213> ORGANISM: Homo sapiens

<400> SEQUENCE: 216
cccaggagcc gccggcactc tcttcycctc ccaccccctc agttctcaga g    51

<210> SEQ ID NO 217
<211> LENGTH: 51
<212> TYPE: DNA
<213> ORGANISM: Homo sapiens

<400> SEQUENCE: 217
tctgtcaccc aagctggagt gcagtrgcac aatcttggct cactgcaacc t    51

<210> SEQ ID NO 218
<211> LENGTH: 51
<212> TYPE: DNA
<213> ORGANISM: Homo sapiens

<400> SEQUENCE: 218
ctcccaaagt tctgggaata caggcdtgag ccactgcaac cagccagtag c    51

<210> SEQ ID NO 219
<211> LENGTH: 51
<212> TYPE: DNA
<213> ORGANISM: Homo sapiens

<400> SEQUENCE: 219
ccagctcaga gcttccagtc cctgtmagcc caggggccc ccctacttcc c          51

<210> SEQ ID NO 220
<211> LENGTH: 51
<212> TYPE: DNA
<213> ORGANISM: Homo sapiens

<400> SEQUENCE: 220
aggaggggcg tcagagggtg aataaragca gatagagtgt ttgggggagg t          51

<210> SEQ ID NO 221
<211> LENGTH: 51
<212> TYPE: DNA
<213> ORGANISM: Homo sapiens

<400> SEQUENCE: 221
ccaccacgct cggctaattt ttgaaytttt ttgtagagat gaggtctccc t          51

<210> SEQ ID NO 222
<211> LENGTH: 51
<212> TYPE: DNA
<213> ORGANISM: Homo sapiens

<400> SEQUENCE: 222
caccgtggtc tcgatctcct gacttygtga tccgcctgcc tcgacctccc a          51

<210> SEQ ID NO 223
<211> LENGTH: 51
<212> TYPE: DNA
<213> ORGANISM: Homo sapiens

<400> SEQUENCE: 223
atttttggcc gggcagggtg gctcaygcct gtaatcccag cactttggga g          51

<210> SEQ ID NO 224
<211> LENGTH: 51
<212> TYPE: DNA
<213> ORGANISM: Homo sapiens

<400> SEQUENCE: 224
actctgtctc aaaaaaaaaa aaaamaaaa aaaaaacaag atggtcttgc c          51

<210> SEQ ID NO 225
<211> LENGTH: 51
<212> TYPE: DNA
<213> ORGANISM: Homo sapiens

<400> SEQUENCE: 225
ccaaaaaaga aaaaaactc ctggcrcggt ggctcacgcc agtaatccca g          51

<210> SEQ ID NO 226
<211> LENGTH: 51
<212> TYPE: DNA
<213> ORGANISM: Homo sapiens

<400> SEQUENCE: 226
tctcgatctc ctgacctggt gatccrcccg cctcggcctc ccaaagtgct g          51

<210> SEQ ID NO 227
<211> LENGTH: 51
<212> TYPE: DNA
<213> ORGANISM: Homo sapiens

```
<400> SEQUENCE: 227
cgaactcctg acctcaagtg atcagsctac ctcggcctcc caaagtgttg g          51

<210> SEQ ID NO 228
<211> LENGTH: 51
<212> TYPE: DNA
<213> ORGANISM: Homo sapiens

<400> SEQUENCE: 228
tcccataagg gcattgaggc ccagaraggt gaagttactt gtataaggtc a          51

<210> SEQ ID NO 229
<211> LENGTH: 51
<212> TYPE: DNA
<213> ORGANISM: Homo sapiens

<400> SEQUENCE: 229
aatgtcacta tgctacactt ttcctrgtgt ggtctacccg agatgagggg c          51

<210> SEQ ID NO 230
<211> LENGTH: 51
<212> TYPE: DNA
<213> ORGANISM: Homo sapiens

<400> SEQUENCE: 230
gtgaggagcg cctcttcccg gccgcmcatc gtctgagatg tggggagcgc c          51

<210> SEQ ID NO 231
<211> LENGTH: 51
<212> TYPE: DNA
<213> ORGANISM: Homo sapiens

<400> SEQUENCE: 231
acctcctggg ttcaagcgat tctcaygcct cagcctactg agtagctggg a          51

<210> SEQ ID NO 232
<211> LENGTH: 51
<212> TYPE: DNA
<213> ORGANISM: Homo sapiens

<400> SEQUENCE: 232
ggtggtgggt gcctgtagtc tcagcwactt gggaggctga ggcatgagaa t          51

<210> SEQ ID NO 233
<211> LENGTH: 51
<212> TYPE: DNA
<213> ORGANISM: Homo sapiens

<400> SEQUENCE: 233
attacaggcc tgtgccacca cacccrgcta attttttcta tttttgacag g          51

<210> SEQ ID NO 234
<211> LENGTH: 51
<212> TYPE: DNA
<213> ORGANISM: Homo sapiens

<400> SEQUENCE: 234
tctagggaca cggtgtgaat gagggsggga tgagatcaca gggttattac t          51

<210> SEQ ID NO 235
<211> LENGTH: 51
<212> TYPE: DNA
<213> ORGANISM: Homo sapiens
```

```
<400> SEQUENCE: 235
tcttgtatga ctagatgtag tcactrcagt ggaaaccaac atacgaaaga g            51

<210> SEQ ID NO 236
<211> LENGTH: 51
<212> TYPE: DNA
<213> ORGANISM: Homo sapiens

<400> SEQUENCE: 236
gctgaggcgc ttcaggactc cctccrgcat cttatgaaag tacaggggac c            51

<210> SEQ ID NO 237
<211> LENGTH: 51
<212> TYPE: DNA
<213> ORGANISM: Homo sapiens

<400> SEQUENCE: 237
attcccagaa aggcctctag tttgaytccc ttggctgccc agaagcaata g            51

<210> SEQ ID NO 238
<211> LENGTH: 51
<212> TYPE: DNA
<213> ORGANISM: Homo sapiens

<400> SEQUENCE: 238
agaaaggcct ctagtttgac tccctyggct gcccagaagc aatagtgcct g            51

<210> SEQ ID NO 239
<211> LENGTH: 51
<212> TYPE: DNA
<213> ORGANISM: Homo sapiens

<400> SEQUENCE: 239
tgttttttct ataaaaataa aaaaawttta aaagaaaca aacattaaaa a             51

<210> SEQ ID NO 240
<211> LENGTH: 51
<212> TYPE: DNA
<213> ORGANISM: Homo sapiens

<400> SEQUENCE: 240
actcccagaa gacctagcgc gccagvcagg cacttccttt tctctttatc c            51

<210> SEQ ID NO 241
<211> LENGTH: 51
<212> TYPE: DNA
<213> ORGANISM: Homo sapiens

<400> SEQUENCE: 241
gacctagcgc gccaggcagg cacttycttt tctctttatc cccaacttcc t            51

<210> SEQ ID NO 242
<211> LENGTH: 51
<212> TYPE: DNA
<213> ORGANISM: Homo sapiens

<400> SEQUENCE: 242
tcagaaactc cctttctagc cgggcrcggt agctcacgcc tgtaatttac a            51

<210> SEQ ID NO 243
<211> LENGTH: 51
<212> TYPE: DNA
```

```
<213> ORGANISM: Homo sapiens

<400> SEQUENCE: 243
tgatggcacc aggccgtcac caccgyggtg acagcacaca cacatccaca c         51

<210> SEQ ID NO 244
<211> LENGTH: 51
<212> TYPE: DNA
<213> ORGANISM: Homo sapiens

<400> SEQUENCE: 244
tgaggagtga ttggaggagt ggacgraggt agaagggagc tgggacgaga g         51

<210> SEQ ID NO 245
<211> LENGTH: 34
<212> TYPE: DNA
<213> ORGANISM: Homo sapiens

<400> SEQUENCE: 245
gcgcgtatcg ggccgccctg tggtcagcag gtgg                            34

<210> SEQ ID NO 246
<211> LENGTH: 16
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Any amino acid

<400> SEQUENCE: 246

Ala Asp Ser Gly Glu Gly Asp Phe Xaa Ala Glu Gly Gly Gly Val Arg
1               5                   10                  15
```